US009499837B2

(12) United States Patent
Bidney et al.

(10) Patent No.: US 9,499,837 B2
(45) Date of Patent: Nov. 22, 2016

(54) METHODS AND COMPOSITIONS FOR PRODUCING MALE STERILE PLANTS

(75) Inventors: Dennis Bidney, Urbandale, IA (US); Andrew Mark Cigan, Johnston, IA (US); Saverio Carl Falco, Wilmington, DE (US); Huirong Gao, Johnston, IA (US); Derek Jantz, Durham, NC (US); Mike Lassner, Urbandale, IA (US); Keith Lowe, Johnston, IA (US); Leszek A Lyznik, Johnston, IA (US); James Jefferson Smith, Durham, NC (US)

(73) Assignees: E.I. du Pont de Nemours and Company, Wilmington, DE (US); Pioneer Hi-Bred International, Inc., Johnston, IA (US)

( * ) Notice: Subject to any disclaimer, the term of this patent is extended or adjusted under 35 U.S.C. 154(b) by 601 days.

(21) Appl. No.: 13/526,912

(22) Filed: Jun. 19, 2012

(65) Prior Publication Data

US 2014/0020131 A1    Jan. 16, 2014

Related U.S. Application Data

(60) Provisional application No. 61/499,441, filed on Jun. 21, 2011.

(51) Int. Cl.
*C12N 15/82* (2006.01)
*C12N 15/09* (2006.01)

(52) U.S. Cl.
CPC ....... *C12N 15/8289* (2013.01); *C12N 15/8213* (2013.01)

(58) Field of Classification Search
None
See application file for complete search history.

(56) References Cited

U.S. PATENT DOCUMENTS

| | | | |
|---|---|---|---|
| 4,654,465 A | 3/1987 | Brar | 800/1 |
| 4,727,219 A | 2/1988 | Brar | 800/1 |
| 5,478,369 A | 12/1995 | Albertsen | 47/58 |
| 5,750,868 A | 5/1998 | Cigan | 800/205 |
| 6,140,466 A | 10/2000 | Barbas | 530/350 |
| 6,281,348 B1 | 8/2001 | Cigan | 536/24.1 |
| 6,453,242 B1 | 9/2002 | Eisenberg | 702/190 |
| 6,511,808 B2 | 1/2003 | Wolffe | 514/100 |
| 6,743,968 B2 | 6/2004 | Dellaporta | 800/278 |
| 6,790,941 B2 | 9/2004 | Barbas | 530/400 |
| 7,154,024 B2 | 12/2006 | Albertsen | 800/287 |
| 7,517,975 B2 * | 4/2009 | Albertsen | C07K 14/415 536/23.6 |
| 7,612,251 B2 | 11/2009 | Albertsen | 800/274 |
| 7,919,676 B2 | 4/2011 | Albertsen | 800/274 |
| 7,973,152 B2 | 7/2011 | Albertsen | 536/23.6 |
| 8,338,157 B2 * | 12/2012 | Jantz | C12N 9/22 435/199 |
| 2002/0076711 A1 | 6/2002 | Wolffe | 514/100 |
| 2002/0144305 A1 | 10/2002 | Dellaporta | 800/278 |
| 2003/0059767 A1 | 3/2003 | Barbas | 530/400 |
| 2003/0108880 A1 | 6/2003 | Rebar | 800/278 |
| 2004/0221331 A1 | 11/2004 | Albertsen | 800/287 |
| 2006/0015968 A1 | 1/2006 | Albertsen | 536/23.6 |
| 2006/0288440 A1 | 12/2006 | Albertsen | 800/274 |
| 2008/0086783 A1 | 4/2008 | Albertsen | 536/23.6 |
| 2008/0244765 A1 | 10/2008 | Zhao | 800/278 |
| 2009/0038026 A1 | 2/2009 | Albertsen | 800/274 |
| 2009/0133152 A1 * | 5/2009 | Lyznik | C12N 9/22 800/275 |
| 2011/0202479 A1 * | 8/2011 | Jantz | C12N 9/22 705/500 |
| 2014/0020131 A1 | 1/2014 | Bidney | 800/278 |

FOREIGN PATENT DOCUMENTS

| | | |
|---|---|---|
| AU | 2012333207 | 6/2012 |
| BR | 1120130331763 | 6/2012 |
| CN | 201280040579.3 | 6/2012 |
| EA | 201490056 | 6/2012 |
| EP | 12823277.4 | 6/2012 |
| ID | P00201400327 | 6/2012 |
| IN | 11330/DELNP/2013 | 6/2012 |
| MX | MX/a/2013/015174 | 6/2012 |
| TH | 1301007217 | 6/2012 |
| UA | a201400354 | 6/2012 |
| WO | PCT/US2012/043082 | 6/2012 |
| ZA | 2014/00368 | 6/2012 |

OTHER PUBLICATIONS

Seligman et al (2002) Nucleic Acids Research vol. 30 pp. 3870-3879.*
Nelson et al, Pharmocogenetics (1996) 6: 1-42.*
U.S. Appl. No. 61/499,441, filed Jun. 21, 2011, Dennis L. Bidney.
U.S. Appl. No. 13/526,912, filed Jun. 19, 2012, Dennis L. Bidney.
U.S. Appl. No. 14/129,038, filed Jun. 19, 2012, Dennis L. Bidney.
Aarts M.G., et al. (1993) Transposon tagging of a male sterility gene in Arabidopsis. Nature 363: 715-717.
Albertsen M.C. et al., (1993) Cloning and utilizing a maize nuclear male sterility gene. Proc Annu Corn Sorghum Ind Res Conf 48:224-233.

(Continued)

*Primary Examiner* — Brent Page
(74) *Attorney, Agent, or Firm* — Ballard Spahr LLP

(57) ABSTRACT

Methods of making a targeted modification in a male fertility gene in the genome of a plant are disclosed. The methods involve contacting a plant cell with an engineered double-strand-break-inducing agent capable of inducing a double-strand break in a target sequence in the male fertility gene and identifying a cell comprising an alteration in the target sequence. Also disclosed are plants, plant cells, plant parts, and seeds comprising a male fertility gene with an alteration in a male fertility gene. Nucleic acid molecules comprising male fertility genes with at least one targeted modification therein, optimized nucleic acid molecules encoding endonucleases that are engineered double-strand-break-inducing agents and expression cassettes, host cells, and plants comprising one or more of the nucleic acid molecules are further disclosed.

14 Claims, 18 Drawing Sheets

(56) References Cited

OTHER PUBLICATIONS

Figure 1:
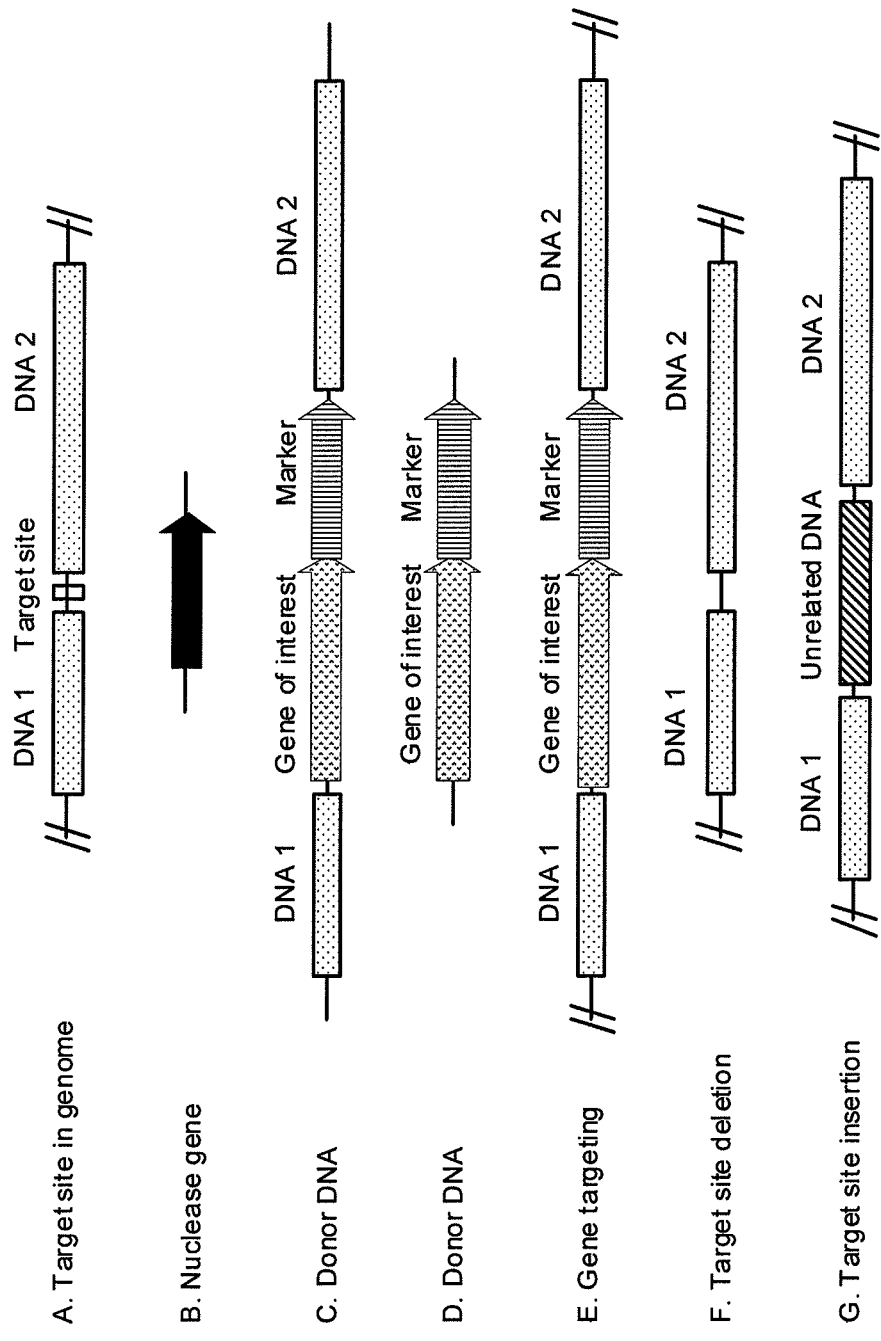

Chames et al., (2005) In vivo selection of engineered homing endonucleases using double-strand break induced homologous recombination. Nucleic Acids Res 33(20):e178 [10 pages].

Chaubal et al., (2000) Two male-sterile mutants of Zea mays (Poaceae) with an extra cell division in the anther wall. Am J Bot 87:1193-1201.

Chen and Zhao, (2005) A highly sensitive selection method for directed evolution of homing endonucleases. Nucleic Acids Res 33(18):e154 [7 pages].

Chevalier et al., (2002) Design, activity, and structure of a highly specific artificial endonuclease. Mol Cell 10:895-905.

Durai et al., (2005) Zinc finger nucleases: custom-designed molecular scissors for genome engineering of plant and mammalian cells. Nucleic Acids Res 33(18):5978-5990.

Epinat et al., (2003) A novel engineered meganuclease induces homologous recombination in yeast and mammalian cells. Nucleic Acids Res 31(11):2952-2962.

Gao et al., (2010) Heritable targeted mutagenesis in maize using a designed endonuclease. Plant J 61:176-187.

Gimble et al., (2003) Assessing the plasticity of DNA target site recognition of the PI-SceI homing endonuclease using a bacterial two-hybrid selection system. Mol Biol 334:993-1008.

Gruen et al., (2002) An in vivo selection system for homing endonuclease activity. Nucleic Acids Res 30(7):e29 [6 pages].

Li et al., (2010) Cytochrome P450 family member CYP704B2 catalyzes the ω-hydroxylation of fatty acids and is required for anther cutin biosynthesis and pollen exine formation in rice. Plant Cell 22:173-190.

Mani et al., (2005) Design, engineering, and characterization of zinc finger nucleases. Biochem Biophys Res Comm 335:447-457.

Neuffer et al., (1977) Mutants of maize. Cold Spring Harbor Laboratory Press, Cold Spring Harbor, NY.

Puchta et al., (1996) Two different but related mechanisms are used in plants for the repair of genomic double-strand breaks by homologous recombination. Proc. Natl. Acad. Sci. USA 93:5055-5060.

Rosen et al., (2006) Homing endonuclease I-CreI derivatives with novel DNA target specificities. Nucleic Acids Res 34(17):4791-4800.

Sadowski, (1993) Site-specific genetic recombination: hops, flips, and flops. FASEB J 7:760-767.

Sauer, (1994) Site-specific recombination: developments and applications. Curr Op Biotechnol 5:521-527.

Seligman et al., (2002) Mutations altering the cleavage specificity of a homing endonuclease. Nucleic Acids Res 30(17):3870-3879.

Smith et al., (2006) A combinatorial approach to create artificial homing endonucleases cleaving chosen sequences. Nucleic Acids Res 34(22):e149 [12 pages].

Sussman et al., (2004) Isolation and characterization of new homing endonuclease specificities at individual target site positions. J Mol Biol 342:31-41.

Unger et al. (2002) A chimeric ecdysone receptor facilitates methoxyfenozide-dependent restoration of male fertility in ms45 maize. Transgenic Research 11(5): 455-465.

Walbot, (2000) Saturation mutagenesis using maize transposons. Curr Opin Plant . Biol 3(2): 103-107.

West et al., (1985) Three new male-sterile genes. Maize Newsletter 59:87 [2 pages].

Yang et al., (2009) Targeted mutagenesis in the progeny of maize transgenic plants. Plant Mol Biol 70:669-679.

Preliminary Amendment filed Dec. 23, 2013 with the USPTO for U.S. Appl. No. 14/129,038, filed Dec. 23, 2013 [Inventor—Bidney; Applicant—Pioneer Hi-Bred International, Inc.;] [4 pages].

International Search Report and Written Opinion mailed Jul. 16, 2013 by the International Searching Authority for PCT/US2012/043082, filed Jun. 19, 2012 [Inventor—Bidney; Applicant—Pioneer Hi-Bred International, Inc.;] [17 pages].

International Preliminary Report on Patentability mailed Dec. 23, 2013 by the International Bureau for PCT/US2012/043082, filed Jun. 19, 2012 [Inventor—Bidney; Applicant—Pioneer Hi-Bred International, Inc.;] [12 pages].

* cited by examiner

FIG. 2

| | |
|---|---|
| Wild type | CGGCGGGATGGTGACGTACGTGCCCTACTCGAT |
| 3281 | CGGCGGGATGGTGACG          TACTCGAT |
| 2963 | CGGCGGGATGGTGACGT CGTGCCCTACTCGAT |
| 2980 | CGGCGGGATGGTGACG ACGTGCCCTACTCGAT |
| 3861 | CGGCGGGATGGTG    ACGTGCCCTACTCGAT |
| 3956 | CGGCGGGATGGTGAC TACGTGCCCTACTCGAT |
| 3990 | CGGCGGGATGGTGACGT CGTGCCCTACTCGAT |
| 6227 | CGGCGGGATGGTGACG ACGTGCCCTACTCGAT |

FIG. 3

```
MS26 TS       ------------------------GATGGTGACGTACGTGCCCTAC---------------------
maize MS26    AGGTGAGGGCCGGGGATGGTGACGTACGTGCCCTACTCGATCGATGGGGCGG
sorghum MS26  AGGTGAGGGCCGGGGATGGTGACGTACGTGCCCTACTCGATCGATGGGGCGG
rice MS26     AGGTGCGCGCCGGGGATGGTGACGTACGTGCCCTACTCCATCCATGGGGCGG
rye MS26      AGGTGCGGCCCGGGGATGGTGACGTACGTGCCCTACTCCATGGGGAGG
              AGGTGCGCGCCGGGGATGGTGACGTACGTGCCCTACTCCATGGGGCGG
```

FIG. 5

FIG. 7

```
MS26WT   GTGCTCCCCGACGGCACCAAGGTGCGCGCCGGCGGGATGGTGACGTACGTGCCCTACTCCATGGGGAGGATGGAGTACAACTGGGGCCCCGACGCGGGCGA
MS26.1   GTGCTCCCCGACGGCACCAAGGTGCGCGCCGGCGGGATGGTGACGTACGTGCCCTACTCCATGGGGAGGATGGAGTACAACTGGGGCCCCGACGCGGGCGA
MS26.2   GTGCTCCCCGACGGCACCAAGGTGCGCGCCGGCGGGATGGTG----ACGTGCCCTACTCCATGGGGAGGATGGAGTACAACTGGGGCCCCGACGCGGGCGA
MS26.3   GTGCTCCCCGACGGCACCAAGGTGCGCGCCGGCGGGATGGTGA---------GCGTGCCCTACTCCATGGGGAGGATGGAGTACAACTGGGGCCCCGACGCGGGCGA
MS26.4   GTGCTCCCCGACGGCACCAAGGT---------------------------GTACGTGCCCTACTCCATGGGGAGGATGGAGTACAACTGGGGCCCCGACGCGGGCGA
MS26.5   GTGCTCCCCGACGGCACCAAGGTGCGCGCCGGCGGGATGGTGA--------------GGATGGAGTACAACTGGGGCCCCGACGCGGGCGA
MS26.6   GTGCTCCCCGACGGCACCAAGGTGCGCGCCGGCGGGATG--------GTGCCCTACTCCATGGGGAGGATGGAGTACAACTGGGGCCCCGACGCGGGCGA
MS26.7   GTGCTCCCCGACGGCACCAAGGTGCGCGCCGGCGGGATGGTGAC-----------------GGGGAGGATGGAGTACAACTGGGGCCCCGACGCGGGCGA
MS26.8   GTGCTCCCCGACGGCACCAAGGTGCGCGCCGGCGGGATGGTG-------------TACAACTGGGGAGGATGGAGTACAACTGGGGCCCCGACGCGGGCGA
MS26.9   GTGCTCCCCGACGGCACCAAGGTGCGCGCCGGCGGGATGGTGACG-----------TACTCCATGGGGAGGATGGAGTACAACTGGGGCCCCGACGCGGGCGA
MS26.9   --------------------------------238bp Deletion------------------------------
MS26.10  --------------------------------192bp Deletion------------------------------
```

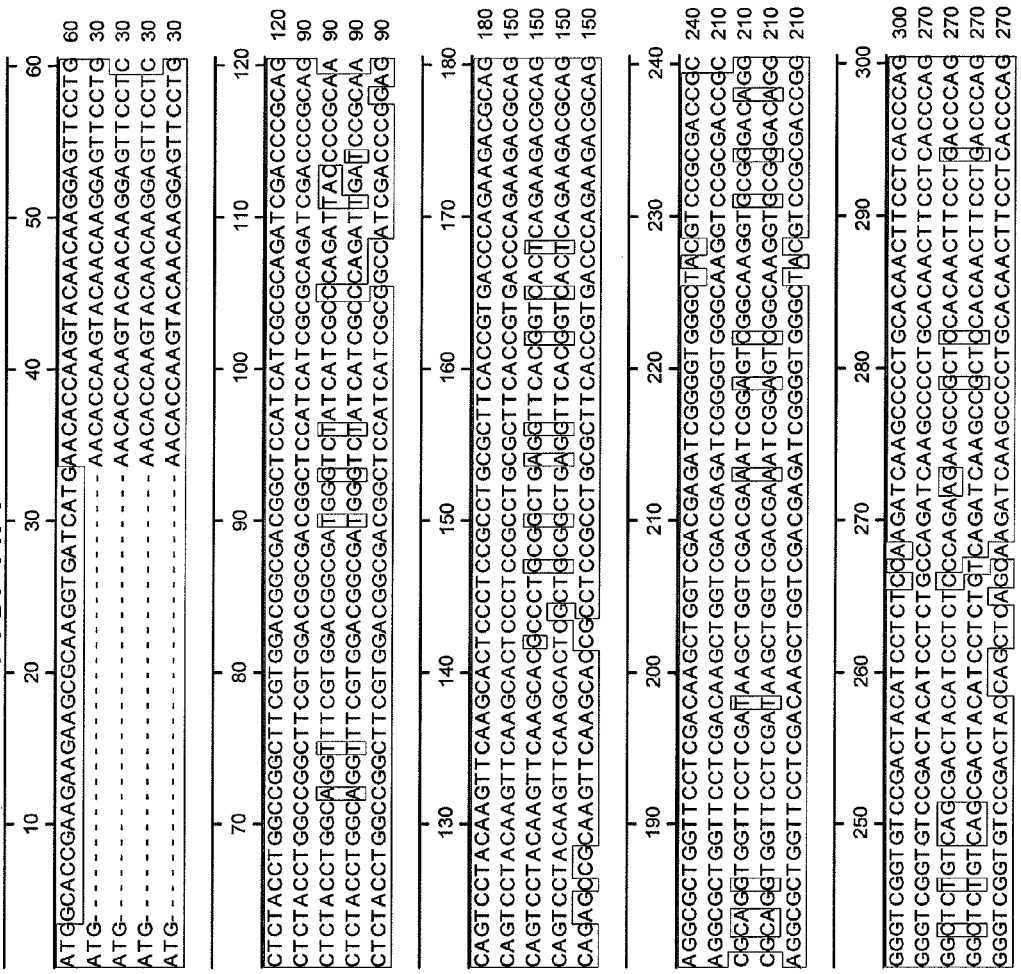

Sorghum MS26 mutations and deletions

Flowers from MS26/ ms26.78Δ (A) and ms26.78Δ / ms26.78Δ (B) sorghum plants.

Stigmas, anthers and pollen from MS26/ ms26.78Δ (A, C) and ms26.78Δ / ms26.78Δ (B, D) sorghum plants.

```
                          SEQUENCE LISTING

<160> NUMBER OF SEQ ID NOS: 78

<210> SEQ ID NO 1
<211> LENGTH: 22
<212> TYPE: DNA
<213> ORGANISM: Zea mays
<220> FEATURE:
<221> NAME/KEY: misc_feature
<222> LOCATION: (0)...(0)
<223> OTHER INFORMATION: TS-MS26 target site

<400> SEQUENCE: 1
gatggtgacg tacgtgccct ac                                              22

<210> SEQ ID NO 2
<211> LENGTH: 10
<212> TYPE: PRT
<213> ORGANISM: Simian virus 40
<220> FEATURE:
<221> NAME/KEY: DOMAIN
<222> LOCATION: (1)...(10)
<223> OTHER INFORMATION: Nuclear localization signal (SV40 NLS-1)

<400> SEQUENCE: 2

Met Ala Pro Lys Lys Lys Arg Lys Val Ile
1               5                   10

<210> SEQ ID NO 3
<211> LENGTH: 10
<212> TYPE: PRT
<213> ORGANISM: Simian virus 40
<220> FEATURE:
<221> NAME/KEY: DOMAIN
<222> LOCATION: (1)...(10)
<223> OTHER INFORMATION: Nuclear localization signal (SV40 NLS-2)

<400> SEQUENCE: 3

Met Ala Pro Lys Lys Lys Arg Lys Val His
1               5                   10

<210> SEQ ID NO 4
<211> LENGTH: 1083
<212> TYPE: DNA
<213> ORGANISM: Artificial Sequence
<220> FEATURE:
<223> OTHER INFORMATION: Plant-optimized nucleotide sequence (without an
      intron) encoding the engineered MS26 endonuclease

<400> SEQUENCE: 4
atggcaccga agaagaagcg caaggtgatc atgaacacca agtacaacaa ggagttcctg      60
ctctacctgg ccggcttcgt ggacggcgac ggctccatca tcgcgcagat cgaccccgcag    120 cagtcctaca gttcaagca ctccctccgc ctgcgcttca ccgtgaccca aagacgcag       180 aggcgctggt tcctcgacaa gctggtcgac gagatcgggg tgggctacgt ccgcgaccgc    240
gggtcggtgt ccgactacat cctctccaag atcaagcccc tgcacaactt cctcacccag    300
ctccagccgt tcctcaagct gaagcagaag caggcgaacc tcgtcctgaa gatcatcgag    360
cagctcccct cggccaagga gtccccggac aagttcctgg aggtgtgcac gtgggtcgac    420
cagatcgcgg ccctcaacga cagcaagacc cgcaagacga cctcggagac ggtgcgggcg    480
```

```
gtcctggact ccctctcagg atccgtggga ggtctatcgc catctcaggc atccagcgcc    540
gcatcctcgg cttcctcaag cccgggttca gggatctccg aagcactcag agctggagca    600
actaagtcca aggaattcct gctctacctg gccggcttcg tggacggcga cggctccatc    660
tgcgcgtcca tcgacccgaa ccagtcctgc aagttcaagc accagctccg cctgcgcttc    720
accgtgaccc agaagacgca gaggcgctgg ttcctcgaca gctggtcga cgagatcgggg    780 gtgggctacg tctacgaccg cgggtcggtg tccgactacc gcctctccaa gatcaagccc    840
ctgcacaact tcctcaccca gctccagccg ttcctcaagc tgaagcagaa gcaggcgaac    900
ctcgtcctga gatcatcga gcagctcccc tcggccaagg agtccccgga caagttcctg    960
gaggtgtgca cgtgggtcga ccagatcgcg ccctcaacg acagcaagac ccgcaagacg   1020
acctcggaga cggtgcgggc ggttctagac tccctcagcg agaagaagaa gtcgtccccc   1080
tga                                                                 1083

<210> SEQ ID NO 5
<211> LENGTH: 929
<212> TYPE: DNA
<213> ORGANISM: Artificial Sequence
<220> FEATURE:
<223> OTHER INFORMATION: Plant-optimized nucleotide sequence (without an
      intron) encoding the engineered MS26+ endonuclease

<400> SEQUENCE: 5
atgaacacca agtacaacaa ggagttcctg ctctacctgg ccggcttcgt ggacggcgac     60
ggctccatca tcgcgcagat cgacccgcag cagtcctaca agttcaagca ctccctccgc    120
ctgcgcttca ccgtgaccca gaagacgcag aggcgctggt tcctcgacaa gctggtcgac    180
gagatcgggg tgggcaaggt ccgcgaccgc gggtcggtgt ccgactacat cctctgccag    240
atcaagcccc tgcacaactt cctcacccag ctccagccgt tcctcaagct gaagcagaag    300
caggcgaacc tcgtcctgaa gatcatcgag cagctcccct cggccaagga gtccccggac    360
aagttcctgg aggtgtgcac gtgggtcgac cagatcgcgg ccctcaacga cagcaagacc    420
cgcaagacga cctcggagac ggtgcgggcg gtcctggact ccctcccagg atccgtggga    480
ggtctatcgc catctcaggc atccagcgcc gcatcctcgg cttcctcaag cccgggttca    540
gggatctccg aagcactcag agctggagca actaagtcca aggaattcct gctctacctg    600
gcgggcttcg tggacggcga cggctccatc tgcgcgtcca tcgacccgaa ccagtcctgc    660
aagttcaagc accagctccg cctgcgcttc accgtgaccc agaagacgca gaggcgctgg    720
ttcctcgaca gctggtcga cgagatcgggg gtgggcaagg tctacgaccg cgggtcggtg    780
tccgactacc gcctctgcca gatcaagccc ctgcacaact tcctcaccca gctccagccg    840
ttcctcaagc tgaagcagaa gcaggcgaac ctcgtcctga gatcatcga gcagctcccc    900 tcggccaagg agtccccgga caagttcct                                      929

<210> SEQ ID NO 6
<211> LENGTH: 1242
<212> TYPE: DNA
<213> ORGANISM: Artificial Sequence
<220> FEATURE:
<223> OTHER INFORMATION: Plant-optimized nucleotide sequence (with an
      intron) encoding the engineered MS26++
      endonuclease

<400> SEQUENCE: 6
atgaacacca agtacaacaa ggagttcctc ctctacctgg caggtttcgt ggacggcgat     60
```

```
gggtctatca tcgcccagat taccccgcaa cagtcctaca agttcaagca cgccctgcgg      120
ctgaggttca cggtcactca gaagacgcag cgcaggtggt tcctcgataa gctggtcgac      180
gaaatcggag tcggcaaggt gcgggacagg ggctctgtca gcgactacat cctctcccag      240
aagaagccgc tccacaactt cctgacccag ctgcagccct tcctcaagct caagcagaag      300
caggccaacc tggtgctcaa gatcatcgag cagctgccat ctgccaagga gtcaccagac      360
aagttccttg aggtaagttt ctgcttctac ctttgatata tatataataa ttatcattaa      420
ttagtagtaa tataatattt caaatatttt tttcaaaata aaagaatgta gtatatagca      480
attgcttttc tgtagtttat aagtgtgtat atttttaattt ataacttttc taatatatga     540
ccaaaacatg gtgatgtgca ggtctgcacc tgggtcgatc agatcgctgc cctgaacgac      600
tccaagacga ggaagaccac ctccgagacc gtcagggctg tgctggactc actcccagga      660
tccgttggcg gtctcagccc ttctcaggct agctcggctg cttcctcagc cagcagctca      720
cctggctccg gtatcagcga ggctctcaga gcaggtgcca ccaagtccaa ggagttcctc      780
ctgtacctgg caggcttcgt tgacggcgac ggctcgatca tggcgtccat taccccgaac      840
cagtcgtgta agttcaagca tcagctgcgc ctgcgcttta ccgtcacgca gaagacccag      900
aggcgctggt tcctggacaa actggtggac gagatcgggg tcgggaaggt gtacgacaga      960
gggagcgtta gcgactaccg gctgtcccag aagaagccgc tccacaactt cctgacgcag     1020
ctccaaccct tcctgaagct gaagcagaag caggcgaacc ttgtgctgaa gatcattgag     1080
cagctgccga cgccaaggag gagccctgac aagttcctgg aggtctgcac ctgggtcgac     1140
cagatcgctg ccctcaacga ctccaagacc aggaagacca cgagcgagac cgttcgggct     1200
gtcctggaca gcctctccga agaagaag tcgagcccgt ag                          1242
```

<210> SEQ ID NO 7
<211> LENGTH: 1242
<212> TYPE: DNA
<213> ORGANISM: Artificial Sequence
<220> FEATURE:
<223> OTHER INFORMATION: Plant-optimized nucleotide sequence (with an intron) encoding the engineered MS26+ endonuclease

<400> SEQUENCE: 7

```
atgaacacca gtacaacaa ggagttcctc ctctacctgg caggtttcgt ggacggcgat        60
gggtctatca tcgcccagat tgatccgcaa cagtcctaca agttcaagca ctcgctgcgg      120
ctgaggttca cggtcactca gaagacgcag cgcaggtggt tcctcgataa gctggtcgac      180
gaaatcggag tcggcaaggt gcgggacagg ggctctgtca gcgactacat cctctgtcag      240
atcaagccgc tccacaactt cctgacccag ctgcagccct tcctcaagct caagcagaag      300
caggccaacc tggtgctcaa gatcatcgag cagctgccat ctgccaagga gtcaccagac      360
aagttccttg aggtaagttt ctgcttctac ctttgatata tatataataa ttatcattaa      420
ttagtagtaa tataatattt caaatatttt tttcaaaata aaagaatgta gtatatagca      480
attgcttttc tgtagtttat aagtgtgtat atttttaattt ataacttttc taatatatga     540
ccaaaacatg gtgatgtgca ggtctgcacc tgggtcgatc agatcgctgc cctgaacgac      600
tccaagacga ggaagaccac ctccgagacc gtcagggctg tgctggactc actcccagga      660
tccgttggcg gtctcagccc ttctcaggct agctcggctg cttcctcagc cagcagctca      720
cctggctccg gtatcagcga ggctctcaga gcaggtgcca ccaagtccaa ggagttcctc      780
ctgtacctgg caggcttcgt tgacggcgac ggctcgatct gcgcgtccat tgacccgaac      840
```

```
cagtcgtgta agttcaagca tcagctgcgc ctgcgcttta ccgtcacgca gaagacccag      900
aggcgctggt tcctggacaa actggtggac gagatcgggg tcgggaaggt gtacgacaga      960
gggagcgtta gcgactaccg gctgtgccag atcaagccgc tccacaactt cctgacgcag     1020
ctccaaccct tcctgaagct gaagcagaag caggcgaacc ttgtgctgaa gatcattgag     1080
cagctgccga gcgccaagga gagccctgac aagttcctgg aggtctgcac ctgggtcgac     1140
cagatcgctg ccctcaacga ctccaagacc aggaagacca cgagcgagac cgttcgggct     1200
gtcctggaca gcctctccga agaagaag tcgagcccgt ag                           1242
```

<210> SEQ ID NO 8
<211> LENGTH: 1890
<212> TYPE: DNA
<213> ORGANISM: Zea mays
<220> FEATURE:
<221> NAME/KEY: misc_feature
<222> LOCATION: (0)...(0)
<223> OTHER INFORMATION: Nucleotide sequence of a male fertility gene
      encoding a cytochrome P450 (MS26) in maize
      (AF366297)

<400> SEQUENCE: 8

```
atggaggaag ctcacctcac gccggcgacg ccatcgccat tcttcccact agcagggcct       60
cacaagtaca tcgcgctcct tctggttgtc ctctcatgga tcctggtcca gaggtggagc      120
ctgaggaagc agaaaggccc gagatcatgg ccagtcatcg gcgcaacggt ggagcagctg      180
aggaactacc accggatgca cgactggctt gtcgggtacc tgtcacggca caggacagtg      240
accgtcgaca tgccgttcac ttcctacacc tacatcgctg acccggtgaa tgtcgagcat      300
gtcctcaaga ctaacttcac caattacccc aagggaatcg tgtacagatc ctacatggac      360
gtgctcctcg gtgacggcat cttcaacgcc gacggcgagc tgtggaggaa gcagaggaag      420
acggcgagtt tcgagttcgc ctccaagaac ctgagggatt tcagcgccat tgtgttcaga      480
gagtactccc tgaagctgtc gggtatactg agccaggcat ccaaggcagg caaagttgtg      540
gacatgcagg aactttacat gaggatgacg ctggactcca tctgcaaggt tgggttcggg      600
gtcgagatcg gcacgctgtc gccagatctc cccgagaaca gcttcgcgca ggcgttcgat      660
gccgccaaca tcatcatcac gctgcggttc atcgacccgc tgtggcgcat caagaggttc      720
ttccacgtcg ggtcagaggc cctcctagcg cagagcatca agctcgtgga cgagttcacc      780
tacagcgtga tccgccggag gaaggccgag atcgtcgagg tccgggccag cggcaaacag      840
gagaagatga agcacgacat cctgtcacgg ttcatcgagc tgggcgaggc cggcgacgac      900
ggcggcggct tcgggacga taagagcctc cgggacgtgg tgctcaactt cgtgatcgcc      960
gggcgggaca cgacgcgac gacgctgtcg tggttcacgc acatggccat gtcccacccg     1020
gacgtggccg agaagctgcg ccgcgagctg tgcgcgttcg aggcggagcg cgcgcgcgag     1080
gagggcgtca cgctcgtgct ctgcggcggc gctgacgccg acgacaaggc gttcgccgcc     1140
cgcgtggcgc agttcgcggg cctcctcacc tacgacagcc tcggcaagct ggtctacctc     1200
cacgcctgcg tcaccgagac gctccgcctg taccccgccg tccctcagga ccccaagggg     1260
atcctggagc acgacgtgct gccggacggg acgaaggtga gggccggcgg gatggtgacg     1320
tacgtgccct actcgatggg gcggatggag tacaactggg gccccgacgc ggcgagcttc     1380
cggccggagc ggtggatcaa cgaggatggc gcgttccgca acgcgtcgcc gttcaagttc     1440
acggcgttcc aggcggggcc gaggatctgc ctgggcaagg actcggcgta cctgcagatg     1500
```

| aagatggcgc | tggccatcct | cttccgcttc | tacagcttcc | ggctgctgga | ggggcacccg | 1560 |
| gtgcagtacc | gcatgatgac | catcctctcc | atggcgcacg | gcctcaaggt | ccgcgtctct | 1620 |
| agggccgtct | gatgtcatgg | cgatttggat | atggatatcg | tcccgcttaa | tccacgacaa | 1680 |
| ataacgctcg | tgttacaaat | ttgcatgcat | gcatgtaagg | gaaagcgatg | ggtttcattg | 1740 |
| gtggcttggc | ttaagcctta | aaaactccgt | cgggtcttgc | gaaccaccac | atcactagtg | 1800 |
| ttttgtactc | tactcctcag | tggaagtgta | gtgacagcat | acaagttcat | catatatatt | 1860 |
| atcctctttc | ttaaaaaaaa | aaaaaaaaaa | | | | 1890 |

<210> SEQ ID NO 9
<211> LENGTH: 1930
<212> TYPE: DNA
<213> ORGANISM: Oryza sativa
<220> FEATURE:
<221> NAME/KEY: misc_feature
<222> LOCATION: (0)...(0)
<223> OTHER INFORMATION: Nucleotide sequence of a male fertility gene
      encoding a cytochrome P450 (MS26) in rice
      (LOC_Os03g07250)

<400> SEQUENCE: 9

| atgaagagcc | ccatggagga | agctcatgca | atgccagtga | catcattctt | cccagtagca | 60 |
| ggaatccaca | agctcatagc | tatcttcctt | gttgtcctct | catggatctt | ggtccacaag | 120 |
| tggagcctga | ggaaccagaa | agggccaaga | tcatggccaa | tcatcggcgc | gacagtggag | 180 |
| caactgaaga | actaccacag | gatgcatgac | tggcttgtcg | agtacttgtc | gaaggacagg | 240 |
| acggtgaccg | tcgacatgcc | tttcacctcc | tacacctaca | ttgccgaccc | ggtgaacgtc | 300 |
| gagcatgtcc | tgaagaccaa | cttccaccaat | taccccaagg | taaaagaacc | ataggatctt | 360 |
| cagtgtactg | taaaatgtgc | cttgcacagt | actaacactg | acacaaaaaa | tgtctgaaaa | 420 |
| tatgcagggt | gaagtgtaca | ggtcttacat | ggatgtgctg | ctcggtgatg | gcatattcaa | 480 |
| tgccgacggc | gagatgtgga | ggaagcaaag | gaagacggcg | agcttcgagt | ttgcctccaa | 540 |
| gaacttgaga | gacttcagca | ctgtggtgtt | cagggagtac | tccctgaagc | tatcaagcat | 600 |
| tctgagccaa | gcatgcaagg | ccggcagagt | tgtagacatg | caggtaacca | actgaattcc | 660 |
| ttgcctaata | cctaaacatt | tcttgagaaa | ccaaattgtt | cagaattctg | atgcaagaac | 720 |
| taaccaaaat | tcaggaattg | ttcatgagga | tgacactgga | ctcgatctgc | aaggtcgggt | 780 |
| ttggggttga | gatcgggacg | ctgtcacctg | atctcccgga | gaacagcttt | gcccaggcat | 840 |
| tcgacgctgc | caacatcatc | gtcacgctgc | ggttcatcga | tcctctgtgg | cgtctgaaga | 900 |
| agttcttgca | cgtcggatca | gaggctctcc | tcgagcagag | catgaagctg | gttgatgact | 960 |
| tcacctacag | cgtgatccgc | cgccgcaagg | ctgagatctt | gcaggctcga | gccagcggca | 1020 |
| agcaagagaa | ggtgatcctt | cctctcttgc | tcaaagaatc | agtagaactg | aactgacatg | 1080 |
| gtaatggtga | tgatcagatc | ggaaaaggtt | ttgtttcttg | atatcgttga | tttgtaatgg | 1140 |
| cgagcagatc | aagcacgaca | tactgtcgcg | gttcatcgag | ctcggggagg | ccggcggcga | 1200 |
| cgaggggggc | ggcagcttcg | gggacgacaa | gagcctccgc | gacgtggtgc | tcaacttcgt | 1260 |
| gatcgccggg | cgtgacacga | cggcgacgac | gctgtcgtgg | ttcacgtaca | tggcgatgac | 1320 |
| gcacccggcc | gtcgccgaca | agctccggcg | cgagctggcc | gcgttcgagg | atgagcgcgc | 1380 |
| gcgcgaggag | ggcgtcgcgc | tcgccgacgc | cgccggcgag | gcgtcgttcg | cggcgcgcgt | 1440 |
| ggcgcagttc | gcgtcgctgc | tgagctacga | cgcggtgggg | aagctggtgt | acctgcacgc | 1500 |
| gtgcgtgacg | gagacgctcc | gcctctaccc | ggcggtgccg | caggaccccca | agggatcgt | 1560 |

```
ggaggacgac gtgctccccg acggcaccaa ggtgcgcgcc ggcgggatgg tgacgtacgt    1620
gccctactcc atggggagga tggagtacaa ctggggcccc gacgcggcga gcttccggcc    1680
ggagcggtgg ctcagcggcg acggcggcgc gttccggaac cgtcgccgt tcaagttcac    1740 cgcgttccag gccgggccgc ggatctgcct cggcaaggac tccgcctacc tccagatgaa    1800
gatggcgctc gccatcctct tccgcttcta caccttcgac ctcgtcgagg accacccgt    1860 caagtaccgg atgatgacca tcctctccat ggctcacggc tcaaggtcc gcgtctccac    1920 ctccgtctga                                                          1930
```

<210> SEQ ID NO 10
<211> LENGTH: 2735
<212> TYPE: DNA
<213> ORGANISM: Sorghum bicolor
<220> FEATURE:
<221> NAME/KEY: misc_feature
<222> LOCATION: (0)...(0)
<223> OTHER INFORMATION: Nucleotide sequence of a male fertility gene encoding a cytochrome P450 (MS26) in sorghum

<400> SEQUENCE: 10

```
gatggcaact acatgctata ttcatcagct ataaacttgc agaaaataat tcgcaatggg     60
ctcacaaatt tttgttcagg atgtactttt cacttgaact ttcatgtagg aacaacgaat    120
gtatcattgt gcctaaattt ttaaagaatt gtggacaatt tctggtaggc tgagtttcag    180
actttcagta ccaagctgat ggatcacatt ctggatccga agtatgataa cataatctgg    240
caactcctaa ttgtaataac aatgaataac ctgcaaatac agtataagag tggctcattt    300
tcttggttgg cagatcacaa aaaggaacac aaaggctaag cgccaacttg tccgggagtt    360
aggtcatgga taccatatga atgaaagaaa tcttaatttc cggtcacacc aagattgtct    420
ctctcaaggt tggtaacagc aatacccaat atatcaccta caaacccag acaacactac    480 atacataaca tccatcactt ggagactgga cccttcatca agagcaccat ggaggaagct    540
cacctcatgc cggcgacacc attgttccca ctagcagggc tccacaagta catcgcgatc    600
ctcctcgttg tcctctcatg ggccctggtc cataggtgga gcctgaggaa gcagaaaggc    660
ccgagatcat ggccggtcat tggcgccacg ttggagcagc tgaggaacta ccaccggatg    720
cacgactggc ttgttgggta cctgtcacgg cacaagacag tgaccgtcga catgccgttc    780
acttcctaca cctacatcgc tgacccggtg aatgtcgagc atgtcctcaa gactaacttc    840
accaattacc caaggtcag tgatctaaac tcaccgatgt tcagtcttct gtgatgctgt    900
gctaaaggtt cagaaatcag aattgaaagc tgattccaat gcctgaacac tgtgcagggg    960
gacgtgtaca gatcctacat ggatgtgctc ctcggtgacg gcatattcaa cgctgacggc   1020
gagctgtgga ggaagcagag gaagacggcg agtttcgagt tcgcctccaa gaacctgagg   1080
gatttcagtg ccaatgtttt cagagagtac tccctgaagc tgtcgggcat actgagtcag   1140
gcatccaagg caggcaaagt tgttgacatg caggtgaact cactgctccc ttgccaatgc   1200
cagcatgagg atttcttggg cactctcact cactgtgaat ctgagactga caaacgtcct   1260
aattaacacg agagctactt tgtgattcag gaactttaca tgaggatgac actggactcg   1320
atctgcaagg ttggggttcgg ggtcgagatc ggcacgctgt cgccggatct ccccgagaac   1380
agcttcgccc aggcgttcga tgccgctaac atcatcgtca cgctgcggtt catcgacccg   1440
ctgtggcgcg tcaagagggtt cttccacgtc ggctcagagg ccctcctggc gcagagcatc   1500
aagctcgtgg acgagttcac ctacagcgtg atccgccgga ggaaggccga gatcgtcgag   1560
```

```
gcccgggcca gcggcaaaca ggagaaggtt agcttgtttc gttcttcaat tcaccatctt    1620
ggttgggacg aacctgatcc tgattgatta tatatgtgtg tgacttgtga gggaaaatta    1680
aatgggcaga tgaagcacga catcctgtca cggttcatcg agctgggcga ggccggcgac    1740 gacgcggct  tcggggacga caagagcctc cgagacgtgg tgctcaactt cgtgatcgcc    1800
gggcgggaca cgacggcgac gacgctgtcg tggttcacgc acatggccat gtcccacccg    1860
gacgtggcca gaagctgcg  gcgcgagctg tgcgcgttcg aggcggagcg cgcgcgcgag    1920
gagggcgtcg cggtgccctg ctgcggccct gacgacgaca aggcgttcgc cgcccgcgtg    1980
gcgcagttcg cggggctcct cacctacgac agcctcggca gctggtcta  cctccacgcc    2040 tgcgtcaccg agacgctccg cttgtacccc gccgtccctc aggtgagcgc gcacgcacga    2100
ccaccggact ccggtccgat gcaatgcgat gcagatgtgg ctgctgggtg agagtgaaaa    2160
cctgcaatgc aaatgcactt ggacgcagga ccccaagggg atcctggagg acgacgtgct    2220 gccgacggg  acgaaggtga gggccggcgg gatggtgacg tacgtgccct actcgatggg    2280
gcggatggag tacaactggg gacccgacgc ggcgagcttc cggccggagc ggtggatcaa    2340
cgaggagggc gcgttccgca acgcgtcgcc gttcaagttc acggcgttcc aggcggggcc    2400
gaggatctgc ctgggcaagg actcggcgta cctgcagatg aagatggcgc tcgccatcct    2460
cttccgcttc tacagcttcc agctgctgga ggggcacccg gtccagtacc gcatgatgac    2520
catcctctcc atggcgcacg gcctcaaggt ccgcgtctcc agggccgttt gatgccatat    2580
atgatgactc gcttaatgcc ttaatccacg ccaaataatg ttcatgttac atatttccat    2640
gcatgtaagg ggaaatgatg ggtttcattg gtggtttggt cttaaaattg cgtcggatca    2700
tgcatgagaa cgatcgacca ccaccagtgt tttgt                               2735
```

<210> SEQ ID NO 11
<211> LENGTH: 1079
<212> TYPE: DNA
<213> ORGANISM: Secale cereale
<220> FEATURE:
<221> NAME/KEY: misc_feature
<222> LOCATION: (0)...(0)
<223> OTHER INFORMATION: Partial nucleotide sequence of a male fertility
      gene encoding a cytochrome P450 (MS26) in rye
      (FJ539083)

<400> SEQUENCE: 11

```
cgaattcagg agctgtacat gaggatgacg ctggactcga tctgcaaggt ggggttcggg     60
gtggagatcg gcacgctgtc gccggagctg ccggagaaca gcttcgcgca ggcgttcgac    120
gccgccaaca tcatcgtgac gctgcggttc atcgacccgc tgtggcgcgt gaagaagttc    180
ctgcacgtcg gctcggaggc gctgctggag cagagcatca agctcgtcga cgagttcacc    240
tacagcgtca tccgccgccg caaggccgag atcgtgcagg cccgggccag cggcaagcag    300
gagaaggtgc gtgcgtgatg atcatcgtcg tcaagcttcg gctcgctggt ctgtgcaggt    360
gtcattgatc actaacacat caactgggtg cgcagatcaa gcacgacata ctgtcgcggt    420
tcatcgagct gggcgaggcc ggcggcgacg acgcggcag  cctgttcggg gacgacaagg    480
gcctccgcga cgtggtgctc aacttcgtga tcgccgggcg ggacacgacg ccacgacgc    540 tgtcctggtt cacctacatg gccatgacgc acccggacgt ggccgagaag ctccgccgcg    600
agctggccgc cttcgaggcc gaccgcgccc gcgaggatgg cgtcgctctg gtcccctgca    660
gcgacggcga gggctccgac gaggccttcg ccgcccgcgt ggcgcagttc gcggggctcc    720
```

```
tgagctacga cgggctcggg aaactggtgt acctccacgc gtgcgtgacg gagacgctcc    780
gcctgtaccc ggcggtgccg caggacccca agggcatcgc ggaggacgac gtgctcccgg    840
acggcaccaa ggtgcgcgcc ggcgggatgg tgacgtacgt gccctactcc atggggcgga    900
tggagtacaa ctgggggccc gacgccgcca gcttccggcc ggagcggtgg atcggcgacg    960
acggcgcctt ccgcaacgcg tcgccgttca agttcacggc gttccaggcg ggccgcgga   1020 tctgcctcgg caaggactcg gcgtacctgc agatgaagat ggcgctggcc atcctgtgc   1079
```

<210> SEQ ID NO 12
<211> LENGTH: 543
<212> TYPE: PRT
<213> ORGANISM: Zea mays
<220> FEATURE:
<221> NAME/KEY: DOMAIN
<222> LOCATION: (0)...(0)
<223> OTHER INFORMATION: Amino acid sequence of a male fertility gene
encoding a cytochrome P450 (MS26) in maize
(AAK52956.1)

<400> SEQUENCE: 12

```
Met Glu Glu Ala His Leu Thr Pro Ala Thr Pro Ser Pro Phe Phe Pro
 1               5                  10                  15

Leu Ala Gly Pro His Lys Tyr Ile Ala Leu Leu Val Val Leu Ser
             20                  25                  30

Trp Ile Leu Val Gln Arg Trp Ser Leu Arg Lys Gln Lys Gly Pro Arg
         35                  40                  45

Ser Trp Pro Val Ile Gly Ala Thr Val Glu Gln Leu Arg Asn Tyr His
     50                  55                  60

Arg Met His Asp Trp Leu Val Gly Tyr Leu Ser Arg His Arg Thr Val
 65                  70                  75                  80

Thr Val Asp Met Pro Phe Thr Ser Tyr Thr Tyr Ile Ala Asp Pro Val
                 85                  90                  95

Asn Val Glu His Val Leu Lys Thr Asn Phe Thr Asn Tyr Pro Lys Gly
            100                 105                 110

Ile Val Tyr Arg Ser Tyr Met Asp Val Leu Leu Gly Asp Gly Ile Phe
        115                 120                 125

Asn Ala Asp Gly Glu Leu Trp Arg Lys Gln Arg Lys Thr Ala Ser Phe
    130                 135                 140

Glu Phe Ala Ser Lys Asn Leu Arg Asp Phe Ser Ala Ile Val Phe Arg
145                 150                 155                 160

Glu Tyr Ser Leu Lys Leu Ser Gly Ile Leu Ser Gln Ala Ser Lys Ala
                165                 170                 175

Gly Lys Val Val Asp Met Gln Glu Leu Tyr Met Arg Met Thr Leu Asp
            180                 185                 190

Ser Ile Cys Lys Val Gly Phe Gly Val Glu Ile Gly Thr Leu Ser Pro
        195                 200                 205

Asp Leu Pro Glu Asn Ser Phe Ala Gln Ala Phe Asp Ala Ala Asn Ile
    210                 215                 220

Ile Ile Thr Leu Arg Phe Ile Asp Pro Leu Trp Arg Ile Lys Arg Phe
225                 230                 235                 240

Phe His Val Gly Ser Glu Ala Leu Leu Ala Gln Ser Ile Lys Leu Val
                245                 250                 255

Asp Glu Phe Thr Tyr Ser Val Ile Arg Arg Lys Ala Glu Ile Val
            260                 265                 270

Glu Val Arg Ala Ser Gly Lys Gln Glu Lys Met Lys His Asp Ile Leu
        275                 280                 285
```

Ser Arg Phe Ile Glu Leu Gly Glu Ala Gly Asp Gly Gly Phe
    290                 295                 300

Gly Asp Asp Lys Ser Leu Arg Asp Val Val Leu Asn Phe Val Ile Ala
305                 310                 315                 320

Gly Arg Asp Thr Thr Ala Thr Thr Leu Ser Trp Phe Thr His Met Ala
                325                 330                 335

Met Ser His Pro Asp Val Ala Glu Lys Leu Arg Arg Glu Leu Cys Ala
                340                 345                 350

Phe Glu Ala Glu Arg Ala Arg Glu Glu Gly Val Thr Leu Val Leu Cys
            355                 360                 365

Gly Gly Ala Asp Ala Asp Lys Ala Phe Ala Ala Arg Val Ala Gln
        370                 375                 380

Phe Ala Gly Leu Leu Thr Tyr Asp Ser Leu Gly Lys Leu Val Tyr Leu
385                 390                 395                 400

His Ala Cys Val Thr Glu Thr Leu Arg Leu Tyr Pro Ala Val Pro Gln
                405                 410                 415

Asp Pro Lys Gly Ile Leu Glu Asp Asp Val Leu Pro Asp Gly Thr Lys
                420                 425                 430

Val Arg Ala Gly Gly Met Val Thr Tyr Val Pro Tyr Ser Met Gly Arg
                435                 440                 445

Met Glu Tyr Asn Trp Gly Pro Asp Ala Ala Ser Phe Arg Pro Glu Arg
450                 455                 460

Trp Ile Asn Glu Asp Gly Ala Phe Arg Asn Ala Ser Pro Phe Lys Phe
465                 470                 475                 480

Thr Ala Phe Gln Ala Gly Pro Arg Ile Cys Leu Gly Lys Asp Ser Ala
                485                 490                 495

Tyr Leu Gln Met Lys Met Ala Leu Ala Ile Leu Phe Arg Phe Tyr Ser
                500                 505                 510

Phe Arg Leu Leu Glu Gly His Pro Val Gln Tyr Arg Met Met Thr Ile
            515                 520                 525

Leu Ser Met Ala His Gly Leu Lys Val Arg Val Ser Arg Ala Val
            530                 535                 540

<210> SEQ ID NO 13
<211> LENGTH: 50
<212> TYPE: DNA
<213> ORGANISM: Zea mays
<220> FEATURE:
<221> NAME/KEY: misc_feature
<222> LOCATION: (0)...(0)
<223> OTHER INFORMATION: Maize genomic region comprising the maize MS26
      target site of Figure 3

<400> SEQUENCE: 13
aggtgagggc cggcgggatg gtgacgtacg tgccctactc gatggggcgg          50

<210> SEQ ID NO 14
<211> LENGTH: 50
<212> TYPE: DNA
<213> ORGANISM: Oryza sativa
<220> FEATURE:
<221> NAME/KEY: misc_feature
<222> LOCATION: (0)...(0)
<223> OTHER INFORMATION: Rice genomic region comprising the rice MS26
      target site of Figure 3

<400> SEQUENCE: 14
aggtgcgcgc cggcgggatg gtgacgtacg tgccctactc catggggagg          50

```
<210> SEQ ID NO 15
<211> LENGTH: 50
<212> TYPE: DNA
<213> ORGANISM: Sorghum bicolor
<220> FEATURE:
<221> NAME/KEY: misc_feature
<222> LOCATION: (0)...(0)
<223> OTHER INFORMATION: Sorghum genomic region comprising the
      sorghumMS26 target site of Figure 3

<400> SEQUENCE: 15
aggtgagggc cggcgggatg gtgacgtacg tgccctactc gatggggcgg            50

<210> SEQ ID NO 16
<211> LENGTH: 50
<212> TYPE: DNA
<213> ORGANISM: Secale cereale
<220> FEATURE:
<221> NAME/KEY: misc_feature
<222> LOCATION: (0)...(0)
<223> OTHER INFORMATION: Rye genomic region comprising the rye MS26
      target site of Figure 3

<400> SEQUENCE: 16
aggtgcgcgc cggcgggatg gtgacgtacg tgccctactc catggggagg            50

<210> SEQ ID NO 17
<211> LENGTH: 23
<212> TYPE: DNA
<213> ORGANISM: Artificial Sequence
<220> FEATURE:
<223> OTHER INFORMATION: primer UNIMS26 5'-2

<400> SEQUENCE: 17
gacgtggtgc tcaacttcgt gat                                        23

<210> SEQ ID NO 18
<211> LENGTH: 23
<212> TYPE: DNA
<213> ORGANISM: Artificial Sequence
<220> FEATURE:
<223> OTHER INFORMATION: primer UNIMS26 3'-1

<400> SEQUENCE: 18
gccatggaga ggatggtcat cat                                        23

<210> SEQ ID NO 19
<211> LENGTH: 90
<212> TYPE: DNA
<213> ORGANISM: Zea mays
<220> FEATURE:
<221> NAME/KEY: misc_feature
<222> LOCATION: (0)...(0)
<223> OTHER INFORMATION: maize genomic region comprising the maize
      TS-MS26 target sequence

<400> SEQUENCE: 19
ggagttctgc ggccggccgc tcggcctgag gttccacggg gagaccggcg agctctacgt  60
cgccgacgcg tactacggtc tcatggtcgt                                  90

<210> SEQ ID NO 20
<211> LENGTH: 22
<212> TYPE: DNA
<213> ORGANISM: Zea mays
<220> FEATURE:
<221> NAME/KEY: misc_feature
<222> LOCATION: (0)...(0)
```

<223> OTHER INFORMATION: TS-MS45 target sequence from maize

<400> SEQUENCE: 20
cggggagacc ggcgagctct ac            22

<210> SEQ ID NO 21
<211> LENGTH: 9
<212> TYPE: PRT
<213> ORGANISM: Simian virus 40
<220> FEATURE:
<221> NAME/KEY: DOMAIN
<222> LOCATION: (1)...(9)
<223> OTHER INFORMATION: nuclear localization sequence used in MAY1/MAY
      fusions

<400> SEQUENCE: 21

Met Ala Pro Lys Lys Lys Arg Lys Val
 1               5

<210> SEQ ID NO 22
<211> LENGTH: 492
<212> TYPE: DNA
<213> ORGANISM: Artificial Sequence
<220> FEATURE:
<223> OTHER INFORMATION: plant-optimized nucleotide sequence encoding
      MAY1

<400> SEQUENCE: 22
atgaacacca agtacaacaa ggagttcctg ctctacctgg ccggcttcgt ggacggcgac     60
ggctccatca tcgcggccat cgacccggag cagagccgca agttcaagca ccgcctccgc    120
ctgcgcttca ccgtgaccca agagacgcag aggcgctggt tcctcgacaa gctggtcgac    180
gagatcgggg tgggctacgt ccgcgaccgg gggtcggtgt ccgactacca gctcagcaag    240
atcaagcccc tgcacaactt cctcacccag ctccagccgt tcctcaagct gaagcagaag    300
caggcgaacc tcgtcctgaa gatcatcgag cagctcccct cggccaagga gtccccggac    360
aagttcctgg aggtgtgcac gtgggtcgac cagatcgcgg ccctcaacga cagcaagacc    420
cgcaagacga cctcggagac ggtgcgggcg gtcctggact ccctcagcga gaagaagaag    480
tcgtccccct ga                                                       492

<210> SEQ ID NO 23
<211> LENGTH: 492
<212> TYPE: DNA
<213> ORGANISM: Artificial Sequence
<220> FEATURE:
<223> OTHER INFORMATION: plant-optimized nucleotide sequence encoding
      MAY2

<400> SEQUENCE: 23
atgaacacca agtacaacaa ggagttcctg ctctacctgg ccggcttcgt ggacggcgac     60
ggctccatca aggcgagcat cagcccgaac cagagctgca agttcaagca ccagctccgc    120
ctgaccttcc aggtgaccca agagacgcag aggcgctggt tcctcgacaa gctggtcgac    180
gagatcgggg tgggctacgt ctacgaccgg gggtcggtgt ccgactaccg cctcagcaag    240
atcaagcccc tgcacaactt cctcacccag ctccagccgt tcctcaagct gaagcagaag    300
caggcgaacc tcgtcctgaa gatcatcgag cagctcccct cggccaagga gtccccggac    360
aagttcctgg aggtgtgcac gtgggtcgac cagatcgcgg ccctcaacga cagcaagacc    420
cgcaagacga cctcggagac ggtgcgggcg gtcctggact ccctcagcga gaagaagaag    480
tcgtccccct ga                                                       492

<210> SEQ ID NO 24
<211> LENGTH: 1485
<212> TYPE: DNA
<213> ORGANISM: Zea mays
<220> FEATURE:
<221> NAME/KEY: misc_feature
<222> LOCATION: (0)...(0)
<223> OTHER INFORMATION: nucleotide sequence of a male fertility gene
      encoding a chalcone and stilbene synthase (5126)
      in maize (AX060770)

<400> SEQUENCE: 24

| | | | | | |
|---|---|---|---|---|---|
| ggaattcggc | acgagctcgg | tgccgccttc | cttccttcaa | ttctaaatac | cacaaatcaa | 60 |
| agttgctttg | cgatggtgag | cagcagcatg | gacacgacga | gtgacaagcg | tgcgtcatcc | 120 |
| atgctggccc | ctaaccctgg | caaggccacg | atcctcgccc | ttggccacgc | cttcccgcag | 180 |
| cagcttgtca | tgcaggacta | cgtcgtcgac | ggcttcatga | agaacaccaa | ctgtgacgac | 240 |
| ccggagctca | aggagaagct | caccagactc | tgcaagacga | cgaccgtgag | gactcggtac | 300 |
| gtggtgatgt | cggatgagat | cctcaagaac | tacccggagc | tggcccagga | ggggctgccg | 360 |
| acgatgaacc | agcgtctgga | catctcgaac | gcggcggtga | cgcagatggc | gacgaggcg | 420 |
| tccctgtcgt | gcgtccgctc | gtggggcggc | gcgctctcgt | ccattaccca | cctggtgtac | 480 |
| gtctcgtcga | gcgaggcgcg | cttcccgggc | ggcgacctgc | acctggcgcg | cgcgctgggg | 540 |
| ctgagcccgg | acgtccgccg | cgtcatgctg | gccttcaccg | gctgctcggg | cggcgtggcg | 600 |
| gggctccgcg | tggccaaggg | cctggccgag | agctgcccgg | gcgcgcgcgt | gctgctggcc | 660 |
| acctccgaga | ccaccatcgt | ggggttccgc | ccgcccagcc | ccgaccgccc | ctacgacctc | 720 |
| gtgggcgtgg | cgctcttcgg | cgacggcgcg | ggcgccgccg | tcatcggcac | cgaccccgcc | 780 |
| cccgccgagc | gcccgctctt | cgagctccac | tcggcgctcc | agcgcttcct | cccggacacg | 840 |
| gagaggacca | tcgagggccg | gctgacggag | gaaggcatca | agttccagct | ggggcgggag | 900 |
| ctgccccaca | tcatcgaggc | gcacgtggag | gacttctgcc | agaagctgat | gaaggagcgg | 960 |
| cagagcggcg | aggacgccga | cggtggcggc | cccgagccga | tgagctacgg | ggacatgttc | 1020 |
| tgggcggtcc | accccggcgg | gccggccatc | ctaaccaaga | tggaggggcg | cctgggcctc | 1080 |
| ggcgccgaca | gctccgcgc | cagccggtgc | gcgctccggg | acttcggcaa | cgccagcagc | 1140 |
| aacaccatcg | tgtacgtgct | ggagaacatg | gtggaggaca | cccggcggag | gaggctgctg | 1200 |
| gctgctgacg | acggtggaga | ggactgcgag | tggggtctca | tcctcgcgtt | cgggccgggg | 1260 |
| atcacgttcg | agggcatcct | agccaggaac | ttgcaggcaa | ccgcgcgcgc | ctcagcccag | 1320 |
| ctctgatcac | ctcttgctgt | gttgcttttc | tgcttgctct | gcacctctgc | ttccgtgtga | 1380 |
| ttgctgcttt | gagggagaat | gctgagcatc | aacattgctc | atgagcatca | atgaaataag | 1440 |
| gggccccgaa | attcactgct | caaaaaaaaa | aaaaaaaaac | tcgag | | 1485 |

<210> SEQ ID NO 25
<211> LENGTH: 1346
<212> TYPE: DNA
<213> ORGANISM: Oryza sativa
<220> FEATURE:
<221> NAME/KEY: misc_feature
<222> LOCATION: (0)...(0)
<223> OTHER INFORMATION: nucleotide sequence of a male fertility gene
      encoding a chalcone and stilbene synthase (5126)
      in rice (LOC_Os07g22850)

<400> SEQUENCE: 25

| | |
|---|---|
| atggtgagca ccaatgccgg cggtactgcg agcaagcagg cgtcgtccat ggcccccaac | 60 |
| ccgggcaagg ccacgatcct cgccctcggc cacgccttcc cgcagcagct ggtcatgcag | 120 |
| gactacgtcg tcgacggctt catgaggaac accaactgcg acgacccgga gctcaaggag | 180 |
| aagctcacca gactctgtac cgtacctgat ccaaatctga tcatttgcag ttacaaatat | 240 |
| atatactcca ctattatcga acttgcgtgt gagctcacct gcatgcgtat ttgcaattaa | 300 |
| tttgcatgtc gttgctgacg aaaggcaaga cgacgacggt gaagacgagg tacgtggtga | 360 |
| tgtcggagga gatcctcaag agctacccgg agctggcgca ggagggccag ccgacgatga | 420 |
| agcagcggct ggacatctcc aacaaggcgt gacgcagat ggcgacggag gcgtcgctcg | 480 |
| cctgcgtccg ctcctggggc ggcgcgctct cggagatcac ccaccttgtc tacgtctcct | 540 |
| ccagcgaggc gcggttcccc ggcggagacc tccacctggc gcgcgcgctg ggcctcagcc | 600 |
| cggacgtccg ccgcgtcatg ctggcgttca ccggctgctc gggcggcgtc gcgggcctcc | 660 |
| gcgtcgccaa gggcctcgcc gagagctgcc cgggtgcgcg cgtcctcctc gccacctccg | 720 |
| agaccaccat cgtcgggttc cgcccgccca gccccgaccg cccctacgac ctcgtcggcg | 780 |
| tcgccctctt cggcgacggc gccggcgcgg ccgtggtcgg cgccgacccg acaccggtgg | 840 |
| agcgcccgct gttcgagctc cactcggcgc tgcagcggtt cctccccgac accgacaaga | 900 |
| ccatcgacgg gcggctgacg gaggagggca tcaagttcca gctcggccgc gaactccccc | 960 |
| acatcatcga ggccaacgtg gaggccttct gccagaagct gatgcaggag cacccctcagg | 1020 |
| cggcggacaa gctcacctac ggcgacatgt tctgggcggt gcaccccggc gggccggcga | 1080 |
| tcctgaccaa gatggaggc aggctggggc tggacggcgg gaagctccgc ccagccggaa | 1140 |
| gcgcgctccg ggacttcggg aacgcgagca gcaacaccat cgtgtacgtg ctggagaaca | 1200 |
| tggtggagga gaccccggcag aggagggagg aggcggcgga agaggaggat tgcgagtggg | 1260 |
| ggctcatact ggcgttcggg ccggggatca cgttcgaggg gatcctggcc agaaatctgc | 1320 |
| aggcgcgcgc gcgcgcgcgc gactga | 1346 |

<210> SEQ ID NO 26
<211> LENGTH: 1193
<212> TYPE: DNA
<213> ORGANISM: Zea mays
<220> FEATURE:
<221> NAME/KEY: misc_feature
<222> LOCATION: (0)...(0)
<223> OTHER INFORMATION: nucleotide sequence of a male fertility gene
      encoding a dihydroflavonol 4-reductase (BS7) in
      maize (AF366295)

<400> SEQUENCE: 26

| | |
|---|---|
| atggtgacct caagcaaggg caaggtatgc gtaaccgggg cctcaggctt tgttgcctct | 60 |
| tggcttatca aacggctcct cgagtctgga tatcatgtgg tagggactgt cagggaccca | 120 |
| ggaaatcacc aaaaaacagc ccacctttgg aaattacctg cgctaaaga gaggctgcaa | 180 |
| atcgtgcgag ctaatctgtt ggaagaaggg agcttcgaca cgccgtgat ggcctgtgag | 240 |
| ggtgtattcc acactgcatc ccccgtcctc gctaaacccg actctactag caaggaggac | 300 |
| acgctcgtcc ctgcggtgaa cggtactctg aacgtgctga tcgtgcaa gaagaacccc | 360 |
| ttcctgaaaa gggtcgtcct acgtcttcg tcgtctgcgg tgaggatcag ggacgacggt | 420 |
| ggccagtcca gtaacatctc gctggacgaa acgacatgga gctccgtgcc actctgcgag | 480 |
| aagatgcatc tatggtatgc cctagccaag gtatttgcag agaaagcggc gtgggagttc | 540 |
| gccaaggaga acggcatcga ccttgtgact gtcctcccgt cgttcgtgat cgggcccagt | 600 |

```
ttgtcccacg agctatgcgt taccgcttca gacgtcctag gcctattcca aggcgacacg    660
gcaaggttca gctcgtacgg aagaatgggg tacgtccaca tcgacgacgt tgcgagcagc    720
cacatcctgg tgtacgaggt cccccaggcc gccgggaggt acctgtgcag ctcagtggtg    780
ctggacaacg acgagctggt ctcctcgctc gcgaaacgct acccgatatt ccccataccc    840
cggaggctga acagcccta cggcaagcag tcgtaccagc tgaacacgtc gaagctgcag    900
gggctgggct tcaagttcag aggggtgcag gagatgttcg acgactgcgt gcagtcgctc    960
aaagaccagg gccacctgct ggagtgcccc ctgtgaactg cgatgggggt gcctcctgtg   1020
aacgcccgtt ttttttttttc ttcaataatt ccacgtcatg tcacggtgtc ctcgcgcaga   1080
ctgctactgt caggtgtcag ggcgtcatag ctcacgggct ctacggctac atgaataaaa   1140
tgtcacgcta gctcgtcatt tgctttgcca tttaaaaaaa aaaaaaaaaa aaa           1193

<210> SEQ ID NO 27
<211> LENGTH: 1346
<212> TYPE: DNA
<213> ORGANISM: Oryza sativa
<220> FEATURE:
<221> NAME/KEY: misc_feature
<222> LOCATION: (0)...(0)
<223> OTHER INFORMATION: nucleotide sequence of a male fertility gene
      encoding a a dihydroflavonol 4-reductase (BS7) in
      rice (LOC_Os08g40440)

<400> SEQUENCE: 27
atggtgagca ccaatgccgg cggtactgcg agcaagcagg cgtcgtccat ggcccccaac     60
ccgggcaagg ccacgatcct cgccctcggc cacgccttcc cgcagcagct ggtcatgcag    120
gactacgtcg tcgacggctt catgaggaac accaactgcg acgacccgga gctcaaggag    180
aagctcacca gactctgtac cgtacctgat ccaaatctga tcatttgcag ttacaaatat    240
atatactcca ctattatcga acttgcgtgt gagctcacct gcatgcgtat ttgcaattaa    300
tttgcatgtc gttgctgacg aaaggcaaga cgacgacggt gaagacgagg tacgtggtga    360
tgtcggagga gatcctcaag agctaccccg agctggcgca ggagggccag ccgacgatga    420
agcagcggct ggacatctcc aacaaggcgg tgacgcagat ggcgacggag gcgtcgctcg    480
cctgcgtccg ctcctggggc ggcgcgctct cggagatcac ccaccttgtc tacgtctcct    540
ccagcgaggc gcggttcccc ggcggagacc tccacctggc gcgcgcgctg ggcctcagcc    600
cggacgtccg ccgcgtcatg ctggcgttca ccggctgctc gggcggcgtc gcgggcctcc    660
gcgtcgccaa gggcctcgcc gagagctgcc cgggtgcgcg cgtcctcctc gccacctccg    720
agaccaccat cgtcgggttc cgcccgccca gccccgaccg ccctacgac ctcgtcggcg    780 tcgccctctt cggcgacggc gccggcgcgg ccgtggtcgg cgccgacccg acaccggtgg    840
agcgcccgct gttcgagctc cactcggcgc tgcagcggtt cctccccgac accgacaaga    900
ccatcgacgg gcgctgacg gaggaggca tcaagttcca gctcggccgc gaactccccc    960
acatcatcga ggccaacgtg gaggccttct gccagaagct gatgcaggag cacctcagg   1020 cggcggacaa gctcacctac ggcgacatgt tctgggcggt gcaccccggc gggccggcga   1080
tcctgaccaa gatggagggc aggctggggc tggacgcgcg gaagctccgc gccagccgga   1140
gcgcgctccg ggacttcggg aacgcgagca gcaacaccat cgtgtacgtg ctggagaaca   1200
tggtggagga gacccggcag aggagggagg aggcggcgga agaggaggat tgcgagtggg   1260
ggctcatact ggcgttcggg ccgggggatca cgttcgaggg gatcctggcc agaaatctgc   1320
```
aggcgcgcgc gcgcgcgcgc gactga                                          1346

<210> SEQ ID NO 28
<211> LENGTH: 3343
<212> TYPE: DNA
<213> ORGANISM: Zea mays
<220> FEATURE:
<221> NAME/KEY: misc_feature
<222> LOCATION: (0)...(0)
<223> OTHER INFORMATION: nucleotide sequence of a male fertility gene
      encoding a strictosidine synthase (MS45) in maize
      (AF360356)

<400> SEQUENCE: 28

| | | |
|---|---|---|
| ccatggtgtc tctatgaaaa agatgagtac aatgtgtcta tatccgtttt cttagggtcc | 60 |
| cttcttctgc cttattactg actgaatcgg ggttacaaaa aacttccacg ggtgcatgat | 120 |
| ctccatgttc cacttctccc acctcgcgtt gcacatttct tggatgtcgg tggttcccat | 180 |
| ctgaccgagg cccatcagac acctttcggg acacccatca agggcctttc ggatggccca | 240 |
| cgagacgtat cgggtcgtgg tgatccaggg gatatatgtc ccccacaatc gtcacctata | 300 |
| ttattattct ttagatatta tttaattttt ggaaaaataa caaacttata cttttgtgta | 360 |
| gggcctcagc atagattttc gcttagggcc cagaaatgcg aggaccagcc atgtctagtg | 420 |
| tccactattg gcactaccca gaacaagatt taaaaaaata accaaagtaa ctaatccact | 480 |
| cgaaagctat catgtaatgt ttaaagaaac atctattaaa accacgatcc tcttaaaaaa | 540 |
| caagcatatt tcgaaagaga caaattatgt tacagtttac aaacatctaa gagcgacaaa | 600 |
| ttatatcgaa aggtaagcta tgacgttcag attttttcttt ttcattcttg ttattttgtt | 660 |
| attgttttta tatacatttt cttctcttac aatagagtga ttttcttccg atttttataaa | 720 |
| atgactataa agtcatttt atataagagc acgcatgtcg tagattctcg ttcaaaaatc | 780 |
| tttctgattt ttttaagagc tagtttggca accctgtttc tttcaaagaa ttttgatttt | 840 |
| ttcaaaaaaa attagtttat tttctcttta taaaatagaa aacacttaga aaaatagagt | 900 |
| tgccagacta gccctagaat gttttcccaa taaattacaa tcactgtgta taattatttg | 960 |
| gccagcccca taaattattt aaaccgaaac tgaaatcgag cgaaaccaaa tctgagctat | 1020 |
| ttctctagat tagtaaaaag ggagagagag aggaagaaat cagttttaag tcattgtccc | 1080 |
| tgagatgtgc ggtttggcaa cgatagccac cgtaatcata gctcataggt gcctacgtca | 1140 |
| ggttcggcag ctctcgtgtc atctcacatg gcatactaca tgcttgttca accgttcgtc | 1200 |
| ttgttccatc gtccaagcct tgcctattct gaaccaagag gatacctact cccaaacaat | 1260 |
| ccatcttact catgcaactt ccatgcaaac acgcacatat gtttcctgaa ccaatccatt | 1320 |
| aaagatcaca acagctagcg ttctcccgct agcttccctc tctcctctgc cgatcttttt | 1380 |
| cgtccaccag catggagaag aggaacctgc agtggcggcg agggcgtgat ggcatcgtgc | 1440 |
| agtaccctca cctcttcttc gcggccctgg cgctggccct cctagtcgcg gacccgttcg | 1500 |
| gcctcagtcc gctggccgag gtcgactacc ggccggtgaa gcacgagctc gcgccgtacg | 1560 |
| gggaggtcat gggcagctgg cccagagaca atgccagccg gctcaggcgc gggaggctgg | 1620 |
| agttcgtcgg cgaggtgttc gggccggagt ctatcgagtt cgatctccag ggccgcgggc | 1680 |
| cgtacgccgg cctcgccgac ggccgcgtcg tgcggtggat gggcgaggag gccgggtggg | 1740 |
| agacgttcgc cgtcatgaat cctgactggt aagtgctcga tatcgctccg gcgtccactc | 1800 |
| gttacatgct ataatatagt agtactaaga tattttgatc tgattttttg cattcttggg | 1860 |
| agaaacgtca tgcaaaattt gttgtttctt ggcaaaggtc agaagaagtc tgtgccaatg | 1920 |

```
gagtgaactc aacgacgagg aagcagcacg agaaggagga gttctgcggc cggccgctcg    1980
gcctgaggtt ccacggggag accggcgagc tctacgtcgc cgacgcgtac tacggtctca    2040
tggtcgttgg ccagagcggc ggcgtggcgt cctccgtcgc gagggaagcc gacgggacc     2100 ccatccggtt cgcgaacgac ctcgatgtgc acaggaatgg atccgtattc ttcactgaca    2160
cgagcatgag atacagcaga aagtgagcaa agcgacgtaa caatccggct tctcattttc    2220
aaacgcctct gtattctctg ctgaaagagt agctcaccag acaagagctg aatttgcagg    2280
gaccatctga acatcctgtt agaaggagaa ggcaccggga ggctgctcag gtatgatcca    2340
gaaacaagcg gtgtccatgt cgtgctcaag gggctggtgt tcccaaacgg cgtgcagatc    2400
tcagaggacc atcagtttct tctcttctcc gagacaacaa actgcaggta caaaaatac     2460 tatctgacga tgctcatgat tctaccgtat ccatagtcat gaacacaaac cacacgaatc    2520
tggccttgac caggataatg aggtactggc tggaaggccc aagagcgggc gaggtagagg    2580
tgttcgcgaa cctgccgggc ttccccgaca acgtgcgctc caacggcagg ggccagttct    2640
gggtggcgat cgactgctgc cggacgccgg cgcaggaggt gttcgccaag aggccgtggc    2700
tccggaccct gtacttcaag ttcccgctgt cgctcaaggt gctcacttgg aaggccgcca    2760
ggaggatgca cacggtgctc gcgctcctcg acggcgaagg gcgcgtcgtg gaggtgctcg    2820
aggaccgggg ccacgaggtg atgaagctgg tgagcgaggt gcgggaggtg ggccgcaagc    2880
tgtggatcgg aaccgtggcg cacaaccaca tcgccaccat cccctaccct ttagaggact    2940
aaccatgatc tatgctgttt caatgcctcc taatctgtgt acgtctataa atgtctaatg    3000
cagtcactgg ttgtaatctt gtttgtgttt ggcaaattgg cataataatg gacagattca    3060
atgggcattg gtgctgtagt cgcatcacac taattgaatg ggatcatgtt gagctctcac    3120
tttgctacaa tttgctccag cttgtacggt tgtaccctct tgctcgtcta tagtaagggc    3180
catctaaaaa aaactcaaat tagatctgca atacaagtat gattgggccg aatttggatt    3240
gtcacgggtc cgcgaccgcg aattgggctc ggtttgattt agccgacata gtagtgaccg    3300
acccgagccg gcggcgagcc aaaccgagcg gacgccgcca tgg                      3343
```

<210> SEQ ID NO 29
<211> LENGTH: 1570
<212> TYPE: DNA
<213> ORGANISM: Oryza sativa
<220> FEATURE:
<221> NAME/KEY: misc_feature
<222> LOCATION: (0)...(0)
<223> OTHER INFORMATION: nucleotide sequence of male fertility gene
      encoding a strictosidine synthase (MS45) in rice
      (LOC_Os03g15710)

<400> SEQUENCE: 29

```
atggaagaga agaagcagca gcagcagcgt ccacagagag ggcgcgatgg catcctgcag      60
tatccgcacc ttttcttcgc ggcgctggcg ctggccctgc tcctcaccga cccgttccac     120
ctcggcccgc tcgccggggt ggactaccgg ccggtgaggc acgagctggc gccgtaccgc     180
gaggtgatgg cgcggtggcc gcgggacaac ggcagccggc tcaggcacgg caggctggag     240
ttcgtcggag aggtgttcgg gccggagtcc atcgagttcg accgccacgg ccgcggcccc     300
tacgccggcc tcgccgacgg ccgcgtcgtg cggtggatgg gggaggacgc cgggtgggag     360
acgttcgccg tcatgagccc tgactggtaa cgaacacctc gcctgcattt tgctctcgcc     420
ctccacgaaa acacctctcg tagcagtgta caattacgtg ttcttatatt gcaaaaaaag     480
```

```
gtcggagaaa gtttgtgcca atggggtgga gtcgacgacg aagaagcagc acgagatgga    540
gcgacggtgc ggccggcctc tcgggctgag gtttcacggc gagaccggcg agctctacgt    600
cgccgacgca tactacgggc tcatgtccgt cggtccgaac ggcggggtgg cgacctctct    660
cgcgagagaa gtcggcggga gcccggtcaa cttcgcgaac gacctcgaca tccaccgcaa    720
cggctccgtg ttcttcaccg acacgagcac gagatacaac agaaagtgtg cagctgcagt    780
atcactctct tcagttgtat cgattctcta tttccttcta tcgttcaaga ttttctgatt    840
agaatcagtt gtgcagggat catctgaacg ttctgctaga aggtgaaggc acagggaggc    900
tgctcagata tgacccagaa accaaagctg cccatgtcgt gctgagcggg ctggtcttcc    960
cgaatggcgt gcagatttct gacgaccagc agttcctcct cttctccgaa acaacaaact   1020
gcaggtgaaa tggcacaagc tttcacaggt tctgaaaata ctaaaggtta acaagattc    1080 agaattgatt aacattgcac gcatatgctg ttctaggata atgcggtact ggctggaagg   1140
gccaagagcc gggcaggtgg aggtgttcgc cgacctgccg ggggttccgg acaacgtgcg   1200
actgagcagc ggcggcggcg gcggacggtt ctgggtggcg atcgactgct gcaggacggc   1260
ggcgcaggag gtgttcgcca agcggccgtg gctgcgaacg ctctacttca agctgcccct   1320
gacgatgcgc acgctgggga agatggtcag catgcggatg cacaccctcg tcgcgctcct   1380
cgacggcgaa ggggacgtcg tcgaggtgct cgaggaccgg ggcggcgagg tgatgcggct   1440
ggtgagcgag gtgagggagg tggggcgcaa gctgtggatc ggcaccgtgg ctcataacca   1500
catcgccacg atcccttacc cgttggaaga gcagagtagc agcagcagca gcaacgtgct   1560
tggtgattga                                                          1570

<210> SEQ ID NO 30
<211> LENGTH: 52256
<212> TYPE: DNA
<213> ORGANISM: Artificial Sequence
<220> FEATURE:
<223> OTHER INFORMATION: plasmid PHP31457

<400> SEQUENCE: 30
gggggggggg gggggggggtt ccattgttca ttccacggac aaaaacagag aaaggaaacg     60
acagaggcca aaaagctcgc tttcagcacc tgtcgtttcc tttcttttca gagggtattt    120
taaataaaaa cattaagtta tgacgaagaa gaacggaaac gccttaaacc ggaaaatttt    180
cataaatagc gaaaacccgc gaggtcgccg ccccgtaacc tgtcggatca ccggaaagga    240
cccgtaaagt gataatgatt atcatctaca tatcacaacg tgcgtggagg ccatcaaacc    300
acgtcaaata atcaattatg acgcaggtat cgtattaatt gatctgcatc aacttaacgt    360
aaaaacaact tcagacaata caaatcagcg acactgaata cggggcaacc tcatgtcccc    420
cccccccccc cccctgcagg catcgtggtg tcacgctcgt cgtttggtat ggcttcattc    480
agctccggtt cccaacgatc aaggcgagtt acatgatccc ccatgttgtg caaaaaagcg    540
gttagctcct tcggtcctcc gatcgttgtc agaagtaagt tggccgcagt gttatcactc    600
atggttatgg cagcactgca taattctctt actgtcatgc catccgtaag atgcttttct    660
gtgactggtg agtactcaac caagtcattc tgagaatagt gtatgcggcg accgagttgc    720
tcttgcccgg cgtcaacacg ggataatacc gcgccacata gcagaacttt aaaagtgctc    780
atcattggaa aacgttcttc ggggcgaaaa ctctcaagga tcttaccgct gttgagatcc    840
agttcgatgt aacccactcg tgcacccaac tgatcttcag catctttac tttcaccagc    900 gtttctgggt gagcaaaaac aggaaggcaa aatgccgcaa aaaagggaat aagggcgaca    960
```

```
cggaaatgtt gaatactcat actcttcctt tttcaatatt attgaagcat ttatcagggt    1020
tattgtctca tgagcggata catatttgaa tgtatttaga aaaataaaca aatagggggtt   1080 ccgcgcacat ttccccgaaa agtgccacct gacgtctaag aaaccattat tatcatgaca   1140
ttaacctata aaataggcg tatcacgagg cccttttcgtc ttcaagaatt cggagctttt   1200
gccattctca ccggattcag tcgtcactca tggtgatttc tcacttgata accttatttt   1260
tgacgagggg aaattaatag gttgtattga tgttggacga gtcggaatcg cagaccgata   1320
ccaggatctt gccatcctat ggaactgcct cggtgagttt tctccttcat tacagaaacg   1380 gcttttcaa aaatatggta ttgataatcc tgatatgaat aaattgcagt ttcatttgat    1440
gctcgatgag tttttctaat cagaattggt taattggttg taacactggc agagcattac   1500
gctgacttga cgggacggcg gctttgttga ataaatcgaa cttttgctga gttgaaggat   1560
cagatcacgc atcttcccga caacgcagac cgttccgtgg caaagcaaaa gttcaaaatc   1620
accaactggt ccacctacaa caaagctctc atcaaccgtg ctccctcac tttctggctg     1680 gatgatgggg cgattcaggc ctggtatgag tcagcaacac cttcttcacg aggcagacct   1740
cagcgccaga aggccgccag agaggccgag cgcggccgtg aggcttggac gctagggcag   1800
ggcatgaaaa agcccgtagc gggctgctac gggcgtctga cgcggtggaa aggggagggg   1860
gatgttgtct acatggctct gctgtagtga gtgggttgcg ctccggcagc ggtcctgatc   1920
aatcgtcacc ctttctcggt ccttcaacgt tcctgacaac gagcctcctt ttcgccaatc   1980
catcgacaat caccgcgagt ccctgctcga acgctgcgtc cggaccggct tcgtcgaagg   2040
cgtctatcgc ggcccgcaac agcggcgaga gcggagcctg ttcaacggtg ccgccgcgct   2100
cgccggcatc gctgtcgccg gcctgctcct caagcacggc cccaacagtg aagtagctga   2160
ttgtcatcag cgcattgacg gcgtccccgg ccgaaaaacc cgcctcgcag aggaagcgaa   2220
gctgcgcgtc ggccgtttcc atctgcggtg cgcccggtcg cgtgccggca tggatgcgcg   2280
cgccatcgcg gtaggcgagc agcgcctgcc tgaagctgcg ggcattcccg atcagaaatg   2340
agcgccagtc gtcgtcggct ctcggcaccg aatgcgtatg attctccgcc agcatggctt   2400
cggccagtgc gtcgagcagc gcccgcttgt tcctgaagtg ccagtaaagc gccggctgct   2460 gaaccccaa ccgttccgcc agtttgcgtg tcgtcagacc gtctacgccg acctcgttca    2520
acaggtccag ggcggcacgg atcactgtat tcggctgcaa ctttgtcatg cttgacactt   2580
tatcactgat aaacataata tgtccaccaa cttatcagtg ataaagaatc cgcgcgttca   2640
atcggaccag cggaggctgg tccggaggcc agacgtgaaa cccaacatac ccctgatcgt   2700
aattctgagc actgtcgcgc tcgacgctgt cggcatcggc ctgattatgc cggtgctgcc   2760
gggcctcctg cgcgatctgg ttcactcgaa cgacgtcacc gcccactatg gcattctgct   2820
ggcgctgtat gcgttggtgc aatttgcctg cgcacctgtg ctgggcgcgc tgtcggatcg   2880
tttcgggcgg cggccaatct tgctcgtctc gctggccggc gccactgtcg actacgccat   2940
catggcgaca gcgccttcc tttgggttct ctatatcggg cggatcgtgg ccggcatcac    3000
cggggcgact ggggcggtag ccggcgctta tattgccgat atcactgatg gcgatgagcg   3060
cgcgcggcac ttcggcttca tgagcgcctg tttcgggttc gggatggtcg cgggacctgt   3120
gctcggtggg ctgatgggcg gtttctcccc ccacgctccg ttcttcgccg cggcagcctt   3180
gaacggcctc aatttcctga cgggctgttt ccttttgccg gagtcgcaca aaggcgaacg   3240
ccggccgtta cgccgggagg ctctcaaccc gctcgcttcg ttccggtggg cccggggcat   3300
```

```
gaccgtcgtc gccgccctga tggcggtctt cttcatcatg caacttgtcg gacaggtgcc    3360
ggccgcgctt tgggtcattt tcggcgagga tcgctttcac tgggacgcga ccacgatcgg    3420
catttcgctt gccgcatttg gcattctgca ttcactcgcc caggcaatga tcaccggccc    3480
tgtagccgcc cggctcggcg aaaggcgggc actcatgctc ggaatgattg ccgacggcac    3540
aggctacatc ctgcttgcct tcgcgacacg gggatggatg gcgttcccga tcatggtcct    3600
gcttgcttcg ggtggcatcg gaatgccggc gctgcaagca atgttgtcca ggcaggtgga    3660
tgaggaacgt caggggcagc tgcaaggctc actggcggcg ctcaccagcc tgacctcgat    3720
cgtcggaccc ctcctcttca cggcgatcta tgcggcttct ataacaacgt ggaacgggtg    3780
ggcatggatt gcaggcgctg ccctctactt gctctgcctg ccggcgctgc gtcgcgggct    3840
ttggagcggc gcagggcaac gagccgatcg ctgatcgtgg aaacgatagg cctatgccat    3900
gcgggtcaag gcgacttccg gcaagctata cgcgccctag gagtgcggtt ggaacgttgg    3960
cccagccaga tactcccgat cacgagcagg acgccgatga tttgaagcgc actcagcgtc    4020
tgatccaaga acaaccatcc tagcaacacg gcggtccccg ggctgagaaa gcccagtaag    4080
gaaacaactg taggttcgag tcgcgagatc ccccggaacc aaaggaagta ggttaaaccc    4140
gctccgatca ggccgagcca cgccaggccg agaacattgg ttcctgtagg catcgggatt    4200
ggcggatcaa acactaaagc tactggaacg agcagaagtc ctccggccgc cagttgccag    4260
gcggtaaagg tgagcagagg cacggaggt tgccacttgc gggtcagcac ggttccgaac    4320
gccatggaaa ccgccccgc caggcccgct gcgacgccga caggatctag cgctgcgttt    4380
ggtgtcaaca ccaacagcgc cacgcccgca gttccgcaaa tagcccccag gaccgccatc    4440
aatcgtatcg ggctacctag cagagcggca gagatgaaca cgaccatcag cggctgcaca    4500
gcgcctaccg tcgccgcgac cccgcccggc aggcggtaga ccgaaataaa caacaagctc    4560
cagaatagcg aaatattaag tgcgccgagg atgaagatgc catccacca gattcccgtt    4620 ggaatctgtc ggacgatcat cacgagcaat aaacccgccg gcaacgcccg cagcagcata    4680
ccggcgaccc ctcggcctcg ctgttcgggc tccacgaaaa cgccggacag atgcgccttg    4740
tgagcgtcct tggggccgtc ctcctgtttg aagaccgaca gcccaatgat ctcgccgtcg    4800
atgtaggcgc cgaatgccac ggcatctcgc aaccgttcag cgaacgcctc catgggcttt    4860
ttctcctcgt gctcgtaaac ggacccgaac atctctggag cttttcttcag ggccgacaat    4920 cggatctcgc ggaaatcctg cacgtcggcc gctccaagcc gtcgaatctg agccttaatc    4980
acaattgtca attttaatcc tctgtttatc ggcagttcgt agagcgcgcc gtgcgtcccg    5040
agcgatactg agcgaagcaa gtgcgtcgag cagtgcccgc ttgttcctga aatgccagta    5100
aagcgctggc tgctgaaccc ccagccggaa ctgaccccac aaggccctag cgtttgcaat    5160
gcaccaggtc atcattgacc caggcgtgtt ccaccaggcc gctgcctcgc aactcttcgc    5220
aggcttcgcc gacctgctcg cgccacttct tcacgcgggt ggaatccgat ccgcacatga    5280
ggcggaaggt ttccagcttg agcgggtacg gctcccggtg cgagctgaaa tagtcgaaca    5340
tccgtcgggc cgtcggcgac agcttgcggt acttctccca tatgaatttc gtgtagtggt    5400
cgccagcaaa cagcacgacg atttcctcgt cgatcaggac ctggcaacgg gacgttttct    5460
tgccacggtc caggacgcgg aagcggtgca gcagcgacac cgattccagg tgcccaacgc    5520
ggtcggacgt gaagcccatc gccgtcgcct gtaggcgcga caggcattcc tcggccttcg    5580
tgtaataccg gccattgatc gaccagccca ggtcctggca aagctcgtag aacgtgaagg    5640
tgatcggctc gccgataggg gtgcgcttcg cgtactccaa cacctgctgc cacaccagtt    5700
```

```
cgtcatcgtc ggcccgcagc tcgacgccgg tgtaggtgat cttcacgtcc ttgttgacgt    5760
ggaaaatgac cttgttttgc agcgcctcgc gcgggatttt cttgttgcgc gtggtgaaca    5820
gggcagagcg ggccgtgtcg tttggcatcg ctcgcatcgt gtccggccac ggcgcaatat    5880
cgaacaagga aagctgcatt tccttgatct gctgcttcgt gtgtttcagc aacgcggcct    5940
gcttggcctc gctgacctgt tttgccaggt cctcgccggc ggttttcgc ttcttggtcg     6000
tcatagttcc tcgcgtgtcg atggtcatcg acttcgccaa acctgccgcc tcctgttcga    6060
gacgacgcga acgctccacg gcggccgatg gcgcgggcag ggcaggggga gccagttgca    6120
cgctgtcgcg ctcgatcttg gccgtagctt gctggaccat cgagccgacg gactggaagg    6180
tttcgcgggg cgcacgcatg acggtgcggc ttgcgatggt ttcggcatcc tcggcggaaa    6240
accccgcgtc gatcagttct tgcctgtatg ccttccggtc aaacgtccga ttcattcacc    6300
ctccttgcgg gattgccccg actcacgccg gggcaatgtg cccttattcc tgatttgacc    6360
cgcctggtgc cttggtgtcc agataatcca ccttatcggc aatgaagtcg gtcccgtaga    6420
ccgtctggcc gtccttctcg tacttggtat tccgaatctt gccctgcacg aataccagcg    6480
accccttgcc caaatacttg ccgtgggcct cggcctgaga gccaaaacac ttgatgcgga    6540
agaagtcggt gcgctcctgc ttgtcgccgg catcgttgcg ccactcttca ttaaccgcta    6600
tatcgaaaat tgcttgcggc ttgttagaat tgccatgacg tacctcggtg tcacgggtaa    6660
gattaccgat aaactggaac tgattatggc tcatatcgaa agtctccttg agaaaggaga    6720
ctctagttta gctaaacatt ggttccgctg tcaagaactt tagcggctaa aattttgcgg    6780
gccgcgacca aaggtgcgag gggcggcttc cgctgtgtac aaccagatat tttttcaccaa   6840
catccttcgt ctgctcgatg agcggggcat gacgaaacat gagctgtcgg agagggcagg    6900
ggtttcaatt tcgtttttat cagacttaac caacggtaag gccaaccccct cgttgaaggt   6960
gatggaggcc attgccgacg ccctggaaac tcccctacct cttctcctgg agtccaccga    7020
ccttgaccgc gaggcactcg cggagattgc gggtcatcct ttcaagagca gcgtgccgcc    7080
cggatacgaa cgcatcagtg tggttttgcc gtcacataag gcgtttatcg taaagaaatg    7140
gggcgacgac acccgaaaaa agctgcgtgg aaggctctga cgccaagggt tagggcttgc    7200
acttccttct ttagccgcta aaacggcccc ttctctgcgg gccgtcggct cgcgcatcat    7260
atcgacatcc tcaacggaag ccgtgccgcg aatggcatcg ggcgggtgcg ctttgacagt    7320
tgtttttctat cagaacccct acgtcgtgcg gttcgattag ctgtttgtct tgcaggctaa   7380
acactttcgg tatatcgttt gcctgtgcga taatgttgct aatgatttgt tgcgtagggg    7440
ttactgaaaa gtgagcggga aagaagagtt tcagaccatc aaggagcggg ccaagcgcaa    7500
gctggaacgc gacatgggtg cggacctgtt ggccgcgctc aacgacccga aaaccgttga    7560
agtcatgctc aacgcggacg gcaaggtgtg gcacgaacgc cttggcgagc cgatgcggta    7620
catctgcgac atgcggccca gccagtcgca ggcgattata gaaacggtgg ccggattcca    7680
cggcaaagag gtcacgcggc attcgcccat cctggaaggc gagttcccct ggatggcag    7740
ccgctttgcc ggccaattgc cgccggtcgt ggccgcgcca acctttgcga tccgcaagcg    7800
cgcggtcgcc atcttcacgc tggaacagta cgtcgaggcg ggcatcatga cccgcgagca    7860
atacgaggtc attaaaagcg ccgtcgcggc gcatcgaaac atcctcgtca ttggcggtac    7920
tggctcgggc aagaccacgc tcgtcaacgc gatcatcaat gaaatggtcg ccttcaaccc    7980
gtctgagcgc gtcgtcatca tcgaggacac cggcgaaatc cagtgcgccg cagagaacgc    8040
```

```
cgtccaatac cacaccagca tcgacgtctc gatgacgctg ctgctcaaga caacgctgcg   8100
tatgcgcccc gaccgcatcc tggtcggtga ggtacgtggc cccgaagccc ttgatctgtt   8160
gatggcctgg aacaccgggc atgaaggagg tgccgccacc ctgcacgcaa caacccccaa   8220
agcgggcctg agccggctcg ccatgcttat cagcatgcac ccggattcac cgaaacccat   8280
tgagccgctg attggcgagg cggttcatgt ggtcgtccat atcgccagga cccctagcgg   8340
ccgtcgagtg caagaaattc tcgaagttct tggttacgag aacggccagt acatcaccaa   8400
aaccctgtaa ggagtatttc caatgacaac ggctgttccg ttccgtctga ccatgaatcg   8460
cggcattttg ttctaccttg ccgtgttctt cgttctcgct ctcgcgttat ccgcgcatcc   8520
ggcgatggcc tcggaaggca ccggcggcag cttgccatat gagagctggc tgacgaacct   8580
gcgcaactcc gtaaccggcc cggtggcctt cgcgctgtcc atcatcggca tcgtcgtcgc   8640
cggcggcgtg ctgatcttcg gcggcgaact caacgccttc ttccgaaccc tgatcttcct   8700
ggttctggtg atggcgctgc tggtcggcgc gcagaacgtg atgagcacct tcttcggtcg   8760
tggtgccgaa atcgcggccc tcggcaacgg ggcgctgcac caggtgcaag tcgcggcggc   8820
ggatgccgtg cgtgcggtag cggctggacg gctcgcctaa tcatggctct gcgcacgatc   8880
cccatccgtc gcgcaggcaa ccgagaaaac ctgttcatgg gtggtgatcg tgaactggtg   8940
atgttctcgg gcctgatggc gtttgcgctg attttcagcg cccaagagct gcgggccacc   9000
gtggtcggtc tgatcctgtg gttcggggcg ctctatgcgt tccgaatcat ggcgaaggcc   9060
gatccgaaga tgcggttcgt gtacctgcgt caccgccggt acaagccgta ttacccggcc   9120
cgctcgaccc cgttccgcga gaacaccaat agccaaggga agcaataccg atgatccaag   9180
caattgcgat tgcaatcgcg ggcctcggcg cgcttctgtt gttcatcctc tttgcccgca   9240
tccgcgcggt cgatgccgaa ctgaaactga aaaagcatcg ttccaaggac gccggcctgg   9300
ccgatctgct caactacgcc gctgtcgtcg atgacggcgt aatcgtgggc aagaacggca   9360
gctttatggc tgcctggctg tacaagggcg atgacaacgc aagcagcacc gaccagcagc   9420
gcgaagtagt gtccgcccgc atcaaccagg ccctcgcggg cctgggaagt gggtggatga   9480
tccatgtgga cgccgtgcgg cgtcctgctc cgaactacgc ggagcggggc ctgtcggcgt   9540
tccctgaccg tctgacggca gcgattgaag aagagcgctc ggtcttgcct tgctcgtcgg   9600
tgatgtactt caccagctcc gcgaagtcgc tcttcttgat ggagcgcatg gggacgtgct   9660
tggcaatcac gcgcaccccc cggccgtttt agcggctaaa aaagtcatgg ctctgccctc   9720
gggcggacca cgcccatcat gaccttgcca agctcgtcct gcttctcttc gatcttcgcc   9780
agcagggcga ggatcgtggc atcaccgaac cgcgccgtgc gcgggtcgtc ggtgagccag   9840
agtttcagca ggccgcccag gcggcccagg tcgccattga tgcgggccag ctcgcggacg   9900
tgctcatagt ccacgacgcc cgtgattttg tagccctggc cgacggccag caggtaggcc   9960
gacaggctca tgccggccgc cgccgccttt cctcaatcg ctcttcgttc gtctggaagg  10020
cagtacacct tgataggtgg gctgcccttc ctggttggct tggtttcatc agccatccgc  10080
ttgccctcat ctgttacgcc ggcggtagcc ggccagcctc gcagagcagg attcccgttg  10140
agcaccgcca ggtgcgaata agggacagtg aagaaggaac accgctcgc gggtgggcct  10200 acttcaccta tcctgcccgg ctgacgccgt tggatacacc aaggaaagtc tacacgaacc  10260
ctttggcaaa atcctgtata tcgtgcgaaa aaggatggat ataccgaaaa atcgctata  10320 atgacccga agcagggtta tgcagcgaa aagcgctgct tccctgctgt tttgtggaat  10380
atctaccgac tggaaacagg caaatgcagg aaattactga actgagggga caggcgagag  10440
```

```
acgatgccaa agagctacac cgacgagctg gccgagtggg ttgaatcccg cgcggccaag   10500
aagcgccggc gtgatgaggc tgcggttgcg ttcctggcgg tgagggcgga tgtcgaggcg   10560
gcgttagcgt ccggctatgc gctcgtcacc atttgggagc acatgcggga acggggaag    10620
gtcaagttct cctacgagac gttccgctcg cacgccaggc ggcacatcaa ggccaagccc   10680
gccgatgtgc ccgcaccgca ggccaaggct gcggaacccg cgccggcacc caagacgccg   10740
gagccacggc ggccgaagca gggggggcaag gctgaaaagc cggcccccgc tgcggccccg   10800
accggcttca ccttcaaccc aacaccggac aaaaaggatc tactgtaatg cgaaaattc    10860
acatggtttt gcagggcaag gcggggtcg gcaagtcggc catcgccgcg atcattgcgc    10920
agtacaagat ggacaagggg cagacaccct tgtgcatcga caccgacccg gtgaacgcga   10980
cgttcgaggg ctacaaggcc ctgaacgtcc gccggctgaa catcatggcc ggcgacgaaa   11040
ttaactcgcg caacttcgac accctggtcg agctgattgc gccgaccaag gatgacgtgg   11100
tgatcgacaa cggtgccagc tcgttcgtgc ctctgtcgca ttacctcatc agcaaccagg   11160
tgccggctct gctgcaagaa atggggcatg agctggtcat ccataccgtc gtcaccggcg   11220
gccaggctct cctggacacg gtgagcggct cgcccagct cgccagccag ttcccggccg    11280
aagcgctttt cgtggtctgg ctgaacccgt attgggggcc tatcgagcat gagggcaaga   11340
gctttgagca gatgaaggcg tacacggcca acaaggcccg cgtgtcgtcc atcatccaga   11400
ttccggccct caaggaagaa acctacggcc gcgatttcag cgacatgctg caagagcggc   11460
tgacgttcga ccaggcgctg gccgatgaat cgctcacgat catgacgcgg caacgcctca   11520
agatcgtgcg gcgcggcctg tttgaacagc tcgacgcggc ggccgtgcta tgagcgacca   11580
gattgaagag ctgatccggg agattgcggc caagcacggc atcgccgtcg ccgcgacga    11640
cccggtgctg atcctgcata ccatcaacgc ccggctcatg gccgacagtg cggccaagca   11700
agaggaaatc cttgccgcgt tcaaggaaga gctggaaggg atcgcccatc gttggggcga   11760
ggacgccaag gccaaagcgg agcggatgct gaacgcggcc ctggcggcca gcaaggacgc   11820
aatggcgaag gtaatgaagg acagcgccgc gcaggcggcc gaagcgatcc gcagggaaat   11880
cgacgacggc cttggccgcc agctcgcggc caaggtcgcg gacgcgcggc gcgtggcgat   11940
gatgaacatg atcgccggcg gcatggtgtt gttcgcggcc gccctggtgg tgtgggcctc   12000
gttatgaatc gcagaggcgc agatgaaaaa gcccggcgtt gccgggcttt gttttgcgt    12060
tagctgggct tgtttgacag gcccaagctc tgactgcgcc cgcgctcgcg ctcctgggcc   12120
tgtttcttct cctgctcctg cttgcgcatc agggcctggt gccgtcgggc tgcttcacgc   12180
atcgaatccc agtcgccggc cagctcggga tgctccgcgc gcatcttgcg cgtcgccagt   12240
tcctcgatct tgggcgcgtg aatgcccatg ccttccttga tttcgcgcac catgtccagc   12300
cgcgtgtgca gggtctgcaa gcgggcttgc tgttgggcct gctgctgctg ccaggcggcc   12360
tttgtacgcg gcagggacag caagccgggg gcattggact gtagctgctg caaacgcgcc   12420
tgctgacggt ctacgagctg ttctaggcgg tcctcgatgc gctccacctg gtcatgcttt   12480
gcctgcacgt agagcgcaag ggtctgctgg taggtctgct cgatgggcgc ggattctaag   12540
agggcctgct gttccgtctc ggcctcctgg gccgcctgta gcaaatcctc gccgctgttg   12600
ccgctggact gctttactgc cggggactgc tgttgccctg ctcgcgccgt cgtcgcagtt   12660
cggcttgccc ccactcgatt gactgcttca tttcgagccg cagcgatgcg atctcggatt   12720
gcgtcaacgg acggggcagc gcggaggtgt ccggcttctc cttgggtgag tcggtcgatg   12780
```

```
ccatagccaa aggtttcctt ccaaaatgcg tccattgctg gaccgtgttt ctcattgatg    12840
cccgcaagca tcttcggctt gaccgccagg tcaagcgcgc cttcatgggc ggtcatgacg    12900
gacgccgcca tgaccttgcc gccgttgttc tcgatgtagc cgcgtaatga ggcaatggtg    12960
ccgcccatcg tcagcgtgtc atcgacaacg atgtacttct ggccggggat cacctccccc    13020
tcgaaagtcg ggttgaacgc caggcgatga tctgaaccgg ctccggttcg ggcgaccttc    13080
tcccgctgca caatgtccgt ttcgacctca aggccaaggc ggtcggccag aacgaccgcc    13140
atcatggccg gaatcttgtt gttccccgcc gcctcgacgg cgaggactgg aacgatgcgg    13200
ggcttgtcgt cgccgatcag cgtcttgagc tgggcaacag tgtcgtccga aatcaggcgc    13260
tcgaccaaat taagcgccgc ttccgcgtcg ccctgcttcg cagcctggta ttcaggctcg    13320
ttggtcaaag aaccaaggtc gccgttgcga accaccttcg ggaagtctcc ccacggtgcg    13380
cgctcggctc tgctgtagct gctcaagacg cctcccttt tagccgctaa aactctaacg     13440
agtgcgcccg cgactcaact tgacgctttc ggcacttacc tgtgccttgc cacttgcgtc    13500
ataggtgatg cttttcgcac tcccgatttc aggtacttta tcgaaatctg accgggcgtg    13560
cattacaaag ttcttcccca cctgttggta aatgctgccg ctatctgcgt ggacgatgct    13620
gccgtcgtgg cgctgcgact tatcggcctt ttgggccata tagatgttgt aaatgccagg    13680
tttcagggcc ccggctttat ctaccttctg gttcgtccat gcgccttggt tctcggtctg    13740
gacaattctt tgcccattca tgaccaggag gcggtgtttc attgggtgac tcctgacggt    13800
tgcctctggt gttaaacgtg tcctggtcgc ttgccggcta aaaaaagcc gacctcggca     13860
gttcgaggcc ggctttccct agagccgggc gcgtcaaggt tgttccatct attttagtga    13920
actgcgttcg atttatcagt tactttcctc ccgctttgtg tttcctccca ctcgtttccg    13980
cgtctagccg accccctcaac atagcggcct cttcttgggc tgccttttgcc tcttgccgcg   14040
cttcgtcacg ctcggcttgc accgtcgtaa agcgctcggc ctgcctggcc gcctcttgcg    14100
ccgccaactt cctttgctcc tggtgggcct cggcgtcggc ctgcgccttc gctttcaccg    14160
ctgccaactc cgtgcgcaaa ctctccgctt cgcgcctggt ggcgtcgcgc tcgccgcgaa    14220
gcgcctgcat ttcctggttg gccgcgtcca gggtcttgcg gctctcttct ttgaatgcgc    14280
gggcgtcctg gtgagcgtag tccagctcgg cgcgcagctc ctgcgctcga cgctccacct    14340
cgtcggcccg ctgcgtcgcc agcgcggccc gctgctcggc tcctgccagg gcggtgcgtg    14400
cttcggccag ggcttgccgc tggcgtgcgg ccagctcggc cgcctcggcg gcctgctgct    14460
ctagcaatgt aacgcgcgcc tgggcttctt ccagctcgcg ggcctgcgcc tcgaaggcgt    14520
cggccagctc cccgcgcacg gcttccaact cgttgcgctc acgatcccag ccggcttgcg    14580
ctgcctgcaa cgattcattg gcaagggcct gggcggcttg ccagagggcg gccacggcct    14640
ggttgccggc ctgctgcacc gcgtccggca cctggactgc cagcggggcg gcctgcgccg    14700
tgcgctggcg tcgccattcg cgcatgccgg cgctggcgtc gttcatgttg acgcgggcgg    14760
ccttacgcac tgcatccacg gtcgggaagt tctcccggtc gccttgctcg aacagctcgt    14820
ccgcagccgc aaaaatgcgg tcgcgcgtct cttttgttcag ttccatgttg gctccggtaa   14880
ttggtaagaa taataatact cttacctacc ttatcagcgc aagagtttag ctgaacagtt    14940
ctcgacttaa cggcaggttt tttagcggct gaagggcagg caaaaaaagc cccgcacggt    15000
cggcgggggc aaagggtcag cgggaagggg attagcgggc gtcgggcttc ttcatgcgtc    15060
ggggccgcgc ttcttgggat ggagcacgac gaagcgcgca cgcgcatcgt cctcggccct    15120
atcggcccgc gtcgcggtca ggaacttgtc gcgcgctagg tcctccctgg tgggcaccag    15180
```

```
gggcatgaac tcggcctgct cgatgtaggt ccactccatg accgcatcgc agtcgaggcc    15240
gcgttccttc accgtctctt gcaggtcgcg gtacgcccgc tcgttgagcg gctggtaacg    15300
ggccaattgg tcgtaaatgg ctgtcggcca tgagcggcct ttcctgttga gccagcagcc    15360
gacgacgaag ccggcaatgc aggccctgg cacaaccagg ccgacgccgg gggcagggga    15420
tggcagcagc tcgccaacca ggaaccccgc cgcgatgatg ccgatgccgg tcaaccagcc    15480
cttgaaacta tccggccccg aaacacccct gcgcattgcc tggatgctgc gccggatagc    15540
ttgcaacatc aggagccgtt tcttttgttc gtcagtcatg gtccgccctc accagttgtt    15600
cgtatcggtg tcggacgaac tgaaatcgca agagctgccg gtatcggtcc agccgctgtc    15660
cgtgtcgctg ctgccgaagc acggcgaggg gtccgcgaac gccgcagacg gcgtatccgg    15720
ccgcagcgca tcgcccagca tggccccggt cagcgagccg ccggccaggt agcccagcat    15780
ggtgctgttg gtcgccccgg ccaccagggc cgacgtgacg aaatcgccgt cattccctct    15840
ggattgttcg ctgctcggcg gggcagtgcg ccgcgccggc ggcgtcgtgg atggctcggg    15900
ttggctggcc tgcgacggcc ggcgaaaggt gcgcagcagc tcgttatcga ccggctgcgg    15960
cgtcggggcc gccgccttgc gctgcggtcg gtgttccttc ttcggctcgc gcagcttgaa    16020
cagcatgatc gcggaaacca gcagcaacgc cgcgcctacg cctcccgcga tgtagaacag    16080
catcggattc attcttcggt cctccttgta gcggaaccgt tgtctgtgcg gcgcgggtgg    16140
cccgcgccgc tgtctttggg gatcagccct cgatgagcgc gaccagtttc acgtcggcaa    16200
ggttcgcctc gaactcctgg ccgtcgtcct cgtacttcaa ccaggcatag ccttccgccg    16260
gcggccgacg gttgaggata aggcgggcag ggcgctcgtc gtgctcgacc tggacgatgg    16320 ccttttttcag cttgtccggg tccggctcct tcgcgccctt ttccttggcg tccttaccgt    16380
cctggtcgcc gtcctcgccg tcctggccgt cgccggcctc cgcgtcacgc tcggcatcag    16440
tctggccgtt gaaggcatcg acggtgttgg gatcgcggcc cttctcgtcc aggaactcgc    16500
gcagcagctt gaccgtgccg cgcgtgattt cctgggtgtc gtcgtcaagc cacgcctcga    16560
cttcctccgg gcgcttcttg aaggccgtca ccagctcgtt caccacggtc acgtcgcgca    16620
cgcggccggt gttgaacgca tcggcgatct tctccggcag gtccagcagc gtgacgtgct    16680
gggtgatgaa cgccggcgac ttgccgattt ccttggcgat atcgcctttc ttcttgccct    16740
tcgccagctc gcggccaatg aagtcggcaa tttcgcgcgg ggtcagctcg ttgcgttgca    16800
ggttctcgat aacctggtcg gcttcgttgt agtcgttgtc gatgaacgcc gggatggact    16860
tcttgccggc ccactcgag ccacggtagc ggcgggcgcc gtgattgatg atatagcggc    16920
ccggctgctc ctggttctcg cgcaccgaaa tgggtgactt caccccgcgc tctttgatcg    16980
tggcaccgat ttccgcgatg ctctccgggg aaaagccggg gttgtcggcc gtccgcggct    17040
gatgcggatc ttcgtcgatc aggtccaggt ccagctcgat agggccggaa ccgccctgag    17100
acgccgcagg agcgtccagg aggctcgaca ggtcgccgat gctatccaac cccaggccgg    17160
acggctgcgc cgcgcctgcg gcttcctgag cggccgcagc ggtgtttttc ttggtggtct    17220
tggcttgagc cgcagtcatt gggaaatctc catcttcgtg aacacgtaat cagccagggc    17280
gcgaacctct ttcgatgcct tgcgcgcggc cgttttcttg atcttccaga ccggcacacc    17340
ggatgcgagg gcatcggcga tgctgctgcg caggccaacg gtggccggaa tcatcatctt    17400
ggggtacgcg gccagcagct cggcttggtg gcgcgcgtgg cgcggattcc gcgcatcgac    17460
cttgctgggc accatgccaa ggaattgcag cttggcgttc ttctggcgca cgttcgcaat    17520
```

```
ggtcgtgacc atcttcttga tgccctggat gctgtacgcc tcaagctcga tgggggacag   17580
cacatagtcg gccgcgaaga gggcggccgc caggccgacg ccaagggtcg ggccgtgtc   17640 gatcaggcac acgtcgaagc cttggttcgc cagggccttg atgttcgccc cgaacagctc   17700
gcgggcgtcg tccagcgaca gccgttcggc gttcgccagt accgggttgg actcgatgag   17760
ggcgaggcgc gcggcctggc cgtcgccggc tgcgggtgcg gtttcggtcc agccgccggc   17820
agggacagcg ccgaacagct tgcttgcatg caggccggta gcaaagtcct tgagcgtgta   17880
ggacgcattg ccctgggggt ccaggtcgat cacggcaacc cgcaagccgc gctcgaaaaa   17940
gtcgaaggca agatgcacaa gggtcgaagt cttgccgacg ccgcctttct ggttggccgt   18000
gaccaaagtt ttcatcgttt ggtttcctgt tttttcttgg cgtccgcttc ccacttccgg   18060
acgatgtacg cctgatgttc cggcagaacc gccgttaccc gcgcgtaccc ctcgggcaag   18120
ttcttgtcct cgaacgcggc ccacacgcga tgcaccgctt gcgacactgc gccctggtc   18180 agtcccagcg acgttgcgaa cgtcgcctgt ggcttcccat cgactaagac gccccgcgct   18240
atctcgatgg tctgctgccc cacttccagc ccctggatcg cctcctggaa ctggctttcg   18300
gtaagccgtt tcttcatgga taacacccat aatttgctcc gcgccttggt tgaacatagc   18360
ggtgacagcc gccagcacat gagagaagtt tagctaaaca tttctcgcac gtcaacacct   18420
ttagccgcta aaactcgtcc ttggcgtaac aaaacaaaag cccggaaacc gggctttcgt   18480
ctcttgccgc ttatggctct gcacccggct ccatcaccaa caggtcgcgc acgcgcttca   18540
ctcggttgcg gatcgacact gccagcccaa caaagccggt tgccgccgcc gcaggatcg   18600 cgccgatgat gccggccaca ccggccatcg cccaccaggt cgccgccttc cggttccatt   18660
cctgctggta ctgcttcgca atgctggacc tcggctcacc ataggctgac cgctcgatgg   18720
cgtatgccgc ttctcccctt ggcgtaaaac ccagcgccgc aggcggcatt gccatgctgc   18780
ccgccgcttt cccgaccacg acgcgcgcac caggcttgcg gtccagacct tcggccacgg   18840
cgagctgcgc aaggacataa tcagccgccg acttggctcc acgcgcctcg atcagctctt   18900
gcactcgcgc gaaatccttg gcctccacgg ccgccatgaa tcgcgcacgc ggcgaaggct   18960
ccgcagggcc ggcgtcgtga tcgccgccga gaatgcccct taccaagttc gacgacacga   19020
aaatcatgct gacggctatc accatcatgc agacggatcg cacgaacccg ctgaattgaa   19080
cacgagcacg gcaccgcgca ccactatgcc aagaatgccc aaggtaaaaa ttgccggccc   19140
cgccatgaag tccgtgaatg ccccgacggc cgaagtgaag ggcaggccgc cacccaggcc   19200
gccgccctca ctgcccggca cctggtcgct gaatgtcgat gccagcacct gcggcacgtc   19260
aatgcttccg ggcgtcgcgc tcgggctgat cgccatccc gttactgccc cgatcccggc   19320
aatggcaagg actgccagcg ctgccatttt tggggtgagg ccgttcgcgg ccgaggggcg   19380
cagcccctgg ggggatggga ggcccgcgtt agcgggccgg gagggttcga aagggggggg   19440
cacccccctt cggcgtgcgc ggtcacgcgc acagggcgca gccctggtta aaaacaaggt   19500
ttataaatat tggtttaaaa gcaggttaaa agacaggtta gcgtggccg aaaaacgggc   19560 ggaaaccctt gcaaatgctg gattttctgc ctgtggacag ccccctcaaat gtcaataggt   19620 gcgcccctca tctgtcagca ctctgcccct caagtgtcaa ggatcgcgcc cctcatctgt   19680
cagtagtcgc gcccctcaag tgtcaatacc gcagggcact tatccccagg cttgtccaca   19740
tcatctgtgg gaaactcgcg taaaatcagg cgttttcgcc gatttgcgag gctggccagc   19800
tccacgtcgc cggccgaaat cgagcctgcc cctcatctgt caacgccgcg ccgggtgagt   19860
cggcccctca agtgtcaacg tccgcccctc atctgtcagt gagggccaag ttttccgcga   19920
```

```
ggtatccaca acgccggcgg ccgcggtgtc tcgcacacgg cttcgacggc gtttctggcg    19980
cgtttgcagg gccatagacg gccgccagcc cagcggcgag ggcaaccagc ccggtgagcg    20040
tcggaaaggc gctggaagcc ccgtagcgac gcggagaggg gcgagacaag ccaagggcgc    20100
aggctcgatg cgcagcacga catagccggt tctcgcaagg acgagaattt ccctgcggtg    20160
cccctcaagt gtcaatgaaa gtttccaacg cgagccattc gcgagagcct tgagtccacg    20220
ctagatgaga gctttgttgt aggtggacca gttggtgatt ttgaactttt gctttgccac    20280
ggaacggtct gcgttgtcgg gaagatgcgt gatctgatcc ttcaactcag caaaagttcg    20340
atttattcaa caaagccacg ttgtgtctca aaatctctga tgttacattg cacaagataa    20400
aaatatatca tcatgaacaa taaaactgtc tgcttacata aacagtaata caagggtgt    20460 tatgagccat attcaacggg aaacgtcttg ctcgactcta gagctcgttc ctcgaggcct    20520
cgaggcctcg aggaacggta cctgcgggga agcttacaat aatgtgtgtt gttaagtctt    20580
gttgcctgtc atcgtctgac tgactttcgt cataaatccc ggcctccgta acccagcttt    20640
gggcaagctc acggatttga tccggcggaa cgggaatatc gagatgccgg gctgaacgct    20700
gcagttccag ctttcccttt cgggacaggt actccagctg attgattatc tgctgaaggg    20760
tcttggttcc acctcctggc acaatgcgaa tgattacttg agcgcgatcg ggcatccaat    20820
tttctcccgt caggtgcgtg gtcaagtgct acaaggcacc tttcagtaac gagcgaccgt    20880
cgatccgtcg ccgggatacg gacaaaatgg agcgcagtag tccatcgagg gcggcgaaag    20940
cctcgccaaa agcaatacgt tcatctcgca cagcctccag atccgatcga gggtcttcgg    21000
cgtaggcaga tagaagcatg gatacattgc ttgagagtat tccgatggac tgaagtatgg    21060
cttccatctt ttctcgtgtg tctgcatcta tttcgagaaa gcccccgatg cggcgcaccg    21120
caacgcgaat tgccatacta tccgaaagtc ccagcaggcg cgcttgatag gaaaaggttt    21180
catactcggc cgatcgcaga cgggcactca cgacccttgaa cccttcaact ttcagggatc    21240
gatgctggtt gatggtagtc tcactcgacg tggctctggt gtgttttgac atagcttcct    21300
ccaaagaaag cggaaggtct ggatactcca gcacgaaatg tgcccgggta gacggatgga    21360
agtctagccc tgctcaatat gaaatcaaca gtacatttac agtcaatact gaatatactt    21420
gctacatttg caattgtctt ataacgaatg tgaaataaaa atagtgtaac aacgctttta    21480
ctcatcgata atcacaaaaa catttatacg aacaaaaata caaatgcact ccggtttcac    21540
aggataggcg ggatcagaat atgcaacttt tgacgttttg ttctttcaaa gggggtgctg    21600
gcaaaaccac cgcactcatg ggcctttgcg ctgctttggc aaatgacggt aaacgagtgg    21660
ccctctttga tgccgacgaa aaccggcctc tgacgcgatg gagagaaaac gccttacaaa    21720
gcagtactgg gatcctcgct gtgaagtcta ttccgccgac gaaatgcccc ttcttgaagc    21780
agcctatgaa aatgccgagc tcgaaggatt tgattatgcg ttggccgata cgcgtggcgg    21840
ctcgagcgag ctcaacaaca caatcatcgc tagctcaaac ctgcttctga tccccaccat    21900
gctaacgccg ctcgacatcg atgaggcact atctacctac cgctacgtca tcgagctgct    21960
gttgagtgaa aatttggcaa ttcctacagc tgtttttgcgc caacgcgtcc cggtcggccg    22020
attgacaaca tcgcaacgca ggatgtcaga gacgctagag agccttccag ttgtaccgtc    22080
tcccatgcat gaaagagatg catttgccgc gatgaaagaa cgcggcatgt tgcatcttac    22140
attactaaac acgggaactg atccgacgat gcgcctcata gagaggaatc ttcggattgc    22200
gatggaggaa gtcgtggtca tttcgaaact gatcagcaaa atcttggagg cttgaagatg    22260
```

-continued

```
gcaattcgca agcccgcatt gtcggtcggc gaagcacggc ggcttgctgg tgctcgaccc   22320
gagatccacc atcccaaccc gacacttgtt ccccagaagc tggacctcca gcacttgcct   22380
gaaaaagccg acgagaaaga ccagcaacgt gagcctctcg tcgccgatca catttacagt   22440
cccgatcgac aacttaagct aactgtggat gcccttagtc cacctccgtc cccgaaaaag   22500
ctccaggttt ttcttccagc gcgaccgccc gcgcctcaag tgtcgaaaac atatgacaac   22560
ctcgttcggc aatacagtcc ctcgaagtcg ctacaaatga ttttaaggcg cgcgttggac   22620
gatttcgaaa gcatgctggc agatggatca tttcgcgtgg ccccgaaaag ttatccgatc   22680
ccttcaacta cagaaaaatc cgttctcgtt cagacctcac gcatgttccc ggttgcgttg   22740
ctcgaggtcg ctcgaagtca ttttgatccg ttggggttgg agaccgctcg agctttcggc   22800
cacaagctgg ctaccgccgc gctcgcgtca ttctttgctg gagagaagcc atcgagcaat   22860
tggtgaagag ggacctatcg gaacccctca ccaaatattg agtgtaggtt tgaggccgct   22920
ggccgcgtcc tcagtcacct tttgagccag ataattaaga gccaaatgca attggctcag   22980
gctgccatcg tccccccgtg cgaaacctgc acgtccgcgt caaagaaata accggcacct   23040
cttgctgttt ttatcagttg agggcttgac ggatccgcct caagtttgcg gcgcagccgc   23100
aaaatgagaa catctatact cctgtcgtaa acctcctcgt cgcgtactcg actggcaatg   23160
agaagttgct cgcgcgatag aacgtcgcgg ggtttctcta aaaacgcgag gagaagattg   23220
aactcacctg ccgtaagttt cacctcaccg ccagcttcgg acatcaagcg acgttgcctg   23280
agattaagtg tccagtcagt aaaacaaaaa gaccgtcggt ctttggagcg acaacgttg   23340 gggcgcacgc gcaaggcaac ccgaatgcgt gcaagaaact ctctcgtact aaacggctta   23400
gcgataaaat cacttgctcc tagctcgagt gcaacaactt tatccgtctc ctcaaggcgg   23460
tcgccactga taattatgat tggaatatca gactttgccg ccagatttcg aacgatctca   23520
agcccatctt cacgacctaa atttagatca acaaccacga catcgaccgt cgcggaagag   23580
agtactctag tgaactgggt gctgtcggct accgcggtca ctttgaaggc gtggatcgta   23640
aggtattcga taataagatg ccgcatagcg acatcgtcat cgataagaag aacgtgtttc   23700
aacggctcac ctttcaatct aaaatctgaa cccttgttca cagcgcttga gaaattttca   23760
cgtgaaggat gtacaatcat ctccagctaa atgggcagtt cgtcagaatt gcggctgacc   23820
gcggatgacg aaaatgcgaa ccaagtattt caattttatg acaaaagttc tcaatcgttg   23880
ttacaagtga aacgcttcga ggttacagct actattgatt aaggagatcg cctatggtct   23940
cgccccggcg tcgtgcgtcc gccgcgagcc agatctcgcc tacttcataa acgtcctcat   24000
aggcacggaa tggaatgatg acatcgatcg ccgtagagag catgtcaatc agtgtgcgat   24060
cttccaagct agcaccttgg gcgctacttt tgacaaggga aaacagtttc ttgaatcctt   24120
ggattggatt cgcgccgtgt attgttgaaa tcgatcccgg atgtcccgag acgacttcac   24180
tcagataagc ccatgctgca tcgtcgcgca tctcgccaag caatatccgg tccgccgca   24240 tacgcagact tgcttggagc aagtgctcgg cgctcacagc acccagccca gcaccgttct   24300
tggagtagag tagtctaaca tgattatcgt gtggaatgac gagttcgagc gtatcttcta   24360
tggtgattag cctttcctgg gggggatgg cgctgatcaa ggtcttgctc attgttgtct   24420
tgccgcttcc ggtagggcca catagcaaca tcgtcagtcg gctgacgacg catgcgtgca   24480
gaaacgcttc caaatccccg ttgtcaaaat gctgaaggat agcttcatca tcctgatttt   24540
ggcgtttcct tcgtgtctgc cactggtcc acctcgaagc atcataacgg gaggagactt   24600
ctttaagacc agaaacacgc gagcttggcc gtcgaatggt caagctgacg gtgcccgagg   24660
```

```
gaacggtcgg cggcagacag atttgtagtc gttcaccacc aggaagttca gtggcgcaga    24720
gggggttacg tggtccgaca tcctgctttc tcagcgcgcc cgctaaaata gcgatatctt    24780
caagatcatc ataagagacg ggcaaaggca tcttggtaaa aatgccggct tggcgcacaa    24840
atgcctctcc aggtcgattg atcgcaattt cttcagtctt cgggtcatcg agccattcca    24900
aaatcggctt cagaagaaag cgtagttgcg gatccacttc catttacaat gtatcctatc    24960
tctaagcgga aatttgaatt cattaagagc ggcggttcct cccccgcgtg gcgccgccag    25020
tcaggcggag ctggtaaaca ccaaagaaat cgaggtcccg tgctacgaaa atggaaacgg    25080
tgtcaccctg attcttcttc agggttggcg gtatgttgat ggttgcctta agggctgtct    25140
cagttgtctg ctcaccgtta ttttgaaagc tgttgaagct catcccgcca cccgagctgc    25200
cggcgtaggt gctagctgcc tggaaggcgc cttgaacaac actcaagagc atagctccgc    25260
taaaacgctg ccagaagtgg ctgtcgaccg agcccggcaa tcctgagcga ccgagttcgt    25320
ccgcgcttgg cgatgttaac gagatcatcg catggtcagg tgtctcggcg cgatcccaca    25380
acacaaaaac gcgcccatct ccctgttgca agccacgctg tatttcgcca acaacggtgg    25440
tgccacgatc aagaagcacg atattgttcg ttgttccacg aatatcctga ggcaagacac    25500
actttacata gcctgccaaa tttgtgtcga ttgcggtttg caagatgcac ggaattattg    25560
tcccttgcgt taccataaaa tcggggtgcg gcaagagcgt ggcgctgctg ggctgcagct    25620
cggtgggttt catacgtatc gacaaatcgt tctcgccgga cacttcgcca ttcggcaagg    25680
agttgtcgtc acgcttgcct tcttgtcttc ggcccgtgtc gccctgaatg gcgcgtttgc    25740
tgaccccttg atcgccgctg ctatatgcaa aaatcggtgt ttcttccggc cgtggctcat    25800
gccgctccgg ttcgcccctc ggcggtagag gagcagcagg ctgaacagcc tcttgaaccg    25860
ctggaggatc cggcggcacc tcaatcggag ctggatgaaa tggcttggtg tttgttgcga    25920
tcaaagttga cggcgatgcg ttctcattca ccttctttg gcgcccacct agccaaatga    25980
ggcttaatga taacgcgaga acgacacctc cgacgatcaa tttctgagac cccgaaagac    26040
gccggcgatg tttgtcggag accagggatc cagatgcatc aacctcatgt gccgcttgct    26100
gactatcgtt attcatccct tcgcccccct caggacgcgt ttcacatcgg gcctcaccgt    26160
gcccgtttgc ggccttttggc caacgggatc gtaagcggtg ttccagatac atagtactgt    26220
gtggccatcc ctcagacgcc aacctcggga aaccgaagaa atctcgacat cgctcccttt    26280
aactgaatag ttggcaacag cttccttgcc atcaggattg atggtgtaga tggagggtat    26340
gcgtacattg cccggaaagt ggaataccgt cgtaaatcca ttgtcgaaga cttcgagtgg    26400
caacagcgaa cgatcgcctt gggcgacgta gtgccaatta ctgtccgccg caccaagggc    26460
tgtgacaggc tgatccaata aattctcagc tttccgttga tattgtgctt ccgcgtgtag    26520
tctgtccaca acagccttct gttgtgcctc ccttcgccga gccgccgcat cgtcggcggg    26580
gtaggcgaat tggacgctgt aatagagatc gggctgctct ttatcgaggt gggacagagt    26640
cttgaacttt atactgaaaa cataacggcg catcccggag tcgcttgcgg ttagcacgat    26700
tactggctga ggcgtgagga cctggcttgc cttgaaaaat agataatttc cccgcggtag    26760
ggctgctaga tctttgctat ttgaaacggc aaccgctgtc accgtttcgt tcgtggcgaa    26820
tgttacgacc aaagtagctc caaccgccgt cgagaggcgc accacttgat cgggattgta    26880
agccaaataa cgcatcgcgcg gatctagctt gcccgccatt ggagtgtctt cagcctccgc    26940
accagtcgca gcggcaaata acatgctaa aatgaaaagt gcttttctga tcatggttcg    27000
```

```
ctgtggccta cgtttgaaac ggtatcttcc gatgtctgat aggaggtgac aaccagacct   27060
gccgggttgg ttagtctcaa tctgccgggc aagctggtca ccttttcgta gcgaactgtc   27120
gcggtccacg tactcaccac aggcattttg ccgtcaacga cgagggtcct tttatagcga   27180
atttgctgcg tgcttggagt tacatcattt gaagcgatgt gctcgacctc caccctgccg   27240
cgtttgccaa gaatgacttg aggcgaactg ggattgggat agttgaagaa ttgctggtaa   27300
tcctggcgca ctgttgggc actgaagttc gataccaggt cgtaggcgta ctgagcggtg    27360
tcggcatcat aactctcgcg caggcgaacg tactcccaca atgaggcgtt aacgacggcc   27420
tcctcttgag ttgcaggcaa tcgcgagaca gacacctcgc tgtcaacggt gccgtccggc   27480
cgtatccata gatatacggg cacaagcctg ctcaacggca ccattgtggc tatagcgaac   27540
gcttgagcaa catttcccaa aatcgcgata gctgcgacag ctgcaatgag tttggagaga   27600
cgtcgcgccg atttcgctcg cgcggtttga aaggcttcta cttccttata gtgctcggca   27660
aggctttcgc gcgccactag catggcatat tcaggccccg tcatagcgtc cacccgaatt   27720
gccgagctga agatctgacg gagtaggctg ccatcgcccc acattcagcg ggaagatcgg   27780
gcctttgcag ctcgctaatg tgtcgtttgt ctggcagccg ctcaaagcga caactaggca   27840
cagcaggcaa tacttcatag aattctccat tgaggcgaat ttttgcgcga cctagcctcg   27900
ctcaacctga gcgaagcgac ggtacaagct gctggcagat tgggttgcgc cgctccagta   27960
actgcctcca atgttgccgg cgatcgccgg caaagcgaca atgagcgcat cccctgtcag   28020
aaaaaacata tcgagttcgt aaagaccaat gatcttggcc gcggtcgtac cggcgaaggt   28080
gattacacca agcataaggg tgagcgcagt cgcttcggtt aggatgacga tcgttgccac   28140
gaggtttaag aggagaagca agagaccgta ggtgataagt tgcccgatcc acttagctgc   28200
gatgtcccgc gtgcgatcaa aaatatatcc gacgaggatc agaggcccga tcgcgagaag   28260
cactttcgtg agaattccaa cggcgtcgta aactccgaag gcagaccaga gcgtgccgta   28320
aaggacccac tgtgccccctt ggaaagcaag gatgtcctgg tcgttcatcg gaccgatttc   28380
ggatgcgatt ttctgaaaaa cggcctgggt cacggcgaac attgtatcca actgtgccgg   28440
aacagtctgc agaggcaagc cggttacact aaactgctga acaaagtttg gaccgtcttt   28500
ttcgaagatg gaaaccacat agtcttggta gttagcctgc ccaacaatta gagcaacaac   28560
gatggtgacc gtgatcaccc gagtgatacc gctacgggta tcgacttcgc cgcgtatgac   28620 taaaatacccc tgaacaataa tccaaagagt gacacaggcg atcaatggcg cactcaccgc   28680
ctcctggata gtctcaagca tcgagtccaa gcctgtcgtg aaggctacat cgaagatcgt   28740
atgaatggcc gtaaacggcg ccggaatcgt gaaattcatc gattggaccct gaacttgact   28800 ggtttgtcgc ataatgttgg ataaaatgag ctcgcattcg gcgaggatgc gggcggatga   28860
acaaatcgcc cagccttagg ggagggcacc aaagatgaca gcggtctttt gatgctcctt   28920
gcgttgagcg gccgcctctt ccgcctcgtg aaggccggcc tgcgcggtag tcatcgttaa   28980
taggcttgtc gcctgtacat tttgaatcat tgcgtcatgg atctgcttga gaagcaaacc   29040
attggtcacg gttgcctgca tgatattgcg agatcgggaa agctgagcag acgtatcagc   29100
attcgccgtc aagcgtttgt ccatcgtttc cagattgtca gccgcaatgc cagcgctgtt   29160
tgcggaaccg gtgatctgcg atcgcaacag gtccgcttca gcatcactac ccacgactgc   29220
acgatctgta tcgctggtga tcgcacgtgc cgtggtcgac attggcattc gcggcgaaaa   29280
catttcattg tctaggtcct tcgtcgaagg atactgattt ttctggttga gcgaagtcag   29340
tagtccagta acgccgtagg ccgacgtcaa catcgtaacc atcgctatag tctgagtgag   29400
```

```
attctccgca gtcgcgagcg cagtcgcgag cgtctcagcc tccgttgccg ggtcgctaac   29460
aacaaactgc gcccgcgcgg gctgaatata tagaaagctg caggtcaaaa ctgttgcaat   29520
aagttgcgtc gtcttcatcg tttcctacct tatcaatctt ctgcctcgtg gtgacgggcc   29580
atgaattcgc tgagccagcc agatgagttg ccttcttgtg cctcgcgtag tcgagttgca   29640
aagcgcaccg tgttggcacg ccccgaaagc acggcgacat attcacgcat atcccgcaga   29700
tcaaattcgc agatgacgct tccactttct cgtttaagaa gaaacttacg gctgccgacc   29760
gtcatgtctt cacggatcgc ctgaaattcc ttttcggtac atttcagtcc atcgacataa   29820
gccgatcgat ctgcgttgg tgatggatag aaaatcttcg tcatacattg cgcaaccaag   29880
ctggctccta gcggcgattc cagaacatgc tctggttgct gcgttgccag tattagcatc   29940
ccgttgtttt ttcgaacggt caggaggaat tgtcgacga cagtcgaaaa tttgggttt   30000 aacaaatagg cgcgaaactc atcgcagctc atcacaaaac ggcggccgtc gatcatggct   30060
ccaatccgat gcaggagata tgctgcagcg ggagcgcata cttcctcgta ttcgagaaga   30120
tgcgtcatgt cgaagccggt aatcgacgga tctaacttta cttcgtcaac ttcgccgtca   30180
aatgcccagc caagcgcatg gccccggcac cagcgttgga gccgcgctcc tgcgccttcg   30240
gcgggcccat gcaacaaaaa ttcacgtaac cccgcgattg aacgcatttg tggatcaaac   30300
gagagctgac gatggatacc acggaccaga cggcggttct cttccggaga atcccaccc   30360 cgaccatcac tctcgatgag agccacgatc cattcgcgca gaaaatcgtg tgaggctgct   30420
gtgttttcta ggccacgcaa cggcgccaac ccgctgggtg tgcctctgtg aagtgccaaa   30480
tatgttcctc ctgtggcgcg aaccagcaat tcgccacccc ggtccttgtc aaagaacacg   30540
accgtacctg cacggtcgac catgctctgt tcgagcatgg ctagaacaaa catcatgagc   30600
gtcgtcttac ccctcccgat aggcccgaat attgccgtca tgccaacatc gtgctcatgc   30660
gggatatagt cgaaaggcgt tccgccattg gtacgaaatc gggcaatcgc gttgccccag   30720
tggcctgagc tggcgccctc tggaaagttt tcgaaagaga caaaccctgc gaaattgcgt   30780
gaagtgattg cgccagggcg tgtgcgccac ttaaaattcc ccggcaattg ggaccaatag   30840
gccgcttcca taccaatacc ttcttggaca accacggcac ctgcatccgc cattcgtgtc   30900
cgagcccgcg cgcccctgtc cccaagacta ttgagatcgt ctgcatagac gcaaaggctc   30960
aaatgatgtg agcccataac gaattcgttg ctcgcaagtg cgtcctcagc ctcggataat   31020
ttgccgattt gagtcacggc tttatcgccg gaactcagca tctggctcga tttgaggcta   31080
agtttcgcgt gcgcttgcgg gcgagtcagg aacgaaaaac tctgcgtgag aacaagtgga   31140
aaatcgaggg atagcagcgc gttgagcatg cccggccgtg ttttgcagg gtattcgcga   31200 aacgaataga tggatccaac gtaactgtct tttggcgttc tgatctcgag tcctcgcttg   31260
ccgcaaatga ctctgtcggt ataaatcgaa gcgccgagtg agccgctgac gaccggaacc   31320
ggtgtgaacc gaccagtcat gatcaaccgt agcgcttcgc caattcggt gaagagcaca   31380 ccctgcttct cgcggatgcc aagacgatgc aggccatacg ctttaagaga gccagcgaca   31440
acatgccaaa gatcttccat gttcctgatc tggcccgtga gatcgttttc ccttttccg   31500 cttagcttgg tgaacctcct cttaccttc cctaaagccg cctgtgggta gacaatcaac   31560
gtaaggaagt gttcattgcg gaggagttgg ccggagagca cgcgctgttc aaaagcttcg   31620
ttcaggctag cggcgaaaac actacggaag tgtcgcggcg ccgatgatgg cacgtcggca   31680
tgacgtacga ggtgagcata tattgacaca tgatcatcag cgatattgcg caacagcgtg   31740
```

```
ttgaacgcac gacaacgcgc attgcgcatt tcagtttcct caagctcgaa tgcaacgcca    31800
tcaattctcg caatggtcat gatcgatccg tcttcaagaa ggacgatatg gtcgctgagg    31860
tggccaatat aagggagata gatctcaccg gatctttcgg tcgttccact cgcgccgagc    31920
atcacaccat tcctctccct cgtgggggaa ccctaattgg atttgggcta acagtagcgc    31980
ccccccaaac tgcactatca atgcttcttc ccgcggtccg caaaaatagc aggacgacgc    32040
tcgccgcatt gtagtctcgc tccacgatga gccgggctgc aaaccataac ggcacgagaa    32100
cgacttcgta gagcgggttc tgaacgataa cgatgacaaa gccggcgaac atcatgaata    32160
accctgccaa tgtcagtggc accccaagaa acaatgcggg ccgtgtggct gcgaggtaaa    32220
gggtcgattc ttccaaacga tcagccatca actaccgcca gtgagcgttt ggccgaggaa    32280
gctcgcccca acatgataa caatgccgcc gacgacgccg gcaaccagcc caagcgaagc    32340
ccgcccgaac atccaggaga tcccgatagc gacaatgcca agaacagcga gtgactggcc    32400
gaacggacca aggataaacg tgcatatatt gttaaccatt gtggcggggt cagtgccgcc    32460
acccgcagat tgcgctgcgg cgggtccgga tgaggaaatg ctccatgcaa ttgcaccgca    32520
caagcttggg gcgcagctcg atatcacgcg catcatcgca ttcgagagcg agaggcgatt    32580
tagatgtaaa cggtatctct caaagcatcg catcaatgcg cacctcctta gtataagtcg    32640
aataagactt gattgtcgtc tgcggatttg ccgttgtcct ggtgtggcgg tggcggagcg    32700
attaaaccgc cagcgccatc ctcctgcgag cggcgctgat atgaccccca acatcccac    32760 gtctcttcgg attttagcgc ctcgtgatcg tcttttggag gctcgattaa cgcgggcacc    32820
agcgattgag cagctgtttc aacttttcgc acgtagccgt ttgcaaaacc gccgatgaaa    32880
ttaccggtgt tgtaagcgga gatcgcccga cgaagcgcaa attgcttctc gtcaatcgtt    32940
tcgccgcctg cataacgact tttcagcatg tttgcagcgg cagataatga tgtgcacgcc    33000
tggagcgcac cgtcaggtgt cagaccgagc atagaaaaat ttcgagagtt tatttgcatg    33060
aggccaacat ccagcgaatg ccgtgcatcg agacggtgcc tgacgacttg ggttgcttgg    33120
ctgtgatctt gccagtgaag cgtttcgccg gtcgtgttgt catgaatcgc taaaggatca    33180
aagcgactct ccaccttagc tatcgccgca agcgtagatg tcgcaactga tggggcacac    33240
ttgcgagcaa catggtcaaa ctcagcagat gagagtggcg tggcaaggct cgacgaacag    33300
aaggagacca tcaaggcaag agaaagcgac cccgatctct taagcatacc ttatctcctt    33360
agctcgcaac taacaccgcc tctcccgttg gaagaagtgc gttgttttat gttgaagatt    33420
atcgggaggg tcggttactc gaaaattttc aattgcttct ttatgatttc aattgaagcg    33480
agaaacctcg cccggcgtct tggaacgcaa catggaccga gaaccgcgca tccatgacta    33540
agcaaccgga tcgacctatt caggccgcag ttggtcaggt caggctcaga acgaaaatgc    33600
tcggcgaggt tacgctgtct gtaaacccat tcgatgaacg ggaagcttcc ttccgattgc    33660
tcttggcagg aatattggcc catgcctgct tgcgctttgc aaatgctctt atcgcgttgg    33720
tatcatatgc cttgtccgcc agcagaaacg cactctaagc gattatttgt aaaaatgttt    33780
cggtcatgcg gcggtcatgg gcttgacccg ctgtcagcgc aagacggatc ggtcaaccgt    33840
cggcatcgac aacagcgtga atcttggtgg tcaaaccgcc acgggaacgt cccatacagc    33900
catcgtcttg atcccgctgt ttcccgtcgc cgcatgttgg tggacgcgga cacaggaact    33960
gtcaatcatg acgacattct atcgaaagcc ttggaaatca cactcagaat atgatcccag    34020
acgtctgcct cacgccatcg tacaaagcga ttgtagcagg ttgtacagga accgtatcga    34080
tcaggaacgt ctgcccaggg cgggcccgtc cggaagcgcc acaagatgac attgatcacc    34140
```

```
cgcgtcaacg cgcggcacgc gacgcggctt atttgggaac aaaggactga acaacagtcc   34200
attcgaaatc ggtgacatca aagcggggac gggttatcag tggcctccaa gtcaagcctc   34260
aatgaatcaa aatcagaccg atttgcaaac ctgatttatg agtgtgcggc ctaaatgatg   34320
aaatcgtcct tctagatcgc ctccgtggtg tagcaacacc tcgcagtatc gccgtgctga   34380
ccttggccag ggaattgact ggcaaggtg cttcacatg accgctcttt tggccgcgat     34440
agatgatttc gttgctgctt tgggcacgta aaggagaga agtcatatcg gagaaattcc   34500
tcctggcgcg agagcctgct ctatcgcgac ggcatcccac tgtcgggaac agaccggatc   34560
attcacgagg cgaaagtcgt caacacatgc gttataggca tcttcccttg aaggatgatc   34620
ttgttgctgc caatctggag gtgcggcagc cgcaggcaga tgcgatctca gcgcaacttg   34680
cggcaaaaca tctcactcac ctgaaaacca ctagcgagtc tcgcgatcag acgaaggcct   34740
tttacttaac gacacaatat ccgatgtctg catcacaggc gtcgctatcc cagtcaatac   34800
taaagcggtg caggaactaa agattactga tgacttaggc gtgccacgag gcctgagacg   34860
acgcgcgtag acagttttt gaaatcatta tcaaagtgat ggcctccgct gaagcctatc    34920
acctctgcgc cggtctgtcg gagagatggg caagcattat tacggtcttc gcgcccgtac   34980
atgcattgga cgattgcagg gtcaatggat ctgagatcat ccagaggatt gccgccctta   35040
ccttccgttt cgagttggag ccagccccta aatgagacga catagtcgac ttgatgtgac   35100
aatgccaaga gagagatttg cttaacccga ttttttttgct caagcgtaag cctattgaag   35160
cttgccggca tgacgtccgc gccgaaagaa tatcctacaa gtaaaacatt ctgcacaccg   35220
aaatgcttgg tgtagacatc gattatgtga ccaagatcct tagcagtttc gcttggggac   35280
cgctccgacc agaaatacccg aagtgaactg acgccaatga caggaatccc ttccgtctgc   35340
agataggtac catcgataga tctgctgcct cgcgcgtttc ggtgatgacg gtgaaaacct   35400
ctgacacatg cagctcccgg agacggtcac agcttgtctg taagcggatg ccgggagcag   35460
acaagcccgt cagggcgcgt cagcgggtgt tggcgggtgt cggggcgcag ccatgaccca   35520
gtcacgtagc gatagcggag tgtatactgg cttaactatg cggcatcaga gcagattgta   35580
ctgagagtgc accatatgcg gtgtgaaata ccgcacagat gcgtaaggag aaaataccgc   35640
atcaggcgct cttccgcttc ctcgctcact gactcgctgc gctcggtcgt tcggctgcgg   35700
cgagcggtat cagctcactc aaaggcggta atacggttat ccacagaatc agggggataac   35760 gcaggaaaga acatgtgagc aaaaggccag caaaaggcca ggaaccgtaa aaaggccgcg   35820
ttgctggcgt ttttccatag gctccgcccc cctgacgagc atcacaaaaa tcgacgctca   35880
agtcagaggt ggcgaaaccc gacaggacta taaagatacc aggcgtttcc ccctggaagc   35940
tccctcgtgc gctctcctgt tccgaccctg ccgcttaccg gatacctgtc cgcctttctc   36000
ccttcgggaa gcgtggcgct ttctcatagc tcacgctgta ggtatctcag ttcggtgtag   36060
gtcgttcgct ccaagctggg ctgtgtgcac gaaccccccg ttcagcccga ccgctgcgcc   36120
ttatccggta actatcgtct tgagtccaac ccggtaagac acgacttatc gccactggca   36180
gcagccactg gtaacaggat tagcagagcg aggtatgtag gcggtgctac agagttcttg   36240
aagtggtggc ctaactacgg ctacactaga aggacagtat ttggtatctg cgctctgctg   36300
aagccagtta ccttcggaaa aagagttggt agctcttgat ccggcaaaca aaccaccgct   36360
ggtagcggtg gtttttttgt ttgcaagcag cagattacgc gcagaaaaaa aggatctcaa   36420
gaagatcctt tgatcttttc tacggggtct gacgctcagt ggaacgaaaa ctcacgttaa   36480
```

```
gggattttgg tcatgagatt atcaaaaagg atcttcacct agatccttt  aaattaaaaa    36540 tgaagtttta aatcaatcta aagtatatat gagtaaactt ggtctgacag ttaccaatgc    36600
ttaatcagtg aggcacctat ctcagcgatc tgtctatttc gttcatccat agttgcctga    36660
ctccccgtcg tgtagataac tacgatacgg agggcttac  catctggccc cagtgctgca    36720
atgataccgc gagacccacg ctcaccggct ccagatttat cagcaataaa ccagccagcc    36780
ggaagggccg agcgcagaag tggtcctgca actttatccg cctccatcca gtctattaat    36840
tgttgccggg aagctagagt aagtagttcg ccagttaata gtttgcgcaa cgttgttgcc    36900
attgctgcag ggggggggggg gggggggggac ttccattgtt cattccacgg acaaaaacag   36960
agaaaggaaa cgacagaggc caaaaagcct cgctttcagc acctgtcgtt tcctttcttt    37020
tcagagggta tttaaataa  aaacattaag ttatgacgaa gaagaacgga aacgccttaa    37080
accggaaaat tttcataaat agcgaaaacc cgcgaggtcg ccgccccgta acctgtcgga    37140
tcaccgaaaa ggaccgtaa  agtgataatg attatcatct acatatcaca acgtgcgtgg    37200
aggccatcaa accacgtcaa ataatcaatt atgacgcagg tatcgtatta attgatctgc    37260
atcaacttaa cgtaaaaaca acttcagaca atacaaatca gcgacactga atacggggca    37320
acctcatgtc cccccccccc cccccctgc  aggcatcgtg gtgtcacgct cgtcgtttgg    37380
tatggcttca ttcagctccg gttcccaacg atcaaggcga gttacatgat cccccatgtt    37440
gtgcaaaaaa gcggttagct ccttcggtcc tccgatcgtt gtcagaagta agttggccgc    37500
agtgttatca ctcatggtta tggcagcact gcataattct cttactgtca tgccatccgt    37560
aagatgcttt tctgtgactg gtgagtactc aaccaagtca ttctgagaat agtgtatgcg    37620
gcgaccgagt tgctcttgcc cggcgtcaac acgggataat accgcgccac atagcagaac    37680
tttaaaagtg ctcatcattg gaaaacgttc ttcggggcga aaactctcaa ggatcttacc    37740
gctgttgaga tccagttcga tgtaacccac tcgtgcaccc aactgatctt cagcatcttt    37800
tactttcacc agcgtttctg ggtgagcaaa aacaggaagg caaaatgccg caaaaaaggg    37860
aataagggcg acacggaaat gttgaatact catactcttc ctttttcaat attattgaag    37920
catttatcag ggttattgtc tcatgagcgg atacatattt gaatgtattt agaaaaataa    37980
acaaataggg gttccgcgca catttccccg aaaagtgcca cctgacgtct aagaaaccat    38040
tattatcatg acattaacct ataaaaatag gcgtatcacg aggccctttc gtcttcaaga    38100
attggtcgac gatcttgctg cgttcggata ttttcgtgga gttcccgcca cagacccgga    38160
ttgaaggcga gatccagcaa ctcgcgccag atcatcctgt gacggaactt tggcgcgtga    38220
tgactggcca ggacgtcggc cgaaagagcg acaagcagat cacgcttttc gacagcgtcg    38280
gatttgcgat cgaggatttt tcggcgctgc gctacgtccg cgaccgcgtt gagggatcaa    38340
gccacagcag cccactcgac cttctagccg acccagacga gccaagggat cttttggaa    38400 tgctgctccg tcgtcaggct ttccgacgtt tgggtggttg aacagaagtc attatcgtac    38460
ggaatgccaa gcactcccga ggggaaccct gtggttggca tgcacataca aatggacgaa    38520
cggataaacc ttttcacgcc cttttaaata tccgttattc taataaacgc tcttttctct    38580
taggtttacc cgccaatata tcctgtcaaa cactgatagt ttaaactgaa ggcgggaaac    38640
gacaatctga tcatgagcgg agaattaagg gagtcacgtt atgacccccg ccgatgacgc    38700
gggacaagcc gttttacgtt tggaactgac agaaccgcaa cgttgaagga gccactcagc    38760
ccaagctggt acgattgtaa tacgactcac tatagggcga attgagcgct gtttaaacgc    38820
tcttcaactg gaagagcggt taccagaggc cagaatggcc atctcggacc gatatcgcta    38880
```

```
tcaactttgt atagaaaagt tgggccgaat tcgagctcgg tacgccagga atggcccgga   38940
ccgggttacc cggaccgaag cttgcatgcc tgcagtgcag cgtgacccgg tcgtgcccct   39000
ctctagagat aatgagcatt gcatgtctaa gttataaaaa attaccacat attttttttg   39060
tcacacttgt ttgaagtgca gtttatctat ctttatacat atatttaaac tttactctac   39120
gaataatata atctatagta ctacaataat atcagtgttt tagagaatca tataaatgaa   39180
cagttagaca tggtctaaag gacaattgag tattttgaca acaggactct acagttttat   39240
cttttagtg tgcatgtgtt ctccttttt tttgcaaata gcttcaccta tataatactt    39300
catccatttt attagtacat ccatttaggg tttagggtta atggttttta tagactaatt   39360
tttttagtac atctatttta ttctatttta gcctctaaat taagaaaact aaaactctat   39420
tttagttttt ttatttaata atttagatat aaaatagaat aaaataaagt gactaaaaat   39480
taaacaaata ccctttaaga aattaaaaaa actaaggaaa cattttttctt gtttcgagta   39540
gataatgcca gcctgttaaa cgccgtcgac gagtctaacg gacaccaacc agcgaaccag   39600
cagcgtcgcg tcgggccaag cgaagcagac ggcacggcat ctctgtcgct gcctctggac   39660
ccctctcgag agttccgctc caccgttgga cttgctccgc tgtcggcatc cagaaattgc   39720
gtggcggagc ggcagacgtg agccggcacg gcaggcggcc tcctcctcct ctcacggcac   39780
cggcagctac gggggattcc tttcccaccg ctccttcgct ttcccttcct cgcccgccgt   39840
aataaataga caccccctcc acaccctctt tccccaacct cgtgttgttc ggagcgcaca   39900
cacacacaac cagatctccc ccaaatccac ccgtcggcac ctccgcttca aggtacgccg   39960
ctcgtcctcc cccccccccc tctctacctt ctctagatcg gcgttccggt ccatgcatgg   40020
ttagggcccg gtagttctac ttctgttcat gtttgtgtta gatccgtgtt tgtgttagat   40080
ccgtgctgct agcgttcgta cacgatgcg acctgtacgt cagacacgtt ctgattgcta    40140
acttgccagt gtttctcttt ggggaatcct gggatggctc tagccgttcc gcagacggga   40200
tcgatttcat gatttttttt gtttcgttgc atagggtttg gtttgccctt ttcctttatt   40260
tcaatatatg ccgtgcactt gttttgtcggg tcatctttttc atgctttttt ttgtcttggt   40320
tgtgatgatg tggtctggtt gggcggtcgt tctagatcgg agtagaattc tgtttcaaac   40380
tacctggtgg atttattaat tttggatctg tatgtgtgtg ccatacatat tcatagttac   40440
gaattgaaga tgatggatgg aaatatcgat ctaggatagg tatacatgtt gatgcgggtt   40500
ttactgatgc atatacagag atgctttttg ttcgcttggt tgtgatgatg tggtgtggtt   40560
gggcggtcgt tcattcgttc tagatcggag tagaatactt tttcaaacta cctggtgtat   40620
ttattaattt tggaactgta tgtgtgtgtc atacatcttc atagttacga gtttaagatg   40680
gatggaaata tcgatctagg ataggtatac atgttgatgt gggttttact gatgcatata   40740
catgatggca tatgcagcat ctattcatat gctctaacct tgagtaccta tctattataa   40800
taaacaagta tgttttataa ttattttgat cttgatatac ttggatgatg gcatatgcag   40860
cagctatatg tggattttttt tagccctgcc ttcatacgct atttatttgc ttggtactgt   40920
ttcttttgtc gatgctcacc ctgttgtttg gtgttacttc tgcaggtcga ctctagagga   40980
tccaccacca tgaacaccaa gtacaacaag gagttcctgc tctacctggc cggcttcgtg   41040
gacggcgacg gctccatcat cgcggccatc gacccggagc agagccgcaa gttcaagcac   41100
cgcctccgcc tgcgcttcac cgtgacccag aagacgcaga ggcgctggtt cctcgacaag   41160
ctggtcgacg agatcggggt gggctacgtc cgcgaccggg ggtcggtgtc cgactaccag   41220
```

```
ctcagcaaga tcaagcccct gcacaacttc ctcacccagc tccagccgtt cctcaagctg   41280
aagcagaagc aggcgaacct cgtcctgaag atcatcgagc agctcccctc ggccaaggag   41340
tccccggaca agttcctgga ggtgtgcacg tgggtcgacc agatcgcggc cctcaacgac   41400
agcaagaccc gcaagacgac ctcggagacg gtgcgggcgg tcctggactc cctcagcgag   41460
aagaagaagt cgtccccctg aggtaccaca tggttaacct agacttgtcc atcttctgga   41520
ttggccaact taattaatgt atgaaataaa aggatgcaca catagtgaca tgctaatcac   41580
tataatgtgg gcatcaaagt tgtgtgttat gtgtaattac tagttatctg aataaaagag   41640
aaagagatca tccatatttc ttatcctaaa tgaatgtcac gtgtctttat aattctttga   41700
tgaaccagat gcatttcatt aaccaaatcc atatacatat aaatattaat catatataat   41760
taatatcaat tgggttagca aaacaaatct agtctaggtg tgttttgcga atgcggccgc   41820
caccgcggtg gagctcgaat tccggtccgg gtcacccggt ccgggcctag aaggccagct   41880
tcaagtttgt acaaaaaagc aggctccggc cagaatggcc cggaccgggt taccgaattc   41940
gagctcggta ccctgggatc cgatatcgat gggccctggc cgaagctggc cgctcattaa   42000
ttaagtcagg cgcgcctcta gttgaagaca cgttcatgtc ttcatcgtaa gaagacactc   42060
agtagtcttc ggccagaatg gccatctgga ttcagcaggc ctagaaggcc atttaaatcc   42120
tgaggatctg gtcttcctaa ggacccggga tatcggaccg attaaacttt aattcggtcc   42180
gaagcttgca tgcctgcagt gcagcgtgac ccggtcgtgc ccctctctag agataatgag   42240
cattgcatgt ctaagttata aaaaattacc acatattttt tttgtcacac ttgtttgaag   42300
tgcagtttat ctatctttat acatatattt aaactttact ctacgaataa tataatctat   42360
agtactacaa taatatcagt gttttagaga atcatataaa tgaacagtta gacatggtct   42420
aaaggacaat tgagtatttt gacaacagga ctctacagtt ttatctttt agtgtgcatg    42480 tgttctcctt ttttttgca aatagcttca cctatataat acttcatcca ttttattagt    42540
acatccattt agggtttagg gttaatggtt tttatagact aatttttta gtacatctat    42600 tttattctat tttagcctct aaattaagaa aactaaaact ctattttagt ttttttattt   42660
aataatttag atataaaata gaataaaata aagtgactaa aaattaaaca aatacccttt   42720
aagaaattaa aaaactaag gaaacatttt tcttgtttcg agtagataat gccagcctgt   42780
taaacgccgt cgacgagtct aacggacacc aaccagcgaa ccagcagcgt cgcgtcgggc   42840
caagcgaagc agacggcacg gcatctctgt cgctgcctct ggacccctct cgagagttcc   42900
gctccaccgt tggacttgct ccgctgtcgg catccagaaa ttgcgtggcg gagcggcaga   42960
cgtgagccgg cacggcaggc ggcctcctcc tcctctcacg gcaccggcag ctacggggga   43020
ttcctttccc accgctcctt cgctttccct tcctcgcccg ccgtaataaa tagacacccc   43080
ctccacaccc tctttcccca acctcgtgtt gttcggagcg cacacacaca caaccagatc   43140
tcccccaaat ccaccgtcg gcacctccgc ttcaaggtac gccgctcgtc ctccccccc    43200 cccctctcta ccttctctag atcggcgttc cggtccatgc atggttaggg cccggtagtt   43260
ctacttctgt tcatgtttgt gttagatccg tgtttgtgtt agatccgtgc tgctagcgtt   43320
cgtacacgga tgcgacctgt acgtcagaca cgttctgatt gctaacttgc cagtgtttct   43380 cttgggaa tcctgggatg gctctagccg ttccgcagac gggatcgatt tcatgatttt    43440
ttttgtttcg ttgcataggg tttggtttgc cctttccctt tatttcaata tatgccgtgc   43500 acttgttgt cgggtcatct tttcatgctt tttttgtct tggttgtgat gatgtggtct     43560
ggttgggcgg tcgttctaga tcggagtaga attctgtttc aaactacctg gtggatttat   43620
```

```
taattttgga tctgtatgtg tgtgccatac atattcatag ttacgaattg aagatgatgg   43680
atggaaatat cgatctagga taggtataca tgttgatgcg ggttttactg atgcatatac   43740
agagatgctt tttgttcgct tggttgtgat gatgtggtgt ggttgggcgg tcgttcattc   43800
gttctagatc ggagtagaat actgtttcaa actacctggt gtatttatta attttggaac   43860
tgtatgtgtg tgtcatacat cttcatagtt acgagtttaa gatggatgga aatatcgatc   43920
taggataggt atacatgttg atgtgggttt tactgatgca tatacatgat ggcatatgca   43980
gcatctattc atatgctcta accttgagta cctatctatt ataataaaca agtatgtttt   44040
ataattattt tgatcttgat atacttggat gatggcatat gcagcagcta tatgtggatt   44100
tttttagccc tgccttcata cgctatttat ttgcttggta ctgtttcttt tgtcgatgct   44160
caccctgttg tttggtgtta cttctgcagg tcgactctag aggatccacc accatgaaca   44220
ccaagtacaa caaggagttc ctgctctacc tggccggctt cgtggacggc gacggctcca   44280
tcaaggcgag catcagcccg aaccagagct gcaagttcaa gcaccagctc cgcctgacct   44340
tccaggtgac ccagaagacg cagaggcgct ggttcctcga caagctggtc gacgagatcg   44400
gggtgggcta cgtctacgac cggggtcgg tgtccgacta ccgcctcagc aagatcaagc   44460
ccctgcacaa cttcctcacc cagctccagc cgttcctcaa gctgaagcag aagcaggcga   44520
acctcgtcct gaagatcatc gagcagctcc cctcggccaa ggagtccccg acaagttcc   44580 tggaggtgtg cacgtgggtc gaccagatcg cggccctcaa cgacagcaag acccgcaaga   44640
cgacctcgga gacggtgcgg gcggtcctgg actccctcag cgagaagaag aagtcgtccc   44700
cctgaggtac cacatggtta acctagactt gtccatcttc tggattggcc aacttaatta   44760
atgtatgaaa taaaggatg cacacatagt gacatgctaa tcactataat gtgggcatca   44820
aagttgtgtg ttatgtgtaa ttactagtta tctgaataaa agagaaagag atcatccata   44880
tttcttatcc taaatgaatg tcacgtgtct ttataattct ttgatgaacc agatgcattt   44940
cattaaccaa atccatatac atataaatat taatcatata taattaatat caattgggtt   45000
agcaaaacaa atctagtcta ggtgtgtttt gcgaattgcg gccagcttgg tcacccggtc   45060
cgggcctaga aggccgatct cccgggcacc cagctttctt gtacaaagtg gccgttaacg   45120
gatcggccag aatggcccgg accgggttac ccggaccgaa gctggccgcg atctgagctt   45180
ctagaaatcc gtcaacatgg tggagcacga cactctcgtc tactccaaga atatcaaaga   45240
tacagtctca gaagaccaaa gggctattga gactttttcaa caagggtaa tatcgggaaa   45300 cctcctcgga ttccattgcc cagctatctg tcacttcatc aaaaggacag tagaaaagga   45360
aggtggcacc tacaaatgcc atcattgcga taaaggaaag gctatcgttc aagatgcctc   45420
tgccgacagt ggtcccaaag atggaccccc acccacgagg agcatcgtgg aaaaagaaga   45480
cgttccaacc acgtcttcaa gcaagtggat tgatgtgat gctctagaaa ccgtcaaca   45540 tggtggagca cgacactctc gtctactcca agaatatcaa agatacagtc tcagaagacc   45600
aaagggctat tgagactttt caacaaaggg taatatcggg aaacctcctc ggattccatt   45660
gcccagctat ctgtcacttc atcaaaagga cagtagaaaa ggaaggtggc acctacaaat   45720
gccatcattg cgataaagga aaggctatcg ttcaagatgc ctctgccgac agtggtccca   45780
aagatggacc cccacccacg aggagcatcg tggaaaaaga agacgttcca accacgtctt   45840
caaagcaagt ggattgatgt gatatctcca ctgacgtaag gatgacgca caatcccact   45900 atccttcgca agacccttcc tctatataag gaagttcatt tcatttggag aggacgagct   45960
```

```
gcagcttatt tttacaacaa ttaccaacaa caacaaacaa caaacaacat tacaattact   46020
atttacaatt acagtcgacg gatcaagtgc aaaggtccgc cttgtttctc ctctgtctct   46080
tgatctgact aatcttggtt tatgattcgt tgagtaattt tggggaaagc ttcgtccaca   46140 gtttttttt cgatgaacag tgccgcagtg gcgctgatct tgtatgctat cctgcaatcg   46200
tggtgaactt atgtctttta tatccttcac taccatgaaa agactagtaa tctttctcga   46260
tgtaacatcg tccagcactg ctattaccgt gtggtccatc cgacagtctg gctgaacaca   46320
tcatacgata ttgagcaaag atcgatctat cttccctgtt ctttaatgaa agacgtcatt   46380
ttcatcagta tgatctaaga atgttgcaac ttgcaaggag gcgtttcttt ctttgaatt    46440 aactaactcg ttgagtggcc ctgtttctcg gacgtaaggc ctttgctgct ccacacatgt   46500
ccattcgaat tttaccgtgt ttagcaaggg cgaaaagttt gcatcttgat gatttagctt   46560
gactatgcga ttgctttcct ggacccgtgc agctgcggac gggatccacc atgagcccag   46620
aacgacgccc ggccgacatc cgccgtgcca ccgaggcgga catgccggcg gtctgcacca   46680
tcgtcaacca ctacatcgag acaagcacgg tcaacttccg taccgagccg caggaaccgc   46740
aggactggac ggacgacctc gtccgtctgc gggagcgcta tccctggctc gtcgccgagg   46800
tggacggcga ggtcgccggc atcgcctacg cgggcccctg gaaggcacgc aacgcctacg   46860
actggacggc cgagtcgacc gtgtacgtct ccccccgcca ccagcggacg ggactgggct   46920
ccacgctcta cacccacctg ctgaagtccc tggaggcaca gggcttcaag agcgtggtcg   46980
ctgtcatcgg gctgcccaac gacccgagcg tgcgcatgca cgaggcgctc ggatatgccc   47040
cccgcggcat gctgcgggcg gccggcttca agcacgggaa ctggcatgac gtgggttct    47100 ggcagctgga cttcagcctg ccggtaccgc cccgtccggt cctgcccgtc accgagatct   47160
gatccgtcga ccaacctaga cttgtccatc ttctggattg gccaacttaa ttaatgtatg   47220
aaataaaagg atgcacacat agtgacatgc taatcactat aatgtgggca tcaaagttgt   47280
gtgttatgtg taattactag ttatctgaat aaaagagaaa gagatcatcc atatttctta   47340
tcctaaatga atgtcacgtg tctttataat tctttgatga accagatgca tttcattaac   47400
caaatccata tacatataaa tattaatcat atataattaa tatcaattgg gttagcaaaa   47460
caaatctagt ctaggtgtgt tttgcgaatg cggccgccac cgcggtggag ctcgaattcc   47520
ggtccgggtc acccggtccg ggcctagaag gccagcttgc ggccgccccg ggcaacttta   47580
ttatacaaag ttgatagata tcggtccgag cggcctagaa ggcctttggt cacctttgtc   47640
caccaagatg gaactgcggc cgctcattaa ttaagtcagg cgcgcctcta gttgaagaca   47700
cgttcatgtc ttcatcgtaa gaagacactc agtagtcttc ggccagaatg gcctaactca   47760
aggccatcgt ggcctcttgc tcttcaggat gaagagctat gtttaaacgt gcaagcgcta   47820
ctagacaatt cagtacatta aaaacgtccg caatgtgtta ttaagttgtc taagcgtcaa   47880
tttgtttaca ccacaatata tcctgccacc agccagccaa cagctccccg accggcagct   47940
cggcacaaaa tcaccactcg atacaggcag cccatcagtc cggacggcg tcagcggag    48000 agccgttgta aggcggcaga ctttgctcat gttaccgatg ctattcggaa gaacggcaac   48060
taagctgccg ggtttgaaac acggatgatc tcgcggaggg tagcatgttg attgtaacga   48120
tgacagagcg ttgctgcctg tgatcaaata tcatctcct cgcagagatc cgaattatca    48180
gccttcttat tcatttctcg cttaaccgtg acaggctgtc gatcttgaga actatgccga   48240
cataatagga aatcgctgga taaagccgct gaggaagctg agtggcgcta tttctttaga   48300
agtgaacgtt gacgatcgtc gaccgtaccc cgatgaatta attcggacgt acgttctgaa   48360
```

```
cacagctgga tacttacttg ggcgattgtc atacatgaca tcaacaatgt acccgtttgt   48420
gtaaccgtct cttggaggtt cgtatgacac tagtggttcc cctcagcttg cgactagatg   48480
ttgaggccta acattttatt agagagcagg ctagttgctt agatacatga tcttcaggcc   48540
gttatctgtc agggcaagcg aaaattggcc atttatgacg accaatgccc cgcagaagct   48600
cccatctttg ccgccataga cgccgcgccc cccttttggg gtgtagaaca tccttttgcc   48660
agatgtggaa aagaagttcg ttgtcccatt gttggcaatg acgtagtagc cggcgaaagt   48720
gcgagaccca tttgcgctat atataagcct acgatttccg ttgcgactat tgtcgtaatt   48780
ggatgaacta ttatcgtagt tgctctcaga gttgtcgtaa tttgatggac tattgtcgta   48840
attgcttatg gagttgtcgt agttgcttgg agaaatgtcg tagttggatg gggagtagtc   48900
atagggaaga cgagcttcat ccactaaaac aattggcagg tcagcaagtg cctgcccga   48960 tgccatcgca agtacgaggc ttagaaccac cttcaacaga tcgcgcatag tcttccccag   49020
ctctctaacg cttgagttaa gccgcgccgc gaagcggcgt cggcttgaac gaattgttag   49080
acattatttg ccgactacct tggtgatctc gcctttcacg tagtgaacaa attcttccaa   49140
ctgatctgcg cgcgaggcca agcgatcttc ttgtccaaga taagcctgcc tagcttcaag   49200
tatgacgggc tgatactggg ccggcaggcg ctccattgcc cagtcggcag cgacatcctt   49260
cggcgcgatt ttgccggtta ctgcgctgta ccaaatgcgg acaacgtaa gcactacatt   49320 tcgctcatcg ccagcccagt cgggcggcga gttccatagc gttaaggttt catttagcgc   49380
ctcaaataga tcctgttcag gaaccggatc aaagagttcc tccgccgctg gacctaccaa   49440
ggcaacgcta tgttctcttg cttttgtcag caagatagcc agatcaatgt cgatcgtggc   49500
tggctcgaag atacctgcaa gaatgtcatt gcgctgccat tctccaaatt gcagttcgcg   49560
cttagctgga taacgccacg gaatgatgtc gtcgtgcaca acaatggtga cttctacagc   49620
gcggagaatc tcgctctctc caggggaagc cgaagtttcc aaaaggtcgt tgatcaaagc   49680
tcgccgcgtt gtttcatcaa gccttacagt caccgtaacc agcaaatcaa tatcactgtg   49740
tggcttcagg ccgccatcca ctgcggagcc gtacaaatgt acggccagca acgtcggttc   49800
gagatggcgc tcgatgacgc caactacctc tgatagttga gtcgatactt cggcgatcac   49860
cgcttccctc atgatgttta actcctgaat taagccgcgc cgcgaagcgg tgtcggcttg   49920
aatgaattgt taggcgtcat cctgtgctcc cgagaaccag taccagtaca tcgctgtttc   49980
gttcgagact tgaggtctag ttttatacgt gaacaggtca atgccgccga gagtaaagcc   50040
acattttgcg tacaaattgc aggcaggtac attgttcgtt tgtgtctcta atcgtatgcc   50100
aaggagctgt ctgcttagtg cccactttt cgcaaattcg atgagactgt gcgcgactcc   50160
tttgcctcgg tgcgtgtgcg acacaacaat gtgttcgata gaggctagat cgttccatgt   50220
tgagttgagt tcaatcttcc cgacaagctc ttggtcgatg aatgcgccat agcaagcaga   50280
gtcttcatca gagtcatcat ccgagatgta atccttccgg tagggctca cacttctggt   50340 agatagttca aagccttggt cggataggtg cacatcgaac acttcacgaa caatgaaatg   50400
gttctcagca tccaatgttt ccgccacctg ctcagggatc accgaaatct tcatatgacg   50460
cctaacgcct ggcacagcgg atcgcaaacc tggcgcggct tttggcacaa aaggcgtgac   50520
aggtttgcga atccgttgct gccacttgtt aaccctttg ccagatttgg taactataat   50580
ttatgttaga ggcgaagtct tgggtaaaaa ctggcctaaa attgctgggg atttcaggaa   50640
agtaaacatc accttccggc tcgatgtcta ttgtagatat atgtagtgta tctacttgat   50700
```

```
cgggggatct gctgcctcgc gcgtttcggt gatgacggtg aaaacctctg acacatgcag   50760
ctcccggaga cggtcacagc ttgtctgtaa gcggatgccg ggagcagaca agcccgtcag   50820
ggcgcgtcag cgggtgttgg cgggtgtcgg ggcgcagcca tgacccagtc acgtagcgat   50880
agcggagtgt atactggctt aactatgcgg catcagagca gattgtactg agagtgcacc   50940
atatgcggtg tgaaataccg cacagatgcg taaggagaaa ataccgcatc aggcgctctt   51000
ccgcttcctc gctcactgac tcgctgcgct cggtcgttcg gctgcggcga gcggtatcag   51060
ctcactcaaa ggcggtaata cggttatcca cagaatcagg ggataacgca ggaaagaaca   51120
tgtgagcaaa aggccagcaa aaggccagga accgtaaaaa ggccgcgttg ctggcgtttt   51180
tccataggct ccgcccccct gacgagcatc acaaaaatcg acgctcaagt cagaggtggc   51240
gaaacccgac aggactataa agataccagg cgtttccccc tggaagctcc ctcgtgcgct   51300
ctcctgttcc gaccctgccg cttaccggat acctgtccgc ctttctccct tcgggaagcg   51360
tggcgctttc tcatagctca cgctgtaggt atctcagttc ggtgtaggtc gttcgctcca   51420
agctgggctg tgtgcacgaa ccccccgttc agcccgaccg ctgcgcctta tccggtaact   51480
atcgtcttga gtccaacccg gtaagacacg acttatcgcc actggcagca gccactggta   51540
acaggattag cagagcgagg tatgtaggcg gtgctacaga gttcttgaag tggtggccta   51600
actacggcta cactagaagg acagtatttg gtatctgcgc tctgctgaag ccagttacct   51660
tcggaaaaag agttggtagc tcttgatccg gcaaacaaac caccgctggt agcggtggtt   51720
tttttgtttg caagcagcag attacgcgca gaaaaaagg atctcaagaa gatcctttga   51780
tcttttctac ggggtctgac gctcagtgga acgaaaactc acgttaaggg attttggtca   51840
tgagattatc aaaaaggatc ttcacctaga tccttttaaa ttaaaaatga agttttaaat   51900
caatctaaag tatatatgag taaacttggt ctgacagtta ccaatgctta atcagtgagg   51960
cacctatctc agcgatctgt ctatttcgtt catccatagt tgcctgactc cccgtcgtgt   52020
agataactac gatacgggag ggcttaccat ctggccccag tgctgcaatg ataccgcgag   52080
acccacgctc accggctcca gatttatcag caataaacca gccagccgga agggccgagc   52140
gcagaagtgg tcctgcaact ttatccgcct ccatccagtc tattaattgt tgccgggaag   52200
ctagagtaag tagttcgcca gttaatagtt tgcgcaacgt tgttgccatt gctgca       52256
```

<210> SEQ ID NO 31
<211> LENGTH: 52316
<212> TYPE: DNA
<213> ORGANISM: Artificial Sequence
<220> FEATURE:
<223> OTHER INFORMATION: plasmid PHP31459

<400> SEQUENCE: 31

```
gggggggggg ggggggggtt ccattgttca ttccacggac aaaaacagag aaaggaaacg     60
acagaggcca aaaagctcgc tttcagcacc tgtcgtttcc tttcttttca gagggtattt    120
taaataaaaa cattaagtta tgacgaagaa gaacggaaac gccttaaacc ggaaaatttt    180
cataaatagc gaaaacccgc gaggtcgccg ccccgtaacc tgtcggatca ccggaaagga    240
cccgtaaagt gataatgatt atcatctaca tatcacaacg tgcgtggagg ccatcaaacc    300
acgtcaaata atcaattatg acgcaggtat cgtattaatt gatctgcatc aacttaacgt    360
aaaaacaact tcagacaata caaatcagcg acactgaata cggggcaacc tcatgtcccc    420
cccccccccc cccctgcagg catcgtggtg tcacgctcgt cgtttggtat ggcttcattc    480
agctccggtt cccaacgatc aaggcgagtt acatgatccc ccatgttgtg caaaaaagcg    540
```

```
gttagctcct tcggtcctcc gatcgttgtc agaagtaagt tggccgcagt gttatcactc    600
atggttatgg cagcactgca taattctctt actgtcatgc catccgtaag atgcttttct    660
gtgactggtg agtactcaac caagtcattc tgagaatagt gtatgcggcg accgagttgc    720
tcttgcccgg cgtcaacacg ggataatacc gcgccacata gcagaacttt aaaagtgctc    780
atcattggaa aacgttcttc ggggcgaaaa ctctcaagga tcttaccgct gttgagatcc    840
agttcgatgt aacccactcg tgcacccaac tgatcttcag catcttttac tttcaccagc    900
gtttctgggt gagcaaaaac aggaaggcaa aatgccgcaa aaagggaat aagggcgaca     960
cggaaatgtt gaatactcat actcttcctt tttcaatatt attgaagcat ttatcagggt   1020
tattgtctca tgagcggata catatttgaa tgtatttaga aaaataaaca aatagggggtt  1080
ccgcgcacat ttccccgaaa agtgccacct gacgtctaag aaaccattat tatcatgaca   1140
ttaacctata aaaataggcg tatcacgagg ccctttcgtc ttcaagaatt cggagctttt   1200
gccattctca ccggattcag tcgtcactca tggtgatttc tcacttgata accttatttt   1260
tgacgagggg aaattaatag gttgtattga tgttggacga gtcggaatcg cagaccgata   1320
ccaggatctt gccatcctat ggaactgcct cggtgagttt tctccttcat tacagaaacg   1380
gcttttttcaa aaatatggta ttgataatcc tgatatgaat aaattgcagt ttcatttgat  1440
gctcgatgag tttttctaat cagaattggt taattggttg taacactggc agagcattac   1500
gctgacttga cgggacggcg ctttgttga ataaatcgaa cttttgctga gttgaaggat    1560
cagatcacgc atcttcccga caacgcagac cgttccgtgg caaagcaaaa gttcaaaatc   1620
accaactggt ccacctacaa caaagctctc atcaaccgtg gctccctcac tttctggctg   1680
gatgatgggg cgattcaggc ctggtatgag tcagcaacac cttcttcacg aggcagacct   1740
cagcgccaga aggccgccag agaggccgag cgcggccgtg aggcttggac gctagggcag   1800
ggcatgaaaa agcccgtagc gggctgctac gggcgtctga cgcggtggaa aggggaggg    1860
gatgttgtct acatggctct gctgtagtga gtgggttgcg ctccggcagc ggtcctgatc   1920
aatcgtcacc ctttctcggt ccttcaacgt tcctgacaac gagcctcctt ttcgccaatc   1980
catcgacaat caccgcgagt ccctgctcga acgctgcgtc cggaccggct tcgtcgaagg   2040
cgtctatcgc ggcccgcaac agcggcgaga gcggagcctg ttcaacggtg ccgccgcgct   2100
cgccggcatc gctgtcgccg gcctgctcct caagcacggc ccaacagtg aagtagctga    2160
ttgtcatcag cgcattgacg gcgtccccgg ccgaaaaacc cgcctcgcag aggaagcgaa   2220
gctgcgcgtc ggccgtttcc atctgcggtg cgcccggtcg cgtgccggca tggatgcgcg   2280
cgccatcgcg gtaggcgagc agcgcctgcc tgaagctgcg ggcattcccg atcagaaatg   2340
agcgccagtc gtcgtcggct ctcggcaccg aatgcgtatg attctccgcc agcatggctt   2400
cggccagtgc gtcgagcagc gcccgcttgt tcctgaagtg ccagtaaagc gccggctgct   2460
gaaccccaa ccgttccgcc agtttgcgtg tcgtcagacc gtctacgccg acctcgttca    2520
acaggtccag ggcggcacgg atcactgtat tcggctgcaa cttgtcatg cttgacactt    2580
tatcactgat aaacataata tgtccaccaa cttatcagtg ataaagaatc cgcgcgttca   2640
atcgaccag cggaggctgg tccggaggcc agacgtgaaa cccaacatac ccctgatcgt    2700
aattctgagc actgtcgcgc tcgacgctgt cggcatcggc ctgattatgc cggtgctgcc   2760
gggcctcctg cgcgatctgg ttcactcgaa cgacgtcacc gcccactatg gcattctgct   2820
ggcgctgtat gcgttggtgc aatttgcctg cgcacctgtg ctgggcgcgc tgtcggatcg   2880
```

```
tttcgggcgg cggccaatct tgctcgtctc gctggccggc gccactgtcg actacgccat   2940
catggcgaca gcgcctttcc tttgggttct ctatatcggg cggatcgtgg ccggcatcac   3000
cggggcgact ggggcggtag ccggcgctta tattgccgat atcactgatg gcgatgagcg   3060
cgcgcggcac ttcggcttca tgagcgcctg tttcgggttc gggatggtcg cgggacctgt   3120
gctcggtggg ctgatgggcg gtttctcccc ccacgctccg ttcttcgccg cggcagcctt   3180
gaacggcctc aatttcctga cgggctgttt ccttttgccg gagtcgcaca aaggcgaacg   3240
ccggccgtta cgccgggagg ctctcaaccc gctcgcttcg ttccggtggg cccggggcat   3300
gaccgtcgtc gccgccctga tggcggtctt cttcatcatg caacttgtcg gacaggtgcc   3360
ggccgcgctt tgggtcattt tcggcgagga tcgctttcac tgggacgcga ccacgatcgg   3420
catttcgctt gccgcatttg gcattctgca ttcactcgcc caggcaatga tcaccggccc   3480
tgtagccgcc cggctcggcg aaaggcgggc actcatgctc ggaatgattg ccgacggcac   3540
aggctacatc ctgcttgcct tcgcgacacg gggatggatg gcgttcccga tcatggtcct   3600
gcttgcttcg ggtggcatcg gaatgccggc gctgcaagca atgttgtcca ggcaggtgga   3660
tgaggaacgt caggggcagc tgcaaggctc actgcggcg ctcaccagcc tgacctcgat   3720
cgtcggaccc ctcctcttca cggcgatcta tgcggcttct ataacaacgt ggaacgggtg   3780
ggcatggatt gcaggcgctg ccctctactt gctctgcctg ccggcgctgc gtcgcgggct   3840
ttggagcggc gcagggcaac gagccgatcg ctgatcgtgg aaacgatagg cctatgccat   3900
gcgggtcaag gcgacttccg gcaagctata cgcgccctag gagtgcggtt ggaacgttgg   3960
cccagccaga tactcccgat cacgagcagg acgccgatga tttgaagcgc actcagcgtc   4020
tgatccaaga acaaccatcc tagcaacacg gcggtccccg ggctgagaaa gcccagtaag   4080
gaaacaactg taggttcgag tcgcgagatc ccccggaacc aaaggaagta ggttaaaccc   4140
gctccgatca ggccgagcca cgccaggccg agaacattgg ttcctgtagg catcgggatt   4200
ggcggatcaa acactaaagc tactggaacg agcagaagtc ctccggccgc cagttgccag   4260
gcggtaaagg tgagcagagg cacgggaggt tgccacttgc gggtcagcac ggttccgaac   4320
gccatggaaa ccgcccccgc caggcccgct gcgacgccga caggatctag cgctgcgttt   4380
ggtgtcaaca ccaacagcgc cacgcccgca gttccgcaaa tagcccccag gaccgccatc   4440
aatcgtatcg ggctacctag cagagcggca gagatgaaca cgaccatcag cggctgcaca   4500
gcgcctaccg tcgccgcgac cccgcccggc aggcggtaga ccgaaataaa caacaagctc   4560
cagaatagcg aaatattaag tgcgccgagg atgaagatgc gcatccacca gattcccgtt   4620
ggaatctgtc ggacgatcat cacgagcaat aaacccgccg gcaacgcccg cagcagcata   4680
ccggcgaccc ctcggcctcg ctgttcgggc tccacgaaaa cgccggacag atgcgccttg   4740
tgagcgtcct tggggccgtc ctcctgtttg aagaccgaca gcccaatgat ctcgccgtcg   4800
atgtaggcgc cgaatgccac ggcatctcgc aaccgttcag cgaacgcctc catgggcttt   4860
ttctcctcgt gctcgtaaac ggacccgaac atctctggag cttcttcag ggccgacaat   4920
cggatctcgc ggaaatcctg cacgtcggcc gctccaagcc gtcgaatctg agccttaatc   4980
acaattgtca attttaatcc tctgtttatc ggcagttcgt agagcgcgcc gtgcgtcccg   5040
agcgatactg agcgaagcaa gtgcgtcgag cagtgcccgc ttgttcctga aatgccagta   5100
aagcgctggc tgctgaaccc ccagccggaa ctgaccccac aaggccctag cgtttgcaat   5160
gcaccaggtc atcattgacc caggcgtgtt ccaccaggcc gctgcctcgc aactcttcgc   5220
aggcttcgcc gacctgctcg cgccacttct tcacgcgggt ggaatccgat ccgcacatga   5280
```

```
ggcggaaggt tccagcttg agcgggtacg gctcccggtg cgagctgaaa tagtcgaaca    5340
tccgtcgggc cgtcggcgac agcttgcggt acttctccca tatgaatttc gtgtagtggt    5400
cgccagcaaa cagcacgacg atttcctcgt cgatcaggac ctggcaacgg gacgttttct    5460
tgccacggtc caggacgcgg aagcggtgca gcagcgacac cgattccagg tgcccaacgc    5520
ggtcggacgt gaagcccatc gccgtcgcct gtaggcgcga caggcattcc tcggccttcg    5580
tgtaataccg gccattgatc gaccagccca ggtcctggca aagctcgtag aacgtgaagg    5640
tgatcggctc gccgataggg gtgcgcttcg cgtactccaa cacctgctgc cacaccagtt    5700
cgtcatcgtc ggcccgcagc tcgacgccgg tgtaggtgat cttcacgtcc ttgttgacgt    5760
ggaaaatgac cttgttttgc agcgcctcgc gcgggatttt cttgttgcgc gtggtgaaca    5820
gggcagagcg ggccgtgtcg tttggcatcg ctcgcatcgt gtccggccac ggcgcaatat    5880
cgaacaagga aagctgcatt tccttgatct gctgcttcgt gtgtttcagc aacgcggcct    5940
gcttggcctc gctgacctgt tttgccaggt cctcgccggc ggttttttcgc ttcttggtcg    6000 tcatagttcc tcgcgtgtcg atggtcatcg acttcgccaa acctgccgcc tcctgttcga    6060
gacgacgcga acgctccacg gcggccgatg gcgcgggcag ggcaggggga gccagttgca    6120
cgctgtcgcg ctcgatcttg gccgtagctt gctggaccat cgagccgacg gactggaagg    6180
tttcgcgggg cgcacgcatg acggtgcggc ttgcgatggt ttcggcatcc tcggcggaaa    6240
accccgcgtc gatcagttct tgcctgtatg ccttccggtc aaacgtccga ttcattcacc    6300
ctccttgcgg gattgccccg actcacgccg gggcaatgtg cccttattcc tgatttgacc    6360
cgcctggtgc cttggtgtcc agataatcca ccttatcggc aatgaagtcg gtcccgtaga    6420
ccgtctggcc gtccttctcg tacttggtat tccgaatctt gccctgcacg aataccagcg    6480
accccttgcc caaatacttg ccgtgggcct cggcctgaga gccaaaacac ttgatgcgga    6540
agaagtcggt gcgctcctgc ttgtcgccgg catcgttgcg ccactcttca ttaaccgcta    6600
tatcgaaaat tgcttgcggc ttgttagaat tgccatgacg tacctcggtg tcacgggtaa    6660
gattaccgat aaactggaac tgattatggc tcatatcgaa agtctccttg agaaaggaga    6720
ctctagttta gctaaacatt ggttccgctg tcaagaactt tagcggctaa aattttgcgg    6780
gccgcgacca aagtgcgag gggcggcttc cgctgtgtac aaccagatat ttttcaccaa    6840
catccttcgt ctgctcgatg agcggggcat gacgaaacat gagctgtcgg agagggcagg    6900
ggtttcaatt tcgtttttat cagacttaac caacggtaag gccaacccct cgttgaaggt    6960
gatggaggcc attgccgacg ccctggaaac tcccctacct cttctcctgg agtccaccga    7020
ccttgaccgc gaggcactcg cggagattgc gggtcatcct ttcaagagca gcgtgccgcc    7080
cggatacgaa cgcatcagtg tggttttgcc gtcacataag gcgtttatcg taagaaaatg    7140
gggcgacgac acccgaaaaa agctgcgtgg aaggctctga cgccaagggt tagggcttgc    7200
acttccttct ttagccgcta aaacggcccc ttctctgcgg gccgtcggct cgcgcatcat    7260
atcgacatcc tcaacggaag ccgtgccgcg aatggcatcg ggcgggtgcg ctttgacagt    7320
tgttttctat cagaacccct acgtcgtgcg gttcgattag ctgtttgtct tgcaggctaa    7380
acactttcgg tatatcgttt gcctgtgcga taatgttgct aatgatttgt tgcgtagggg    7440
ttactgaaaa gtgagcggga agaagagtt tcagaccatc aaggagcggg ccaagcgcaa    7500 gctgaacgc gacatgggtg cggacctgtt ggccgcgctc aacgacccga aaaccgttga    7560
agtcatgctc aacgcggacg gcaaggtgtg gcacgaacgc cttggcgagc cgatgcggta    7620
```

```
catctgcgac atgcggccca gccagtcgca ggcgattata gaaacggtgg ccggattcca    7680
cggcaaagag gtcacgcggc attcgcccat cctggaaggc gagttcccct tggatggcag    7740
ccgctttgcc ggccaattgc cgccggtcgt ggccgcgcca acctttgcga tccgcaagcg    7800
cgcggtcgcc atcttcacgc tggaacagta cgtcgaggcg ggcatcatga cccgcgagca    7860
atacgaggtc attaaaagcg ccgtcgcggc gcatcgaaac atcctcgtca ttggcggtac    7920
tggctcgggg aagaccacgc tcgtcaacgc gatcatcaat gaaatggtcg ccttcaaccc    7980
gtctgagcgc gtcgtcatca tcgaggacac cggcgaaatc cagtgcgccg cagagaacgc    8040
cgtccaatac cacaccagca tcgacgtctc gatgacgctg ctgctcaaga caacgctgcg    8100
tatgcgcccc gaccgcatcc tggtcggtga ggtacgtggc cccgaagccc ttgatctgtt    8160
gatggcctgg aacaccgggc atgaaggagg tgccgccacc ctgcacgcaa acaaccccaa    8220
agcgggcctg agccggctcg ccatgcttat cagcatgcac ccggattcac cgaaacccat    8280
tgagccgctg attggcgagg cggttcatgt ggtcgtccat atcgccagga cccctagcgg    8340
ccgtcgagtg caagaaattc tcgaagttct tggttacgag aacggccagt acatcaccaa    8400
aaccctgtaa ggagtatttc caatgacaac ggctgttccg ttccgtctga ccatgaatcg    8460
cggcattttg ttctaccttg ccgtgttctt cgttctcgct ctcgcgttat ccgcgcatcc    8520
ggcgatggcc tcggaaggca ccggcggcag cttgccatat gagagctggc tgacgaacct    8580
gcgcaactcc gtaaccggcc cggtggcctt cgcgctgtcc atcatcggca tcgtcgtcgc    8640
cggcggcgtg ctgatcttcg gcggcgaact caacgccttc ttccgaaccc tgatcttcct    8700
ggttctggtg atggcgctgc tggtcggcgc gcagaacgtg atgagcacct tcttcggtcg    8760
tggtgccgaa atcgcggccc tcggcaacgg ggcgctgcac caggtgcaag tcgcggcggc    8820
ggatgccgtg cgtgcggtag cggctggacg gctcgcctaa tcatggctct gcgcacgatc    8880
cccatccgtc gcgcaggcaa ccgagaaaac ctgttcatgg gtggtgatcg tgaactggtg    8940
atgttctcgg gcctgatggc gtttgcgctg attttcagcg cccaagagct gcgggccacc    9000
gtggtcggtc tgatcctgtg gttcggggcg ctctatgcgt tccgaatcat ggcgaaggcc    9060
gatccgaaga tgcggttcgt gtacctgcgt caccgccggt acaagccgta ttacccggcc    9120
cgctcgaccc cgttccgcga gaacaccaat agccaaggga agcaataccg atgatccaag    9180
caattgcgat tgcaatcgcg ggcctcggcg cgcttctgtt gttcatcctc tttgcccgca    9240
tccgcgcggt cgatgccgaa ctgaaactga aaaagcatcg ttccaaggac gccggcctgg    9300
ccgatctgct caactacgcc gctgtcgtcg atgacgcgt aatcgtgggc aagaacggca    9360
gctttatggc tgcctggctg tacaagggcg atgacaacgc aagcagcacc gaccagcagc    9420
gcgaagtagt gtccgcccgc atcaaccagg ccctcgcggg cctgggaagt gggtggatga    9480
tccatgtgga cgccgtgcgg cgtcctgctc cgaactacgc ggagcggggc ctgtcggcgt    9540
tccctgaccg tctgacggca gcgattgaag aagagcgctc ggtcttgcct tgctcgtcgg    9600
tgatgtactt caccagctcc gcgaagtcgc tcttcttgat ggagcgcatg gggacgtgct    9660
tggcaatcac gcgcaccccc cggccgtttt agcggctaaa aaagtcatgg ctctgccctc    9720
gggcggacca cgcccatcat gaccttgcca agctcgtcct gcttctcttc gatcttcgcc    9780
agcagggcga ggatcgtggc atcaccgaac cgcgccgtgc gcgggtcgtc ggtgagccag    9840
agtttcagca ggccgcccag gcggcccagg tcgccattga tgcgggccag ctcgcggacg    9900
tgctcatagt ccacgacgcc cgtgattttg tagccctggc cgacggccag caggtaggcc    9960
gacaggctca tgccggccgc cgccgccttt tcctcaatcg ctcttcgttc gtctggaagg   10020
```

```
cagtacacct tgataggtgg gctgcccttc ctggttggct tggtttcatc agccatccgc    10080
ttgccctcat ctgttacgcc ggcggtagcc ggccagcctc gcagagcagg attcccgttg    10140
agcaccgcca ggtgcgaata agggacagtg aagaaggaac acccgctcgc gggtgggcct    10200
acttcaccta tcctgcccgg ctgacgccgt tggatacacc aaggaaagtc tacacgaacc    10260 cctttggcaaa atcctgtata tcgtgcgaaa aaggatggat ataccgaaaa atcgctata    10320 atgaccccga agcagggtta tgcagcgaaa aagcgctgct tccctgctgt tttgtggaat    10380
atctaccgac tggaaacagg caaatgcagg aaattactga actgagggga caggcgagag    10440
acgatgccaa agagctacac cgacgagctg gccgagtggg ttgaatcccg cgcggccaag    10500
aagcgccggc gtgatgaggc tgcggttgcg ttcctggcgg tgagggcgga tgtcgaggcg    10560
gcgttagcgt ccggctatgc gctcgtcacc atttgggagc acatgcggga aacggggaag    10620
gtcaagttct cctacgagac gttccgctcg cacgccaggc ggcacatcaa ggccaagccc    10680
gccgatgtgc ccgcaccgca ggccaaggct gcggaacccg cgccggcacc caagacgccg    10740
gagccacggc ggccgaagca gggggggcaag gctgaaaagc cggcccccgc tgcggccccg    10800
accggcttca ccttcaaccc aacaccggac aaaaaggatc tactgtaatg gcgaaaattc    10860
acatggtttt gcagggcaag ggcggggtcg gcaagtcggc catcgccgcg atcattgcgc    10920
agtacaagat ggacaagggg cagacaccct tgtgcatcga caccgacccg gtgaacgcga    10980
cgttcgaggg ctacaaggcc ctgaacgtcc gccggctgaa catcatggcc ggcgacgaaa    11040
ttaactcgcg caacttcgac accctggtcg agctgattgc gccgaccaag gatgacgtgg    11100
tgatcgacaa cggtgccagc tcgttcgtgc ctctgtcgca ttacctcatc agcaaccagg    11160
tgccggctct gctgcaagaa atggggcatg agctggtcat ccataccgtc gtcaccggcg    11220
gccaggctct cctggacacg gtgagcggct tcgcccagct cgccagccag ttcccggccg    11280
aagcgctttt cgtggtctgg ctgaacccgt attgggggcc tatcgagcat gagggcaaga    11340
gctttgagca gatgaaggcg tacacggcca acaaggcccg cgtgtcgtcc atcatccaga    11400
ttccggccct caaggaagaa acctacggcc gcgatttcag cgacatgctg caagagcggc    11460
tgacgttcga ccaggcgctg gccgatgaat cgctcacgat catgacgcgg caacgcctca    11520
agatcgtgcg gcgcggcctg tttgaacagc tcgacgcggc ggccgtgcta tgagcgacca    11580
gattgaagag ctgatccggg agattgcggc caagcacgga atcgccgtcg gccgcgacga    11640
cccggtgctg atcctgcata ccatcaacgc ccggctcatg gccgacagtg cggccaagca    11700
agaggaaatc cttgccgcgt tcaaggaaga gctggaaggg atcgcccatc gttggggcga    11760
ggacgccaag gccaaagcgg agcggatgct gaacgcggcc ctggcggcca gcaaggacgc    11820
aatggcgaag gtaatgaagg acagcgccgc gcaggcggcc gaagcgatcc gcagggaaat    11880
cgacgacggc cttggccgcc agctcgcggc caaggtcgcg gacgcgcggc gcgtggcgat    11940
gatgaacatg atcgccggcg gcatggtgtt gttcgcggcc gccctggtgg tgtgggcctc    12000
gttatgaatc gcagaggcgc agatgaaaaa gcccggcgtt gccgggcttt gtttttgcgt    12060
tagctgggct tgtttgacag gcccaagctc tgactgcgcc cgcgctcgcg ctcctgggcc    12120
tgtttcttct cctgctcctg cttgcgcatc agggcctggt gccgtcgggc tgcttcacgc    12180
atcgaatccc agtcgccggc cagctcggga tgctccgcgc gcatcttgcg cgtcgccagt    12240
tcctcgatct tgggcgcgtg aatgcccatg ccttccttga tttcgcgcac catgtccagc    12300
cgcgtgtgca gggtctgcaa gcgggcttgc tgtttgggcct gctgctgctg ccaggcggcc    12360
```

```
tttgtacgcg gcagggacag caagccgggg gcattggact gtagctgctg caaacgcgcc   12420
tgctgacggt ctacgagctg ttctaggcgg tcctcgatgc gctccacctg gtcatgcttt   12480
gcctgcacgt agagcgcaag ggtctgctgg taggtctgct cgatgggcgc ggattctaag   12540
agggcctgct gttccgtctc ggcctcctgg gccgcctgta gcaaatcctc gccgctgttg   12600
ccgctggact gctttactgc cggggactgc tgttgccctg ctcgcgccgt cgtcgcagtt   12660
cggcttgccc ccactcgatt gactgcttca tttcgagccg cagcgatgcg atctcggatt   12720
gcgtcaacgg acggggcagc gcggaggtgt ccggcttctc cttgggtgag tcggtcgatg   12780
ccatagccaa aggtttcctt ccaaaatgcg tccattgctg gaccgtgttt ctcattgatg   12840
cccgcaagca tcttcggctt gaccgccagg tcaagcgcgc cttcatgggc ggtcatgacg   12900
gacgccgcca tgaccttgcc gccgttgttc tcgatgtagc cgcgtaatga ggcaatggtg   12960
ccgcccatcg tcagcgtgtc atcgacaacg atgtacttct ggccggggat caccctcccc   13020
tcgaaagtcg ggttgaacgc caggcgatga tctgaaccgg ctccggttcg ggcgaccttc   13080
tcccgctgca caatgtccgt ttcgacctca aggccaaggc ggtcggccag aacgaccgcc   13140
atcatggccg gaatcttgtt gttccccgcc gcctcgacgg cgaggactgg aacgatgcgg   13200
ggcttgtcgt cgccgatcag cgtcttgagc tgggcaacag tgtcgtccga aatcaggcgc   13260
tcgaccaaat taagcgccgc ttccgcgtcg ccctgcttcg cagcctggta ttcaggctcg   13320
ttggtcaaag aaccaaggtc gccgttgcga accaccttcg ggaagtctcc ccacggtgcg   13380
cgctcggctc tgctgtagct gctcaagacg cctcccttt tagccgctaa aactctaacg   13440
agtgcgcccg cgactcaact tgacgctttc ggcacttacc tgtgccttgc cacttgcgtc   13500
ataggtgatg cttttcgcac tcccgatttc aggtacttta tcgaaatctg accgggcgtg   13560
cattacaaag ttcttcccca cctgttggta aatgctgccg ctatctgcgt ggacgatgct   13620
gccgtcgtgg cgctgcgact tatcggcctt ttgggccata tagatgttgt aaatgccagg   13680
tttcagggcc ccggctttat ctaccttctg gttcgtccat gcgccttggt tctcggtctg   13740
gacaattctt tgcccattca tgaccaggag gcggtgtttc attgggtgac tcctgacggt   13800
tgcctctggt gttaaacgtg tcctggtcgc ttgccggcta aaaaaaagcc gacctcggca   13860
gttcgaggcc ggcttttcct agagccgggc gcgtcaaggt tgttccatct attttagtga   13920
actgcgttcg atttatcagt tactttcctc ccgctttgtg tttcctccca ctcgtttccg   13980
cgtctagccg acccctcaac atagcggcct cttcttgggc tgccttttgcc tcttgccgcg   14040
cttcgtcacg ctcggcttgc accgtcgtaa agcgctcggc ctgcctggcc gcctcttgcg   14100
ccgccaactt cctttgctcc tggtgggcct cggcgtcggc ctgcgccttc gctttcaccg   14160
ctgccaactc cgtgcgcaaa ctctccgctt cgcgcctggt ggcgtcgcgc tcgccgcgaa   14220
gcgcctgcat ttcctggttg gccgcgtcca gggtcttgcg gctctcttct ttgaatgcgc   14280
gggcgtcctg gtgagcgtag tccagctcgg cgcgcagctc ctgcgctcga cgctccacct   14340
cgtcggcccg ctgcgtcgcc agcgcggccc gctgctcggc tcctgccagg gcggtgcgtg   14400
cttcggccag ggcttgccgc tggcgtgcgg ccagctcggc cgcctcggcg gcctgctgct   14460
ctagcaatgt aacgcgcgcc tgggcttctt ccagctcgcg ggcctgcgcc tcgaaggcgt   14520
cggccagctc cccgcgcacg gcttccaact cgttgcgctc acgatcccag ccggcttgcg   14580
ctgcctgcaa cgattcattg gcaagggcct gggcggcttg ccagagggcg gccacggcct   14640
ggttgccggc ctgctgcacc gcgtccggca cctggactgc cagcggggcg gcctgcgccg   14700
tgcgctggcg tcgccattcg cgcatgccgg cgctggcgtc gttcatgttg acgcgggcgg   14760
```

```
ccttacgcac tgcatccacg gtcgggaagt tctcccggtc gccttgctcg aacagctcgt   14820
ccgcagccgc aaaaatgcgg tcgcgcgtct ctttgttcag ttccatgttg gctccggtaa   14880
ttggtaagaa taataatact cttacctacc ttatcagcgc aagagtttag ctgaacagtt   14940
ctcgacttaa cggcaggttt tttagcggct gaagggcagg caaaaaaagc cccgcacggt   15000 cggcggggggc aaagggtcag cgggaagggg attagcgggc gtcgggcttc ttcatgcgtc   15060
ggggccgcgc ttcttgggat ggagcacgac gaagcgcgca cgcgcatcgt cctcggccct   15120
atcggcccgc gtcgcggtca ggaacttgtc gcgcgctagg tcctccctgg tgggcaccag   15180
gggcatgaac tcggcctgct cgatgtaggt ccactccatg accgcatcgc agtcgaggcc   15240
gcgttccttc accgtctctt gcaggtcgcg gtacgcccgc tcgttgagcg gctggtaacg   15300
ggccaattgg tcgtaaatgg ctgtcggcca tgagcggcct ttcctgttga gccagcagcc   15360
gacgacgaag ccggcaatgc aggcccctgg cacaaccagg ccgacgccgg gggcagggga   15420
tggcagcagc tcgccaacca ggaacccgcc gcgatgatg ccgatgccgg tcaaccagcc    15480
cttgaaacta tccggccccg aaacacccct gcgcattgcc tggatgctgc gccggatagc   15540
ttgcaacatc aggagccgtt tcttttgttc gtcagtcatg gtccgccctc accagttgtt   15600
cgtatcggtg tcggacgaac tgaaatcgca agagctgccg gtatcggtcc agccgctgtc   15660
cgtgtcgctg ctgccgaagc acggcgaggg gtccgcgaac gccgcagacg gcgtatccgg   15720
ccgcagcgca tcgcccagca tggcccccggt cagcgagccg ccggccaggt agcccagcat   15780
ggtgctgttg gtcgccccgg ccaccagggc cgacgtgacg aaatcgccgt cattccctct   15840
ggattgttcg ctgctcggcg gggcagtgcg ccgcgccggc ggcgtcgtgg atggctcggg   15900
ttggctggcc tgcgacggcc ggcgaaaggt gcgcagcagc tcgttatcga ccggctgcgg   15960
cgtcggggcc gccgccttgc gctgcggtcg gtgttccttc ttcggctcgc gcagcttgaa   16020
cagcatgatc gcggaaacca gcagcaacgc cgcgcctacg cctcccgcga tgtagaacag   16080
catcggattc attcttcggt cctccttgta gcggaaccgt tgtctgtgcg gcgcgggtgg   16140
cccgcgccgc tgtctttggg gatcagccct cgatgagcgc gaccagtttc acgtcggcaa   16200
ggttcgcctc gaactcctgg ccgtcgtcct cgtacttcaa ccaggcatag ccttccgccg   16260
gcggccgacg gttgaggata aggcgggcag ggcgctcgtc gtgctcgacc tggacgatgg   16320
cctttttcag cttgtccggg tccggctcct tcgcgccctt ttccttggcg tccttaccgt   16380
cctggtcgcc gtcctcgccg tcctggccgt cgccggcctc cgcgtcacgc tcggcatcag   16440
tctggccgtt gaaggcatcg acggtgttgg gatcgcggcc cttctcgtcc aggaactcgc   16500
gcagcagctt gaccgtgccg cgcgtgattt cctgggtgtc gtcgtcaagc cacgcctcga   16560
cttcctccgg gcgcttcttg aaggccgtca ccagctcgtt caccacggtc acgtcgcgca   16620
cgcggccggt gttgaacgca tcggcgatct tctccggcag gtccagcagc gtgacgtgct   16680
gggtgatgaa cgccgcgac ttgccgattt ccttggcgat atcgcctttc ttcttgccct    16740
tcgccagctc gcggccaatg aagtcggcaa tttcgcgcgg ggtcagctcg ttgcgttgca   16800
ggttctcgat aacctggtcg gcttcgttgt agtcgttgtc gatgaacgcc gggatggact   16860
tcttgccggc ccacttcgag ccacggtagc ggcgggcgcc gtgattgatg atatagcggc   16920
ccggctgctc ctggttctcg cgcaccgaaa tgggtgactt caccccgcgc tctttgatcg   16980
tggcaccgat ttccgcgatg ctctccgggg aaaagccggg gttgtcggcc gtccgcggct   17040
gatgcggatc ttcgtcgatc aggtccaggt ccagctcgat agggccggaa ccgccctgag   17100
```

```
acgccgcagg agcgtccagg aggctcgaca ggtcgccgat gctatccaac cccaggccgg   17160
acggctgcgc cgcgcctgcg gcttcctgag cggccgcagc ggtgtttttc ttggtggtct   17220
tggcttgagc cgcagtcatt gggaaatctc catcttcgtg aacacgtaat cagccagggc   17280
gcgaacctct ttcgatgcct tgcgcgcggc cgtttcttg atcttccaga ccggcacacc    17340
ggatgcgagg gcatcggcga tgctgctgcg caggccaacg gtggccggaa tcatcatctt   17400
ggggtacgcg gccagcagct cggcttggtg gcgcgcgtgg cgcggattcc gcgcatcgac   17460
cttgctgggc accatgccaa ggaattgcag cttggcgttc ttctggcgca cgttcgcaat   17520
ggtcgtgacc atcttcttga tgccctggat gctgtacgcc tcaagctcga tgggggacag   17580
cacatagtcg gccgcgaaga gggcggccgc caggccgacg ccaagggtcg gggccgtgtc   17640
gatcaggcac acgtcgaagc cttggttcgc cagggccttg atgttcgccc cgaacagctc   17700
gcgggcgtcg tccagcgaca gccgttcggc gttcgccagt accgggttgg actcgatgag   17760
ggcgaggcgc gcggcctggc cgtcgccggc tgcgggtgcg gtttcggtcc agccgccggc   17820
agggacagcg ccgaacagct tgcttgcatg caggccggta gcaaagtcct tgagcgtgta   17880
ggacgcattg ccctgggggt ccaggtcgat cacggcaacc cgcaagccgc gctcgaaaaa   17940
gtcgaaggca agatgcacaa gggtcgaagt cttgccgacg ccgcctttct ggttggccgt   18000
gaccaaagtt ttcatcgttt ggtttcctgt tttttcttgg cgtccgcttc ccacttccgg   18060
acgatgtacg cctgatgttc cggcagaacc gccgttaccc gcgcgtaccc ctcgggcaag   18120
ttcttgtcct cgaacgcggc ccacacgcga tgcaccgctt gcgacactgc gcccctggtc   18180
agtcccagcg acgttgcgaa cgtcgcctgt ggcttcccat cgactaagac gccccgcgct   18240
atctcgatgg tctgctgccc cacttccagc ccctggatcg cctcctggaa ctggctttcg   18300
gtaagccgtt tcttcatgga taacacccat aatttgctcc gcgccttggt tgaacatagc   18360
ggtgacagcc gccagcacat gagagaagtt tagctaaaca tttctcgcac gtcaacacct   18420
ttagccgcta aaactcgtcc ttggcgtaac aaaacaaaag cccggaaacc gggctttcgt   18480
ctcttgccgc ttatggctct gcacccggct ccatcaccaa caggtcgcgc acgcgcttca   18540
ctcggttgcg gatcgacact gccagcccaa caaagccggt tgccgccgcc gccaggatcg   18600
cgccgatgat gccggccaca ccggccatcg cccaccaggt cgccgccttc cggttccatt   18660
cctgctggta ctgcttcgca atgctggacc tcggctcacc ataggctgac cgctcgatgg   18720
cgtatgccgc ttctccccctt ggcgtaaaac ccagcgccgc aggcggcatt gccatgctgc   18780
ccgccgcttt cccgaccacg acgcgcgcac caggcttgcg gtccagacct tcggccacgg   18840
cgagctgcgc aaggacataa tcagccgccg acttggctcc acgcgcctcg atcagctctt   18900
gcactcgcgc gaaatccttg gcctccacgg ccgccatgaa tcgcgcacgc ggcgaaggct   18960
ccgcagggcc ggcgtcgtga tcgccgccga gaatgcccctt caccaagttc gacgacacga   19020
aaatcatgct gacggctatc accatcatgc agacggatcg cacgaacccg ctgaattgaa   19080
cacgagcacg gcacccgcga ccactatgcc aagaatgccc aaggtaaaaa ttgccggccc   19140
cgccatgaag tccgtgaatg ccccgacggc cgaagtgaag ggcaggccgc cacccaggcc   19200
gccgccctca ctgccggca cctggtcgct gaatgtcgat gccagcacct gcggcacgtc   19260
aatgcttccg ggcgtcgcgc tcgggctgat cgcccatccc gttactgccc cgatcccggc   19320
aatggcaagg actgccagcg ctgccatttt tggggtgagg ccgttcgcgg ccgaggggcg   19380 cagccccctgg ggggatggga ggcccgcgtt agcgggccgg gagggttcga gaaggggggg   19440
cacccccctt cggcgtgcgc ggtcacgcgc acagggcgca gccctggtta aaaacaaggt   19500
```

```
ttataaatat tggtttaaaa gcaggttaaa agacaggtta gcggtggccg aaaaacgggc    19560
ggaaacccct gcaaatgctg gattttctgc ctgtggacag cccctcaaat gtcaataggt    19620
gcgcccctca tctgtcagca ctctgcccct caagtgtcaa ggatcgcgcc cctcatctgt    19680
cagtagtcgc gccccctcaag tgtcaatacc gcagggcact tatccccagg cttgtccaca   19740
tcatctgtgg gaaactcgcg taaaatcagg cgttttcgcc gatttgcgag gctggccagc    19800
tccacgtcgc cggccgaaat cgagcctgcc cctcatctgt caacgccgcg ccgggtgagt    19860
cggcccctca agtgtcaacg tccgcccctc atctgtcagt gagggccaag ttttccgcga    19920
ggtatccaca acgccggcgg ccgcggtgtc tcgcacacgg cttcgacggc gtttctggcg    19980
cgtttgcagg gccatagacg gccgccagcc cagcggcgag ggcaaccagc ccggtgagcg    20040
tcggaaaggc gctggaagcc ccgtagcgac gcggagaggg gcgagacaag ccaagggcgc    20100
aggctcgatg cgcagcacga catagccggt tctcgcaagg acgagaattt ccctgcggtg    20160
cccctcaagt gtcaatgaaa gtttccaacg cgagccattc gcgagagcct tgagtccacg    20220
ctagatgaga gctttgttgt aggtggacca gttggtgatt ttgaactttt gctttgccac    20280
ggaacggtct gcgttgtcgg gaagatgcgt gatctgatcc ttcaactcag caaaagttcg    20340
atttattcaa caaagccacg ttgtgtctca aaatctctga tgttacattg cacaagataa    20400
aaatatatca tcatgaacaa taaaactgtc tgcttacata aacagtaata caaggggtgt    20460
tatgagccat attcaacggg aaacgtcttg ctcgactcta gagctcgttc ctcgaggcct    20520
cgaggcctcg aggaacggta cctgcgggga agcttacaat aatgtgtgtt gttaagtctt    20580
gttgcctgtc atcgtctgac tgactttcgt cataaatccc ggcctccgta acccagcttt    20640
gggcaagctc acggatttga tccggcgaaa cgggaatatc gagatgccgg gctgaacgct    20700
gcagttccag cttttccttt cgggacaggt actccagctg attgattatc tgctgaaggg    20760
tcttggttcc acctcctggc acaatgcgaa tgattacttg agcgcgatcg ggcatccaat    20820
tttctcccgt caggtgcgtg gtcaagtgct acaaggcacc tttcagtaac gagcgaccgt    20880
cgatccgtcg ccgggatacg gacaaaatgg agcgcagtag tccatcgagg gcggcgaaag    20940
cctcgccaaa agcaatacgt tcatctcgca cagcctccag atccgatcga gggtcttcgg    21000
cgtaggcaga tagaagcatg gatacattgc ttgagagtat tccgatggac tgaagtatgg    21060
cttccatctt ttctcgtgtg tctgcatcta tttcgagaaa gccccgatg cggcgcaccg     21120 caacgcgaat tgccatacta tccgaaagtc ccagcaggcg cgcttgatag gaaaaggttt    21180
catactcggc cgatcgcaga cgggcactca cgaccttgaa cccttcaact ttcagggatc    21240
gatgctggtt gatggtagtc tcactcgacg tggctctggt gtgttttgac atagcttcct    21300
ccaaagaaag cggaaggtct ggatactcca gcacgaaatg tgcccgggta gacggatgga    21360
agtctagccc tgctcaatat gaaatcaaca gtacatttac agtcaatact gaatatactt    21420
gctacatttg caattgtctt ataacgaatg tgaaataaaa atagtgtaac aacgcttta    21480 ctcatcgata atcacaaaaa catttatacg aacaaaaata caaatgcact ccggtttcac    21540
aggataggcg ggatcagaat atgcaacttt tgacgttttg ttctttcaaa gggggtgctg    21600
gcaaaaccac cgcactcatg ggcctttgcg ctgctttggc aaatgacggt aaacgagtgg    21660
ccctctttga tgccgacgaa aaccggcctc tgacgcgatg gagagaaaac gccttacaaa    21720
gcagtactgg gatcctcgct gtgaagtcta ttccgccgac gaaatgcccc ttcttgaagc    21780
agcctatgaa aatgccgagc tcgaaggatt tgattatgcg ttggccgata cgcgtggcgg    21840
```

```
ctcgagcgag ctcaacaaca caatcatcgc tagctcaaac ctgcttctga tccccaccat   21900
gctaacgccg ctcgacatcg atgaggcact atctacctac cgctacgtca tcgagctgct   21960
gttgagtgaa aatttggcaa ttcctacagc tgttttgcgc caacgcgtcc cggtcggccg   22020
attgacaaca tcgcaacgca ggatgtcaga gacgctagag agccttccag ttgtaccgtc   22080
tcccatgcat gaaagagatg catttgccgc gatgaaagaa cgcggcatgt tgcatcttac   22140
attactaaac acgggaactg atccgacgat gcgcctcata gagaggaatc ttcggattgc   22200
gatggaggaa gtcgtggtca tttcgaaact gatcagcaaa atcttggagg cttgaagatg   22260
gcaattcgca agcccgcatt gtcggtcggc gaagcacggc ggcttgctgg tgctcgaccc   22320
gagatccacc atcccaaccc gacacttgtt ccccagaagc tggacctcca gcacttgcct   22380
gaaaaagccg acgagaaaga ccagcaacgt gagcctctcg tcgccgatca catttacagt   22440
cccgatcgac aacttaagct aactgtggat gcccttagtc cacctccgtc cccgaaaaag   22500
ctccaggttt ttctttcagc gcgaccgccc gcgcctcaag tgtcgaaaac atatgacaac   22560
ctcgttcggc aatacagtcc ctcgaagtcg ctacaaatga ttttaaggcg cgcgttggac   22620
gatttcgaaa gcatgctggc agatggatca tttcgcgtgg ccccgaaaag ttatccgatc   22680
ccttcaacta cagaaaaatc cgttctcgtt cagacctcac gcatgttccc ggttgcgttg   22740
ctcgaggtcg ctcgaagtca tttgatccg ttggggttgg agaccgctcg agctttcggc   22800
cacaagctgg ctaccgccgc gctcgcgtca ttctttgctg gagagaagcc atcgagcaat   22860
tggtgaagag ggacctatcg gaacccctca ccaaatattg agtgtaggtt tgaggccgct   22920
ggccgcgtcc tcagtcacct tttgagccag ataattaaga gccaaatgca attggctcag   22980
gctgccatcg tcccccgtg cgaaacctgc acgtccgcgt caaagaaata accggcacct   23040
cttgctgttt ttatcagttg agggcttgac ggatccgcct caagtttgcg gcgcagccgc   23100
aaaatgagaa catctatact cctgtcgtaa acctcctcgt cgcgtactcg actggcaatg   23160
agaagttgct cgcgcgatag aacgtcgcgg ggtttctcta aaaacgcgag gagaagattg   23220
aactcacctg ccgtaagttt cacctcaccg ccagcttcgg acatcaagcg acgttgcctg   23280
agattaagtg tccagtcagt aaaacaaaaa gaccgtcggt cttggagcg acaacgttg   23340 gggcgcacgc gcaaggcaac ccgaatgcgt gcaagaaact ctctcgtact aaacggctta   23400
gcgataaaat cacttgctcc tagctcgagt gcaacaactt tatccgtctc ctcaaggcgg   23460
tcgccactga taattatgat tggaatatca gactttgccg ccagatttcg aacgatctca   23520
agcccatctt cacgacctaa atttagatca acaaccacga catcgaccgt cgcggaagag   23580
agtactctag tgaactgggt gctgtcggct accgcggtca ctttgaaggc gtggatcgta   23640
aggtattcga taataagatg ccgcatagcg acatcgtcat cgataagaag aacgtgtttc   23700
aacggctcac ctttcaatct aaaatctgaa cccttgttca cagcgcttga gaaattttca   23760
cgtgaaggat gtacaatcat ctccagctaa atgggcagtt cgtcagaatt gcggctgacc   23820
gcggatgacg aaaatgcgaa ccaagtattt caattttatg acaaaagttc tcaatcgttg   23880
ttacaagtga aacgcttcga ggttacagct actattgatt aaggagatcg cctatggtct   23940
cgccccggcg tcgtgcgtcc gccgcgagcc agatctcgcc tacttcataa acgtcctcat   24000
aggcacggaa tggaatgatg acatcgatcg ccgtagagag catgtcaatc agtgtgcgat   24060
cttccaagct agcaccttgg gcgctacttt tgacaaggga aaacagtttc ttgaatcctt   24120
ggattggatt cgcgccgtgt attgttgaaa tcgatcccgg atgtcccgag acgacttcac   24180
tcagataagc ccatgctgca tcgtcgcgca tctcgccaag caatatccgg tccggccgca   24240
```

```
tacgcagact tgcttggagc aagtgctcgg cgctcacagc acccagccca gcaccgttct   24300
tggagtagag tagtctaaca tgattatcgt gtggaatgac gagttcgagc gtatcttcta   24360
tggtgattag cctttcctgg gggggatgg cgctgatcaa ggtcttgctc attgttgtct    24420
tgccgcttcc ggtagggcca catagcaaca tcgtcagtcg gctgacgacg catgcgtgca   24480
gaaacgcttc caaatccccg ttgtcaaaat gctgaaggat agcttcatca tcctgatttt   24540
ggcgtttcct tcgtgtctgc cactggttcc acctcgaagc atcataacgg gaggagactt   24600
ctttaagacc agaaacacgc gagcttggcc gtcgaatggt caagctgacg gtgcccgagg   24660
gaacggtcgg cggcagacag atttgtagtc gttcaccacc aggaagttca gtggcgcaga   24720
gggggttacg tggtccgaca tcctgctttc tcagcgcgcc cgctaaaata gcgatatctt   24780
caagatcatc ataagagacg ggcaaaggca tcttggtaaa aatgccggct tggcgcacaa   24840
atgcctctcc aggtcgattg atcgcaattt cttcagtctt cgggtcatcg agccattcca   24900
aaatcggctt cagaagaaag cgtagttgcg gatccacttc catttacaat gtatcctatc   24960
tctaagcgga aatttgaatt cattaagagc ggcggttcct cccccgcgtg gcgccgccag   25020
tcaggcggag ctggtaaaca ccaaagaaat cgaggtcccg tgctacgaaa atggaaacgg   25080
tgtcaccctg attcttcttc agggttggcg gtatgttgat ggttgcctta agggctgtct   25140
cagttgtctg ctcaccgtta ttttgaaagc tgttgaagct catcccgcca cccgagctgc   25200
cggcgtaggt gctagctgcc tggaaggcgc cttgaacaac actcaagagc atagctccgc   25260
taaaacgctg ccagaagtgg ctgtcgaccg agcccggcaa tcctgagcga ccagttcgt    25320 ccgcgcttgg cgatgttaac gagatcatcg catggtcagg tgtctcggcg cgatcccaca   25380
acacaaaaac gcgcccatct ccctgttgca agccacgctg tatttcgcca acaacggtgg   25440
tgccacgatc aagaagcacg atattgttcg ttgttccacg aatatcctga ggcaagacac   25500
actttacata gcctgccaaa tttgtgtcga ttgcggtttg caagatgcac ggaattattg   25560
tcccttgcgt taccataaaa tcggggtgcg gcaagagcgt ggcgctgctg ggctgcagct   25620
cggtgggttt catacgtatc gacaaatcgt tctcgccgga cacttcgcca ttcggcaagg   25680
agttgtcgtc acgcttgcct tcttgtcttc ggcccgtgtc gccctgaatg gcgcgtttgc   25740
tgaccccttg atcgccgctg ctatatgcaa aaatcggtgt tcttccggc cgtggctcat    25800 gccgctccgg ttcgcccctc ggcggtagag gagcagcagg ctgaacagcc tcttgaaccg   25860
ctggaggatc cggcggcacc tcaatcggag ctggatgaaa tggcttggtg tttgttgcga   25920
tcaaagttga cggcgatgcg ttctcattca ccttcttttg gcgcccacct agccaaatga   25980
ggcttaatga taacgcgaga acgacacctc cgacgatcaa tttctgagac cccgaaagac   26040
gccggcgatg tttgtcggag accagggatc cagatgcatc aacctcatgt gccgcttgct   26100
gactatcgtt attcatccct tcgccccctt caggacgcgt ttcacatcgg gcctcaccgt   26160 gcccgttttgc ggcctttggc caacgggatc gtaagcggtg ttccagatac atagtactgt   26220
gtggccatcc ctcagacgcc aacctcggga aaccgaagaa atctcgacat cgctcccttt   26280
aactgaatag ttggcaacag cttccttgcc atcaggattg atggtgtaga tggagggtat   26340
gcgtacattg cccggaaagt ggaataccgt cgtaaatcca ttgtcgaaga cttcgagtgg   26400
caacagcgaa cgatcgcctt gggcgacgta gtgccaatta ctgtccgccg caccaagggc   26460
tgtgacaggt tgatccaata aattctcagc tttccgttga tattgtgctt ccgcgtgtag   26520
tctgtccaca acagccttct gttgtgcctc ccttcgccga gccgccgcat cgtcggcggg   26580
```

```
gtaggcgaat tggacgctgt aatagagatc gggctgctct ttatcgaggt gggacagagt    26640
cttggaactt atactgaaaa cataacggcg catcccggag tcgcttgcgg ttagcacgat    26700
tactggctga ggcgtgagga cctggcttgc cttgaaaaat agataatttc cccgcggtag    26760
ggctgctaga tctttgctat ttgaaacggc aaccgctgtc accgtttcgt tcgtggcgaa    26820
tgttacgacc aaagtagctc caaccgccgt cgagaggcgc accacttgat cgggattgta    26880
agccaaataa cgcatgcgcg gatctagctt gcccgccatt ggagtgtctt cagcctccgc    26940
accagtcgca gcggcaaata acatgctaaa atgaaaagt gcttttctga tcatggttcg      27000
ctgtggccta cgtttgaaac ggtatcttcc gatgtctgat aggaggtgac aaccagacct    27060
gccgggttgg ttagtctcaa tctgccgggc aagctggtca ccttttcgta gcgaactgtc    27120
gcggtccacg tactcaccac aggcattttg ccgtcaacga cgagggtcct tttatagcga    27180
atttgctgcg tgcttggagt tacatcattt gaagcgatgt gctcgacctc caccctgccg    27240
cgtttgccaa gaatgacttg aggcgaactg ggattgggat agttgaagaa ttgctggtaa    27300
tcctggcgca ctgttggggc actgaagttc gataccaggc cgtaggcgta ctgagcggtg    27360
tcggcatcat aactctcgcg caggcgaacg tactcccaca atgaggcgtt aacgacggcc    27420
tcctcttgag ttgcaggcaa tcgcgagaca gacacctcgc tgtcaacggt gccgtccggc    27480
cgtatccata gatatacggg cacaagcctg ctcaacggca ccattgtggc tatagcgaac    27540
gcttgagcaa catttcccaa aatcgcgata gctgcgacag ctgcaatgag tttggagaga    27600
cgtcgcgccg atttcgctcg cgcggtttga aaggcttcta cttccttata gtgctcggca    27660
aggctttcgc gcgccactag catggcatat tcaggccccg tcatagcgtc cacccgaatt    27720
gccgagctga agatctgacg gagtaggctg ccatcgcccc acattcagcg ggaagatcgg    27780
gcctttgcag ctcgctaatg tgtcgtttgt ctggcagccg ctcaaagcga caactaggca    27840
cagcaggcaa tacttcatag aattctccat tgaggcgaat ttttgcgcga cctagcctcg    27900
ctcaacctga gcgaagcgac ggtacaagct gctggcagat tgggttgcgc cgctccagta    27960
actgcctcca atgttgccgg cgatcgccgg caaagcgaca atgagcgcat cccctgtcag    28020
aaaaaacata tcgagttcgt aaagaccaat gatcttggcc gcggtcgtac cggcgaaggt    28080
gattacacca agcataaggg tgagcgcagt cgcttcggtt aggatgacga tcgttgccac    28140
gaggtttaag aggagaagca agagaccgta ggtgataagt tgcccgatcc acttagctgc    28200
gatgtcccgc gtgcgatcaa aaatatatcc gacgaggatc agaggcccga tcgcgagaag    28260
cactttcgtg agaattccaa cggcgtcgta aactccgaag gcagaccaga gcgtgccgta    28320
aaggacccac tgtgcccctt ggaaagcaag gatgtcctgg tcgttcatcg gaccgatttc    28380
ggatgcgatt ttctgaaaaa cggcctgggt cacggcgaac attgtatcca actgtgccgg    28440
aacagtctgc agaggcaagc cggttacact aaactgctga acaaagtttg gaccgtctt     28500 ttcgaagatg gaaccacat agtcttggta gttagcctgc ccaacaatta gcaacaac       28560 gatggtgacc gtgatcaccc gagtgatacc gctacgggta tcgacttcgc cgcgtatgac    28620
taaaataccc tgaacaataa tccaaagagt gacacaggcg atcaatggcg cactcaccgc    28680
ctcctggata gtctcaagca tcgagtccaa gcctgtcgtg aaggctacat cgaagatcgt    28740
atgaatggcc gtaaacggcg ccggaatcgt gaaattcatc gattggacct gaacttgact    28800
ggtttgtcgc ataatgttgg ataaaatgag ctcgcattcg gcgaggatgc gggcggatga    28860
acaaatcgca cagccttagg ggagggcacc aaagatgaca gcggtctttt gatgctcctt    28920
gcgttgagcg gccgcctctt ccgcctcgtg aaggccggcc tgcgcggtag tcatcgttaa    28980
```

```
taggcttgtc gcctgtacat tttgaatcat tgcgtcatgg atctgcttga gaagcaaacc   29040
attggtcacg gttgcctgca tgatattgcg agatcgggaa agctgagcag acgtatcagc   29100
attcgccgtc aagcgtttgt ccatcgtttc cagattgtca gccgcaatgc cagcgctgtt   29160
tgcggaaccg gtgatctgcg atcgcaacag gtccgcttca gcatcactac ccacgactgc   29220
acgatctgta tcgctggtga tcgcacgtgc cgtggtcgac attggcattc gcggcgaaaa   29280
catttcattg tctaggtcct tcgtcgaagg atactgattt ttctggttga gcgaagtcag   29340
tagtccagta acgccgtagg ccgacgtcaa catcgtaacc atcgctatag tctgagtgag   29400
attctccgca gtcgcgagcg cagtcgcgag cgtctcagcc tccgttgccg ggtcgctaac   29460
aacaaactgc gcccgcgcgg gctgaatata tagaaagctg caggtcaaaa ctgttgcaat   29520
aagttgcgtc gtcttcatcg tttcctacct tatcaatctt ctgcctcgtg gtgacgggcc   29580
atgaattcgc tgagccagcc agatgagttg ccttcttgtg cctcgcgtag tcgagttgca   29640
aagcgcaccg tgttggcacg ccccgaaagc acggcgacat attcacgcat atcccgcaga   29700
tcaaattcgc agatgacgct tccactttct cgtttaagaa gaaacttacg gctgccgacc   29760
gtcatgtctt cacggatcgc ctgaaattcc ttttcggtac atttcagtcc atcgacataa   29820
gccgatcgat ctgcggttgg tgatggatag aaaatcttcg tcatacattg cgcaaccaag   29880
ctggctccta gcggcgattc cagaacatgc tctggttgct gcgttgccag tattagcatc   29940
ccgttgtttt ttcgaacggt caggaggaat tgtcgacga cagtcgaaaa tttagggttt   30000
aacaaatagg cgcgaaactc atcgcagctc atcacaaaac ggcggccgtc gatcatggct   30060
ccaatccgat gcaggagata tgctgcagcg ggagcgcata cttcctcgta ttcgagaaga   30120
tgcgtcatgt cgaagccggt aatcgacgga tctaacttta cttcgtcaac ttcgccgtca   30180
aatgcccagc caagcgcatg gccccggcac cagcgttgga gccgcgctcc tgcgccttcg   30240
gcgggcccat gcaacaaaaa ttcacgtaac cccgcgattg aacgcatttg tggatcaaac   30300
gagagctgac gatggatacc acggaccaga cggcggttct cttccggaga atcccaccc   30360 cgaccatcac tctcgatgag agccacgatc cattcgcgca gaaaatcgtg tgaggctgct   30420
gtgttttcta ggccacgcaa cggcgccaac ccgctgggtg tgcctctgtg aagtgccaaa   30480
tatgttcctc ctgtggcgcg aaccagcaat tcgccacccc ggtccttgtc aaagaacacg   30540
accgtacctg cacggtcgac catgctctgt tcgagcatgg ctagaacaaa catcatgagc   30600
gtcgtcttac ccctcccgat aggcccgaat attgccgtca tgccaacatc gtgctcatgc   30660
gggatatagt cgaaaggcgt tccgccattg gtacgaaatc gggcaatcgc gttgccccag   30720
tggcctgagc tggcgccctc tggaaagttt tcgaaagaga caaaccctgc gaaattgcgt   30780
gaagtgattg cgccagggcg tgtgcgccac ttaaaattcc ccggcaattg ggaccaatag   30840
gccgcttcca taccaatacc ttcttggaca accacggcac ctgcatccgc cattcgtgtc   30900
cgagcccgcg cgccctgtc cccaagacta ttgagatcgt ctgcatagac gcaaaggctc   30960
aaatgatgtg agcccataac gaattcgttg ctcgcaagtg cgtcctcagc ctcggataat   31020
ttgccgattt gagtcacggc tttatcgccg gaactcagca tctggctcga tttgaggcta   31080
agtttcgcgt gcgcttgcgg gcgagtcagg aacgaaaaac tctgcgtgag aacaagtgga   31140
aaatcgaggg atagcagcgc gttgagcatg cccggccgtg tttttgcagg gtattcgcga   31200
aacgaataga tggatccaac gtaactgtct tttggcgttc tgatctcgag tcctcgcttg   31260
ccgcaaatga ctctgtcggt ataaatcgaa gcgccgagtg agccgctgac gaccggaacc   31320
```

```
ggtgtgaacc gaccagtcat gatcaaccgt agcgcttcgc caatttcggt gaagagcaca    31380
ccctgcttct cgcggatgcc aagacgatgc aggccatacg ctttaagaga gccagcgaca    31440
acatgccaaa gatcttccat gttcctgatc tggcccgtga gatcgttttc ccttttccg     31500
cttagcttgg tgaacctcct ctttaccttc cctaaagccg cctgtgggta gacaatcaac    31560
gtaaggaagt gttcattgcg gaggagttgg ccggagagca cgcgctgttc aaaagcttcg    31620
ttcaggctag cggcgaaaac actacggaag tgtcgcggcg ccgatgatgg cacgtcggca    31680
tgacgtacga ggtgagcata tattgacaca tgatcatcag cgatattgcg caacagcgtg    31740
ttgaacgcac gacaacgcgc attgcgcatt tcagtttcct caagctcgaa tgcaacgcca    31800
tcaattctcg caatggtcat gatcgatccg tcttcaagaa ggacgatatg gtcgctgagg    31860
tggccaatat aagggagata gatctcaccg gatctttcgg tcgttccact cgcgccgagc    31920
atcacaccat tcctctccct cgtggggaa ccctaattgg atttgggcta acagtagcgc     31980
ccccccaaac tgcactatca atgcttcttc ccgcggtccg caaaaatagc aggacgacgc    32040
tcgccgcatt gtagtctcgc tccacgatga gccgggctgc aaaccataac ggcacgagaa    32100
cgacttcgta gagcgggttc tgaacgataa cgatgacaaa gccggcgaac atcatgaata    32160
accctgccaa tgtcagtggc accccaagaa acaatgcggg ccgtgtggct gcgaggtaaa    32220
gggtcgattc ttccaaacga tcagccatca actaccgcca gtgagcgttt ggccgaggaa    32280
gctcgcccca aacatgataa caatgccgcc gacgacgccg gcaaccagcc caagcgaagc    32340
ccgcccgaac atccaggaga tcccgatagc gacaatgccg agaacagcga gtgactggcc    32400
gaacggacca aggataaacg tgcatatatt gttaaccatt gtggcggggt cagtgccgcc    32460
acccgcagat tgcgctgcgg cgggtccgga tgaggaaatg ctccatgcaa ttgcaccgca    32520
caagcttggg gcgcagctcg atatcacgcg catcatcgca ttcgagagcg agaggcgatt    32580
tagatgtaaa cggtatctct caaagcatcg catcaatgcg cacctcctta gtataagtcg    32640
aataagactt gattgtcgtc tgcggatttg ccgttgtcct ggtgtggcgg tggcggagcg    32700
attaaaccgc cagcgccatc ctcctgcgag cggcgctgat atgaccccca aacatcccac    32760
gtctcttcgg atttttagcgc ctcgtgatcg tcttttggag gctcgattaa cgcgggcacc    32820
agcgattgag cagctgtttc aacttttcgc acgtagccgt ttgcaaaacc gccgatgaaa    32880
ttaccggtgt tgtaagcgga gatcgcccga cgaagcgcaa attgcttctc gtcaatcgtt    32940
tcgccgcctg cataacgact tttcagcatg tttgcagcgg cagataatga tgtgcacgcc    33000
tggagcgcac cgtcaggtgt cagaccgagc atagaaaaat ttcgagagtt tatttgcatg    33060
aggccaacat ccagcgaatg ccgtgcatcg agacggtgcc tgacgacttg ggttgcttgg    33120
ctgtgatctt gccagtgaag cgtttcgccg gtcgtgttgt catgaatcgc taaaggatca    33180
aagcgactct ccaccttagc tatcgccgca agcgtagatg tcgcaactga tggggcacac    33240
ttgcgagcaa catggtcaaa ctcagcagat gagagtggcg tggcaaggct cgacgaacag    33300
aaggagacca tcaaggcaag agaaagcgac cccgatctct taagcatacc ttatctcctt    33360
agctcgcaac taacaccgcc tctcccgttg gaagaagtgc gttgttttat gttgaagatt    33420
atcgggaggg tcggttactc gaaaattttc aattgcttct ttatgatttc aattgaagcg    33480
agaaacctcg cccggcgtct tggaacgcaa catggaccga gaaccgcgca tccatgacta    33540
agcaaccgga tcgacctatt caggccgcag ttggtcaggt caggctcaga acgaaaatgc    33600
tcggcgaggt tacgctgtct gtaaacccat tcgatgaacg ggaagcttcc ttccgattgc    33660
tcttggcagg aatattggcc catgcctgct tgcgctttgc aaatgctctt atcgcgttgg    33720
```

```
tatcatatgc cttgtccgcc agcagaaacg cactctaagc gattatttgt aaaaatgttt    33780
cggtcatgcg gcggtcatgg gcttgacccg ctgtcagcgc aagacggatc ggtcaaccgt    33840
cggcatcgac aacagcgtga atcttggtgg tcaaaccgcc acgggaacgt cccatacagc    33900
catcgtcttg atcccgctgt ttcccgtcgc cgcatgttgg tggacgcgga cacaggaact    33960
gtcaatcatg acgacattct atcgaaagcc ttggaaatca cactcagaat atgatcccag    34020
acgtctgcct cacgccatcg tacaaagcga ttgtagcagg ttgtacagga accgtatcga    34080
tcaggaacgt ctgcccaggg cgggcccgtc cggaagcgcc acaagatgac attgatcacc    34140
cgcgtcaacg cgcggcacgc gacgcggctt atttgggaac aaaggactga acaacagtcc    34200
attcgaaatc ggtgacatca aagcggggac gggttatcag tggcctccaa gtcaagcctc    34260
aatgaatcaa aatcagaccg atttgcaaac ctgatttatg agtgtgcggc ctaaatgatg    34320
aaatcgtcct tctagatcgc ctccgtggtg tagcaacacc tcgcagtatc gccgtgctga    34380
ccttggccag ggaattgact ggcaagggtg cttttcacatg accgctcttt tggccgcgat    34440
agatgatttc gttgctgctt tgggcacgta aaggagaga agtcatatcg gagaaattcc    34500
tcctggcgcg agagcctgct ctatcgcgac ggcatcccac tgtcgggaac agaccggatc    34560
attcacgagg cgaaagtcgt caacacatgc gttataggca tcttcccttg aaggatgatc    34620
ttgttgctgc caatctggag gtgcggcagc cgcaggcaga tgcgatctca gcgcaacttg    34680
cggcaaaaca tctcactcac ctgaaaacca ctagcgagtc tcgcgatcag acgaaggcct    34740
tttacttaac gacacaatat ccgatgtctg catcacaggc gtcgctatcc cagtcaatac    34800
taaagcggtg caggaactaa agattactga tgacttaggc gtgccacgag gcctgagacg    34860
acgcgcgtag acagtttttt gaaatcatta tcaaagtgat ggcctccgct gaagcctatc    34920
acctctgcgc cggtctgtcg gagagatggg caagcattat tacggtcttc gcgcccgtac    34980
atgcattgga cgattgcagg gtcaatggat ctgagatcat ccagaggatt gccgcccttc    35040
ccttccgttt cgagttggag ccagccccta aatgagacga catagtcgac ttgatgtgac    35100
aatgccaaga gagagatttg cttaacccga ttttttttgct caagcgtaag cctattgaag    35160
cttgccggca tgacgtccgc gccgaaagaa tatcctacaa gtaaaacatt ctgcacaccg    35220
aaatgcttgg tgtagacatc gattatgtga ccaagatcct tagcagtttc gcttggggac    35280
cgctccgacc agaaataccg aagtgaactg acgccaatga caggaatccc ttccgtctgc    35340
agataggtac catcgataga tctgctgcct cgcgcgtttc ggtgatgacg gtgaaaacct    35400
ctgacacatg cagctcccgg agacggtcac agcttgtctg taagcggatg ccgggagcag    35460
acaagcccgt cagggcgcgt cagcgggtgt tggcgggtgt cggggcgcag ccatgaccca    35520
gtcacgtagc gatagcggag tgtatactgg cttaactatg cggcatcaga gcagattgta    35580
ctgagagtgc accatatgcg gtgtgaaata ccgcacagat gcgtaaggag aaaataccgc    35640
atcaggcgct cttccgcttc ctcgctcact gactcgctgc gctcggtcgt tcggctgcgg    35700
cgagcggtat cagctcactc aaaggcggta atacggttat ccacagaatc aggggataac    35760
gcaggaaaga acatgtgagc aaaaggccag caaaaggcca ggaaccgtaa aaaggccgcg    35820
ttgctggcgt ttttccatag gctccgcccc cctgacgagc atcacaaaaa tcgacgctca    35880
agtcagaggt ggcgaaaccc gacaggacta taaagatacc aggcgtttcc ccctggaagc    35940
tccctcgtgc gctctcctgt tccgaccctg ccgcttaccg gatacctgtc cgcctttctc    36000
ccttcgggaa gcgtggcgct ttctcatagc tcacgctgta ggtatctcag ttcggtgtag    36060
```

```
gtcgttcgct ccaagctggg ctgtgtgcac gaaccccccg ttcagcccga ccgctgcgcc   36120
ttatccggta actatcgtct tgagtccaac ccggtaagac acgacttatc gccactggca   36180
gcagccactg gtaacaggat tagcagagcg aggtatgtag gcggtgctac agagttcttg   36240
aagtggtggc ctaactacgg ctacactaga aggacagtat ttggtatctg cgctctgctg   36300
aagccagtta ccttcggaaa aagagttggt agctcttgat ccggcaaaca aaccaccgct   36360
ggtagcggtg gttttttgt ttgcaagcag cagattacgc gcagaaaaaa aggatctcaa   36420
gaagatcctt tgatcttttc tacggggtct gacgctcagt ggaacgaaaa ctcacgttaa   36480
gggattttgg tcatgagatt atcaaaaagg atcttcacct agatcctttt aaattaaaaa   36540
tgaagtttta aatcaatcta agtatatat gagtaaactt ggtctgacag ttaccaatgc   36600
ttaatcagtg aggcacctat ctcagcgatc tgtctatttc gttcatccat agttgcctga   36660
ctccccgtcg tgtagataac tacgatacgg gagggcttac catctggccc cagtgctgca   36720
atgataccgc gagacccacg ctcaccggct ccagatttat cagcaataaa ccagccagcc   36780
ggaagggccg agcgcagaag tggtcctgca actttatccg cctccatcca gtctattaat   36840
tgttgccggg aagctagagt aagtagttcg ccagttaata gtttgcgcaa cgttgttgcc   36900
attgctgcag ggggggggg gggggggac ttccattgtt cattccacgg acaaaaacag   36960
agaaaggaaa cgacagaggc caaaaagcct cgctttcagc acctgtcgtt cctttctttt   37020
tcagagggta ttttaaataa aaacattaag ttatgacgaa gaagaacgga aacgccttaa   37080
accggaaaat tttcataaat agcgaaaacc cgcgaggtcg ccgccccgta acctgtcgga   37140
tcaccggaaa ggaccgtaa agtgataatg attatcatct acatatcaca acgtgcgtgg   37200
aggccatcaa accacgtcaa ataatcaatt atgacgcagg tatcgtatta attgatctgc   37260
atcaacttaa cgtaaaaaca acttcagaca atacaaatca gcgacactga atacggggca   37320
acctcatgtc ccccccccc cccccctgc aggcatcgtg gtgtcacgct cgtcgtttgg   37380 tatgcttca ttcagctccg gttcccaacg atcaaggcga gttacatgat cccccatgtt   37440
gtgcaaaaaa gcggttagct ccttcggtcc tccgatcgtt gtcagaagta agttggccgc   37500
agtgttatca ctcatggtta tggcagcact gcataattct cttactgtca tgccatccgt   37560
aagatgcttt tctgtgactg gtgagtactc aaccaagtca ttctgagaat agtgtatgcg   37620
gcgaccgagt tgctcttgcc cggcgtcaac acgggataat accgcgccac atagcagaac   37680
tttaaaagtg ctcatcattg gaaaacgttc ttcggggcga aaactctcaa ggatcttacc   37740
gctgttgaga tccagttcga tgtaacccac tcgtgcaccc aactgatctt cagcatcttt   37800
tactttcacc agcgtttctg ggtgagcaaa aacaggaagg caaaatgccg caaaaaaggg   37860
aataagggcg acacggaaat gttgaatact catactcttc ctttttcaat attattgaag   37920
catttatcag ggttattgtc tcatgagcgg atacatattt gaatgtattt agaaaaataa   37980
acaaataggg gttccgcgca catttccccg aaaagtgcca cctgacgtct aagaaaccat   38040
tattatcatg acattaacct ataaaaatag gcgtatcacg aggccctttc gtcttcaaga   38100
attggtcgac gatcttgctg cgttcggata ttttcgtgga gttcccgcca cagacccgga   38160
ttgaaggcga gatccagcaa ctcgcgccag atcatcctgt gacggaactt ggcgcgtga   38220 tgactggcca ggacgtcggc cgaaagagcg acaagcagat cacgcttttc gacagcgtcg   38280
gatttgcgat cgaggatttt tcggcgctgc gctacgtccg cgaccgcgtt gagggatcaa   38340
gccacagcag cccactcgac cttctagccg acccagacga gccaagggat cttttggaa   38400 tgctgctccg tcgtcaggct ttccgacgtt tgggtggttg aacagaagtc attatcgtac   38460
```

```
ggaatgccaa gcactcccga ggggaaccct gtggttggca tgcacataca aatggacgaa    38520
cggataaacc ttttcacgcc cttttaaata tccgttattc taataaacgc tcttttctct    38580
taggtttacc cgccaatata tcctgtcaaa cactgatagt ttaaactgaa ggcgggaaac    38640
gacaatctga tcatgagcgg agaattaagg gagtcacgtt atgaccccg ccgatgacgc     38700 gggacaagcc gttttacgtt tggaactgac agaaccgcaa cgttgaagga gccactcagc    38760
ccaagctggt acgattgtaa tacgactcac tatagggcga attgagcgct gtttaaacgc    38820
tcttcaactg gaagagcggt taccagaggc cagaatggcc atctcggacc gatatcgcta    38880
tcaactttgt atagaaaagt tgggccgaat tcgagctcgg tacggccaga atggcccgga    38940
ccgggttacc cggaccgaag cttgcatgcc tgcagtgcag cgtgacccgg tcgtgcccct    39000
ctctagagat aatgagcatt gcatgtctaa gttataaaaa attaccacat atttttttg     39060 tcacacttgt ttgaagtgca gtttatctat ctttatacat atatttaaac tttactctac    39120
gaataatata atctatagta ctacaataat atcagtgttt tagagaatca tataaatgaa    39180
cagttagaca tggtctaaag gacaattgag tattttgaca acaggactct acagttttat    39240
ctttttagtg tgcatgtgtt ctcctttttt tttgcaaata gcttcaccta tataatactt    39300
catccatttt attagtacat ccatttaggg tttagggtta atggttttta tagactaatt    39360
tttttagtac atctatttta ttctatttta gcctctaaat taagaaaact aaaactctat    39420
tttagttttt ttatttaata atttagatat aaaatagaat aaaataaagt gactaaaaat    39480
taaacaaata cccttttaaga aattaaaaaa actaaggaaa cattttttctt gtttcgagta   39540 gataatgcca gcctgttaaa cgccgtcgac gagtctaacg gacaccaacc agcgaaccag    39600
cagcgtcgcg tcgggccaag cgaagcagac ggcacggcat ctctgtcgct gcctctggac    39660
ccctctcgag agttccgctc caccgttgga cttgctccgc tgtcggcatc cagaaattgc    39720
gtggcggagc ggcagacgtg agccggcacg gcaggcggcc tcctcctcct ctcacggcac    39780
cggcagctac gggggattcc tttcccaccg ctccttcgct ttcccttcct cgcccgccgt    39840
aataaataga cacccctcc acaccctctt tccccaacct cgtgttgttc ggagcgcaca    39900
cacacacaac cagatctccc ccaaatccac ccgtcggcac ctccgcttca aggtacgccg    39960
ctcgtcctcc cccccccccc tctctacctt ctctagatcg gcgttccggt ccatgcatgg    40020
ttagggcccg gtagttctac ttctgttcat gtttgtgtta gatccgtgtt tgtgttagat    40080
ccgtgctgct agcgttcgta cacggatgcg acctgtacgt cagacacgtt ctgattgcta    40140
acttgccagt gtttctcttt ggggaatcct gggatggctc tagccgttcc gcagacggga    40200
tcgatttcat gatttttttt gtttcgttgc atagggtttg gtttgcccctt tcctttatt    40260 tcaatatatg ccgtgcactt gtttgtcggg tcatcttttc atgcttttt ttgtcttggt     40320 tgtgatgatg tggtctggtt gggcggtcgt tctagatcgg agtagaattc tgtttcaaac    40380
tacctggtgg atttattaat tttggatctg tatgtgtgtg ccatacatat tcatagttac    40440
gaattgaaga tgatggatgg aaatatcgat ctaggatagg tatacatgtt gatgcgggtt    40500
ttactgatgc atatacagag atgcttttg ttcgcttggt tgtgatgatg tggtgtggtt      40560
gggcggtcgt tcattcgttc tagatcggag tagaatactg tttcaaacta cctggtgtat    40620
ttattaattt tggaactgta tgtgtgtgtc atacatcttc atagttacga gtttaagatg    40680
gatggaaata tcgatctagg ataggtatac atgttgatgt gggttttact gatgcatata    40740
catgatggca tatgcagcat ctattcatat gctctaacct tgagtaccta tctattataa    40800
```

```
taaacaagta tgttttataa ttattttgat cttgatatac ttggatgatg gcatatgcag   40860
cagctatatg tggattttt tagccctgcc ttcatacgct atttatttgc ttggtactgt    40920
ttcttttgtc gatgctcacc ctgttgtttg gtgttacttc tgcaggtcga ctctagagga   40980
tccaccacca tggccccgaa gaagaagcgc aaggtgatca tgaacaccaa gtacaacaag   41040
gagttcctgc tctacctggc cggcttcgtg gacggcgacg gctccatcat cgcggccatc   41100
gacccggagc agagccgcaa gttcaagcac cgcctccgcc tgcgcttcac cgtgacccag   41160
aagacgcaga ggcgctggtt cctcgacaag ctggtcgacg agatcggggt gggctacgtc   41220
cgcgaccggg ggtcggtgtc cgactaccag ctcagcaaga tcaagcccct gcacaacttc   41280
ctcacccagc tccagccgtt cctcaagctg aagcagaagc aggcgaacct cgtcctgaag   41340
atcatcgagc agctcccctc ggccaaggag tccccggaca agttcctgga ggtgtgcacg   41400
tgggtcgacc agatcgcggc cctcaacgac agcaagaccc gcaagacgac ctcggagacg   41460
gtgcgggcgg tcctggactc cctcagcgag aagaagaagt cgtcccctg aggtaccaca    41520
tggttaacct agacttgtcc atcttctgga ttggccaact taattaatgt atgaaataaa   41580
aggatgcaca catagtgaca tgctaatcac tataatgtgg gcatcaaagt tgtgtgttat   41640
gtgtaattac tagttatctg aataaaagag aaagagatca tccatatttc ttatcctaaa   41700
tgaatgtcac gtgtctttat aattctttga tgaaccagat gcatttcatt aaccaaatcc   41760
atatacatat aaatattaat catatataat taatatcaat tgggttagca aaacaaatct   41820
agtctaggtg tgttttgcga atgcggccgc caccgcggtg gagctcgaat tccggtccgg   41880
gtcacccggt ccgggcctag aaggccagct tcaagtttgt acaaaaaagc aggctccggc   41940
cagaatggcc cggaccgggt taccgaattc gagctcggta ccctgggatc cgatatcgat   42000
gggccctggc cgaagctggc cgctcattaa ttaagtcagg cgcgcctcta gttgaagaca   42060
cgttcatgtc ttcatcgtaa gaagacactc agtagtcttc ggccagaatg gccatctgga   42120
ttcagcaggc ctagaaggcc atttaaatcc tgaggatctg gtcttcctaa ggaccccgga   42180
tatcggaccg attaaacttt aattcggtcc gaagcttgca tgcctgcagt gcagcgtgac   42240
ccggtcgtgc ccctctctag agataatgag cattgcatgt ctaagttata aaaaattacc   42300
acatatttt tttgtcacac ttgtttgaag tgcagtttat ctatctttat acatatattt    42360
aaactttact ctacgaataa tataatctat agtactacaa taatatcagt gttttagaga   42420
atcatataaa tgaacagtta gacatggtct aaaggacaat tgagtatttt gacaacagga   42480
ctctacagtt ttatcttttt agtgtgcatg tgttctcctt ttttttttgca aatagcttca   42540
cctatataat acttcatcca ttttattagt acatccattt agggtttagg gttaatggtt   42600
tttatagact aatttttta gtacatctat tttattctat tttagcctct aaattaagaa    42660
aactaaaact ctattttagt ttttttattt aataatttag atataaaata gaataaaata   42720
aagtgactaa aaattaaaca aatacccttt aagaaattaa aaaaactaag gaaacatttt   42780
tcttgttcg agtagataat gccagcctgt taaacgccgt cgacgagtct aacggacacc     42840
aaccagcgaa ccagcagcgt cgcgtcgggc caagcgaagc agacggcacg gcatctctgt   42900
cgctgcctct ggaccctct cgagagttcc gctccaccgt tggacttgct ccgctgtcgg    42960
catccagaaa ttgcgtggcg gagcggcaga cgtgagccgg cacggcaggc ggcctcctcc   43020
tcctctcacg gcaccggcag ctacggggga ttccttccc accgctcctt cgctttccct    43080
tcctcgcccg ccgtaataaa tagacacccc ctccacaccc tctttcccca acctcgtgtt   43140
gttcggagcg cacacacaca caaccagatc tcccccaaat ccacccgtcg gcacctccgc   43200
```

```
ttcaaggtac gccgctcgtc ctcccccccc ccctctcta ccttctctag atcggcgttc  43260
cggtccatgc atggttaggg cccggtagtt ctacttctgt tcatgtttgt gttagatccg  43320
tgtttgtgtt agatccgtgc tgctagcgtt cgtacacgga tgcgacctgt acgtcagaca  43380
cgttctgatt gctaacttgc cagtgtttct ctttggggaa tcctgggatg gctctagcca  43440
ttccgcagac gggatcgatt tcatgatttt ttttgtttcg ttgcataggg tttggtttgc  43500
cctttccctt tatttcaata tatgccgtgc acttgtttgt cgggtcatct tttcatgctt  43560 tttttgtct tggttgtgat gatgtggtct ggttgggcgg tcgttctaga tcggagtaga  43620
attctgtttc aaactacctg gtggatttat taattttgga tctgtatgtg tgtgccatac  43680
atattcatag ttacgaattg aagatgatgg atggaaatat cgatctagga taggtataca  43740
tgttgatgcg ggttttactg atgcatatac agagatgctt tttgttcgct tggttgtgat  43800
gatgtggtgt ggttgggcgg tcgttcattc gttctagatc ggagtagaat actgtttcaa  43860
actacctggt gtatttatta atttggaac tgtatgtgtg tgtcatacat cttcatagtt  43920
acgagtttaa gatggatgga aatatcgatc taggataggt atacatgttg atgtgggttt  43980
tactgatgca tatacatgat ggcatatgca gcatctattc atatgctcta accttgagta  44040
cctatctatt ataataaaca agtatgtttt ataattattt tgatcttgat atacttggat  44100
gatggcatat gcagcagcta tatgtggatt tttttagccc tgccttcata cgctatttat  44160
ttgcttggta ctgtttctt tgtcgatgct caccctgttg tttggtgtta cttctgcagg  44220
tcgactctag aggatccacc accatggccc gaagaagaa gcgcaaggtg atcatgaaca  44280
ccaagtacaa caaggagttc ctgctctacc tggccggctt cgtggacggc gacggctcca  44340
tcaaggcgag catcagcccg aaccagagct gcaagttcaa gcaccagctc cgcctgacct  44400
tccaggtgac ccagaagacg cagaggcgct ggttcctcga caagctggtc gacgagatcg  44460
gggtgggcta cgtctacgac cggggggtcgg tgtccgacta ccgcctcagc aagatcaagc  44520
ccctgcacaa cttcctcacc cagctccagc cgttcctcaa gctgaagcag aagcaggcga  44580
acctcgtcct gaagatcatc gagcagctcc cctcggccaa ggagtccccg gacaagttcc  44640
tggaggtgtg cacgtgggtc gaccagatcg cggccctcaa cgacagcaag acccgcaaga  44700
cgacctcgga cacggtgcgg gcggtcctgg actccctcag cgagaagaag aagtcgtccc  44760
cctgaggtac cacatggtta acctagactt gtccatcttc tggattggcc aacttaatta  44820
atgtatgaaa taaaggatg cacacatagt gacatgctaa tcactataat gtgggcatca  44880
aagttgtgtg ttatgtgtaa ttactagtta tctgaataaa agagaaagag atcatccata  44940
tttcttatcc taaatgaatg tcacgtgtct ttataattct ttgatgaacc agatgcattt  45000
cattaaccaa atccatatac atataaatat taatcatata taattaatat caattgggtt  45060
agcaaaacaa atctagtcta ggtgtgtttt gcgaattgcg gccagcttgg tcacccggtc  45120
cgggcctaga aggccgatct cccgggcacc cagctttctt gtacaaagtg gccgttaacg  45180
gatcggccag aatggcccgg accgggttac ccggaccgaa gctggccgcg atctgagctt  45240
ctagaaatcc gtcaacatgg tggagcacga cactctcgtc tactccaaga atatcaaaga  45300
tacagtctca gaagaccaaa gggctattga acttttcaa caaagggtaa tatcgggaaa  45360
cctcctcgga ttccattgcc cagctatctg tcacttcatc aaaaggacag tagaaaagga  45420
aggtggcacc tacaaatgcc atcattgcga taaaggaaag gctatcgttc aagatgcctc  45480
tgccgacagt ggtcccaaag atggacccc acccacgagg agcatcgtgg aaaaagaaga  45540
```

-continued

| | |
|---|---|
| cgttccaacc acgtcttcaa agcaagtgga ttgatgtgat gctctagaaa tccgtcaaca | 45600 |
| tggtggagca cgacactctc gtctactcca agaatatcaa agatacagtc tcagaagacc | 45660 |
| aaagggctat tgagactttt caacaaaggg taatatcggg aaacctcctc ggattccatt | 45720 |
| gcccagctat ctgtcacttc atcaaaagga cagtagaaaa ggaaggtggc acctacaaat | 45780 |
| gccatcattg cgataaagga aaggctatcg ttcaagatgc ctctgccgac agtggtccca | 45840 |
| aagatggacc cccacccacg aggagcatcg tggaaaaaga agacgttcca accacgtctt | 45900 |
| caaagcaagt ggattgatgt gatatctcca ctgacgtaag ggatgacgca caatcccact | 45960 |
| atccttcgca agaccctccc tctatataag gaagttcatt tcatttggag aggacgagct | 46020 |
| gcagcttatt tttacaacaa ttaccaacaa caacaaacaa caaacaacat tacaattact | 46080 |
| atttacaatt acagtcgacg gatcaagtgc aaaggtccgc cttgtttctc ctctgtctct | 46140 |
| tgatctgact aatcttggtt tatgattcgt tgagtaattt tggggaaagc ttcgtccaca | 46200 |
| gttttttttt cgatgaacag tgccgcagtg gcgctgatct tgtatgctat cctgcaatcg | 46260 |
| tggtgaactt atgtctttta tatccttcac taccatgaaa agactagtaa tctttctcga | 46320 |
| tgtaacatcg tccagcactg ctattaccgt gtggtccatc cgacagtctg gctgaacaca | 46380 |
| tcatacgata ttgagcaaag atcgatctat cttccctgtt cttaatgaa agacgtcatt | 46440 |
| ttcatcagta tgatctaaga atgttgcaac ttgcaaggag gcgtttcttt ctttgaattt | 46500 |
| aactaactcg ttgagtggcc ctgtttctcg gacgtaaggc ctttgctgct ccacacatgt | 46560 |
| ccattcgaat tttaccgtgt ttagcaaggg cgaaaagttt gcatcttgat gatttagctt | 46620 |
| gactatgcga ttgcttttcct ggacccgtgc agctgcggac gggatccacc atgagcccag | 46680 |
| aacgacgccc ggccgacatc cgccgtgcca ccgaggcgga catgccggcg gtctgcacca | 46740 |
| tcgtcaacca ctacatcgag acaagcacgg tcaacttccg taccgagccg caggaaccgc | 46800 |
| aggactggac ggacgacctc gtccgtctgc gggagcgcta tccctggctc gtcgccgagg | 46860 |
| tggacggcga ggtcgccggc atcgcctacg cgggcccctg gaaggcacgc aacgcctacg | 46920 |
| actggacggc cgagtcgacc gtgtacgtct ccccccgcca ccagcggacg ggactgggct | 46980 |
| ccacgctcta cacccacctg ctgaagtccc tggaggcaca gggcttcaag agcgtggtcg | 47040 |
| ctgtcatcgg gctgcccaac gacccgagcg tgcgcatgca cgaggcgctc ggatatgccc | 47100 |
| cccgcggcat gctgcgggcg gccggcttca agcacgggaa ctggcatgac gtgggttcct | 47160 |
| ggcagctgga cttcagcctg ccggtaccgc cccgtccggt cctgcccgtc accgagatct | 47220 |
| gatccgtcga ccaacctaga cttgtccatc ttctggattg gccaacttaa ttaatgtatg | 47280 |
| aaataaaagg atgcacacat agtgacatgc taatcactat aatgtgggca tcaaagttgt | 47340 |
| gtgttatgtg taattactag ttatctgaat aaaagagaaa gagatcatcc atatttctta | 47400 |
| tcctaaatga atgtcacgtg tctttataat tctttgatga accagatgca tttcattaac | 47460 |
| caaatccata tacatataaa tattaatcat atataattaa tatcaattgg gttagcaaaa | 47520 |
| caaatctagt ctaggtgtgt tttgcgaatg cggccgccac cgcggtggag ctcgaattcc | 47580 |
| ggtccgggtc acccggtccg ggcctagaag gccagcttgc ggccgccccg gcaacttta | 47640 |
| ttatacaaag ttgatagata tcggtccgag cggcctagaa ggcctttggt cacctttgtc | 47700 |
| caccaagatg gaactgcggc cgctcattaa ttaagtcagg cgcgcctcta gttgaagaca | 47760 |
| cgttcatgtc ttcatcgtaa gaagacactc agtagtcttc ggccagaatg gcctaactca | 47820 |
| aggccatcgt ggcctcttgc tcttcaggat gaagagctat gtttaaacgt gcaagcgcta | 47880 |
| ctagacaatt cagtacatta aaaacgtccg caatgtgtta ttaagttgtc taagcgtcaa | 47940 |

```
tttgtttaca ccacaatata tcctgccacc agccagccaa cagctccccg accggcagct   48000
cggcacaaaa tcaccactcg atacaggcag cccatcagtc cgggacggcg tcagcgggag   48060
agccgttgta aggcggcaga ctttgctcat gttaccgatg ctattcggaa gaacggcaac   48120
taagctgccg ggtttgaaac acggatgatc tcgcggaggg tagcatgttg attgtaacga   48180
tgacagagcg ttgctgcctg tgatcaaata tcatctccct cgcagagatc cgaattatca   48240
gccttcttat tcatttctcg cttaaccgtg acaggctgtc gatcttgaga actatgccga   48300
cataatagga aatcgctgga taaagccgct gaggaagctg agtggcgcta tttctttaga   48360
agtgaacgtt gacgatcgtc gaccgtaccc cgatgaatta attcggacgt acgttctgaa   48420
cacagctgga tacttacttg ggcgattgtc atacatgaca tcaacaatgt acccgtttgt   48480
gtaaccgtct cttggaggtt cgtatgacac tagtggttcc cctcagcttg cgactagatg   48540
ttgaggccta acatttttatt agagagcagg ctagttgctt agatacatga tcttcaggcc   48600
gttatctgtc agggcaagcg aaaattggcc atttatgacg accatgccc cgcagaagct   48660 cccatctttg ccgccataga cgccgcgccc cccttttggg gtgtagaaca tccttttgcc   48720
agatgtggaa aagaagttcg ttgtcccatt gttggcaatg acgtagtagc cggcgaaagt   48780
gcgagaccca tttgcgctat atataagcct acgatttccg ttgcgactat tgtcgtaatt   48840
ggatgaacta ttatcgtagt tgctctcaga gttgtcgtaa tttgatggac tattgtcgta   48900
attgcttatg gagttgtcgt agttgcttgg agaaatgtcg tagttggatg gggagtagtc   48960
atagggaaga cgagcttcat ccactaaaac aattggcagg tcagcaagtg cctgccccga   49020
tgccatcgca agtacgaggc ttagaaccac cttcaacaga tcgcgcatag tcttccccag   49080
ctctctaacg cttgagttaa gccgcgccgc gaagcggcgt cggcttgaac gaattgttag   49140
acattatttg ccgactacct tggtgatctc gcctttcacg tagtgaacaa attcttccaa   49200
ctgatctgcg cgcgaggcca agcgatcttc ttgtccaaga taagcctgcc tagcttcaag   49260
tatgacgggc tgatactggg ccggcaggcg ctccattgcc cagtcggcag cgacatcctt   49320
cggcgcgatt ttgccggtta ctgcgctgta ccaaatgcgg gacaacgtaa gcactacatt   49380
tcgctcatcg ccagcccagt cgggcggcga gttccatagc gttaaggttt catttagcgc   49440
ctcaaataga tcctgttcag gaaccggatc aaagagttcc tccgccgctg gacctaccaa   49500
ggcaacgcta tgttctcttg cttttgtcag caagatagcc agatcaatgt cgatcgtggc   49560
tggctcgaag atacctgcaa gaatgtcatt gcgctgccat tctccaaatt gcagttcgcg   49620
cttagctgga taacgccacg gaatgatgtc gtcgtgcaca acaatggtga cttctacagc   49680
gcggagaatc tcgctctctc caggggaagc cgaagtttcc aaaaggtcgt tgatcaaagc   49740
tcgccgcgtt gtttcatcaa gccttacagt caccgtaacc agcaaatcaa tatcactgtg   49800
tggcttcagg ccgccatcca ctgcggagcc gtacaaatgt acggccagca acgtcggttc   49860
gagatggcgc tcgatgacgc caactacctc tgatagttga gtcgatactt cggcgatcac   49920
cgcttccctc atgatgttta actcctgaat taagccgcgc gcgaagcgg tgtcggcttg   49980 aatgaattgt taggcgtcat cctgtgctcc cgagaaccag taccagtaca tcgctgtttc   50040
gttcgagact tgaggtctag ttttatacgt gaacaggtca atgccgccga gagtaaagcc   50100
acattttgcg tacaaattgc aggcaggtac attgttcgtt tgtgtctcta atcgtatgcc   50160
aaggagctgt ctgcttagtg cccactttttt cgcaaattcg atgagactgt gcgcgactcc   50220
tttgcctcgg tgcgtgtgcg acacaacaat gtgttcgata gaggctagat cgttccatgt   50280
```

```
tgagttgagt tcaatcttcc cgacaagctc ttggtcgatg aatgcgccat agcaagcaga    50340
gtcttcatca gagtcatcat ccgagatgta atccttccgg tagggctca cacttctggt    50400 agatagttca aagccttggt cggataggtg cacatcgaac acttcacgaa caatgaaatg    50460
gttctcagca tccaatgttt ccgccacctg ctcaggatc accgaaatct tcatatgacg    50520
cctaacgcct ggcacagcgg atcgcaaacc tggcgcggct tttggcacaa aaggcgtgac    50580
aggtttgcga atccgttgct gccacttgtt aacccttttg ccagatttgg taactataat    50640
ttatgttaga ggcgaagtct tgggtaaaaa ctggcctaaa attgctgggg atttcaggaa    50700
agtaaacatc accttccggc tcgatgtcta ttgtagatat atgtagtgta tctacttgat    50760
cgggggatct gctgcctcgc gcgtttcggt gatgacggtg aaaacctctg acacatgcag    50820
ctcccggaga cggtcacagc ttgtctgtaa gcggatgccg ggagcagaca agcccgtcag    50880
ggcgcgtcag cgggtgttgg cgggtgtcgg ggcgcagcca tgacccagtc acgtagcgat    50940
agcggagtgt atactggctt aactatgcgg catcagagca gattgtactg agagtgcacc    51000
atatgcggtg tgaaataccg cacagatgcg taaggagaaa ataccgcatc aggcgctctt    51060
ccgcttcctc gctcactgac tcgctgcgct cggtcgttcg gctgcggcga gcggtatcag    51120
ctcactcaaa ggcggtaata cggttatcca cagaatcagg ggataacgca ggaaagaaca    51180
tgtgagcaaa aggccagcaa aaggccagga accgtaaaaa ggccgcgttg ctggcgtttt    51240
tccataggct ccgcccccct gacgagcatc acaaaaatcg acgctcaagt cagaggtggc    51300
gaaacccgac aggactataa agataccagg cgtttccccc tggaagctcc ctcgtgcgct    51360
ctcctgttcc gaccctgccg cttaccggat acctgtccgc ctttctccct tcgggaagcg    51420
tggcgctttc tcatagctca cgctgtaggt atctcagttc ggtgtaggtc gttcgctcca    51480
agctgggctg tgtgcacgaa ccccccgttc agcccgaccg ctgcgcctta tccggtaact    51540
atcgtcttga gtccaacccg gtaagacacg acttatcgcc actggcagca gccactggta    51600
acaggattag cagagcgagg tatgtaggcg gtgctacaga gttcttgaag tggtggccta    51660
actacggcta cactagaagg acagtatttg gtatctgcgc tctgctgaag ccagttacct    51720
tcggaaaaag agttggtagc tcttgatccg gcaaacaaac caccgctggt agcggtggtt    51780
tttttgtttg caagcagcag attacgcgca gaaaaaaagg atctcaagaa gatcctttga    51840
tcttttctac ggggtctgac gctcagtgga acgaaaactc acgttaaggg attttggtca    51900
tgagattatc aaaaaggatc ttcacctaga tccttttaaa ttaaaaatga agttttaaat    51960
caatctaaag tatatatgag taaacttggt ctgacagtta ccaatgctta atcagtgagg    52020
cacctatctc agcgatctgt ctatttcgtt catccatagt tgcctgactc cccgtcgtgt    52080
agataactac gatacgggag ggcttaccat ctggccccag tgctgcaatg ataccgcgag    52140
acccacgctc accggctcca gatttatcag caataaacca gccagccgga agggccgagc    52200
gcagaagtgg tcctgcaact ttatccgcct ccatccagtc tattaattgt tgccgggaag    52260
ctagagtaag tagttcgcca gttaatagtt tgcgcaacgt tgttgccatt gctgca        52316
```

<210> SEQ ID NO 32
<211> LENGTH: 3052
<212> TYPE: DNA
<213> ORGANISM: Zea mays
<220> FEATURE:
<221> NAME/KEY: misc_feature
<222> LOCATION: (0)...(0)
<223> OTHER INFORMATION: nucleotide sequence of a male fertility gene
      encoding a MS22  protein in maize

```
<400> SEQUENCE: 32
aattcgcggg acgtggcgtt gtcggctccg tgtcggcggc cgaaccacca cgaatcactg    60
acgtatctcg tctcctctct cctctagact cccacgatac ggccaacgaa gtgtatgtac   120
atatataccc atggtcatat ggcaacaaac gccaacgcca gcagagcact gcccggcggc   180 cttttttccca tctctctctc tctctctgat ggggtgtgca tgcctgactg actgatagat   240
agatagatgg tcaggtccgt ctgatcctca tcggcctagc tcaccccacg cgaaaaaagc   300
cactgctggc tggcgcccag ttgcgcttgc aacagtcact ttaacgagct ccgtccttgc   360
gtttgccctc ctcgctctgc ccctgccgcc gctgccgctg cgtggtggtg ctggtgcatg   420
aggcaggcag gcgtactagt gcatgcaatt gcaatgcaac cgtaggagtg cgttgcgtac   480
cctggtctgt ccctgcggcc tggcctgccc ttgttcgttg cggatgcggg gggtgccggg   540
tgggtactgt actgtactac tgggtagaga gatactacta gatagagaga gagagaggtc   600
ggtcaccccg ggcgcgggac acagcctctg cgaaaaagcg atccatgtcg cgcctagctt   660
tgacccggaa cggatccccc aaccaggaac cagcagagca ggagggccag gccaccacct   720
ctcgccattc cattcccggt cctagctagt cctgttctgt tcctgtagca gtagcagtag   780
ctacggtact acgagtcctc ctcgacgtcc caggcactac tccactccac gcagcagcag   840
gcagcgagca tctctcgacc agatgcatac aagctacacc ctcctcggct ccgatcctac   900
ccatgccggc ccaggcggcc tataaaagcg cacccccggc ccgtcttcct cccactgcat   960
gcccattgcc cctcccccgg ccttcgccgt gccaacgaca cacctcatca ccggccggaa  1020
cattccacga ccgaagaaac cagtccctag ctagtccacg cacgaccaac aaggcaggcg  1080
agcgacgaca gtccaagcct ccaagaagaa gaagaagaag aagaagaaga agatgctgcg  1140
gatggaggtg cagcagcagg agtcgggagt gagcggcggc gtggtggcgg acgcggcggc  1200
ggcgggatcc gtggcggaag ccgcgacgac gacgatggtg gccgcggcgc cgcactcggc  1260
gtcggcgctg gcggtgtacg agcgggtggc gcgcatggcg ggcgggaacg cggtggtggt  1320
gttcagcgcc agcggctgct gcatgtgcca cgtcgtcaag cgcctgctgc tgggcctcgg  1380
cgtcggcccc accgtgtacg agctcgacca gatggccggc ggcggcgggg cagggagat  1440 ccaggcggcg ctggcgcagc tgctgccgcc gggccagccg cccctgcccg tcgtcttcgt  1500
tggcggccgc ctcctcggcg gcgtcgagaa ggtcatggcg tgccacatca acggcaccct  1560
cgtcccgctc ctcaagcagg ccggcgcgct ctggctctga tcgcgccgtc gtcgtcgtcg  1620
tcgtcgtcga tcggccactg caacagacaa cagtgtgcgt gtgtgtgtgg ctgtgtgcgc  1680
atctccgtgc atgcgatcga tcgctgcccc ttagttagtt actcactact tactaccttg  1740
cgttttaatg taacctctac taagctagct agctcttgtc ctgttccgtg catgagagag  1800
gtcgagtaat gccgcaatcg cctgctgcag ttaatgcagc agcgcacgac gacgtcgccg  1860
atgatggttg atggtgcatc gattattgca ctccatggat atcatccatc ttaaccggac  1920
gtggacgtac ggtgccccgg ccggtgcagc aggggccag tcagcagcct tgtaaaagcg  1980
tacccgtacg tacgtcgtcg agacatcaac gacgtacggg gacgcaacgc aaccagccaa  2040
aacgggatcg ttcgaactag agcaagacgt acggctttcg atgagctggc ggtgtgttag  2100
actgttagac ataaaaaaaa tacataatat aataaacata gaagctatcc atggtttcta  2160
gctttatgtt gggactgcac taatgaccat agcaatgcgc tcatcaagtt atcaaatttt  2220
actccctcca tggtgcctca caacagtacg tacgtagtcg tttcgtgatg aaacacaata  2280
cacaaaattt tactccctcc gtttcatttt acaagtcgtt tccaacagcc aatgcataaa  2340
```

-continued

```
tagcagcgac aactaaaatg aaacggagta atacgtaaaa agtctttata ggaaacaaaa    2400
cacgagcgtc aaccgtcaat cttcattata cgatgagagt ttgtagaaca tagaatacaa    2460
ttagtcgaat cccttctcgt gcgatatgta tatatacata cgacggacga actaaaccag    2520
taccataatc aaaatcaatg tattcagtaa gcccatctct aaatttccta aagtgcaaac    2580
aaagattaga ggtacgtcgc aaatatatat aaaaaaatcc actacacacg atcctctaat    2640
tactgctcct tattatcatg gttaggccac gtacaacggg tgtcttaagc tgtgtcttgt    2700
tgaaggaggg taaatgtaaa aaaactcaag acacatatct taacgaagat attgtgtttg    2760
gctttatgct cgatacatat gggaacagct gattggtaaa attaatttat tgaatgttcc    2820
gattgatgca atgaatatag caagacatat gttttaatta gacacgtcca ctgtattata    2880
ttgtgtttta gctatatctt atacttggag tatcgtgcag cggtgtcagg gttgtacata    2940
catgccctta gccatctacc gacggcattc aatgcgtgtg agataaatca ggataagagc    3000
gaaccatgag atgcataaga gaaccgattt ccctgaaata tgaaactgta gg            3052
```

<210> SEQ ID NO 33
<211> LENGTH: 27
<212> TYPE: DNA
<213> ORGANISM: Simian virus 40
<220> FEATURE:
<221> NAME/KEY: misc_feature
<222> LOCATION: (0)...(0)
<223> OTHER INFORMATION: nuclear localization DNA sequence used in
      MAY1/MAY fusions

<400> SEQUENCE: 33

```
atggccccga agaagaagcg caaggtg                                           27
```

<210> SEQ ID NO 34
<211> LENGTH: 1242
<212> TYPE: DNA
<213> ORGANISM: Artificial Sequence
<220> FEATURE:
<223> OTHER INFORMATION: plant optimized gene encoding a
      MAY1-linker-MAY2 protein

<400> SEQUENCE: 34

```
atgaacacca gtacaacaa ggagttcctg ctctacctgg ccggcttcgt ggacggcgac      60
ggctccatca tcgcggccat cgacccggag cagagccgca agttcaagca ccgcctccgc    120
ctgcgcttca ccgtgaccca gaagacgcag aggcgctggt tcctcgacaa gctggtcgac    180
gagatcgggg tgggctacgt ccgcgaccgg gggtcggtgt ccgactacca gctcagcaag    240
atcaagcccc tgcacaactt cctcacccag ctccagccgt tcctcaagct gaagcagaag    300
caggcgaacc tcgtcctgaa gatcatcgag cagctcccct cggccaagga gtccccggac    360
aagttcctgg aggtaagttt ctgcttctac ctttgatata tatataataa ttatcattaa    420
ttagtagtaa tataatattt caaatatttt tttcaaaata aaagaatgta gtatatagca    480
attgcttttc tgtagtttat aagtgtgtat atttttaattt ataactttc taatatatga    540 ccaaaacatg gtgatgtgca ggtgtgcacg tgggtcgacc agatcgcggc cctcaacgac    600
agcaagaccc gcaagacgac ctcggagacg gtgcgggcgg tcctggactc cctcccagga    660
tccgttggcg gtctcagccc ttctcaggct agctcggctg cttcctcagc cagcagctca    720
cctggctccg gtatcagcga ggctctcaga gcaggtgcca ccaagtccaa ggagttcctg    780
ctctacctgg ccggcttcgt ggacggcgac ggctccatca aggcgagcat cagcccgaac    840
```

```
cagagctgca agttcaagca ccagctccgc ctgaccttcc aggtgaccca gaagacgcag    900
aggcgctggt tcctcgacaa gctggtcgac gagatcgggg tgggctacgt ctacgaccgg    960
gggtcggtgt ccgactaccg cctcagcaag atcaagcccc tgcacaactt cctcacccag   1020
ctccagccgt tcctcaagct gaagcagaag caggcgaacc tcgtcctgaa gatcatcgag   1080
cagctcccct cggccaagga gtccccggac aagttcctgg aggtgtgcac gtgggtcgac   1140
cagatcgcgg ccctcaacga cagcaagacc cgcaagacga cctcggagac ggtgcgggcg   1200
gtcctggact ccctcagcga aagaagaag tcgtcccct ga                        1242
```

<210> SEQ ID NO 35
<211> LENGTH: 33
<212> TYPE: DNA
<213> ORGANISM: Zea mays
<220> FEATURE:
<221> NAME/KEY: allele
<222> LOCATION: (0)...(0)
<223> OTHER INFORMATION: Wild-type TS-MS26 target site DNA fragment of
      Figure 2

<400> SEQUENCE: 35
cggcgggatg gtgacgtacg tgccctactc gat                                  33

<210> SEQ ID NO 36
<211> LENGTH: 24
<212> TYPE: DNA
<213> ORGANISM: Zea mays
<220> FEATURE:
<221> NAME/KEY: allele
<222> LOCATION: (0)...(0)
<223> OTHER INFORMATION: 3281 TS-MS26 target site DNA fragment of
      Figure 2

<400> SEQUENCE: 36
cggcgggatg gtgacgtact cgat                                            24

<210> SEQ ID NO 37
<211> LENGTH: 32
<212> TYPE: DNA
<213> ORGANISM: Zea mays
<220> FEATURE:
<221> NAME/KEY: allele
<222> LOCATION: (0)...(0)
<223> OTHER INFORMATION: 2963 TS-MS26 target site DNA fragment of
      Figure 2

<400> SEQUENCE: 37
cggcgggatg gtgacgtcgt gccctactcg at                                   32

<210> SEQ ID NO 38
<211> LENGTH: 32
<212> TYPE: DNA
<213> ORGANISM: Zea mays
<220> FEATURE:
<221> NAME/KEY: allele
<222> LOCATION: (0)...(0)
<223> OTHER INFORMATION: 2980 TS-MS26 target site DNA fragment of
      Figure 2

<400> SEQUENCE: 38
cggcgggatg gtgacgacgt gccctactcg at                                   32

<210> SEQ ID NO 39
<211> LENGTH: 29
<212> TYPE: DNA
<213> ORGANISM: Zea mays

-continued

```
<220> FEATURE:
<221> NAME/KEY: allele
<222> LOCATION: (0)...(0)
<223> OTHER INFORMATION: 3861 TS-MS26 target site DNA fragment of
      Figure 2

<400> SEQUENCE: 39
cggcgggatg gtgacgtgcc ctactcgat                                       29

<210> SEQ ID NO 40
<211> LENGTH: 32
<212> TYPE: DNA
<213> ORGANISM: Zea mays
<220> FEATURE:
<221> NAME/KEY: allele
<222> LOCATION: (0)...(0)
<223> OTHER INFORMATION: 3956 TS-MS26 target site DNA fragment of
      Figure 2

<400> SEQUENCE: 40
cggcgggatg gtgactacgt gccctactcg at                                   32

<210> SEQ ID NO 41
<211> LENGTH: 32
<212> TYPE: DNA
<213> ORGANISM: Zea mays
<220> FEATURE:
<221> NAME/KEY: allele
<222> LOCATION: (0)...(0)
<223> OTHER INFORMATION: 3990 TS-MS26 target site DNA fragment of
      Figure 2

<400> SEQUENCE: 41
cggcgggatg gtgacgtcgt gccctactcg at                                   32

<210> SEQ ID NO 42
<211> LENGTH: 32
<212> TYPE: DNA
<213> ORGANISM: Zea mays
<220> FEATURE:
<221> NAME/KEY: allele
<222> LOCATION: (0)...(0)
<223> OTHER INFORMATION: 6227 TS-MS26 target site DNA fragment of
      Figure 2

<400> SEQUENCE: 42
cggcgggatg gtgacgacgt gccctactcg at                                   32

<210> SEQ ID NO 43
<211> LENGTH: 51
<212> TYPE: DNA
<213> ORGANISM: Oryza sativa
<220> FEATURE:
<221> NAME/KEY: allele
<222> LOCATION: (0)...(0)
<223> OTHER INFORMATION: Wild-type TS-MS26 target site DNA fragment of
      Figure 5

<400> SEQUENCE: 43
caaggtgcgc gccggcggga tggtgacgta cgtgccctac tccatgggga g              51

<210> SEQ ID NO 44
<211> LENGTH: 105
<212> TYPE: DNA
<213> ORGANISM: Oryza sativa
<220> FEATURE:
<221> NAME/KEY: allele
<222> LOCATION: (0)...(0)
<223> OTHER INFORMATION: Ev48 TS-MS26 target site DNA fragment of
```

-continued

```
      Figure 5

<400> SEQUENCE: 44
caaggtgcgc gccggcggga tggtgacgta catcgtggag cagtacgagc gcgccgaggg    60
ccgccaccac ctgttcctgt agtacgtgcc ctactccatg gggag                  105

<210> SEQ ID NO 45
<211> LENGTH: 19
<212> TYPE: DNA
<213> ORGANISM: Oryza sativa
<220> FEATURE:
<221> NAME/KEY: allele
<222> LOCATION: (0)...(0)
<223> OTHER INFORMATION: Ev62.1 TS-MS26 target site DNA fragment of
      Figure 5

<400> SEQUENCE: 45
tgccctactc catgggag                                                 19

<210> SEQ ID NO 46
<211> LENGTH: 50
<212> TYPE: DNA
<213> ORGANISM: Oryza sativa
<220> FEATURE:
<221> NAME/KEY: allele
<222> LOCATION: (0)...(0)
<223> OTHER INFORMATION: Ev62.13 TS-MS26 target site DNA fragment of
      Figure 5

<400> SEQUENCE: 46
caaggtgcgc gccggcggga tggtgacgta ctgccctact ccatggggag               50

<210> SEQ ID NO 47
<211> LENGTH: 50
<212> TYPE: DNA
<213> ORGANISM: Oryza sativa
<220> FEATURE:
<221> NAME/KEY: allele
<222> LOCATION: (0)...(0)
<223> OTHER INFORMATION: Ev62.14 TS-MS26 target site DNA fragment of
      Figure 5

<400> SEQUENCE: 47
caaggtgcgc gccggcggga tggtgacgac gtgccctact ccatggggag               50

<210> SEQ ID NO 48
<211> LENGTH: 42
<212> TYPE: DNA
<213> ORGANISM: Oryza sativa
<220> FEATURE:
<221> NAME/KEY: allele
<222> LOCATION: (0)...(0)
<223> OTHER INFORMATION: Ev67 TS-MS26 target site DNA fragment of
      Figure 5

<400> SEQUENCE: 48
caaggtgcgc gccggcggga tggtgacgta ctccatgggg ag                      42

<210> SEQ ID NO 49
<211> LENGTH: 100
<212> TYPE: DNA
<213> ORGANISM: Oryza sativa
<220> FEATURE:
<221> NAME/KEY: allele
<222> LOCATION: (0)...(0)
<223> OTHER INFORMATION: Wild-type TS-MS26 target site DNA fragment of
      Figure 7
```

```
<400> SEQUENCE: 49
gtgctccccg acggcaccaa ggtgcgcgcc ggcgggatgg tgacgtacgt gccctactcc      60
atggggagga tggagtacaa ctggggcccc gacgcggcga                           100

<210> SEQ ID NO 50
<211> LENGTH: 96
<212> TYPE: DNA
<213> ORGANISM: Oryza sativa
<220> FEATURE:
<221> NAME/KEY: allele
<222> LOCATION: (0)...(0)
<223> OTHER INFORMATION: ms26.1 TS-MS26 target site DNA fragment of
      Figure 7

<400> SEQUENCE: 50
gtgctccccg acggcaccaa ggtgcgcgcc ggcgggatgg tgacgtgccc tactccatgg      60
ggaggatgga gtacaactgg ggccccgacg cggcga                               96

<210> SEQ ID NO 51
<211> LENGTH: 97
<212> TYPE: DNA
<213> ORGANISM: Oryza sativa
<220> FEATURE:
<221> NAME/KEY: allele
<222> LOCATION: (0)...(0)
<223> OTHER INFORMATION: ms26.2 TS-MS26 target site DNA fragment of
      Figure 7

<400> SEQUENCE: 51
gtgctccccg acggcaccaa ggtgcgcgcc ggcgggatgg tgagcgtgcc ctactccatg      60
gggaggatgg agtacaactg ggccccgac gcggcga                               97

<210> SEQ ID NO 52
<211> LENGTH: 79
<212> TYPE: DNA
<213> ORGANISM: Oryza sativa
<220> FEATURE:
<221> NAME/KEY: allele
<222> LOCATION: (0)...(0)
<223> OTHER INFORMATION: ms26.3 TS-MS26 target site DNA fragment of
      Figure 7

<400> SEQUENCE: 52
gtgctccccg acggcaccaa ggtgtacgtg ccctactcca tggggaggat ggagtacaac      60
tggggccccg acgcggcga                                                  79

<210> SEQ ID NO 53
<211> LENGTH: 76
<212> TYPE: DNA
<213> ORGANISM: Oryza sativa
<220> FEATURE:
<221> NAME/KEY: allele
<222> LOCATION: (0)...(0)
<223> OTHER INFORMATION: ms26.4 TS-MS26 target site DNA fragment of
      Figure 7

<400> SEQUENCE: 53
gtgctccccg acggcaccaa ggtgcgcgcc ggcgggatgg tgaggatgga gtacaactgg      60
ggccccgacg cggcga                                                     76

<210> SEQ ID NO 54
<211> LENGTH: 91
<212> TYPE: DNA
<213> ORGANISM: Oryza sativa
```

```
<220> FEATURE:
<221> NAME/KEY: allele
<222> LOCATION: (0)...(0)
<223> OTHER INFORMATION: ms26.5 TS-MS26 target site DNA fragment of
      Figure 7

<400> SEQUENCE: 54
gtgctccccg acggcaccaa ggtgcgcgcc ggcgggatgg tgccctactc catggggagg    60
atggagtaca actggggccc cgacgcggcg a                                  91

<210> SEQ ID NO 55
<211> LENGTH: 82
<212> TYPE: DNA
<213> ORGANISM: Oryza sativa
<220> FEATURE:
<221> NAME/KEY: allele
<222> LOCATION: (0)...(0)
<223> OTHER INFORMATION: ms26.6 TS-MS26 target site DNA fragment of
      Figure

<400> SEQUENCE: 55
gtgctccccg acggcaccaa ggtgcgcgcc ggcgggatgg tgacggggag gatggagtac    60
aactggggcc ccgacgcggc ga                                            82

<210> SEQ ID NO 56
<211> LENGTH: 67
<212> TYPE: DNA
<213> ORGANISM: Oryza sativa
<220> FEATURE:
<221> NAME/KEY: allele
<222> LOCATION: (0)...(0)
<223> OTHER INFORMATION: ms26.7 TS-MS26 target site DNA fragment of
      Figure 7

<400> SEQUENCE: 56
gtgctccccg acggcaccaa ggtgcgcgcc ggcgggatgg tgtacaactg ggcccccgac    60
gcggcga                                                             67

<210> SEQ ID NO 57
<211> LENGTH: 91
<212> TYPE: DNA
<213> ORGANISM: Oryza sativa
<220> FEATURE:
<221> NAME/KEY: allele
<222> LOCATION: (0)...(0)
<223> OTHER INFORMATION: ms26.8 TS-MS26 target site DNA fragment of
      Figure 7

<400> SEQUENCE: 57
gtgctccccg acggcaccaa ggtgcgcgcc ggcgggatgg tgacgtactc catggggagg    60
atggagtaca actggggccc cgacgcggcg a                                  91

<210> SEQ ID NO 58
<211> LENGTH: 6344
<212> TYPE: DNA
<213> ORGANISM: Artificial Sequence
<220> FEATURE:
<223> OTHER INFORMATION: PHP40082

<400> SEQUENCE: 58
cacatggtta acctagactt gtccatcttc tggattggcc aacttaatta atgtatgaaa    60 taaaggatg cacacatagt gacatgctaa tcactataat gtgggcatca aagttgtgtg   120
ttatgtgtaa ttactagtta tctgaataaa agagaaagag atcatccata tttcttatcc   180
```

```
taaatgaatg tcacgtgtct ttataattct ttgatgaacc agatgcattt cattaaccaa    240
atccatatac atataaatat taatcatata taattaatat caattgggtt agcaaaacaa    300
atctagtcta ggtgtgtttt gcgaattgcg gccagcttgg tcacccggtc cgggcctaga    360
aggccgatct cccgggcacc cagctttctt gtacaaagtg gcattataa gaaagcattg     420 cttatcaatt tgttgcaacg aacaggtcac tatcagtcaa aataaaatca ttatttgcca    480
tccagctgat atccctata gtgagtcgta ttacatggtc atagctgttt cctggcagct     540
ctggcccgtg tctcaaaatc tctgatgtta cattgcacaa gataaaaata tatcatcatg    600
aacaataaaa ctgtctgctt acataaacag taatacaagg ggtgttatga gccatattca    660
acgggaaacg tcgaggccgc gattaaattc caacatggat gctgatttat atgggtataa    720
atgggctcgc gataatgtcg ggcaatcagg tgcgacaatc tatcgcttgt atgggaagcc    780
cgatgcgcca gagttgtttc tgaaacatgg caaaggtagc gttgccaatg atgttacaga    840
tgagatggtc agactaaaact ggctgacgga atttatgcct cttccgacca tcaagcattt    900
tatccgtact cctgatgatg catggttact caccactgcg atccccggaa aaacagcatt    960
ccaggtatta gaagaatatc ctgattcagg tgaaatatt gttgatgcgc tggcagtgtt    1020
cctgcgccgg ttgcattcga ttcctgtttg taattgtcct tttaacagcg atcgcgtatt   1080
tcgtctcgct caggcgcaat cacgaatgaa taacggtttg gttgatgcga gtgattttga   1140
tgacgagcgt aatggctggc ctgttgaaca agtctggaaa gaaatgcata aacttttgcc   1200
attctcaccg gattcagtcg tcactcatgg tgatttctca cttgataacc ttattttga    1260 cgaggggaaa ttaataggtt gtattgatgt tggacgagtc ggaatcgcag accgatacca   1320
ggatcttgcc atcctatgga actgcctcgg tgagttttct ccttcattac agaaacggct   1380
ttttcaaaaa tatggtattg ataatcctga tatgaataaa ttgcagtttc atttgatgct   1440
cgatgagttt ttctaatcag aattggttaa ttggttgtaa cactggcaga gcattacgct   1500
gacttgacgg gacggcgcaa gctcatgacc aaaatccctt aacgtgagtt acgcgtcgtt   1560
ccactgagcg tcagacccg tagaaaagat caaaggatct tcttgagatc ctttttttct    1620
gcgcgtaatc tgctgcttgc aaacaaaaaa accaccgcta ccagcggtgg tttgtttgcc   1680
ggatcaagag ctaccaactc tttttccgaa ggtaactggc ttcagcagag cgcagatacc   1740
aaatactgtc cttctagtgt agccgtagtt aggccaccac ttcaagaact ctgtagcacc   1800
gcctacatac ctcgctctgc taatcctgtt accagtggct gctgccagtg gcgataagtc   1860
gtgtcttacc gggttggact caagacgata gttaccggat aaggcgcagc ggtcgggctg   1920
aacggggggt tcgtgcacac agcccagctt ggagcgaacg acctacaccg aactgagata   1980
cctacagcgt gagcattgag aaagcgccac gcttcccgaa gggagaaagg cggacaggta   2040
tccggtaagc ggcagggtcg aacaggaga gcgcacgagg gagcttccag ggggaaacgc    2100
ctggtatctt tatagtcctg tcgggtttcg ccacctctga cttgagcgtc gatttttgtg   2160
atgctcgtca gggggggcgga gcctatggaa aaacgccagc aacgcggcct ttttacggtt   2220
cctggccttt tgctggcctt tgctcacat gttctttcct gcgttatccc ctgattctgt    2280
ggataaccgt attaccgcct ttgagtgagc tgataccgct cgccgcagcc gaacgaccga   2340
gcgcagcgag tcagtgagcg aggaagcgga agagcgccca atacgcaaac cgcctctccc   2400
cgcgcgttgg ccgattcatt aatgcagctg gcacgacagg tttcccgact ggaaagcggg   2460
cagtgagcgc aacgcaatta atacgcgtac cgctagccag gaagagtttg tagaaacgca   2520
aaaaggccat ccgtcaggat ggccttctgc ttagtttgat gcctggcagt ttatggcggg   2580
```

```
cgtcctgccc gccaccctcc gggccgttgc ttcacaacgt tcaaatccgc tcccggcgga    2640
tttgtcctac tcaggagagc gttcaccgac aaacaacaga taaaacgaaa ggcccagtct    2700
tccgactgag cctttcgttt tatttgatgc ctggcagttc cctactctcg cgttaacgct    2760
agcatggatg ttttcccagt cacgacgttg taaaacgacg gccagtctta agctcgggcc    2820
ccaaataatg attttatttt gactgatagt gacctgttcg ttgcaacaaa ttgatgagca    2880
atgctttttt ataatgccaa gtttgtacaa aaaagcaggc tccggccaga atggcccgga    2940
ccgggttacc gaattcgcct agaaggccat ttaaatcctg aggatctggt cttcctaagg    3000
acccgggata tcgaccgat  taaactttaa ttcggtccga agcttgcatg cctgcagtgc    3060
agcgtgaccc ggtcgtgccc ctctctagag ataatgagca ttgcatgtct aagttataaa    3120
aaattaccac atattttttt tgtcacactt gtttgaagtg cagtttatct atctttatac    3180
atatatttaa actttactct acgaataata taatctatag tactacaata atatcagtgt    3240
tttagagaat catataaatg aacagttaga catggtctaa aggacaattg agtattttga    3300
caacaggact ctacagtttt atctttttag tgtgcatgtg ttctcctttt tttttgcaaa    3360
tagcttcacc tatataatac ttcatccatt ttattagtac atccatttag ggtttagggt    3420
taatggtttt tatagactaa ttttttttagt acatctattt tattctattt tagcctctaa    3480
attaagaaaa ctaaaactct attttagttt ttttatttaa taatttagat ataaaataga    3540
ataaaataaa gtgactaaaa attaaacaaa tacccttttaa gaaattaaaa aaactaagga    3600
aacatttttc ttgtttcgag tagataatgc cagcctgtta aacgccgtcg acagtctaa     3660 cggacaccaa ccagcgaacc agcagcgtcg cgtcgggcca agcgaagcag acggcacggc    3720
atctctgtcg ctgcctctgg accctctcg agagttccgc tccaccgttg gacttgctcc     3780
gctgtcggca tccagaaatt gcgtggcgga gcggcagacg tgagccggca cggcaggcgg    3840
cctcctcctc ctctcacggc accggcagct acggggatt cctttcccac cgctccttcg     3900 cttttcccttc ctcgcccgcc gtaataaata gacacccct ccacaccctc tttccccaac     3960
ctcgtgttgt tcggagcgca cacacacaca accagatctc ccccaaatcc acccgtcggc    4020
acctccgctt caaggtacgc cgctcgtcct ccccccccc cctctctacc ttctctagat     4080
cggcgttccg gtccatgcat ggttagggcc cggtagttct acttctgttc atgtttgtgt    4140
tagatccgtg tttgtgttag atccgtgctg ctagcgttcg tacacggatg cgacctgtac    4200
gtcagacacg ttctgattgc taacttgcca gtgtttctct ttggggaatc ctgggatggc    4260
tctagccgtt ccgcagacgg gatcgatttc atgatttttt ttgtttcgtt gcatagggtt    4320
tggtttgccc ttttcctta tttcaatata tgccgtgcac ttgtttgtcg ggtcatctttt    4380 tcatgctttt ttttgtcttg gttgtgatga tgtggtctgg ttgggcggtc gttctagatc    4440
ggagtagaat tctgtttcaa actacctggt ggatttatta attttggatc tgtatgtgtg    4500
tgccatacat attcatagtt acgaattgaa gatgatggat ggaaatatcg atctaggata    4560
ggtatacatg ttgatgcggg ttttactgat gcatatacag agatgctttt tgttcgcttg    4620
gttgtgatga tgtggtgtgg ttgggcggtc gttcattcgt tctagatcgg agtagaatac    4680
tgtttcaaac tacctggtgt atttattaat tttggaactg tatgtgtgtg tcatacatct    4740
tcatagttac gagtttaaga tggatggaaa tatcgatcta ggataggtat acatgttgat    4800
gtgggtttta ctgatgcata tacatgatgg catatgcagc atctattcat atgctctaac    4860
cttgagtacc tatctattat aataaacaag tatgttttat aattattttg atcttgatat    4920
```

```
acttggatga tggcatatgc agcagctata tgtggatttt tttagccctg ccttcatacg     4980
ctatttattt gcttggtact gtttcttttg tcgatgctca ccctgttgtt tggtgttact     5040
tctgcaggtc gactctagag gatccccatg ctccgaaga agaagcgcaa ggtccacatg      5100
aacaccaagt acaacaagga gttcctcctc tacctggcag gtttcgtgga cggcgatggg     5160
tctatcatcg cccagattga tccgcaacag tcctacaagt tcaagcactc gctgcggctg     5220
aggttcacgg tcactcagaa gacgcagcgc aggtggttcc tcgataagct ggtcgacgaa     5280
atcggagtcg gcaaggtgcg ggacaggggc tctgtcagcg actacatcct ctgtcagatc     5340
aagccgctcc acaacttcct gacccagctg cagcccttcc tcaagctcaa gcagaagcag     5400
gccaacctgg tgctcaagat catcgagcag ctgccatctg ccaaggagtc accagacaag     5460
ttccttgagg taagtttctg cttctacctt tgatatatat ataataatta tcattaatta     5520
gtagtaatat aatatttcaa atatttttt caaaataaaa gaatgtagta tatagcaatt     5580
gcttttctgt agtttataag tgtgtatatt ttaatttata acttttctaa tatatgacca     5640
aaacatggtg atgtgcaggt ctgcacctgg gtcgatcaga tcgctgccct gaacgactcc     5700
aagacgagga agaccacctc cgagaccgtc agggctgtgc tggactcact cccaggatcc     5760
gttggcggtc tcagcccttc tcaggctagc tcggctgctt cctcagccag cagctcacct     5820
ggctccggta tcagcgaggc tctcagagca ggtgccacca gtccaaggga gttcctcctg     5880
tacctggcag gcttcgttga cggcgacggc tcgatctgcg cgtccattga cccgaaccag     5940
tcgtgtaagt tcaagcatca gctgcgcctg cgctttaccg tcacgcagaa gacccagagg     6000
cgctggttcc tggacaaaact ggtggacgag atcggggtcg ggaaggtgta cgacagaggg     6060
agcgttagcg actaccggct gtgccagatc aagccgctcc acaacttcct gacgcagctc     6120
caacccttcc tgaagctgaa gcagaagcag gcgaaccttg tgctgaagat cattgagcag     6180
ctgccgagcg ccaaggagag ccctgacaag ttcctggagg tctgcacctg gtcgaccag      6240 atcgctgccc tcaacgactc caagaccagg aagaccacga gcgagaccgt tcgggctgtc     6300
ctggacagcc tctccgagaa gaagaagtcg agcccgtagg gtac                      6344
```

<210> SEQ ID NO 59
<211> LENGTH: 6021
<212> TYPE: DNA
<213> ORGANISM: Artificial Sequence
<220> FEATURE:
<223> OTHER INFORMATION: PHP40126

<400> SEQUENCE: 59

```
tcgaggtcga cggtatcgat aagcttgata tcgaattccc atggagtcaa agattcaaat       60
agaggaccta acagaactcg ccgtaaagac tggcgaacag ttcatacaga gtctcttacg      120
actcaatgac aagaagaaaa tcttcgtcaa catggtggag cacgacacgc ttgtctactc      180
caaaaatatc aaagatacag tctcagaaga ccaagggca attgagactt tcaacaaag       240 ggtaatatcc ggaaacctcc tcggattcca ttgcccagct atctgtcact ttattgtgaa      300
gatagtggaa aaggaaggtg gctcctacaa atgccatcat tgcgataaag gaaaggccat      360
cgttgaagat gcctctgccg acagtggtcc caaagatgga ccccacccca cgaggagcat      420
cgtggaaaaa gaagacgttc caaccacgtc ttcaaagcaa gtggattgat gtgatatctc      480
cactgacgta agggatgacg cacaatccca ctaagctgac cgaagctggc cgctctagaa      540
ctagatcgaa ttcctgcagc ccgggggatc cagcttcgct tagttttttag tttttggcag     600 aaaaaatgat caatgtttca caaaccaaat attttttataa cttttgatga agaagatca      660
```

-continued

```
ccacggtcat atctaggggt ggtaacaaat tgcgatctaa atgtttcttc ataaaaaata      720
aggcttctta ataaatttta gttcaaaata aatacgaata aagtctgatt ctaatctgat      780
tcgatcctta aattttataa tgcaaaattt agagctcatt accacctcta gtcatatgtc      840
tagtctgagg tatatccaaa aagcccttc  tctaaattcc acacccaact cagatgtttg      900
caaataaata ctccgactcc aaaatgtagg tgaagtgcaa ctttctccat tttatatcaa      960
catttgttat tttttgttta acatttcaca ctcaaaacta attaataaaa tacgtggttg     1020
ttgaacgtgc gcacatgtct cccttacatt atgttttttt atttatgtat tattgttgtt     1080
ttcctccgaa caacttgtca acatatcatc attggtcttt aatatttatg aatatggaag     1140
cctagttatt tacacttggc tacacactag ttgtagtttt gccacttgtc taacatgcaa     1200
ctctagtagt tttgccactt gcctggcatg caactctagt attgacactt gtatagcata     1260
taatgccaat acgacacctg ccttacatga acattatttt ttgacacttg tataccatgc     1320
aacattacca ttgacatttg tccatacaca ttatatcaaa tatattgagc gcatgtcaca     1380
aactcgatac aaagctggat gaccctccct caccacatct ataaaaccc  gagcgctact     1440 gtaaatcact cacaacacaa cacatatctt ttagtaacct ttcaataggc gtcccccaag     1500
aactagtaag atccacacga caccatgtcc cccgagcgcc gccccgtcga tccgcccg      1560 gccaccgccg ccgacatggc cgccgtgtgc gacatcgtga accactacat cgagacctcc     1620
accgtgaact tccgcaccga gccgcagacc ccgcaggagt ggatcgacga cctggagcgc     1680
ctccaggacc gctacccgtg gctcgtggcc gaggtggagg gcgtggtggc cggcatcgcc     1740
tacgccggcc cgtggaaggc ccgcaacgcc tacgactgga ccgtggagtc caccgtgtac     1800
gtgtcccacc gccaccagcg cctcggcctc ggctccaccc tctacaccca cctcctcaag     1860
agcatggagg cccagggctt caagtccgtg gtggccgtga tcggcctccc gaacgacccg     1920
tccgtgcgcc tccacgaggc cctcggctac accgcccgcg gcaccctccg cgccgccggc     1980
tacaagcacg gcggctggca cgacgtcggc ttctggcagc gcgacttcga gctgccggcc     2040
ccgccgcgcc cggtgcgccc ggtgacgcag atctccggtg gaggcggcag cggtggcgga     2100
ggctccggag gcggtggctc catggcctcc tccgaggacg tcatcaagga gttcatgcgc     2160
ttcaaggtgc gcatggaggg ctccgtgaac ggccacgagt tcgagatcga gggcgagggc     2220
gagggccgcc cctacgaggg cacccagacc gccaagctga aggtgaccaa gggcggcccc     2280
ctgcccttcg cctgggacat cctgtccccc cagttccagt acggctccaa ggtgtacgtg     2340
aagcaccccg ccgacatccc cgactacaag aagctgtcct tccccgaggg cttcaagtgg     2400
gagcgcgtga tgaacttcga ggacggcggc gtggtgaccg tgacccagga ctcctccctg     2460
caggacggct ccttcatcta caaggtgaag ttcatcggcg tgaacttccc ctccgacggc     2520
cccgtaatgc agaagaagac tatgggctgg gaggcctcca ccgagcgcct gtaccccgc      2580 gacggcgtgc tgaagggcga gatccacaag gccctgaagc tgaaggacgg cggccactac     2640
ctggtggagt tcaagtccat ctacatggcc aagaagcccg tgcagctgcc cggctactac     2700
tacgtggact ccaagctgga catcacctcc cacaacgagg actacaccat cgtggagcag     2760
tacgagcgcg ccgagggccg ccaccacctg ttcctgtagt caggatctga gtcgaaacct     2820
agacttgtcc atcttctgga ttggccaact taattaatgt atgaaataaa aggatgcaca     2880
catagtgaca tgctaatcac tataatgtgg gcatcaaagt tgtgtgttat gtgtaattac     2940
tagttatctg aataaaagag aaagagatca tccatatttc ttatcctaaa tgaatgtcac     3000
```

```
gtgtctttat aattctttga tgaaccagat gcatttcatt aaccaaatcc atatacatat    3060
aaatattaat catatataat taatatcaat tgggttagca aaacaaatct agtctaggtg    3120
tgttttgcga atgcggccgc aagcttgagc tccaattcgc cctatagtga gtcgtattac    3180
gcgcgctcac tggccgtcgt tttacaacgt cgtgactggg aaaaccctgg cgttacccaa    3240
cttaatcgcc ttgcagcaca tccccctttc gccagctggc gtaatagcga agaggcccgc    3300
accgatcgcc cttcccaaca gttgcgcagc ctgaatggcg aatgggacgc gccctgtagc    3360
ggcgcattaa gcgcggcggg tgtggtggtt acgcgcagcg tgaccgctac acttgccagc    3420
gccctagcgc ccgctccttt cgctttcttc ccttcctttc tcgccacgtt cgccggcttt    3480
ccccgtcaag ctctaaatcg gggctccct  ttagggttcc gatttagtgc tttacggcac    3540
ctcgacccca aaaaacttga ttagggtgat ggttcacgta gtgggccatc gccctgatag    3600
acggttttc  gccctttgac gttggagtcc acgttcttta atagtggact cttgttccaa    3660
actggaacaa cactcaaccc tatctcggtc tattctttg  atttataagg gattttgccg    3720
atttcggcct attggttaaa aaatgagctg atttaacaaa aatttaacgc gaattttaac    3780
aaaatattaa cgcttacaat ttaggtggca cttttcgggg aaatgtgcgc ggaaccccta    3840
tttgtttatt tttctaaata cattcaaata tgtatccgct catgagacaa taaccctgat    3900
aaatgcttca ataatattga aaaggaaga  gtatgagtat tcaacatttc cgtgtcgccc    3960
ttattccctt ttttgcggca ttttgccttc ctgttttgc  tcacccagaa acgctggtga    4020
aagtaaaaga tgctgaagat cagttgggtg cacgagtggg ttacatcgaa ctggatctca    4080
acagcggtaa gatccttgag agttttcgcc ccgaagaacg ttttccaatg atgagcactt    4140
ttaaagttct gctatgtggc gcggtattat cccgtattga cgccgggcaa gagcaactcg    4200
gtcgccgcat acactattct cagaatgact tggttgagta ctcaccagtc acagaaaagc    4260
atcttacgga tggcatgaca gtaagagaat tatgcagtgc tgccataacc atgagtgata    4320
acactgcggc caacttactt ctgacaacga tcggaggacc gaaggagcta accgcttttt    4380
tgcacaacat gggggatcat gtaactcgcc ttgatcgttg ggaaccggag ctgaatgaag    4440
ccataccaaa cgacgagcgt gacaccacga tgcctgtagc aatggcaaca acgttgcgca    4500
aactattaac tggcgaacta cttactctag cttcccggca acaattaata gactggatgg    4560
aggcggataa agttgcagga ccacttctgc gctcggccct tccggctggc tggtttattg    4620
ctgataaatc tggagccggt gagcgtgggt ctcgcggtat cattgcagca ctggggccag    4680
atggtaagcc ctcccgtatc gtagttatct acacgacggg gagtcaggca actatggatg    4740
aacgaaatag acagatcgct gagataggtg cctcactgat taagcattgg taactgtcag    4800
accaagttta ctcatatata ctttagattg atttaaaact tcattttaa  tttaaaagga    4860
tctaggtgaa gatcctttt  gataatctca tgaccaaaat cccttaacgt gagttttcgt    4920
tccactgagc gtcagacccc gtagaaaaga tcaaaggatc ttcttgagat cctttttttc    4980
tgcgcgtaat ctgctgcttg caacaaaaa  aaccaccgct accagcggtg gtttgtttgc    5040
cggatcaaga gctaccaact cttttttccga aggtaactgg cttcagcaga gcgcagatac    5100
caaatactgt ccttctagtg tagccgtagt taggccacca cttcaagaac tctgtagcac    5160
cgcctacata cctcgctctg ctaatcctgt taccagtggc tgctgccagt ggcgataagt    5220
cgtgtcttac cgggttggac tcaagacgat agttaccgga taaggcgcag cggtcgggct    5280
gaacggggg  ttcgtgcaca cagcccagct tggagcgaac gacctacacc gaactgagat    5340
acctacagcg tgagctatga gaaagcgcca cgcttcccga agggagaaag gcggacaggt    5400
```

```
atccggtaag cggcagggtc ggaacaggag agcgcacgag ggagcttcca gggggaaacg    5460
cctggtatct ttatagtcct gtcgggtttc gccacctctg acttgagcgt cgattttgt     5520 gatgctcgtc agggggggcgg agcctatgga aaaacgccag caacgcggcc ttttacggt     5580 tcctggcctt ttgctggcct tttgctcaca tgttctttcc tgcgttatcc cctgattctg    5640
tggataaccg tattaccgcc tttgagtgag ctgataccgc tcgccgcagc cgaacgaccg    5700
agcgcagcga gtcagtgagc gaggaagcgg aagagcgccc aatacgcaaa ccgcctctcc    5760
ccgcgcgttg gccgattcat taatgcagct ggcacgacag gtttcccgac tggaaagcgg    5820
gcagtgagcg caacgcaatt aatgtgagtt agctcactca ttaggcaccc caggctttac    5880
actttatgct tccggctcgt atgttgtgtg gaattgtgag cggataacaa tttcacacag    5940
gaaacagcta tgaccatgat tacgccaagc gcgcaattaa ccctcactaa agggaacaaa    6000
agctgggtac cgggcccccc c                                              6021

<210> SEQ ID NO 60
<211> LENGTH: 54826
<212> TYPE: DNA
<213> ORGANISM: Artificial Sequence
<220> FEATURE:
<223> OTHER INFORMATION: PHP40827

<400> SEQUENCE: 60
gggggggggg ggggggggga cttccattgt tcattccacg acaaaaaaca gagaaaggaa      60
acgacagagg ccaaaaagcc tcgctttcag cacctgtcgt ttcctttctt ttcagagggt    120
attttaaata aaaacattaa gttatgacga agaagaacgg aaacgcctta aaccggaaaa    180
ttttcataaa tagcgaaaac ccgcgaggtc gccgccccgt aacctgtcgg atcaccggaa    240
aggacccgta aagtgataat gattatcatc tacatatcac aacgtgcgtg gaggccatca    300
aaccacgtca aataatcaat tatgacgcag gtatcgtatt aattgatctg catcaactta    360
acgtaaaaac aacttcagac aatacaaatc agcgacactg aatacggggc aacctcatgt    420
cccccccccc ccccccctg caggcatcgt ggtgtcacgc tcgtcgtttg gtatggcttc    480
attcagctcc ggttcccaac gatcaaggcg agttacatga tcccccatgt tgtgcaaaaa    540
agcggttagc tccttcggtc ctccgatcgt tgtcagaagt aagttggccg cagtgttatc    600
actcatggtt atggcagcac tgcataattc tcttactgtc atgccatccg taagatgctt    660
ttctgtgact ggtgagtact caaccaagtc attctgagaa tagtgtatgc ggcgaccgag    720
ttgctcttgc ccggcgtcaa cacgggataa taccgcgcca catagcagaa ctttaaaagt    780
gctcatcatt ggaaaacgtt cttcggggcg aaaactctca aggatcttac cgctgttgag    840
atccagttcg atgtaaccca ctcgtgcacc caactgatct tcagcatctt ttactttcac    900
cagcgtttct gggtgagcaa aaacaggaag gcaaaatgcc gcaaaaaagg gaataagggc    960
gacacggaaa tgttgaatac tcatactctt cctttttcaa tattattgaa gcatttatca    1020
gggttattgt ctcatgagcg gatacatatt tgaatgtatt tagaaaaata aacaaatagg    1080
ggttccgcgc acatttcccc gaaaagtgcc acctgacgtc taagaaacca ttattatcat    1140
gacattaacc tataaaaata ggcgtatcac gaggcccttt cgtcttcaag aattggtcga    1200
cgatcttgct gcgttcggat attttcgtgg agttcccgcc acagacccgg attgaaggcg    1260
agatccagca actcgcgcca gatcatcctg tgacggaact ttggcgcgtg atgactggcc    1320
aggacgtcgg ccgaaagagc gacaagcaga tcacgctttt cgacagcgtc ggatttgcga    1380
```

```
tcgaggattt ttcggcgctg cgctacgtcc gcgaccgcgt tgagggatca agccacagca   1440
gcccactcga ccttctagcc gacccagacg agccaaggga tcttttttgga atgctgctcc   1500
gtcgtcaggc tttccgacgt ttgggtggtt gaacagaagt cattatcgta cggaatgcca   1560
agcactcccg aggggaaccc tgtggttggc atgcacatac aaatggacga acggataaac   1620
cttttcacgc ccttttaaat atccgttatt ctaataaacg ctcttttctc ttaggtttac   1680
ccgccaatat atcctgtcaa acactgatag tttaaactga aggcgggaaa cgacaatctg   1740
atcatgagcg gagaattaag ggagtcacgt tatgacccccc gccgatgacg cgggacaagc   1800
cgttttacgt ttggaactga cagaaccgca acgttgaagg agccactcag cccaagctgg   1860
tacgattgta atacgactca ctatagggcg aattgagcgc tgtttaaacg ctcttcaact   1920
ggaagagcgg ttaccagagg ccagaatggc catctcggac cgatatcgct atcaactttg   1980
tatagaaaag ttgggccgaa ttcgagctcg gtacggccag aatggcccgg accgggttac   2040
cgaattcgag ctcggtaccc gtggagatat aggggaaaga gaacgctgat gtgacaagtg   2100
agtgagatat aggggagaa atttaggggg aacgccgaac acagtctaaa gtagcttggg   2160
acccaaagca ctctgttcgg gggttttttt ttttgtcttt caacttttttg ctgtaatgtt   2220
attcaaaata agaaaagcac ttggcatggc taagaaatag agttcaacaa ctgaacagta   2280
cagtgtatta tcaatggcat aaaaaacaac ccttacagca ttgccgtatt ttattgatca   2340
aacattcaac tcaacactga cgagtggtct tccaccgatc aacggactaa tgctgctttg   2400
tcagatcgtt aacgatgtgt taagacccac tttcacactt cagctgcttc tccaatccgc   2460
atatgatcaa ttcaaggccg aacaggaagg ctggctctgc accttggtga tcgaagagct   2520
cgatagcttg tcggagcagt ggcggcatac tatcagtagt aggtgttttcc ctctcctcct   2580
tagcgacttg gtgctcttga tcttccaata cgcaacccag agtgaagtgc cctacagcgg   2640
agagtgcgta gagggcattc tcaagggaga aaccttgttg gcacaggaag gcgagctggt   2700
tctcgagagt ttcatactgc ttctccgtag gccgtgtacc taggtggacc ttggctccat   2760
cacggtgact gagcaaagca catctgaagc tcttagcgtt gttcctcaag aagtcttgcc   2820
agctttcccc ttccaagggg cagaagtggg tatggtgcct atcgagcatc tcaatggcga   2880
gggcgtctag caaagcccgc ttgttcttga cgtgccaata caatgtaggc tgctctaccc   2940
cgagcttctg ggcgagttta cgggttgtga ggccttcgat tccgacctcg ttcagcagct   3000
ccagtgcgct gttgatcacc ttgctcttgt cgagtctggc catggtggcg accggtggat   3060
cccccgggct gcagaagtaa caccaaacaa cagggtgagc atcgacaaaa gaaacagtac   3120
caagcaaata aatagcgtat gaaggcaggg ctaaaaaaat ccacatatag ctgctgcata   3180
tgccatcatc caagtatatc aagatcaaaa taattataaa acatacttgt ttattataat   3240
agataggtac tcaaggttag agcatatgaa tagatgctgc atatgccatc atgtatatgc   3300
atcagtaaaa cccacatcaa catgtatacc tatcctagat cgatatttcc atccatctta   3360
aactcgtaac tatgaagatg tatgacacac acatacagtt ccaaaattaa taaatacacc   3420
aggtagtttg aaacagtatt ctactccgat ctagaacgaa tgaacgaccg cccaaccaca   3480
ccacatcatc acaaccaagc gaacaaaaag catctctgta tatgcatcag taaacccgc   3540
atcaacatgt atacctatcc tagatcgata tttccatcca tcatcttcaa ttcgtaacta   3600
tgaatatgta tggcacacac atacagatcc aaaattaata aatccaccag gtagtttgaa   3660
acagaattct actccgatct agaacgaccg cccaaccaga ccacatcatc acaaccaaga   3720
caaaaaaaag catgaaaaga tgacccgaca aacaagtgca cggcatatat tgaaataaag   3780
```

```
gaaaagggca aaccaaaccc tatgcaacga aacaaaaaaa atcatgaaat cgatcccgtc   3840
tgcggaacgg ctagagccat cccaggattc cccaaagaga aacactggca agttagcaat   3900
cagaacgtgt ctgacgtaca ggtcgcatcc gtgtacgaac gctagcagca cggatctaac   3960
acaaacacgg atctaacaca aacatgaaca gaagtagaac taccgggccc taaccatgca   4020
tggaccggaa cgccgatcta gagaaggtag agaggggggg ggggaggac gagcggcgta    4080 ccttgaagcg gaggtgccga cgggtggatt tgggggagat ctggttgtgt gtgtgtgcgc   4140
tccgaacaac acgaggttgg ggaaagaggg tgtggagggg tgtctatttt attacggcgg   4200
gcgaggaagg gaaagcgaag gagcggtggg aaaggaatcc cccgtagctg ccggtgccgt   4260
gagaggagga ggaggccgcc tgccgtgccg gctcacgtct gccgctccgc cacgcaattt   4320
ctggatgccg acagcggagc aagtccaacg gtggagcgga actctcgaga ggggtccaga   4380
ggcagcgaca gagatgccgt gccgtctgct tcgcttggcc cgacgcgacg ctgctggttc   4440
gctggttggt gtccgttaga ctcgtcgacg gcgtttaaca ggctggcatt atctactcga   4500
aacaagaaaa atgtttcctt agttttttta atttcttaaa gggtatttgt ttaattttta   4560
gtcactttat tttattctat tttatatcta aattattaaa taaaaaaact aaaatagagt   4620
tttagttttc ttaatttaga ggctaaaata gaataaaata gatgtactaa aaaaattagt   4680
ctataaaaac cattaaccct aaaccctaaa tggatgtact aataaaatgg atgaagtatt   4740 ataggtga agctatttgc aaaaaaaag gagaacacat gcacactaaa aagataaaac      4800
tgtagagtcc tgttgtcaaa atactcaatt gtcctttaga ccatgtctaa ctgttcattt   4860
atatgattct ctaaaacact gatattattg tagtactata gattatatta ttcgtagagt   4920 aaagttaaa tatatgtata aagatagata aactgcactt caaacaagtg tgacaaaaaa    4980
aatatgtggt aatttttat aacttagaca tgcaatgctc attatctcta gagagggca    5040 cgaccgggtc acgctgcact gcaggcatgc aagcttggcg ctctagaact agtggatccc   5100
ccgggctgca ggaattcgat atcaagcttg gtcacccggt ccgggcctag aaggccagct   5160
tcaagtttgt acaaaaaagc aggctccggc cagaatggcc cggaccgggt taccgaattc   5220
gagctcaagc ttgcggccgc attcgcaaaa cacacctaga ctagatttgt tttgctaacc   5280
caattgatat taattatata tgattaatat ttatatgtat atggatttgg ttaatgaaat   5340
gcatctggtt catcaaagaa ttataaagac acgtgacatt catttaggat aagaaatatg   5400
gatgatctct ttctctttta ttcagataac tagtaattac acataacaca caactttgat   5460
gcccacatta tagtgattag catgtcacta tgtgtgcatc cttttatttc atacattaat   5520
taagttggcc aatccagaag atggacaagt ctaggttaac catgtggtac cctacgggct   5580
cgacttcttc ttctcggaga ggctgtccag gacagcccga acgtctcgc tgtggtctt     5640 cctggtcttg gagtcgttga gggcagcgat ctggtcgacc caggtgcaga cctccaggaa   5700
cttgtcaggg ctctccttgg cgctcggcag ctgctcaatg atcttcagca aaggttcgc    5760 ctgcttctgc ttcagcttca ggaagggttg gagctgcgtc aggaagttgt ggagcggctt   5820
gatctggcac agccggtagt cgctaacgct ccctctgtcg tacaccttcc cgaccccgat   5880
ctcgtccacc agtttgtcca ggaaccagcg cctctgggtc ttctgcgtga cggtaaagcg   5940
caggcgcagc tgatgcttga acttacacga ctggttcggg tcaatggacg cgcagatcga   6000
gccgtcgccg tcaacgaagc ctgccaggta caggaggaac tccttggact tggtggcacc   6060
tgctctgaga gcctcgctga taccggagcc aggtgagctg ctggctgagg aagcagccga   6120
```

```
gctagcctga aagggctga gaccgccaac ggatcctggg agtgagtcca gcacagccct      6180
gacggtctcg gaggtggtct tcctcgtctt ggagtcgttc agggcagcga tctgatcgac      6240
ccaggtgcag acctgcacat caccatgttt tggtcatata ttagaaaagt tataaattaa      6300
aatatacaca cttataaact acagaaaagc aattgctata tactacattc ttttatttg      6360 aaaaaaatat ttgaaatatt atattactac taattaatga taattattat atatatatca      6420
aaggtagaag cagaaactta cctcaaggaa cttgtctggt gactccttgg cagatggcag      6480
ctgctcgatg atcttgagca ccaggttggc ctgcttctgc ttgagcttga ggaagggctg      6540
cagctgggtc aggaagttgt ggagcggctt gatctgacag aggatgtagt cgctgacaga      6600
gcccctgtcc cgcaccttgc cgactccgat ttcgtcgacc agcttatcga ggaaccacct      6660
gcgctgcgtc ttctgagtga ccgtgaacct cagccgcagc gagtgcttga acttgtagga      6720
ctgttgcgga tcaatctggg cgatgataga cccatcgccg tccacgaaac ctgccaggta      6780
gaggaggaac tccttgttgt acttggtgtt catgtggacc ttgcgcttct tcttcggagc      6840 catgggatc ctgtaattgt aaatagtaat tgtaatgttg tttgttgttt gttgttgttg      6900
gtaattgttg taaaaataag tacaactcta tcactgatag agttcactct atcactgata      6960
gagtcttata tacactctat cactgataga gtctagtggg attgtgcgtc atcccttacg      7020
tcagtggaga tatcacatca atccacttgc tttgaagacg tggttggaac gtcttctttt      7080
tccacgatgc tcctcgtggg tgggggtcca tctttgggac cactgtcggc agaggcatct      7140
tcaacgatgg cctttccttt atcgcaatga tggcatttgt aggagccacc ttccttttcc      7200
actatcttca caataaagtg acagatagct gggcaatgga atccgaggag gtttccggat      7260
attacccttt gttgaaaagt ctcaattgcc ctttggtctt ctgagactgt atctttgata      7320
tttttggagt agacaagcgt gtcgtgctcc accatgttga cgaagatttt cgaattcctg      7380
cagcccgggg gatccagctt cgcttagttt ttagttttg gcagaaaaaa tgatcaatgt      7440
ttcacaaacc aaatattttt ataacttttg atgaaagaag atcaccacgg tcatatctag      7500
gggtggtaac aaattgcgat ctaaatgttt cttcataaaa aataaggctt cttaataaat      7560
tttagttcaa aataaatacg aataaagtct gattctaatc tgattcgatc cttaaatttt      7620
ataatgcaaa atttagagct cattaccacc tctagtcata tgtctagtct gaggtatatc      7680
caaaaagccc tttctctaaa ttccacaccc aactcagatg tttgcaaata aatactccga      7740
ctccaaaatg taggtgaagt gcaactttct ccatttata tcaacatttg ttattttttg      7800
tttaacattt cacactcaaa actaattaat aaaatacgtg gttgttgaac gtgcgcacat      7860
gtctccctta cattatgttt ttttatttat gtattattgt tgttttcctc cgaacaactt      7920
gtcaacatat catcattggt ctttaatatt tatgaatatg gaagcctagt tatttacact      7980
tggctacaca ctagttgtag ttttgccact tgtctaacat gcaactctag tagttttgcc      8040
acttgcctgg catgcaactc tagtattgac acttgtatag catataatgc caatacgaca      8100
cctgccttac atgaaacatt atttttgaca cttgtatacc atgcaacatt accattgaca      8160
tttgtccata cacattatat caaatatatt gagcgcatgt cacaaactcg atacaaagct      8220
ggatgaccct ccctcaccac atctataaaa acccgagcgc tactgtaaat cactcacaac      8280
acaacacata tcttttagta acctttcaat aggcgtcccc caagaactag taaccatggc      8340
cctgtccaac aagttcatcg gcgacgacat gaagatgacc taccacatgg acggctgcgt      8400
gaacggccac tacttcaccg tgaagggcga gggcagcggc aagccctacg agggcaccca      8460
gacctccacc ttcaaggtga ccatggccaa cggcggcccc ctggccttct ccttcgacat      8520
```

```
cctgtccacc gtgttcatgt acggcaaccg ctgcttcacc gcctacccca ccagcatgcc    8580
cgactacttc aagcaggcct tccccgacgg catgtcctac gagagaacct tcacctacga    8640
ggacggcggc gtggccaccg ccagctggga gatcagcctg aagggcaact gcttcgagca    8700
caagtccacc ttccacggcg tgaacttccc cgccgacggc cccgtgatgg ccaagaagac    8760
caccggctgg gaccectect tcgagaagat accgtgtgc gacggcatct gaagggcga    8820 cgtgaccgcc ttcctgatgc tgcagggcgg cggcaactac agatgccagt ccacacctc    8880 ctacaagacc aagaagcccg tgaccatgcc cccaaccac gtggtggagc accgcatcgc    8940
cagaaccgac ctggacaagg gcggcaacag cgtgcagctg accgagcacg ccgtgggcca    9000
catcacctcc gtggtgccct tctgaagcgg cccatggata ttcgaacgcg taggtaccac    9060
atggttaacc tagacttgtc catcttctgg attggccaac ttaattaatg tatgaaataa    9120
aaggatgcac acatagtgac atgctaatca ctataatgtg ggcatcaaag ttgtgtgtta    9180
tgtgtaatta ctagttatct gaataaaaga gaaagagatc atccatattt cttatcctaa    9240
atgaatgtca cgtgtcttta taattctttg atgaaccaga tgcatttcat taaccaaatc    9300
catatacata taaatattaa tcatatataa ttaatatcaa ttgggttagc aaaacaaatc    9360
tagtctaggt gtgttttgcg aattcccatg gacctcgagg gggggcccgg gcacccagct    9420
ttcttgtaca aagtggccgt taacggatcg gccagaatgg cccggaccgg gttaccgaat    9480
tcgagctcgg taccctggga tcggccgctc tagaactagt ggatccccg ggctgcagga    9540 attcccatgg agtcaaagat tcaaatagag gacctaacag aactcgccgt aaagactggc    9600
gaacagttca tacagagtct cttacgactc aatgacaaga gaaaatctt cgtcaacatg    9660 gtggagcacg acacgcttgt ctactccaaa aatatcaaag atacagtctc agaagaccaa    9720
agggcaattg agactttca acaaagggta atatccggaa acctcctcgg attccattgc    9780
ccagctatct gtcactttat tgtgaagata gtggaaagg aaggtggctc ctacaaatgc    9840
catcattgcg ataaaggaaa ggccatcgtt gaagatgcct ctgccgacag tggtcccaaa    9900
gatggacccc cacccacgag gagcatcgtg gaaaaagaag acgttccaac cacgtcttca    9960
aagcaagtgg attgatgtga tatctccact gacgtaaggg atgacgcaca atcccactaa    10020
gcttcggccg ggcccatcg atctggcgaa aggggaatgt gctgcaaggc gattaagttg    10080
ggtaacgcca gggtttccc agtcacgacg ttgtaaaacg acggcagtg ccaagctcag    10140 atcagcttgg ggctggtatc gataaatgtt tccacataga ttttgcatat cataatgatg    10200
tttgtcgttc cgtatctatg tttcatacaa aattttacg catatcgcaa cacatgggca    10260
catacctagt gactgtataa ctctgcatgt atgagtgtat gactatatga tgtagtaact    10320
aataagaagg gtagacattt gagtgattct tttattcctg gacttgtaag acttgacatt    10380
tctgccttga gtgcgataca tcatatggac aggggttatg catacactgc ttgtttgttg    10440
tttatgttct aagagcatct ccaacaacgt gacatatgaa aatgccctac aatttaaaaa    10500
tggttatatt ttataaaatt tagggcataa ataaaacatc ccgctccaac attaaagcct    10560
taaatctatt atagggaagc ccactatgat atagtatatt tgaggcactt tagagggtgc    10620
cctataattt tttgaccatt tttttatgaa atgagacact attggagtat ttttttttccg    10680 tagagcacca tatttcaatt tgagacacca atttaaggca ttgttggaga tgttctaaat    10740
gttggtttat tttgtctgta tcgttgtggt tttgatagtg gtgcctttgc aatgtacatc    10800
ttacattgac aataataata ggtaaaactc tacaaatttt ttatctaatg gactcttgta    10860
```

```
tgaaacattg tacttgcaca catctgatgt aaacactgca tacttttaac agtgacaaga    10920
ttctgtttca ttttagggct agtttgggaa ccaaatttta ttagggtttt tattttctaa    10980
gaaaaagtaa tttattttac cttgagaaaa tataaattac ttgagaaaat agagttccaa    11040
actagctctt atctttgtcg aatcctcctc tattcaaatg tgacatttct ggcacgtgac    11100
aactggtgat gttgtagact gtgttaagta atacgtgtca ttattactaa atgccatttt    11160
agtaaatgtt gagtatgtac tctactacag taagtattat tggtgtattt acactagaca    11220
gttggcggcc tggcgggtaa agttatcctg tagaaagttg ggccaggcca aaaccaaccg    11280
ccaaaggaaa ggccttccgg cccgcccacc tttgcgcgcc gaaggtcagt tccttcagtc    11340
tcctcccgct tcagactctg accacgtcga caatccgggc cgaaacacat ctgcaccgtc    11400
cacttgcgac agattgaaca caccacttct atccacgtca gcgatccgtg cactagccc    11460
ttccaccaat cagcccaagt tgcccctttc ctttaaattc gccgcaccca ttgctcttct    11520
cacggccata gaaatcgacc gagcgaatcc ctcgcatcgc attcgcagcc tttgctgcat    11580
cacaccaccg cgaaacccca gcagccgcat ctgcaggtcg actctagagg atccatggcc    11640
tcctccgagg acgtcatcaa ggagttcatg cgcttcaagg tgcgcatgga gggctccgtg    11700
aacggccacg agttcgagat cgagggcgag ggcgagggcc gcccctacga gggcacccag    11760
accgccaagc tgaaggtgac caagggcggc cccctgccct tcgcctggga catcctgtcc    11820
ccccagttcc agtacggctc caaggtgtac gtgaagcacc ccgccgacat ccccgactac    11880
aagaagctgt ccttccccga gggcttcaag tgggagcgcg tgatgaactt cgaggacggc    11940
ggcgtggtga cagtgaccca ggactcctcc ctgcaggacg gctccttcat ctacaaggtg    12000
aagttcatcg gcgtgaactt cccctccgac ggccccgtaa tgcagaagaa gactatgggc    12060
tgggaggcct ccaccgagcg cctgtacccc gcgacggcg tgctgaaggg cgagatccac    12120
aaggccctga gctgaagga cggcggccac gctagcatct gatggtgacg tacgtgccct    12180
actcgatggg gctagggata acagggtaat actgaagcta ctcaaaacgt cgtgagacag    12240
tttgcggagg atatatatac ctcacacgta cgcgtagttc gctagcaagg gcggcccct    12300
gcccttcgcc tgggacatcc tgtcccccca gttccagtac ggctccaagg tgtacgtgaa    12360
gcaccccgcc gacatccccg actacaagaa gctgtccttc cccgagggct tcaagtggga    12420
gcgcgtgatg aacttcgagg acggcggcgt ggtgacagtg acccaggact cctccctgca    12480
ggacggctcc ttcatctaca aggtgaagtt catcggcgtg aacttcccct ccgacggccc    12540
cgtaatgcag aagaagacta tgggctggga ggcctccacc gagcgcctgt accccgcga    12600
cggcgtgctg aagggcgaga tccacaaggc cctgaagctg aaggacggcg ccactacct    12660
ggtggagttc aagtccatct acatggccaa gaagcccgtg cagctgcccg gctactacta    12720
cgtggactcc aagctggaca tcacctccca caacgaggac tacaccatcg tggagcagta    12780
cgagcgcgcc gagggccgcc accacctgtt cctgtagtca ggatctgagt cgaaacctag    12840
acttgtccat cttctggatt ggccaactta attaatgtat gaaataaaag gatgcacaca    12900
tagtgacatg ctaatcacta taatgtgggc atcaaagttg tgtgttatgt gtaattacta    12960
gttatctgaa taaagagaa agagatcatc catatttctt atcctaaatg aatgtcacgt    13020
gtctttataa ttctttgatg aaccagatgc atttcattaa ccaaatccat atacatataa    13080
atattaatca tatataatta atatcaattg ggttagcaaa acaaatctag tctaggtgtg    13140
ttttgcgaat gcggccgcca ccgcggtgga gctcgaattc cggtccgggt cacccggtcc    13200
gggcctagaa ggccagcttg cggccgcccc gggcaacttt attatacaaa gttgatagat    13260
```

```
atcggtccga gcggcctaga aggcctttgg tcacctttgt ccaccaagat ggaactgcgg   13320
ccgctcatta attaagtcag gcgcgcctct agttgaagac acgttcatgt cttcatcgta   13380
agaagacact cagtagtctt cggccagaat ggcctaactc aaggccatcg tggcctcttg   13440
ctcttcagga tgaagagcta tgtttaaacg tgcaagcgct actagacaat tcagtacatt   13500
aaaaacgtcc gcaatgtgtt attaagttgt ctaagcgtca atttgtttac accacaatat   13560
atcctgccac cagccagcca acagctcccc gaccggcagc tcggcacaaa atcaccactc   13620
gatacaggca gcccatcagt ccgggacggc gtcagcggga gagccgttgt aaggcggcag   13680
actttgctca tgttaccgat gctattcgga agaacggcaa ctaagctgcc gggtttgaaa   13740
cacggatgat ctcgcggagg gtagcatgtt gattgtaacg atgacagagc gttgctgcct   13800
gtgatcaaat atcatctccc tcgcagagat ccgaattatc agccttctta ttcatttctc   13860
gcttaaccgt gacaggctgt cgatcttgag aactatgccg acataatagg aaatcgctgg   13920
ataaagccgc tgaggaagct gagtggcgct atttctttag aagtgaacgt tgacgatcgt   13980
cgaccgtacc ccgatgaatt aattcggacg tacgttctga acacagctgg atacttactt   14040
gggcgattgt catacatgac atcaacaatg tacccgtttg tgtaaccgtc tcttggaggt   14100
tcgtatgaca ctagtggttc ccctcagctt gcgactagat gttgaggcct aacatttat   14160
tagagagcag gctagttgct tagatacatg atcttcaggc cgttatctgt cagggcaagc   14220
gaaaattggc catttatgac gaccaatgcc ccgcagaagc tcccatcttt gccgccatag   14280
acgccgcgcc ccccttttgg ggtgtagaac atccttttgc cagatgtgga aaagaagttc   14340
gttgtcccat tgttggcaat gacgtagtag ccggcgaaag tgcgagaccc atttgcgcta   14400
tatataagcc tacgatttcc gttgcgacta ttgtcgtaat tggatgaact attatcgtag   14460
ttgctctcag agttgtcgta atttgatgga ctattgtcgt aattgcttat ggagttgtcg   14520
tagttgcttg gagaaatgtc gtagttggat ggggagtagt catagggaag acgagcttca   14580
tccactaaaa caattggcag gtcagcaagt gcctgccccg atgccatcgc aagtacgagg   14640
cttagaacca ccttcaacag atcgcgcata gtcttcccca gctctctaac gcttgagtta   14700
agccgcgccg cgaagcggcg tcggcttgaa cgaattgtta gacattattt gccgactacc   14760
ttggtgatct cgccttttcac gtagtgaaca aattcttcca actgatctgc gcgcgaggcc   14820
aagcgatctt cttgtccaag ataagcctgc ctagcttcaa gtatgacggg ctgatactgg   14880
gccggcaggc gctccattgc ccagtcggca gcgacatcct tcggcgcgat tttgccggtt   14940
actgcgctgt accaaatgcg ggacaacgta agcactacat ttcgctcatc gccagcccag   15000
tcgggcggcg agttccatag cgttaaggtt tcatttagcg cctcaaatag atcctgttca   15060
ggaaccggat caaagagttc ctccgccgct ggacctacca aggcaacgct atgttctctt   15120
gcttttgtca gcaagatagc cagatcaatg tcgatcgtgg ctggctcgaa gatacctgca   15180
agaatgtcat tgcgctgcca ttctccaaat tgcagttcgc gcttagctgg ataacgccac   15240
ggaatgatgt cgtcgtgcac aacaatggtg acttctacag cgcggagaat ctcgctctct   15300
ccaggggaag ccgaagtttc caaaaggtcg ttgatcaaag ctcgccgcgt tgtttcatca   15360
agccttacag tcaccgtaac cagcaaatca atatcactgt gtggcttcag gccgccatcc   15420
actgcggagc cgtacaaatg tacggccagc aacgtcggtt cgagatggcg ctcgatgacg   15480
ccaactacct ctgatagttg agtcgatact tcggcgatca ccgcttccct catgatgttt   15540
aactcctgaa ttaagccgcg ccgcgaagcg gtgtcggctt gaatgaattg ttaggcgtca   15600
```

```
tcctgtgctc ccgagaacca gtaccagtac atcgctgttt cgttcgagac ttgaggtcta   15660
gttttatacg tgaacaggtc aatgccgccg agagtaaagc cacattttgc gtacaaattg   15720
caggcaggta cattgttcgt ttgtgtctct aatcgtatgc caaggagctg tctgcttagt   15780
gcccactttt tcgcaaattc gatgagactg tgcgcgactc ctttgcctcg gtgcgtgtgc   15840
gacacaacaa tgtgttcgat agaggctaga tcgttccatg ttgagttgag ttcaatcttc   15900
ccgacaagct cttggtcgat gaatgcgcca tagcaagcag agtcttcatc agagtcatca   15960
tccgagatgt aatccttccg gtaggggctc acacttctgg tagatagttc aaagccttgg   16020
tcggataggt gcacatcgaa cacttcacga acaatgaaat ggttctcagc atccaatgtt   16080
tccgccacct gctcagggat caccgaaatc ttcatatgac gcctaacgcc tggcacagcg   16140
gatcgcaaac ctggcgcggc ttttggcaca aaggcgtga caggtttgcg aatccgttgc   16200
tgccacttgt taacccttt gccagatttg gtaactataa tttatgttag aggcgaagtc   16260
ttgggtaaaa actggcctaa aattgctggg gatttcagga agtaaacat caccttccgg   16320
ctcgatgtct attgtagata tatgtagtgt atctacttga tcgggggatc tgctgcctcg   16380
cgcgtttcgg tgatgacggt gaaaacctct gacacatgca gctcccggag acggtcacag   16440
cttgtctgta agcggatgcc gggagcagac aagcccgtca gggcgcgtca gcgggtgttg   16500
gcgggtgtcg gggcgcagcc atgacccagt cacgtagcga tagcggagtg tatactggct   16560
taactatgcg gcatcagagc agattgtact gagagtgcac catatgcggt gtgaaatacc   16620
gcacagatgc gtaaggagaa ataccgcat caggcgctct tccgcttcct cgctcactga   16680
ctcgctgcgc tcggtcgttc ggctgcggcg agcggtatca gctcactcaa aggcggtaat   16740
acggttatcc acagaatcag gggataacgc aggaaagaac atgtgagcaa aaggccagca   16800
aaaggccagg aaccgtaaaa aggccgcgtt gctggcgttt ttccataggc tccgccccc   16860
tgacgagcat cacaaaaatc gacgctcaag tcagaggtgg cgaaacccga caggactata   16920
aagataccag gcgtttcccc ctggaagctc cctcgtgcgc tctcctgttc cgaccctgcc   16980
gcttaccgga tacctgtccg cctttctccc ttcgggaagc gtggcgcttt ctcatagctc   17040
acgctgtagg tatctcagtt cggtgtaggt cgttcgctcc aagctgggct gtgtgcacga   17100
accccccgtt cagcccgacc gctgcgcctt atccggtaac tatcgtcttg agtccaaccc   17160
ggtaagacac gacttatcgc cactggcagc agccactggt aacaggatta gcagagcgag   17220
gtatgtaggc ggtgctacag agttcttgaa gtggtggcct aactacggct acactagaag   17280
gacagtattt ggtatctgcg ctctgctgaa gccagttacc ttcggaaaaa gagttggtag   17340
ctcttgatcc ggcaaacaaa ccaccgctgg tagcggtggt ttttttgttt gcaagcagca   17400
gattacgcgc agaaaaaaag gatctcaaga agatcctttg atcttttcta cggggtctga   17460
cgctcagtgg aacgaaaact cacgttaagg gattttggtc atgagattat caaaaaggat   17520
cttcacctag atccttttaa attaaaaatg aagttttaaa tcaatctaaa gtatatatga   17580
gtaaacttgg tctgacagtt accaatgctt aatcagtgag gcacctatct cagcgatctg   17640
tctatttcgt tcatccatag ttgcctgact ccccgtcgtg tagataacta cgatacggga   17700
gggcttacca tctggcccca gtgctgcaat gataccgcga acccacgct caccggctcc   17760
agatttatca gcaataaacc agccagccgg aagggccgag cgcagaagtg gtcctgcaac   17820
tttatccgcc tccatccagt ctattaattg ttgccgggaa gctagagtaa gtagttcgcc   17880
agttaatagt ttgcgcaacg ttgttgccat tgctgcaggg ggggggggg ggggggttcca   17940
ttgttcattc cacggacaaa aacagagaaa ggaaacgaca gaggccaaaa agctcgcttt   18000
```

```
cagcacctgt cgtttccttt cttttcagag ggtattttaa ataaaaacat taagttatga    18060
cgaagaagaa cggaaacgcc ttaaaccgga aaattttcat aaatagcgaa aacccgcgag    18120
gtcgccgccc cgtaacctgt cggatcaccg gaaaggaccc gtaaagtgat aatgattatc    18180
atctacatat cacaacgtgc gtggaggcca tcaaaccacg tcaaataatc aattatgacg    18240
caggtatcgt attaattgat ctgcatcaac ttaacgtaaa aacaacttca gacaatacaa    18300
atcagcgaca ctgaatacgg ggcaacctca tgtccccccc ccccccccc ctgcaggcat     18360 cgtggtgtca cgctcgtcgt ttggtatggc ttcattcagc tccggttccc aacgatcaag    18420
gcgagttaca tgatccccca tgttgtgcaa aaaagcggtt agctccttcg gtcctccgat    18480
cgttgtcaga agtaagttgg ccgcagtgtt atcactcatg gttatggcag cactgcataa    18540
ttctcttact gtcatgccat ccgtaagatg cttttctgtg actggtgagt actcaaccaa    18600
gtcattctga aatagtgta tgcggcgacc gagttgctct tgcccggcgt caacacggga     18660
taataccgcg ccacatagca gaactttaaa agtgctcatc attggaaaac gttcttcggg    18720
gcgaaaactc tcaaggatct taccgctgtt gagatccagt tcgatgtaac ccactcgtgc    18780
acccaactga tcttcagcat cttttacttt caccagcgtt tctgggtgag caaaaacagg    18840
aaggcaaaat gccgcaaaaa agggaataag ggcgacacgg aaatgttgaa tactcatact    18900 cttcctttt caatattatt gaagcattta tcagggttat tgtctcatga gcggatacat      18960
atttgaatgt atttagaaaa ataaacaaat aggggttccg cgcacatttc cccgaaaagt    19020
gccacctgac gtctaagaaa ccattattat catgacatta acctataaaa ataggcgtat    19080
cacgaggccc tttcgtcttc aagaattcgg agcttttgcc attctcaccg gattcagtcg    19140
tcactcatgg tgatttctca cttgataacc ttatttttga cgaggggaaa ttaataggtt    19200
gtattgatgt tggacgagtc ggaatcgcag accgatacca ggatcttgcc atcctatgga    19260
actgcctcgg tgagttttct ccttcattac agaaacggct ttttcaaaaa tatggtattg    19320
ataatcctga tatgaataaa ttgcagtttc atttgatgct cgatgagttt ttctaatcag    19380
aattggttaa ttggttgtaa cactggcaga gcattacgct gacttgacgg gacggcggct    19440
ttgttgaata aatcgaactt tgctgagtt gaaggatcag atcacgcatc ttcccgacaa      19500
cgcagaccgt tccgtggcaa agcaaaagtt caaaatcacc aactggtcca cctacaacaa    19560
agctctcatc aaccgtggct ccctcacttt ctggctggat gatggggcga ttcaggcctg    19620
gtatgagtca gcaacacctt cttcacgagg cagacctcag cgccagaagg ccgccagaga    19680
ggccgagcgc ggccgtgagg cttggacgct agggcagggc atgaaaaagc ccgtagcggg    19740
ctgctacggg cgtctgacgc ggtggaaagg gggagggat gttgtctaca tggctctgct     19800
gtagtgagtg ggttgcgctc cggcagcggt cctgatcaat cgtcacccct tctccggtcct   19860 tcaacgttcc tgacaacgag cctccttttc gccaatccat cgacaatcac cgcgagtccc    19920
tgctcgaacg ctgcgtccgg accggcttcg tcgaaggcgt ctatcgcggc ccgcaacagc    19980
ggcgagagcg gagcctgttc aacggtgccg ccgcgctcgc cggcatcgct gtcgccggcc    20040
tgctcctcaa gcacggcccc aacagtgaag tagctgattg tcatcagcgc attgacggcg    20100
tccccggccg aaaaacccgc ctcgcagagg aagcgaagct gcgcgtcggc cgtttccatc    20160
tgcggtgcgc ccggtcgcgt gccgcatgg atgcgcgcgc catcgcggta ggcgagcagc     20220
gcctgcctga agctgcgggc attcccgatc agaaatgagc gccagtcgtc gtcggctctc    20280
ggcaccgaat gcgtatgatt ctccgccagc atggcttcgg ccagtgcgtc gagcagcgcc    20340
```

```
cgcttgttcc tgaagtgcca gtaaagcgcc ggctgctgaa cccccaaccg ttccgccagt    20400
ttgcgtgtcg tcagaccgtc tacgccgacc tcgttcaaca ggtccagggc ggcacggatc    20460
actgtattcg gctgcaactt tgtcatgctt gacactttat cactgataaa cataatatgt    20520
ccaccaactt atcagtgata aagaatccgc gcgttcaatc ggaccagcgg aggctggtcc    20580
ggaggccaga cgtgaaaccc aacataccccc tgatcgtaat tctgagcact gtcgcgctcg    20640
acgctgtcgg catcggcctg attatgccgg tgctgccggg cctcctgcgc gatctggttc    20700
actcgaacga cgtcaccgcc cactatggca ttctgctggc gctgtatgcg ttggtgcaat    20760
ttgcctgcgc acctgtgctg ggcgcgctgt cggatcgttt cgggcggcgg ccaatcttgc    20820
tcgtctcgct ggccggcgcc actgtcgact acgccatcat ggcgacagcg cctttccttt    20880
gggttctcta tatcgggcgg atcgtggccg gcatcaccgg ggcgactggg gcggtagccg    20940
gcgcttatat tgccgatatc actgatggcg atgagcgcgc gcggcacttc ggcttcatga    21000
gcgcctgttt cgggttcggg atggtcgcgg gacctgtgct cggtgggctg atgggcggtt    21060
tctcccccca cgctccgttc ttccgcgcgg cagccttgaa cggcctcaat ttcctgacgg    21120
gctgtttcct tttgccggag tcgcacaaag gcgaacgccg gccgttacgc cgggaggctc    21180
tcaacccgct cgcttcgttc cggtgggccc ggggcatgac cgtcgtcgcc gccctgatgg    21240
cggtcttctt catcatgcaa cttgtcggac aggtgccggc cgcgctttgg gtcattttcg    21300
gcgaggatcg ctttcactgg gacgcgacca cgatcggcat ttcgcttgcc gcatttggca    21360
ttctgcattc actcgcccag gcaatgatca ccggccctgt agccgcccgg ctcggcgaaa    21420
ggcgggcact catgctcgga atgattgccg acggcacagg ctacatcctg cttgccttcg    21480
cgacacgggg atggatggcg ttcccgatca tggtcctgct tgcttcgggt ggcatcggaa    21540
tgccggcgct gcaagcaatg ttgtccaggc aggtggatga ggaacgtcag gggcagctgc    21600
aaggctcact ggcggcgctc accagcctga cctcgatcgt cggacccctc ctcttcacgg    21660
cgatctatgc ggcttctata acaacgtgga acgggtgggc atggattgca ggcgctgccc    21720
tctacttgct ctgcctgccg gcgctgcgtc gcgggctttg gagcggcgca gggcaacgag    21780
ccgatcgctg atcgtggaaa cgataggcct atgccatgcg ggtcaaggcg acttccggca    21840
agctatacgc gccctaggag tgcggttgga acgttggccc agccagatac tcccgatcac    21900
gagcaggacg ccgatgattt gaagcgcact cagcgtctga tccaagaaca accatcctag    21960
caacacggcg gtccccgggc tgagaaagcc cagtaaggaa acaactgtag gttcgagtcg    22020
cgagatcccc cggaaccaaa ggaagtaggt taaacccgct ccgatcaggc cgagccacgc    22080
caggccgaga acattggttc ctgtaggcat cgggattggc ggatcaaaca ctaaagctac    22140
tggaacgagc agaagtcctc cggccgccag ttgccaggcg gtaaaggtga gcagaggcac    22200
gggaggttgc cacttgcggg tcagcacggt tccgaacgcc atggaaaccg cccccgccag    22260
gcccgctgcg acgccgacag gatctagcgc tgcgtttggt gtcaacacca acagcgccac    22320
gcccgcagtt ccgcaaatag cccccaggac cgccatcaat cgtatcgggc tacctagcag    22380
agcggcagag atgaacacga ccatcagcgg ctgcacagcg cctaccgtcg ccgcgacccc    22440
gcccggcagg cggtagaccg aaataaacaa caagctccag aatagcgaaa tattaagtgc    22500
gccgaggatg aagatgcgca tccaccagat tcccgttgga atctgtcgga cgatcatcac    22560
gagcaataaa cccgcggca acgcccgcag cagcataccg cgacccctc ggcctcgctg    22620 ttcgggctcc acgaaaacgc cggacagatg cgccttgtga cgcgtccttgg ggccgtcctc    22680 ctgtttgaag accgacagcc caatgatctc gccgtcgatg taggcgccga atgccacggc    22740
```

```
atctcgcaac cgttcagcga acgcctccat gggcttttc tcctcgtgct cgtaaacgga   22800
cccgaacatc tctggagctt tcttcagggc cgacaatcgg atctcgcgga aatcctgcac   22860
gtcggccgct ccaagccgtc gaatctgagc cttaatcaca attgtcaatt ttaatcctct   22920
gtttatcggc agttcgtaga gcgcgccgtg cgtcccgagc gatactgagc gaagcaagtg   22980
cgtcgagcag tgcccgcttg ttcctgaaat gccagtaaag cgctggctgc tgaaccccca   23040
gccgaactg accccacaag gccctagcgt ttgcaatgca ccaggtcatc attgacccag    23100
gcgtgttcca ccaggccgct gcctcgcaac tcttcgcagg cttcgccgac ctgctcgcgc   23160
cacttcttca cgcgggtgga atccgatccg cacatgaggc ggaaggtttc cagcttgagc   23220
gggtacggct cccggtgcga gctgaaatag tcgaacatcc gtcgggccgt cggcgacagc   23280
ttgcggtact tctcccatat gaatttcgtg tagtggtcgc cagcaaacag cacgacgatt   23340
tcctcgtcga tcaggacctg gcaacgggac gttttcttgc cacggtccag gacgcggaag   23400
cggtgcagca gcgacaccga ttccaggtgc ccaacgcggt cggacgtgaa gcccatcgcc   23460
gtcgcctgta ggcgcgacag gcattcctcg gccttcgtgt aataccggcc attgatcgac   23520
cagcccaggt cctggcaaag ctcgtagaac gtgaaggtga tcggctcgcc gataggggtg   23580
cgcttcgcgt actccaacac ctgctgccac accagttcgt catcgtcggc ccgcagctcg   23640
acgccggtgt aggtgatctt cacgtccttg ttgacgtgga aaatgacctt gttttgcagc   23700
gcctcgcgcg ggatttcctt gttgcgcgtg gtgaacaggg cagagcgggc cgtgtcgttt   23760
ggcatcgctc gcatcgtgtc cggccacggc gcaatatcga acaaggaaag ctgcatttcc   23820
ttgatctgct gcttcgtgtg tttcagcaac gcggcctgct tggcctcgct gacctgtttt   23880
gccaggtcct cgccggcggt ttttcgcttc ttggtcgtca tagttcctcg cgtgtcgatg   23940
gtcatcgact tcgccaaacc tgccgcctcc tgttcgagac gacgcgaacg ctccacggcg   24000
gccgatggcg cgggcagggc aggggagcc agttgcacgc tgtcgcgctc gatcttggcc    24060
gtagcttgct ggaccatcga gccgacggac tggaaggttt cgcggggcgc acgcatgacg   24120
gtgcggcttg cgatggtttc ggcatcctcg gcggaaaacc ccgcgtcgat cagttcttgc   24180
ctgtatgcct tccggtcaaa cgtccgattc attcaccctc cttgcgggat tgccccgact   24240
cacgccgggg caatgtgccc ttattcctga tttgacccgc ctggtgcctt ggtgtccaga   24300
taatccacct tatcggcaat gaagtcggtc ccgtagaccg tctggccgtc cttctcgtac   24360
ttggtattcc gaatcttgcc ctgcacgaat accagcgacc ccttgcccaa atacttgccg   24420
tgggcctcgg cctgagagcc aaaacacttg atgcggaaga agtcggtgcg ctcctgcttg   24480
tcgccggcat cgttgcgcca ctcttcatta accgctatat cgaaaattgc ttgcggcttg   24540
ttagaattgc catgacgtac ctcggtgtca cgggtaagat taccgataaa ctggaactga   24600
ttatggctca tatcgaaagt ctccttgaga aaggagactc tagtttagct aaacattggt   24660
tccgctgtca agaactttag cggctaaaat tttgcgggcc gcgaccaaag gtgcgagggg   24720
cggcttccgc tgtgtacaac cagatatttt tcaccaacat ccttcgtctg ctcgatgagc   24780
ggggcatgac gaaacatgag ctgtcggaga gggcaggggt ttcaatttcg tttttatcag   24840
acttaaccaa cggtaaggcc aacccctcgt tgaaggtgat ggaggccatt gccgacgccc   24900
tggaaactcc cctacctctt ctcctggagt ccaccgacct tgaccgcgag gcactcgcgg   24960
agattgcggg tcatccttc aagagcagcg tgccgcccgg atacgaacgc atcagtgtgg   25020
ttttgccgtc acataaggcg tttatcgtaa agaaatgggg cgacgacacc cgaaaaaagc   25080
```

| | |
|---|---:|
| tgcgtggaag gctctgacgc caagggttag ggcttgcact tccttcttta gccgctaaaa | 25140 |
| cggccccttc tctgcgggcc gtcggctcgc gcatcatatc gacatcctca acggaagccg | 25200 |
| tgccgcgaat ggcatcgggc gggtgcgctt tgacagttgt tttctatcag aacccctacg | 25260 |
| tcgtgcggtt cgattagctg tttgtcttgc aggctaaaca ctttcggtat atcgtttgcc | 25320 |
| tgtgcgataa tgttgctaat gatttgttgc gtaggggtta ctgaaaagtg agcgggaaag | 25380 |
| aagagtttca gaccatcaag gagcgggcca agcgcaagct ggaacgcgac atgggtgcgg | 25440 |
| acctgttggc cgcgctcaac gacccgaaaa ccgttgaagt catgctcaac gcggacggca | 25500 |
| aggtgtggca cgaacgcctt ggcgagccga tgcggtacat ctgcgacatg cggcccagcc | 25560 |
| agtcgcaggc gattatagaa acggtggccg gattccacgg caaagaggtc acgcggcatt | 25620 |
| cgcccatcct ggaaggcgag ttcccсcttgg atggcagccg cttttgccggc caattgccgc | 25680 |
| cggtcgtggc cgcgccaacc tttgcgatcc gcaagcgcgc ggtcgccatc ttcacgctgg | 25740 |
| aacagtacgt cgaggcgggc atcatgaccc gcgagcaata cgaggtcatt aaaagcgccg | 25800 |
| tcgcggcgca tcgaaacatc ctcgtcattg gcggtactgg ctcgggcaag accacgctcg | 25860 |
| tcaacgcgat catcaatgaa atggtcgcct tcaacccgtc tgagcgcgtc gtcatcatcg | 25920 |
| aggacaccgg cgaaatccag tgcgccgcag agaacgccgt ccaataccac accagcatcg | 25980 |
| acgtctcgat gacgctgctg ctcaagacaa cgctgcgtat gcgccccgac cgcatcctgg | 26040 |
| tcggtgaggt acgtggcccc gaagcccttg atctgttgat ggcctggaac accgggcatg | 26100 |
| aaggaggtgc cgccaccctg cacgcaaaca accccaaagc gggcctgagc cggctcgcca | 26160 |
| tgcttatcag catgcacccg gattcaccga aacccattga gccgctgatt ggcgaggcgg | 26220 |
| ttcatgtggt cgtccatatc gccaggaccc ctagcggccg tcgagtgcaa gaaattctcg | 26280 |
| aagttcttgg ttacgagaac ggccagtaca tcaccaaaac cctgtaagga gtatttccaa | 26340 |
| tgacaacggc tgttccgttc cgtctgacca tgaatcgcgg cattttgttc taccttgccg | 26400 |
| tgttcttcgt tctcgctctc gcgttatccg cgcatccggc gatggcctcg gaaggcaccg | 26460 |
| gcggcagctt gccatatgag agctggctga cgaacctgcg caactccgta accggcccgg | 26520 |
| tggccttcgc gctgtccatc atcggcatcg tcgtcgccgg cggcgtgctg atcttcggcg | 26580 |
| gcgaactcaa cgccttcttc cgaaccctga tcttcctggt tctggtgatg cgctgctgg | 26640 |
| tcggcgcgca gaacgtgatg agcacccttct tcggtcgtgg tgccgaaatc gcggccctcg | 26700 |
| gcaacggggc gctgcaccag gtgcaagtcg cggcggcgga tgccgtgcgt gcggtagcgg | 26760 |
| ctggacggct cgcctaatca tggctctgcg cacgatcccc atccgtcgcg caggcaaccg | 26820 |
| agaaaacctg ttcatggggtg gtgatcgtga actggtgatg ttctcgggcc tgatggcgtt | 26880 |
| tgcgctgatt ttcagcgccc aagagctgcg ggccaccgtg gtcggtctga tcctgtggtt | 26940 |
| cggggcgctc tatgcgttcc gaatcatggc gaaggccgat ccgaagatgc ggttcgtgta | 27000 |
| cctgcgtcac cgccggtaca agccgtatta cccggcccgc tcgaccccgt tccgcgagaa | 27060 |
| caccaatagc caagggaagc aataccgatg atccaagcaa ttgcgattgc aatcgcgggc | 27120 |
| ctcggcgcgc ttctgttgtt catcctcttt gcccgcatcc gcgcggtcga tgccgaactg | 27180 |
| aaactgaaaa agcatcgttc caaggacgcc ggcctggccg atctgctcaa ctacgccgct | 27240 |
| gtcgtcgatg acggcgtaat cgtgggcaag aacggcagct ttatggctgc ctggctgtac | 27300 |
| aagggcgatg acaacgcaag cagcaccgac cagcagcgcg aagtagtgtc cgcccgcatc | 27360 |
| aaccaggccc tcgcgggcct gggaagtggg tggatgatcc atgtggacgc cgtgcggcgt | 27420 |
| cctgctccga actacgcgga gcggggcctg tcggcgttcc ctgaccgtct gacggcagcg | 27480 |

```
attgaagaag agcgctcggt cttgccttgc tcgtcggtga tgtacttcac cagctccgcg    27540
aagtcgctct tcttgatgga gcgcatgggg acgtgcttgg caatcacgcg cacccccccg    27600
ccgttttagc ggctaaaaaa gtcatggctc tgccctcggg cggaccacgc ccatcatgac    27660
cttgccaagc tcgtcctgct tctcttcgat cttcgccagc agggcgagga tcgtggcatc    27720
accgaaccgc gccgtgcgcg ggtcgtcggt gagccagagt ttcagcaggc cgcccaggcg    27780
gcccaggtcg ccattgatgc gggccagctc gcggacgtgc tcatagtcca cgacgcccgt    27840
gattttgtag ccctggccga cggccagcag gtaggccgac aggctcatgc cggccgccgc    27900
cgcctttttcc tcaatcgctc ttcgttcgtc tggaaggcag tacaccttga taggtgggct    27960
gcccttcctg gttggcttgg tttcatcagc catccgcttg ccctcatctg ttacgccggc    28020
ggtagccggc cagcctcgca gagcaggatt cccgttgagc accgccaggt gcgaataagg    28080
gacagtgaag aaggaacacc cgctcgcggg tgggcctact tcacctatcc tgcccggctg    28140
acgccgttgg atacaccaag gaaagtctac acgaacccctt tggcaaaatc ctgtatatcg    28200
tgcgaaaaag gatggatata ccgaaaaaat cgctataatg accccgaagc agggttatgc    28260
agcgaaaaag cgctgcttcc ctgctgtttt gtggaatatc taccgactgg aaacaggcaa    28320
atgcaggaaa ttactgaact gaggggacag gcagagacg atgccaaaga gctacaccga     28380
cgagctggcc gagtgggttg aatcccgcgc ggccaagaag cgccggcgtg atgaggctgc    28440
ggttgcgttc ctggcggtga gggcggatgt cgaggcggcg ttagcgtccg gctatgcgct    28500
cgtcaccatt tgggagcaca tgcgggaaac ggggaaggtc aagttctcct acgagacgtt    28560
ccgctcgcac gccaggcggc acatcaaggc caagcccgcc gatgtgcccg caccgcaggc    28620
caaggctgcg gaacccgcgc cggcacccaa gacgccggag ccacggcggc cgaagcaggg    28680
gggcaaggct gaaaagccgg cccccgctgc ggccccgacc ggcttcacct tcaacccaac    28740
accggacaaa aaggatctac tgtaatggcg aaaattcaca tggttttgca gggcaagggc    28800
ggggtcggca agtcggccat cgccgcgatc attgcgcagt acaagatgga caaggggcag    28860
acacccttgt gcatcgacac cgacccggtg aacgcgacgt tcgagggcta caaggccctg    28920
aacgtccgcc ggctgaacat catggccggc gacgaaatta actcgcgcaa cttcgacacc    28980
ctggtcgagc tgattgcgcc gaccaaggat gacgtggtga tcgacaacgg tgccagctcg    29040
ttcgtgcctc tgtcgcatta cctcatcagc aaccaggtgc cggctctgct gcaagaaatg    29100
gggcatgagc tggtcatcca taccgtcgtc accggcggcc aggctctcct ggacacggtg    29160
agcggcttcg cccagctcgc cagccagttc ccggccgaag cgcttttcgt ggtctggctg    29220
aacccgtatt gggggcctat cgagcatgag ggcaagagct ttgagcagat gaaggcgtac    29280
acggccaaca aggcccgcgt gtcgtccatc atccagattc cggccctcaa ggaagaaacc    29340
tacggccgcg atttcagcga catgctgcaa gagcggctga cgttcgacca ggcgctggcc    29400
gatgaatcgc tcacgatcat gacgcggcaa cgcctcaaga tcgtgcgcgc ggcctgtttt    29460
gaacagctcg acgcggcggc cgtgctatga gcgaccagat tgaagagctg atccgggaga    29520
ttgcggccaa gcacggcatc gccgtcggcc gcgacgaccc ggtgctgatc ctgcatacca    29580
tcaacgcccg gctcatggcc gacagtgcgg ccaagcaaga ggaaatcctt gccgcgttca    29640
aggaagagct ggaagggatc gcccatcgtt ggggcgagga cgccaaggcc aaagcggagc    29700
ggatgctgaa cgcggccctg gcggccagca aggacgcaat ggcgaaggta atgaaggaca    29760
gcgccgcgca ggcggccgaa gcgatccgca gggaaatcga cgacggcctt ggccgccagc    29820
```

```
tcgcggccaa ggtcgcggac gcgcggcgcg tggcgatgat aacatgatc gccggcggca    29880
tggtgttgtt cgcggccgcc ctggtggtgt gggcctcgtt atgaatcgca gaggcgcaga    29940
tgaaaaagcc cggcgttgcc gggctttgtt tttgcgttag ctgggcttgt ttgacaggcc    30000
caagctctga ctgcgcccgc gctcgcgctc ctgggcctgt ttcttctcct gctcctgctt    30060
gcgcatcagg gcctggtgcc gtcgggctgc ttcacgcatc gaatcccagt cgccggccag    30120
ctcgggatgc tccgcgcgca tcttgcgcgt cgccagttcc tcgatcttgg gcgcgtgaat    30180
gcccatgcct tccttgattt cgcgcaccat gtccagccgc gtgtgcaggg tctgcaagcg    30240
ggcttgctgt tgggcctgct gctgctgcca ggcggccttt gtacgcggca gggacagcaa    30300
gccgggggca ttggactgta gctgctgcaa acgcgcctgc tgacggtcta cgagctgttc    30360
taggcggtcc tcgatgcgct ccacctggtc atgctttgcc tgcacgtaga gcgcaagggt    30420
ctgctggtag gtctgctcga tgggcgcgga ttctaagagg gcctgctgtt ccgtctcggc    30480
ctcctgggcc gcctgtagca aatcctcgcc gctgttgccg ctggactgct ttactgccgg    30540
ggactgctgt tgccctgctc gcgccgtcgt cgcagttcgg cttgccccca ctcgattgac    30600
tgcttcattt cgagccgcag cgatgcgatc tcggattgcg tcaacggacg gggcagcgcg    30660
gaggtgtccg gcttctcctt gggtgagtcg gtcgatgcca tagccaaagg tttccttcca    30720
aaatgcgtcc attgctggac cgtgtttctc attgatgccc gcaagcatct tcggcttgac    30780
cgccaggtca agcgcgcctt catgggcggt catgacggac gccgccatga ccttgccgcc    30840
gttgttctcg atgtagccgc gtaatgaggc aatggtgccg cccatcgtca gcgtgtcatc    30900
gacaacgatg tacttctggc cggggatcac ctccccctcg aaagtcgggt tgaacgccag    30960
gcgatgatct gaaccggctc cggttcgggc gaccttctcc cgctgcacaa tgtccgtttc    31020
gacctcaagg ccaaggcggt cggccagaac gaccgccatc atggccggaa tcttgttgtt    31080
ccccgccgcc tcgacggcga ggactggaac gatgcggggc ttgtcgtcgc cgatcagcgt    31140
cttgagctgg gcaacagtgt cgtccgaaat caggcgctcg accaaattaa gcgccgcttc    31200
cgcgtcgccc tgcttcgcag cctggtattc aggctcgttg gtcaaagaac caaggtcgcc    31260
gttgcgaacc accttcggga agtctcccca cggtgcgcgc tcggctctgc tgtagctgct    31320
caagacgcct ccctttttag ccgctaaaac tctaacgagt gcgcccgcga ctcaacttga    31380
cgctttcggc acttacctgt gccttgccac ttgcgtcata ggtgatgctt ttcgcactcc    31440
cgatttcagg tactttatcg aaatctgacc gggcgtgcat tacaaagttc ttccccacct    31500
gttggtaaat gctgccgcta tctgcgtgga cgatgctgcc gtcgtggcgc tgcgacttat    31560
cggccttttg ggccatatag atgttgtaaa tgccaggttt cagggccccg gctttatcta    31620
ccttctggtt cgtccatgcg ccttggttct cggtctggac aattctttgc ccattcatga    31680
ccaggaggcg gtgtttcatt gggtgactcc tgacggttgc ctctggtgtt aaacgtgtcc    31740
tggtcgcttg ccggctaaaa aaagccgac ctcggcagtt cgaggccggc tttccctaga    31800
gccgggcgcg tcaaggttgt tccatctatt ttagtgaact gcgttcgatt tatcagttac    31860
tttcctcccg ctttgtgttt cctcccactc gtttccgcgt ctagccgacc cctcaacata    31920
gcggcctctt cttgggctgc ctttgcctct tgccgcgctt cgtcacgctc ggcttgcacc    31980
gtcgtaaagc gctcggcctg cctggccgcc tcttgcgccg ccaacttcct tgctcctgg    32040
tgggcctcgg cgtcggcctg cgccttcgct ttcaccgctg ccaactccgt gcgcaaactc    32100
tccgcttcgc gcctggtggc gtcgcgctcg ccgcgaagcg cctgcatttc ctggttggcc    32160
gcgtccaggg tcttgcggct ctcttctttg aatgcgcggg cgtcctggtg agcgtagtcc    32220
```

```
agctcggcgc gcagctcctg cgctcgacgc tccacctcgt cggcccgctg cgtcgccagc    32280
gcggcccgct gctcggctcc tgccagggcg gtgcgtgctt cggccagggc ttgccgctgg    32340
cgtgcggcca gctcggccgc ctcggcggcc tgctgctcta gcaatgtaac gcgcgcctgg    32400
gcttcttcca gctcgcgggc ctgcgcctcg aaggcgtcgg ccagctcccc gcgcacggct    32460
tccaactcgt tgcgctcacg atcccagccg gcttgcgctg cctgcaacga ttcattggca    32520
agggcctggg cggcttgcca gagggcgcc acggcctggt tgccggcctg ctgcaccgcg    32580
tccggcacct ggactgccag cggggcggcc tgcgccgtgc gctggcgtcg ccattcgcgc    32640
atgccggcgc tggcgtcgtt catgttgacg cgggcggcct tacgcactgc atccacggtc    32700
gggaagttct cccggtcgcc ttgctcgaac agctcgtccg cagccgcaaa aatgcggtcg    32760
cgcgtctctt tgttcagttc catgttggct ccggtaattg gtaagaataa taatactctt    32820 acctaccttä tcagcgcaag agtttagctg aacagttctc gacttaacgg cagttttttt    32880
agcggctgaa gggcaggcaa aaaaagcccc gcacggtcgg cggggcaaa gggtcagcgg    32940 gaagggatt agcgggcgtc gggcttcttc atgcgtcggg gccgcgcttc ttgggatgga    33000
gcacgacgaa gcgcgcacgc gcatcgtcct cggccctatc ggcccgcgtc gcggtcagga    33060
acttgtcgcg cgctaggtcc tccctggtgg gcaccagggg catgaactcg gcctgctcga    33120
tgtaggtcca ctccatgacc gcatcgcagt cgaggccgcg ttccttcacc gtctcttgca    33180
ggtcgcggta cgcccgctcg ttgagcggct ggtaacgggc caattggtcg taaatggctg    33240
tcggccatga gcggccttc ctgttgagcc agcagccgac gacgaagccg gcaatgcagg    33300
cccctggcac aaccaggccg acgccggggg caggggatgg cagcagctcg ccaaccagga    33360
accccgccgc gatgatgccg atgccggtca accagccctt gaaactatcc ggccccgaaa    33420 caccctgcg cattgcctgg atgctgcgcc ggatagcttg caacatcagg agccgtttct    33480
tttgttcgtc agtcatggtc cgccctcacc agttgttcgt atcggtgtcg gacgaactga    33540
aatcgcaaga gctgccggta tcggtccagc cgctgtccgt gtcgctgctg ccgaagcacg    33600
gcgaggggtc cgcgaacgcc gcagacggcg tatccggccg cagcgcatcg cccagcatgg    33660
ccccggtcag cgagccgccg gccaggtagc ccagcatggt gctgttggtc gccccggcca    33720
ccagggccga cgtgacgaaa tcgccgtcat tccctctgga ttgttcgctg ctcggcgggg    33780
cagtgcgccg cgccggcggc gtcgtggatg gctcgggttg gctggcctgc gacggccggc    33840
gaaaggtgcg cagcagctcg ttatcgaccg gctgcggcgt cggggccgcc gccttgcgct    33900
gcggtcggtg ttccttcttc ggctcgcgca gcttgaacag catgatcgcg gaaaccagca    33960
gcaacgccgc gcctacgcct cccgcgatgt agaacagcat cggattcatt cttcggtcct    34020
ccttgtagcg gaaccgttgt ctgtgcgcg cgggtggccc gcgccgctgt ctttggggat    34080
cagccctcga tgagcgcgac cagtttcacg tcggcaaggt tcgcctcgaa ctcctggccg    34140
tcgtcctcgt acttcaacca ggcatagcct tccgccggcg gccgacggtt gaggataagg    34200
cgggcagggc gctcgtcgtg ctcgacctgg acgatggcct ttttcagctt gtccgggtcc    34260
ggctccttcg cgcccttttc cttggcgtcc ttaccgtcct ggtcgccgtc ctcgccgtcc    34320
tggccgtcgc cggcctccgc gtcacgctcg gcatcagtct ggccgttgaa ggcatcgacg    34380
gtgttgggat cgcggcccgt ctcgtccagg aactcgcgca gcagcttgac cgtgccgcgc    34440
gtgatttcct gggtgtcgtc gtcaagccac gcctcgactt cctccgggcg cttcttgaag    34500
gccgtcacca gctcgttcac cacggtcacg tcgcgcacgc ggccggtgtt gaacgcatcg    34560
```

```
gcgatcttct ccggcaggtc cagcagcgtg acgtgctggg tgatgaacgc cggcgacttg    34620
ccgatttcct tggcgatatc gcctttcttc ttgcccttcg ccagctcgcg gccaatgaag    34680
tcggcaattt cgcgcggggt cagctcgttg cgttgcaggt tctcgataac ctggtcggct    34740
tcgttgtagt cgttgtcgat gaacgccggg atggacttct tgccggccca cttcgagcca    34800
cggtagcggc gggcgccgtg attgatgata tagcggcccg gctgctcctg gttctcgcgc    34860
accgaaatgg gtgacttcac cccgcgctct ttgatcgtgg caccgatttc gcgatgctc    34920 tccggggaaa agccggggtt gtcggccgtc cgcggctgat gcggatcttc gtcgatcagg    34980
tccaggtcca gctcgatagg gccggaaccg ccctgagacg ccgcaggagc gtccaggagg    35040
ctcgacaggt cgccgatgct atccaacccc aggccggacg gctgcgccgc gcctgcggct    35100
tcctgagcgg ccgcagcggt gttttcttg gtggtcttgg cttgagccgc agtcattggg    35160
aaatctccat cttcgtgaac acgtaatcag ccagggcgcg aacctctttc gatgccttgc    35220
gcgcggccgt tttcttgatc ttccagaccg gcacaccgga tgcgagggca tcggcgatgc    35280
tgctgcgcag gccaacggtg gccggaatca tcatcttggg gtacgcggcc agcagctcgg    35340
cttggtggcg cgcgtggcgc ggattccgcg catcgacctt gctgggcacc atgccaagga    35400
attgcagctt ggcgttcttc tggcgcacgt tcgcaatggt cgtgaccatc ttcttgatgc    35460
cctggatgct gtacgcctca agctcgatgg gggacagcac atagtcggcc gcgaagaggg    35520
cggccgccag gccgacgcca agggtcgggg ccgtgtcgat caggcacacg tcgaagcctt    35580
ggttcgccag ggccttgatg ttcgccccga acagctcgcg ggcgtcgtcc agcgacagcc    35640
gttcggcgtt cgccagtacc gggttggact cgatgagggc gaggcgcgcg gcctggccgt    35700
cgccggctgc gggtgcggtt tcggtccagc cgccggcagg gacagcgccg aacagcttgc    35760
ttgcatgcag gccggtagca aagtccttga gcgtgtagga cgcattgccc tgggggtcca    35820
ggtcgatcac ggcaacccgc aagccgcgct cgaaaaagtc gaaggcaaga tgcacaaggg    35880
tcgaagtctt gccgacgccg cctttctggt tggccgtgac caaagttttc atcgtttggt    35940
ttcctgtttt ttcttggcgt ccgcttccca cttccggacg atgtacgcct gatgttccgg    36000
cagaaccgcc gttacccgcg cgtaccccte gggcaagttc ttgtcctcga acgcggccca    36060
cacgcgatgc accgcttgcg acactgcgcc cctggtcagt cccagcgacg ttgcgaacgt    36120
cgcctgtggc ttcccatcga ctaagacgcc ccgcgctatc tcgatggtct gctgccccac    36180
ttccagcccc tggatcgcct cctggaactg gctttcggta agccgtttct tcatggataa    36240
cacccataat ttgctccgcg ccttggttga acatagcggt gacagccgcc agcacatgag    36300
agaagtttag ctaaacattt ctcgcacgtc aacaccttta gccgctaaaa ctcgtccttg    36360
gcgtaacaaa acaaaagccc ggaaaccggg ctttcgtctc ttgccgctta tggctctgca    36420
cccggctcca tcaccaacag gtcgcgcacg cgcttcactc ggttgcggat cgacactgcc    36480
agcccaacaa agccggttgc cgccgccgcc aggatcgcgc cgatgatgcc ggccacaccg    36540
gccatcgccc accaggtcgc cgccttccgg ttcattcct gctggtactg cttcgcaatg    36600
ctggacctcg gctcaccata ggctgaccgc tcgatggcgt atgccgcttc tccccttggc    36660
gtaaaaccca gcgccgcagg cggcattgcc atgctgcccg ccgctttccc gaccacgacg    36720
cgcgcaccag gcttgcggtc cagaccttcg gccacggcga gctgcgcaag gacataatca    36780
gccgccgact ggctccacg cgcctcgatc agctcttgca ctcgcgcgaa atccttggcc    36840
tccacggccg ccatgaatcg cgcacgcggc gaaggctccg cagggccggc gtcgtgatcg    36900
ccgccgagaa tgcccttcac caagttcgac gacacgaaaa tcatgctgac ggctatcacc    36960
```

```
atcatgcaga cggatcgcac gaacccgctg aattgaacac gagcacggca cccgcgacca    37020
ctatgccaag aatgcccaag gtaaaaattg ccggccccgc catgaagtcc gtgaatgccc    37080
cgacggccga agtgaagggc aggccgccac ccaggccgcc gccctcactg cccggcacct    37140
ggtcgctgaa tgtcgatgcc agcacctgcg gcacgtcaat gcttccgggc gtcgcgctcg    37200
ggctgatcgc ccatcccgtt actgcccga tcccggcaat ggcaaggact gccagcgctg    37260
ccatttttgg ggtgaggccg ttcgcggccg aggggcgcag ccctgggg gatgggaggc    37320 ccgcgttagc gggccgggag ggttcgagaa gggggggcac cccccttcgg cgtgcgcggt    37380
cacgcgcaca gggcgcagcc ctggttaaaa acaaggttta taatattgg tttaaaagca    37440 ggttaaaaga caggttagcg gtggccgaaa acgggcgga aacccttgca aatgctggat    37500
tttctgcctg tggacagccc ctcaaatgtc aataggtgcg cccctcatct gtcagcactc    37560
tgcccctcaa gtgtcaagga tcgcgcccct catctgtcag tagtcgcgcc cctcaagtgt    37620
caataccgca gggcacttat ccccaggctt gtccacatca tctgtgggaa actcgcgtaa    37680
aatcaggcgt tttcgccgat ttgcgaggct ggccagctcc acgtcgccgg ccgaaatcga    37740
gcctgcccct catctgtcaa cgccgcgccg ggtgagtcgg cccctcaagt gtcaacgtcc    37800 gccctcatc tgtcagtgag ggccaagttt ccgcgaggt atccacaacg ccggcggccg    37860
cggtgtctcg cacacggctt cgacggcgtt tctggcgcgt ttgcagggcc atagacggcc    37920
gccagcccag cggcgagggc aaccagcccg gtgagcgtcg gaaaggcgct ggaagccccg    37980
tagcgacgcg gagaggggcg agacaagcca agggcgcagg ctcgatgcgc agcacgacat    38040
agccggttct cgcaaggacg agaatttccc tgcggtgccc ctcaagtgtc aatgaaagtt    38100
tccaacgcga gccattcgcg agagccttga gtccacgcta gatgagagct tgttgtagg    38160 tggaccagtt ggtgattttg aacttttgct ttgccacgga acggtctgcg ttgtcgggaa    38220
gatgcgtgat ctgatccttc aactcagcaa aagttcgatt tattcaacaa agccacgttg    38280
tgtctcaaaa tctctgatgt tacattgcac aagataaaaa tatatcatca tgaacaataa    38340
aactgtctgc ttacataaac agtaatacaa ggggtgttat gagccatatt caacgggaaa    38400
cgtcttgctc gactctagag ctcgttcctc gaggcctcga ggcctcgagg aacggtacct    38460
gcggggaagc ttacaataat gtgtgttgtt aagtcttgtt gcctgtcatc gtctgactga    38520 cttttcgtcat aaatcccggc ctccgtaacc cagctttggg caagctcacg gatttgatcc    38580
ggcggaacgg gaatatcgag atgccgggct gaacgctgca gttccagctt tccctttcgg    38640
gacaggtact ccagctgatt gattatctgc tgaagggtct tggttccacc tcctggcaca    38700
atgcgaatga ttacttgagc gcgatcgggc atccaatttt ctcccgtcag gtgcgtggtc    38760
aagtgctaca aggcaccttt cagtaacgag cgaccgtcga tccgtcgccg ggatacggac    38820
aaaatggagc gcagtagtcc atcgagggcg gcgaaagcct cgccaaaagc aatacgttca    38880
tctcgcacag cctccagatc cgatcgaggg tcttcggcgt aggcagatag aagcatggat    38940
acattgcttg agagtattcc gatggactga agtatggctt ccatcttttc tcgtgtgtct    39000
gcatctattt cgagaaagcc cccgatgcgg cgcaccgcaa cgcgaattgc catactatcc    39060
gaaagtccca gcaggcgcgc ttgataggaa aaggtttcat actcggccga tcgcagacgg    39120
gcactcacga ccttgaaccc ttcaactttc agggatcgat gctggttgat ggtagtctca    39180
ctcgacgtgg ctctggtgtg ttttgacata gcttcctcca aagaaagcgg aaggtctgga    39240
tactccagca cgaaatgtgc ccgggtagac ggatggaagt ctagccctgc tcaatatgaa    39300
```

| | |
|---|---|
| atcaacagta catttacagt caatactgaa tatacttgct acatttgcaa ttgtcttata | 39360 |
| acgaatgtga aataaaaata gtgtaacaac gctttactc atcgataatc acaaaaacat | 39420 |
| ttatcgaac aaaaatacaa atgcactccg gtttcacagg ataggcggga tcagaatatg | 39480 |
| caacttttga cgttttgttc tttcaaaggg ggtgctggca aaaccaccgc actcatgggc | 39540 |
| ctttgcgctg ctttggcaaa tgacggtaaa cgagtggccc tctttgatgc cgacgaaaac | 39600 |
| cggcctctga cgcgatggag agaaaacgcc ttacaaagca gtactgggat cctcgctgtg | 39660 |
| aagtctattc cgccgacgaa atgccccttc ttgaagcagc ctatgaaaat gccgagctcg | 39720 |
| aaggatttga ttatgcgttg gccgatacgc gtggcggctc gagcgagctc aacaacacaa | 39780 |
| tcatcgctag ctcaaacctg cttctgatcc ccaccatgct aacgccgctc gacatcgatg | 39840 |
| aggcactatc tacctaccgc tacgtcatcg agctgctgtt gagtgaaaat ttggcaattc | 39900 |
| ctacagctgt tttgcgccaa cgcgtcccgg tcggccgatt gacaacatcg caacgcagga | 39960 |
| tgtcagagac gctagagagc cttccagttg taccgtctcc catgcatgaa agagatgcat | 40020 |
| ttgccgcgat gaaagaacgc ggcatgttgc atcttacatt actaaacacg gaactgatc | 40080 |
| cgacgatgcg cctcatagag aggaatcttc ggattgcgat ggaggaagtc gtggtcattt | 40140 |
| cgaaactgat cagcaaaatc ttggaggctt gaagatggca attcgcaagc ccgcattgtc | 40200 |
| ggtcggcgaa gcacggcggc ttgctggtgc tcgacccgag atccaccatc ccaacccgac | 40260 |
| acttgttccc cagaagctgg acctccagca cttgcctgaa aaagccgacg agaaagacca | 40320 |
| gcaacgtgag cctctcgtcg ccgatcacat ttacagtccc gatcgacaac ttaagctaac | 40380 |
| tgtggatgcc cttagtccac ctccgtcccc gaaaaagctc caggttttc tttcagcgcg | 40440 |
| accgcccgcg cctcaagtgt cgaaaacata tgacaacctc gttcggcaat acagtccctc | 40500 |
| gaagtcgcta caaatgattt taaggcgcgc gttggacgat ttcgaaagca tgctggcaga | 40560 |
| tggatcattt cgcgtggccc cgaaaagtta tccgatccct tcaactacag aaaaatccgt | 40620 |
| tctcgttcag acctcacgca tgttcccggt tgcgttgctc gaggtcgctc gaagtcattt | 40680 |
| tgatccgttg gggttggaga ccgctcgagc tttcggccac aagctggcta ccgccgcgct | 40740 |
| cgcgtcattc tttgctggag agaagccatc gagcaattgg tgaagaggga cctatcggaa | 40800 |
| cccctcacca aatattgagt gtaggtttga ggccgctggc cgcgtcctca gtcacctttt | 40860 |
| gagccagata attaagagcc aaatgcaatt ggctcaggct gccatcgtcc ccccgtgcga | 40920 |
| aacctgcacg tccgcgtcaa agaaataacc ggcacctctt gctgttttta tcagttgagg | 40980 |
| gcttgacgga tccgcctcaa gtttgcggcg cagccgcaaa atgagaacat ctatactcct | 41040 |
| gtcgtaaacc tcctcgtcgc gtactcgact ggcaatgaga agttgctcgc gcgatagaac | 41100 |
| gtcgcggggt ttctctaaaa acgcgaggag aagattgaac tcacctgccg taagtttcac | 41160 |
| ctcaccgcca gcttcggaca tcaagcgacg ttgcctgaga ttaagtgtcc agtcagtaaa | 41220 |
| acaaaaagac cgtcggtctt tggagcggac aacgttgggg cgcacgcgca aggcaacccg | 41280 |
| aatgcgtgca agaaactctc tcgtactaaa cggcttagcg ataaaatcac ttgctcctag | 41340 |
| ctcgagtgca acaactttat ccgtctcctc aaggcggtcg ccactgataa ttatgattgg | 41400 |
| aatatcagac tttgccgcca gatttcgaac gatctcaagc ccatcttcac gacctaaatt | 41460 |
| tagatcaaca accacgacat cgaccgtcgc ggaagagagt actctagtga actgggtgct | 41520 |
| gtcggctacc gcggtcactt tgaaggcgtg gatcgtaagg tattcgataa taagatgccg | 41580 |
| catagcgaca tcgtcatcga taagaagaac gtgtttcaac ggctcacctt tcaatctaaa | 41640 |
| atctgaaccc ttgttcacag cgcttgagaa attttcacgt gaaggatgta caatcatctc | 41700 |

```
cagctaaatg ggcagttcgt cagaattgcg gctgaccgcg gatgacgaaa atgcgaacca   41760
agtatttcaa ttttatgaca aaagttctca atcgttgtta caagtgaaac gcttcgaggt   41820
tacagctact attgattaag gagatcgcct atggtctcgc cccggcgtcg tgcgtccgcc   41880
gcgagccaga tctcgcctac ttcataaacg tcctcatagg cacggaatgg aatgatgaca   41940
tcgatcgccg tagagagcat gtcaatcagt gtgcgatctt ccaagctagc accttgggcg   42000
ctacttttga caagggaaaa cagtttcttg aatccttgga ttggattcgc gccgtgtatt   42060
gttgaaatcg atcccggatg tcccgagacg acttcactca gataagccca tgctgcatcg   42120
tcgcgcatct cgccaagcaa tatccggtcc ggccgcatac gcagacttgc ttggagcaag   42180
tgctcggcgc tcacagcacc cagcccagca ccgttcttgg agtagagtag tctaacatga   42240
ttatcgtgtg gaatgacgag ttcgagcgta tcttctatgg tgattagcct ttcctggggg   42300
gggatggcgc tgatcaaggt cttgctcatt gttgtcttgc cgcttccggt agggccacat   42360
agcaacatcg tcagtcggct gacgacgcat gcgtgcagaa acgcttccaa atccccgttg   42420
tcaaaatgct gaaggatagc ttcatcatcc tgattttggc gtttccttcg tgtctgccac   42480
tggttccacc tcgaagcatc ataacgggag gagacttctt taagaccaga aacacgcgag   42540
cttggccgtc gaatggtcaa gctgacggtg cccgagggaa cggtcggcgg cagacagatt   42600
tgtagtcgtt caccaccagg aagttcagtg gcgcagaggg ggttacgtgg tccgacatcc   42660
tgctttctca gcgcgcccgc taaaatagcg atatcttcaa gatcatcata agagacgggc   42720
aaaggcatct tggtaaaaat gccggcttgg cgcacaaatg cctctccagg tcgattgatc   42780
gcaatttctt cagtcttcgg gtcatcgagc cattccaaaa tcggcttcag aagaaagcgt   42840
agttgcggat ccacttccat ttacaatgta tcctatctct aagcggaaat ttgaattcat   42900
taagagcggc ggttcctccc ccgcgtggcg ccgccagtca ggcggagctg gtaaacacca   42960
aagaaatcga ggtcccgtgc tacgaaaatg gaaacggtgt caccctgatt cttcttcagg   43020
gttggcggta tgttgatggt tgccttaagg gctgtctcag ttgtctgctc accgttattt   43080
tgaaagctgt tgaagctcat cccgccaccc gagctgccgg cgtaggtgct agctgcctgg   43140
aaggcgcctt gaacaacact caagagcata gctccgctaa aacgctgcca gaagtggctg   43200
tcgaccgagc ccggcaatcc tgagcgaccg agttcgtccg cgcttggcga tgttaacgag   43260
atcatcgcat ggtcaggtgt ctcggcgcga tcccacaaca caaaaacgcg cccatctccc   43320
tgttgcaagc cacgctgtat ttcgccaaca acggtggtgc cacgatcaag aagcacgata   43380
ttgttcgttg ttccacgaat atcctgaggc aagacacact ttacatagcc tgccaaattt   43440
gtgtcgattg cggtttgcaa gatgcacgga attattgtcc cttgcgttac cataaaatcg   43500
gggtgcggca agagcgtggc gctgctgggc tgcagctcgg tgggtttcat acgtatcgac   43560
aaatcgttct cgccggacac ttcgccattc ggcaaggagt tgtcgtcacg cttgccttct   43620
tgtcttcggc ccgtgtcgcc ctgaatgcgc cgtttgctga cccctgatc gccgctgcta   43680 tatgcaaaaa tcggtgtttc ttccggccgt ggctcatgcc gctccggttc gccctcggc   43740 ggtagaggag cagcaggctg aacagcctct tgaaccgctg gaggatccgg cggcacctca   43800
atcggagctg atgaaatgg cttggtgttt gttgcgatca aagttgacgg cgatgcgttc   43860
tcattcacct tcttttggcg cccacctagc aaatgaggc ttaatgataa cgcgagaacg   43920
acacctccga cgatcaattt ctgagacccc gaaagacgcc ggcgatgttt gtcggagacc   43980
agggatccag atgcatcaac ctcatgtgcc gcttgctgac tatcgttatt catcccttcg   44040
```

```
ccccettcag gacgcgtttc acatcgggcc tcaccgtgcc cgtttgcggc ctttggccaa    44100
cgggatcgta agcggtgttc cagatacata gtactgtgtg gccatccctc agacgccaac    44160
ctcgggaaac cgaagaaatc tcgacatcgc tcccctttaac tgaatagttg gcaacagctt    44220
ccttgccatc aggattgatg gtgtagatgg agggtatgcg tacattgccc ggaaagtgga    44280
ataccgtcgt aaatccattg tcgaagactt cgagtggcaa cagcgaacga tcgccttggg    44340
cgacgtagtg ccaattactg tccgccgcac caagggctgt gacaggctga tccaataaat    44400
tctcagcttt ccgttgatat tgtgcttccg cgtgtagtct gtccacaaca gccttctgtt    44460
gtgcctccct tcgccgagcc gccgcatcgt cggcggggta ggcgaattgg acgctgtaat    44520
agagatcggg ctgctctttta tcgaggtggg acagagtctt ggaacttata ctgaaaacat    44580
aacggcgcat cccggagtcg cttgcggtta gcacgattac tggctgaggc gtgaggacct    44640
ggcttgcctt gaaaaataga taatttcccc gcggtagggc tgctagatct ttgctatttg    44700
aaacggcaac cgctgtcacc gtttcgttcg tggcgaatgt tacgaccaaa gtagctccaa    44760
ccgccgtcga gaggcgcacc acttgatcgg gattgtaagc caaataacgc atgcgcggat    44820
ctagcttgcc cgccattgga gtgtcttcag cctccgcacc agtcgcagcg gcaaataaac    44880
atgctaaaat gaaaagtgct tttctgatca tggttcgctg tggcctacgt ttgaaacggt    44940
atcttccgat gtctgatagg aggtgacaac cagacctgcc gggttggtta gtctcaatct    45000
gccgggcaag ctggtcacct tttcgtagcg aactgtcgcg gtccacgtac tcaccacagg    45060
cattttgccg tcaacgacga gggtcctttt atagcgaatt tgctgcgtgc ttggagttac    45120
atcatttgaa gcgatgtgct cgacctccac cctgccgcgt ttgccaagaa tgacttgagg    45180
cgaactggga ttgggatagt tgaagaattg ctggtaatcc tggcgcactg ttggggcact    45240
gaagttcgat accaggtcgt aggcgtactg agcggtgtcg gcatcataac tctcgcgcag    45300
gcgaacgtac tcccacaatg aggcgttaac gacggcctcc tcttgagttg caggcaatcg    45360
cgagacagac acctcgctgt caacggtgcc gtccggccgt atccatagat atacgggcac    45420
aagcctgctc aacggcacca ttgtggctat agcgaacgct tgagcaacat ttcccaaaat    45480
cgcgatagct gcgacagctg caatgagttt ggagagacgt cgcgccgatt tcgctcgcgc    45540
ggtttgaaag gcttctactt ccttatagtg ctcggcaagg ctttcgcgcg ccactagcat    45600
ggcatattca ggccccgtca tagcgtccac ccgaattgcc gagctgaaga tctgacggag    45660
taggctgcca tcgccccaca ttcagcggga agatcgggcc tttgcagctc gctaatgtgt    45720
cgtttgtctg gcagccgctc aaagcgacaa ctaggcacag caggcaatac ttcatagaat    45780
tctccattga ggcgaatttt tgcgcgacct agcctcgctc aacctgagcg aagcgacggt    45840
acaagctgct ggcagattgg gttgcgccgc tccagtaact gcctccaatg ttgccggcga    45900
tcgccggcaa agcgacaatg agcgcatccc ctgtcagaaa aaacatatcg agttcgtaaa    45960
gaccaatgat cttggccgcg gtcgtaccgg cgaaggtgat tacaccaagc ataaggtgtga   46020 gcgcagtcgc ttcggttagg atgacgatcg ttgccacgag gtttaagagg agaagcaaga    46080
gaccgtaggt gataagttgc ccgatccact tagctgcgat gtcccgcgtg cgatcaaaaa    46140
tatatccgac gaggatcaga ggcccgatcg cgagaagcac tttcgtgaga attccaacgg    46200
cgtcgtaaac tccgaaggca gaccagagcg tgccgtaaag gacccactgt gccccttgga    46260
aagcaaggat gtcctggtcg ttcatcggac cgatttcgga tgcgattttc tgaaaaacgg    46320
cctgggtcac ggcgaacatt gtatccaact gtgccggaac agtctgcaga ggcaagccgg    46380
ttacactaaa ctgctgaaca aagtttggga ccgtcttttc gaagatggaa accacatagt    46440
```

```
cttggtagtt agcctgccca acaattagag caacaacgat ggtgaccgtg atcacccgag    46500
tgataccgct acgggtatcg acttcgccgc gtatgactaa aatacgctga acaataatcc    46560
aaagagtgac acaggcgatc aatggcgcac tcaccgcctc ctggatagtc tcaagcatcg    46620
agtccaagcc tgtcgtgaag gctacatcga agatcgtatg aatggccgta aacggcgccg    46680
gaatcgtgaa attcatcgat tggacctgaa cttgactggt ttgtcgcata atgttggata    46740
aaatgagctc gcattcggcg aggatgcggg cggatgaaca aatcgcccag ccttagggga    46800
gggcaccaaa gatgacagcg gtcttttgat gctccttgcg ttgagcggcc gcctcttccg    46860
cctcgtgaag gccggcctgc gcggtagtca tcgttaatag gcttgtcgcc tgtacatttt    46920
gaatcattgc gtcatggatc tgcttgagaa gcaaaccatt ggtcacggtt gcctgcatga    46980
tattgcgaga tcgggaaagc tgagcagacg tatcagcatt cgccgtcaag cgttgtcca    47040 tcgtttccag attgtcagcc gcaatgccag cgctgtttgc ggaaccggtg atctgcgatc    47100
gcaacaggtc cgcttcagca tcactaccca cgactgcacg atctgtatcg ctggtgatcg    47160
cacgtgccgt ggtcgacatt ggcattcgcg gcgaaaacat ttcattgtct aggtccttcg    47220
tcgaaggata ctgattttc tggttgagcg aagtcagtag tccagtaacg ccgtaggccg    47280
acgtcaacat cgtaaccatc gctatagtct gagtgagatt ctccgcagtc gcgagcgcag    47340
tcgcgagcgt ctcagcctcc gttgccgggt cgctaacaac aaactgcgcc cgcgcgggct    47400
gaatatatag aaagctgcag gtcaaaactg ttgcaataag ttgcgtcgtc ttcatcgttt    47460
cctaccttat caatcttctg cctcgtggtg acgggccatg aattcgctga ccagccaga    47520 tgagttgcct tcttgtgcct cgcgtagtcg agttgcaaag cgcaccgtgt tggcacgccc    47580
cgaaagcacg gcgacatatt cacgcatatc ccgcagatca aattcgcaga tgacgcttcc    47640
actttctcgt ttaagaagaa acttacggct gccgaccgtc atgtcttcac ggatcgcctg    47700
aaattccttt tcggtacatt tcagtccatc gacataagcc gatcgatctg cggttggtga    47760
tggatagaaa atcttcgtca tacattgcgc aaccaagctg gctcctagcg gcgattccag    47820
aacatgctct ggttgctgcg ttgccagtat tagcatcccg ttgttttttc gaacggtcag    47880
gaggaatttg tcgacgacag tcgaaaattt agggtttaac aaataggcgc gaaactcatc    47940
gcagctcatc acaaaacggc ggccgtcgat catggctcca atccgatgca ggagatatgc    48000
tgcagcggga gcgcatactt cctcgtattc gagaagatgc gtcatgtcga agccggtaat    48060
cgacggatct aactttactt cgtcaacttc gccgtcaaat gcccagccaa gcgcatggcc    48120
ccggcaccag cgttggagcc gcgctcctgc gccttcggcg ggcccatgca acaaaaattc    48180
acgtaacccc gcgattgaac gcatttgtgg atcaaacgag agctgacgat ggataccacg    48240
gaccagacgg cggttctctt ccggagaaat cccaccccga ccatcactct cgatgagagc    48300
cacgatccat tcgcgcagaa aatcgtgtga ggctgctgtg tttttctaggc cacgcaacgg    48360 cgccaacccg ctgggtgtgc ctctgtgaag tgccaaatat gttcctcctg tggcgcgaac    48420
cagcaattcg ccaccccggt ccttgtcaaa gaacacgacc gtacctgcac ggtcgaccat    48480
gctctgttcg agcatggcta gaacaaacat catgagcgtc gtcttacccc tcccgatagg    48540
cccgaatatt gccgtcatgc caacatcgtg ctcatgcggg atatagtcga aaggcgttcc    48600
gccattggta cgaaatcggg caatcgcgtt gccccagtgg cctgagctgg cgccctctgg    48660
aaagttttcg aaagagacaa accctgcgaa attgcgtgaa gtgattgcgc cagggcgtgt    48720
gcgccactta aaattccccg gcaattggga ccaataggcc gcttccatac caataccttc    48780
```

```
ttggacaacc acggcacctg catccgccat tcgtgtccga gcccgcgcgc ccctgtcccc   48840
aagactattg agatcgtctg catagacgca aaggctcaaa tgatgtgagc ccataacgaa   48900
ttcgttgctc gcaagtgcgt cctcagcctc ggataatttg ccgatttgag tcacggcttt   48960
atcgccggaa ctcagcatct ggctcgattt gaggctaagt ttcgcgtgcg cttgcgggcg   49020
agtcaggaac gaaaaactct gcgtgagaac aagtggaaaa tcgagggata gcagcgcgtt   49080
gagcatgccc ggccgtgttt ttgcagggta ttcgcgaaac gaatagatgg atccaacgta   49140
actgtctttt ggcgttctga tctcgagtcc tcgcttgccg caaatgactc tgtcggtata   49200
aatcgaagcg ccgagtgagc cgctgacgac cggaaccggt gtgaaccgac cagtcatgat   49260
caaccgtagc gcttcgccaa tttcggtgaa gagcacaccc tgcttctcgc ggatgccaag   49320
acgatgcagg ccatacgctt taagagagcc agcgacaaca tgccaaagat cttccatgtt   49380
cctgatctgg cccgtgagat cgttttccct ttttccgctt agcttggtga acctcctctt   49440
taccttccct aaagccgcct gtgggtagac aatcaacgta aggaagtgtt cattgcggag   49500
gagttggccg gagagcacgc gctgttcaaa agcttcgttc aggctagcgg cgaaaacact   49560
acggaagtgt cgcggcgccg atgatggcac gtcggcatga cgtacgaggt gagcatatat   49620
tgacacatga tcatcagcga tattgcgcaa cagcgtgttg aacgcacgac aacgcgcatt   49680
gcgcatttca gtttcctcaa gctcgaatgc aacgccatca attctcgcaa tggtcatgat   49740
cgatccgtct tcaagaagga cgatatggtc gctgaggtgg ccaatataag ggagatagat   49800
ctcaccggat ctttcggtcg ttccactcgc gccgagcatc acaccattcc tctccctcgt   49860
gggggaaccc taattggatt tgggctaaca gtagcgcccc cccaaactgc actatcaatg   49920
cttcttcccg cggtccgcaa aaatagcagg acgacgctcg ccgcattgta gtctcgctcc   49980
acgatgagcc gggctgcaaa ccataacggc acgagaacga cttcgtagag cgggttctga   50040
acgataacga tgacaaagcc ggcgaacatc atgaataacc ctgccaatgt cagtggcacc   50100
ccaagaaaca atgcgggccg tgtggctgcg aggtaaaggg tcgattcttc caaacgatca   50160
gccatcaact accgccagtg agcgtttggc cgaggaagct cgccccaaac atgataacaa   50220
tgccgccgac gacgccggca accagcccaa gcgaagcccg cccgaacatc caggagatcc   50280
cgatagcgac aatgccgaga acagcgagtg actggccgaa cggaccaagg ataaacgtgc   50340
atatattgtt aaccattgtg gcggggtcag tgccgccacc cgcagattgc gctgcggcgg   50400
gtccggatga ggaaatgctc catgcaattg caccgcacaa gcttggggcg cagctcgata   50460
tcacgcgcat catcgcattc gagagcgaga ggcgatttag atgtaaacgg tatctctcaa   50520
agcatcgcat caatgcgcac ctccttagta taagtcgaat aagacttgat tgtcgtctgc   50580
ggatttgccg ttgtcctggt gtggcggtgg cggagcgatt aaaccgccag cgccatcctc   50640
ctgcgagcgg cgctgatatg accccaaac atcccacgtc tcttcggatt ttagcgcctc   50700
gtgatcgtct tttggaggct cgattaacgc gggcaccagc gattgagcag ctgtttcaac   50760
ttttcgcacg tagccgtttg caaaaccgcc gatgaaatta ccggtgttgt aagcggagat   50820
cgcccgacga agcgcaaatt gcttctcgtc aatcgtttcg ccgcctgcat aacgactttt   50880
cagcatgttt gcagcggcag ataatgatgt gcacgcctgg agcgcaccgt caggtgtcag   50940
accgagcata gaaaaatttc gagagtttat ttgcatgagg ccaacatcca gcgaatgccg   51000
tgcatcgaga cggtgcctga cgacttgggt tgcttggctg tgatcttgcc agtgaagcgt   51060
ttcgccggtc gtgttgtcat gaatcgctaa aggatcaaag cgactctcca ccttagctat   51120
cgccgcaagc gtagatgtcg caactgatgg ggcacacttg cgagcaacat ggtcaaactc   51180
```

```
agcagatgag agtggcgtgg caaggctcga cgaacagaag gagaccatca aggcaagaga    51240
aagcgacccc gatctcttaa gcatacctta tctccttagc tcgcaactaa caccgcctct    51300
cccgttggaa gaagtgcgtt gttttatgtt gaagattatc gggagggtcg gttactcgaa    51360
aattttcaat tgcttcttta tgatttcaat tgaagcgaga aacctcgccc ggcgtcttgg    51420
aacgcaacat ggaccgagaa ccgcgcatcc atgactaagc aaccggatcg acctattcag    51480
gccgcagttg gtcaggtcag gctcagaacg aaaatgctcg gcgaggttac gctgtctgta    51540
aacccattcg atgaacggga agcttccttc cgattgctct tggcaggaat attggcccat    51600
gcctgcttgc gctttgcaaa tgctcttatc gcgttggtat catatgcctt gtccgccagc    51660
agaaacgcac tctaagcgat tatttgtaaa aatgtttcgg tcatgcggcg gtcatgggct    51720
tgacccgctg tcagcgcaag acggatcggt caaccgtcgg catcgacaac agcgtgaatc    51780
ttggtggtca aaccgccacg ggaacgtccc atacagccat cgtcttgatc ccgctgtttc    51840
ccgtcgccgc atgttggtgg acgcggacac aggaactgtc aatcatgacg acattctatc    51900
gaaagccttg gaaatcacac tcagaatatg atcccagacg tctgcctcac gccatcgtac    51960
aaagcgattg tagcaggttg tacaggaacc gtatcgatca ggaacgtctg cccagggcgg    52020 gccccgtccgg aagcgccaca agatgacatt gatcacccgc gtcaacgcgc ggcacgcgac    52080
gcggcttatt tgggaacaaa ggactgaaca acagtccatt cgaaatcggt gacatcaaag    52140
cggggacggg ttatcagtgg cctccaagtc aagcctcaat gaatcaaaat cagaccgatt    52200
tgcaaacctg atttatgagt gtgcggccta aatgatgaaa tcgtccttct agatcgcctc    52260
cgtggtgtag caacacctcg cagtatcgcc gtgctgacct tggccaggga attgactggc    52320
aagggtgctt tcacatgacc gctcttttgg ccgcgataga tgatttcgtt gctgctttgg    52380
gcacgtagaa ggagagaagt catatcggag aaattcctcc tggcgcgaga gcctgctcta    52440
tcgcgacggc atcccactgt cgggaacaga ccggatcatt cacgaggcga aagtcgtcaa    52500
cacatgcgtt ataggcatct tcccttgaag gatgatcttg ttgctgccaa tctggaggtg    52560
cggcagccgc aggcagatgc gatctcagcg caacttgcgg caaaacatct cactcacctg    52620
aaaaccacta gcgagtctcg cgatcagacg aaggcctttt acttaacgac acaatatccg    52680
atgtctgcat cacaggcgtc gctatcccag tcaatactaa agcggtgcag gaactaaaga    52740
ttactgatga cttaggcgtg ccacgaggcc tgagacgacg cgcgtagaca gttttttgaa    52800
atcattatca aagtgatggc ctccgctgaa gcctatcacc tctgcgccgg tctgtcggag    52860
agatgggcaa gcattattac ggtcttcgcg cccgtacatg cattggacga ttgcagggtc    52920
aatggatctg agatcatcca gaggattgcc gcccttacct tccgtttcga gttggagcca    52980 gccccctaaat gagacgacat agtcgacttg atgtgacaat gccaagagag agatttgctt    53040
aacccgattt ttttgctcaa gcgtaagcct attgaagctt gccggcatga cgtccgcgcc    53100
gaaagaatat cctacaagta aaacattctg cacaccgaaa tgcttggtgt agacatcgat    53160
tatgtgacca agatccttag cagtttcgct tggggaccgc tccgaccaga aataccgaag    53220
tgaactgacg ccaatgacag gaatcccttc cgtctgcaga taggtaccat cgatagatct    53280
gctgcctcgc gcgtttcggt gatgacggtg aaaacctctg acacatgcag ctcccggaga    53340
cggtcacagc ttgtctgtaa gcggatgccg ggagcagaca agcccgtcag ggcgcgtcag    53400
cgggtgttgg cgggtgtcgg ggcgcagcca tgacccagtc acgtagcgat agcggagtgt    53460
atactggctt aactatgcgg catcagagca gattgtactg agagtgcacc atatgcggtg    53520
```

| | |
|---|---|
| tgaaataccg cacagatgcg taaggagaaa ataccgcatc aggcgctctt ccgcttcctc | 53580 |
| gctcactgac tcgctgcgct cggtcgttcg gctgcggcga gcggtatcag ctcactcaaa | 53640 |
| ggcggtaata cggttatcca cagaatcagg ggataacgca ggaaagaaca tgtgagcaaa | 53700 |
| aggccagcaa aaggccagga accgtaaaaa ggccgcgttg ctggcgtttt tccataggct | 53760 |
| ccgcccccct gacgagcatc acaaaaatcg acgctcaagt cagaggtggc gaaacccgac | 53820 |
| aggactataa agataccagg cgtttccccc tggaagctcc ctcgtgcgct ctcctgttcc | 53880 |
| gaccctgccg cttaccggat acctgtccgc ctttctccct tcgggaagcg tggcgctttc | 53940 |
| tcatagctca cgctgtaggt atctcagttc ggtgtaggtc gttcgctcca agctgggctg | 54000 |
| tgtgcacgaa ccccccgttc agcccgaccg ctgcgcctta tccggtaact atcgtcttga | 54060 |
| gtccaacccg gtaagacacg acttatcgcc actggcagca gccactggta acaggattag | 54120 |
| cagagcgagg tatgtaggcg gtgctacaga gttcttgaag tggtggccta actacggcta | 54180 |
| cactagaagg acagtatttg gtatctgcgc tctgctgaag ccagttacct tcggaaaaag | 54240 |
| agttggtagc tcttgatccg gcaaacaaac caccgctggt agcggtggtt tttttgtttg | 54300 |
| caagcagcag attacgcgca gaaaaaaagg atctcaagaa gatcctttga tcttttctac | 54360 |
| ggggtctgac gctcagtgga acgaaaactc acgttaaggg attttggtca tgagattatc | 54420 |
| aaaaaggatc ttcacctaga tccttttaaa ttaaaaatga agttttaaat caatctaaag | 54480 |
| tatatatgag taaacttggt ctgacagtta ccaatgctta atcagtgagg cacctatctc | 54540 |
| agcgatctgt ctatttcgtt catccatagt tgcctgactc cccgtcgtgt agataactac | 54600 |
| gatacgggag ggcttaccat ctggccccag tgctgcaatg ataccgcgag acccacgctc | 54660 |
| accggctcca gatttatcag caataaacca gccagccgga agggccgagc gcagaagtgg | 54720 |
| tcctgcaact ttatccgcct ccatccagtc tattaattgt tgccgggaag ctagagtaag | 54780 |
| tagttcgcca gttaatagtt tgcgcaacgt tgttgccatt gctgca | 54826 |

<210> SEQ ID NO 61
<211> LENGTH: 52300
<212> TYPE: DNA
<213> ORGANISM: artificial sequence
<220> FEATURE:
<223> OTHER INFORMATION: PHP42063

<400> SEQUENCE: 61

| | |
|---|---|
| gggggggggg ggggggggtt ccattgttca ttccacggac aaaaacagag aaaggaaacg | 60 |
| acagaggcca aaaagctcgc tttcagcacc tgtcgtttcc tttcttttca gagggtattt | 120 |
| taaataaaaa cattaagtta tgacgaagaa gaacggaaac gccttaaacc ggaaaatttt | 180 |
| cataaatagc gaaaacccgc gaggtcgccg ccccgtaacc tgtcggatca ccggaaagga | 240 |
| cccgtaaagt gataatgatt atcatctaca tatcacaacg tgcgtggagg ccatcaaacc | 300 |
| acgtcaaata atcaattatg acgcaggtat cgtattaatt gatctgcatc aacttaacgt | 360 |
| aaaaacaact tcagacaata caaatcagcg acactgaata cggggcaacc tcatgtcccc | 420 |
| cccccccccc cccctgcagg catcgtggtg tcacgctcgt cgtttggtat ggcttcattc | 480 |
| agctccggtt cccaacgatc aaggcgagtt acatgatccc ccatgttgtg caaaaaagcg | 540 |
| gttagctcct tcggtcctcc gatcgttgtc agaagtaagt tggccgcagt gttatcactc | 600 |
| atggttatgg cagcactgca taattctctt actgtcatgc catccgtaag atgcttttct | 660 |
| gtgactggtg agtactcaac caagtcattc tgagaatagt gtatgcggcg accgagttgc | 720 |
| tcttgcccgg cgtcaacacg ggataatacc gcgccacata gcagaacttt aaaagtgctc | 780 |

```
atcattggaa aacgttcttc ggggcgaaaa ctctcaagga tcttaccgct gttgagatcc    840
agttcgatgt aacccactcg tgcacccaac tgatcttcag catcttttac tttcaccagc    900
gtttctgggt gagcaaaaac aggaaggcaa aatgccgcaa aaagggaat aagggcgaca     960
cggaaatgtt gaatactcat actcttcctt tttcaatatt attgaagcat ttatcagggt   1020
tattgtctca tgagcggata catatttgaa tgtatttaga aaataaaca aatagggggtt  1080
ccgcgcacat ttccccgaaa agtgccacct gacgtctaag aaaccattat tatcatgaca   1140
ttaacctata aaataggcg tatcacgagg cccttcgtc ttcaagaatt cggagctttt     1200
gccattctca ccggattcag tcgtcactca tggtgatttc tcacttgata accttatttt   1260
tgacgagggg aaattaatag gttgtattga tgttggacga gtcggaatcg cagaccgata   1320
ccaggatctt gccatcctat ggaactgcct cggtgagttt tctccttcat tacagaaacg   1380
gcttttttcaa aaatatggta ttgataatcc tgatatgaat aaattgcagt ttcatttgat  1440
gctcgatgag tttttctaat cagaattggt taattggttg taacactggc agagcattac   1500
gctgacttga cgggacggcg gctttgttga ataaatcgaa cttttgctga gttgaaggat   1560
cagatcacgc atcttcccga caacgcagac cgttccgtgg caaagcaaaa gttcaaaatc   1620
accaactggt ccacctacaa caaagctctc atcaaccgtg gctccctcac tttctggctg   1680
gatgatgggg cgattcaggc ctggtatgag tcagcaacac cttcttcacg aggcagacct   1740
cagcgccaga aggccgccag agaggccgag cgcggccgtg aggcttggac gctagggcag   1800
ggcatgaaaa agcccgtagc gggctgctac gggcgtctga cgcggtggaa aggggggagg   1860
gatgttgtct acatggctct gctgtagtga gtgggttgcg ctccggcagc ggtcctgatc   1920
aatcgtcacc ctttctcggt ccttcaacgt tcctgacaac gagcctcctt ttcgccaatc   1980
catcgacaat caccgcgagt ccctgctcga acgctgcgtc cggaccggct tcgtcgaagg   2040
cgtctatcgc ggcccgcaac agcggcgaga gcggagcctg ttcaacggtg ccgccgcgct   2100
cgccggcatc gctgtcgccg gcctgctcct caagcacggc cccaacagtg aagtagctga   2160
ttgtcatcag cgcattgacg gcgtccccgg ccgaaaaacc cgcctcgcag aggaagcgaa   2220
gctgcgcgtc ggccgtttcc atctgcggtg cgcccggtcg cgtgccggca tggatgcgcg   2280
cgccatcgcg gtaggcgagc agcgcctgcc tgaagctgcg ggcattcccg atcagaaatg   2340
agcgccagtc gtcgtcggct ctcggcaccg aatgcgtatg attctccgcc agcatggctt   2400
cggccagtgc gtcgagcagc gcccgcttgt tcctgaagtg ccagtaaagc gccggctgct   2460
gaaccccaa ccgttccgcc agtttgcgtg tcgtcagacc gtctacgccg acctcgttca    2520
acaggtccag ggcggcacgg atcactgtat tcggctgcaa cttttgtcatg cttgacactt  2580
tatcactgat aaacataata tgtccaccaa cttatcagtg ataaagaatc cgcgcgttca   2640
atcggaccag cggaggctgg tccggaggcc agacgtgaaa cccaacatac ccctgatcgt   2700
aattctgagc actgtcgcgc tcgacgctgt cggcatcggc ctgattatgc cggtgctgcc   2760
gggcctcctg cgcgatctgg ttcactcgaa cgacgtcacc gcccactatg gcattctgct   2820
ggcgctgtat gcgttggtgc aatttgcctg cgcacctgtg ctgggcgcgc tgtcggatcg   2880
tttcgggcgg cggccaatct tgctcgtctc gctggccggc gccactgtcg actacgccat   2940
catggcgaca gcgcctttcc tttgggttct ctatatcggg cggatcgtgg ccggcatcac   3000
cggggcgact ggggcggtag ccggcgctta tattgccgat atcactgatg gcgatgagcg   3060
cgcgcggcac ttcggcttca tgagcgcctg tttcgggttc gggatggtcg cgggacctgt   3120
```

```
gctcggtggg ctgatgggcg gtttctcccc ccacgctccg ttcttcgccg cggcagcctt    3180
gaacggcctc aatttcctga cgggctgttt ccttttgccg gagtcgcaca aaggcgaacg    3240
ccggccgtta cgccgggagg ctctcaaccc gctcgcttcg ttccggtggg cccggggcat    3300
gaccgtcgtc gccgccctga tggcggtctt cttcatcatg caacttgtcg acaggtgcc    3360 ggccgcgctt tgggtcattt tcggcgagga tcgctttcac tgggacgcga ccacgatcgg    3420
catttcgctt gccgcatttg gcattctgca ttcactcgcc caggcaatga tcaccggccc    3480
tgtagccgcc cggctcggcg aaaggcgggc actcatgctc ggaatgattg ccgacggcac    3540
aggctacatc ctgcttgcct tcgcgacacg gggatggatg gcgttcccga tcatggtcct    3600
gcttgcttcg ggtggcatcg gaatgccggc gctgcaagca atgttgtcca ggcaggtgga    3660
tgaggaacgt cagggggcagc tgcaaggctc actggcggcg ctcaccagcc tgacctcgat    3720
cgtcggaccc ctcctcttca cggcgatcta tgcggcttct ataacaacgt ggaacgggtg    3780
ggcatggatt gcaggcgctg ccctctactt gctctgcctg ccggcgctgc gtcgcgggct    3840
ttggagcggc gcagggcaac gagccgatcg ctgatcgtgg aaacgatagg cctatgccat    3900
gcgggtcaag gcgacttccg gcaagctata cgcgccctag gagtgcggtt ggaacgttgg    3960
cccagccaga tactcccgat cacgagcagg acgccgatga tttgaagcgc actcagcgtc    4020
tgatccaaga acaaccatcc tagcaacacg gcggtccccg ggctgagaaa gcccagtaag    4080
gaaacaactg taggttcgag tcgcgagatc ccccggaacc aaaggaagta ggttaaaccc    4140
gctccgatca ggccgagcca cgccaggccg agaacattgg ttcctgtagg catcgggatt    4200
ggcggatcaa acactaaagc tactggaacg agcagaagtc ctccggccgc cagttgccag    4260
gcggtaaagg tgagcagagg cacgggaggt tgccacttgc gggtcagcac ggttccgaac    4320
gccatggaaa ccgcccccgc caggcccgct gcgacgccga caggatctag cgctgcgttt    4380
ggtgtcaaca ccaacagcgc cacgcccgca gttccgcaaa tagcccccag gaccgccatc    4440
aatcgtatcg ggctacctag cagagcggca gagatgaaca cgaccatcag cggctgcaca    4500
gcgcctaccg tcgccgcgac cccgcccggc aggcggtaga ccgaaataaa caacaagctc    4560
cagaatagcg aaatattaag tgcgccgagg atgaagatgc gcatccacca gattcccgtt    4620
ggaatctgtc ggacgatcat cacgagcaat aaacccgccg gcaacgcccg cagcagcata    4680
ccggcgaccc ctcggcctcg ctgttcgggc tccacgaaaa cgccggacag atgcgccttg    4740
tgagcgtcct tggggccgtc ctcctgtttg aagaccgaca gcccaatgat ctcgccgtcg    4800
atgtaggcgc cgaatgccac ggcatctcgc aaccgttcag cgaacgcctc catgggcttt    4860
ttctcctcgt gctcgtaaac ggacccgaac atctctggag cttttcttcag ggccgacaat    4920 cggatctcgc ggaaatcctg cacgtcggcc gctccaagcc gtcgaatctg agccttaatc    4980
acaattgtca atttttaatcc tctgtttatc ggcagttcgt agagcgcgcc gtgcgtcccg    5040
agcgatactg agcgaagcaa gtgcgtcgag cagtgcccgc ttgttcctga aatgccagta    5100
aagcgctggc tgctgaaccc ccagccggaa ctgaccccac aaggccctag cgtttgcaat    5160
gcaccaggtc atcattgacc caggcgtgtt ccaccaggcc gctgcctcgc aactcttcgc    5220
aggcttcgcc gacctgctcg cgccacttct tcacgcgggt ggaatccgat ccgcacatga    5280
ggcggaaggt ttccagcttg agcgggtacg gctcccggtg cgagctgaaa tagtcgaaca    5340
tccgtcgggc cgtcggcgac agcttgcggt acttctccca tatgaatttc gtgtagtggt    5400
cgccagcaaa cagcacgacg atttcctcgt cgatcaggac ctggcaacgg gacgttttct    5460
tgccacggtc caggacgcgg aagcggtgca gcagcgacac cgattccagg tgcccaacgc    5520
```

```
ggtcggacgt gaagcccatc gccgtcgcct gtaggcgcga caggcattcc tcggccttcg    5580
tgtaataccg gccattgatc gaccagccca ggtcctggca agctcgtag aacgtgaagg    5640 tgatcggctc gccgataggg gtgcgcttcg cgtactccaa cacctgctgc cacaccagtt    5700
cgtcatcgtc ggcccgcagc tcgacgccgg tgtaggtgat cttcacgtcc ttgttgacgt    5760
ggaaaatgac cttgttttgc agcgcctcgc gcgggatttt cttgttgcgc gtggtgaaca    5820
gggcagagcg ggccgtgtcg tttggcatcg ctcgcatcgt gtccggccac ggcgcaatat    5880
cgaacaagga aagctgcatt tccttgatct gctgcttcgt gtgtttcagc aacgcggcct    5940
gcttggcctc gctgacctgt tttgccaggt cctcgccggc ggttttcgc ttcttggtcg    6000 tcatagttcc tcgcgtgtcg atggtcatcg acttcgccaa acctgccgcc tcctgttcga    6060
gacgacgcga acgctccacg gcggccgatg gcgcgggcag ggcaggggga gccagttgca    6120
cgctgtcgcg ctcgatcttg gccgtagctt gctggaccat cgagccgacg gactggaagg    6180
tttcgcgggg cgcacgcatg acggtgcggc ttgcgatggt ttcggcatcc tcggcggaaa    6240
accccgcgtc gatcagttct tgcctgtatg ccttccggtc aaacgtccga ttcattcacc    6300
ctccttgcgg gattgccccg actcacgccg gggcaatgtg cccttattcc tgatttgacc    6360
cgcctggtgc cttggtgtcc agataatcca ccttatcggc aatgaagtcg gtcccgtaga    6420
ccgtctggcc gtccttctcg tacttggtat tccgaatctt gccctgcacg aataccagcg    6480
accccttgcc caaatacttg ccgtgggcct cggcctgaga gccaaaacac ttgatgcgga    6540
agaagtcggt gcgctcctgc ttgtcgccgg catcgttgcg ccactcttca ttaaccgcta    6600
tatcgaaaat tgcttgcggc ttgttagaat tgccatgacg tacctcggtg tcacgggtaa    6660
gattaccgat aaactggaac tgattatggc tcatatcgaa agtctccttg agaaaggaga    6720
ctctagttta gctaaacatt ggttccgctg tcaagaactt tagcggctaa aattttgcgg    6780
gccgcgacca aggtgcgag gggcggcttc cgctgtgtac aaccagatat ttttcaccaa    6840
catccttcgt ctgctcgatg agcggggcat gacgaaacat gagctgtcgg agagggcagg    6900
ggtttcaatt tcgttttat cagacttaac caacggtaag gccaacccct cgttgaaggt    6960
gatggaggcc attgccgacg ccctggaaac tcccctacct cttctcctgg agtccaccga    7020
ccttgaccgc gaggcactcg cggagattgc gggtcatcct ttcaagagca gcgtgccgcc    7080
cggatacgaa cgcatcagtg tggttttgcc gtcacataag gcgtttatcg taagaaatg    7140 gggcgacgac acccgaaaaa agctgcgtgg aaggctctga cgccaagggt tagggcttgc    7200
acttccttct ttagccgcta aaacggcccc ttctctgcgg gccgtcggct cgcgcatcat    7260
atcgacatcc tcaacggaag ccgtgccgcg aatggcatcg ggcgggtgcg ctttgacagt    7320
tgttttctat cagaacccct acgtcgtgcg gttcgattag ctgtttgtct tgcaggctaa    7380
acactttcgg tatatcgttt gcctgtgcga taatgttgct aatgatttgt tgcgtagggg    7440
ttactgaaaa gtgagcggga aagaagagtt tcagaccatc aaggagcggg ccaagcgcaa    7500
gctggaacgc gacatgggtg cggacctgtt ggccgcgctc aacgacccga aaccgttga    7560 agtcatgctc aacgcggacg gcaaggtgtg gcacgaacgc cttggcgagc cgatgcggta    7620
catctgcgac atgcggccca gccagtcgca ggcgattata gaaacggtgg ccggattcca    7680
cggcaaagag gtcacgcggc attcgcccat cctggaaggc gagttcccct ggatggcag    7740 ccgctttgcc ggccaattgc cgccggtcgt ggccgcgcca acctttgcga tccgcaagcg    7800
cgcggtcgcc atcttcacgc tggaacagta cgtcgaggcg ggcatcatga cccgcgagca    7860
```

```
atacgaggtc attaaaagcg ccgtcgcggc gcatcgaaac atcctcgtca ttggcggtac    7920
tggctcggga aagaccacgc tcgtcaacgc gatcatcaat gaaatggtcg ccttcaaccc    7980
gtctgagcgc gtcgtcatca tcgaggacac cggcgaaatc cagtgcgccg cagagaacgc    8040
cgtccaatac cacaccagca tcgacgtctc gatgacgctg ctgctcaaga caacgctgcg    8100
tatgcgcccc gaccgcatcc tggtcggtga ggtacgtggc cccgaagccc ttgatctgtt    8160
gatggcctgg aacaccgggc atgaaggagg tgccgccacc ctgcacgcaa acaaccccaa    8220
agcgggcctg agccggctcg ccatgcttat cagcatgcac ccggattcac cgaaacccat    8280
tgagccgctg attggcgagg cggttcatgt ggtcgtccat atcgccagga cccctagcgg    8340
ccgtcgagtg caagaaattc tcgaagttct tggttacgag aacggccagt acatcaccaa    8400
aaccctgtaa ggagtatttc caatgacaac ggctgttccg ttccgtctga ccatgaatcg    8460
cggcattttg ttctaccttg ccgtgttctt cgttctcgct ctcgcgttat ccgcgcatcc    8520
ggcgatggcc tcggaaggca ccggcggcag cttgccatat gagagctggc tgacgaacct    8580
gcgcaactcc gtaaccggcc cggtggcctt cgcgctgtcc atcatcggca tcgtcgtcgc    8640
cggcggcgtg ctgatcttcg gcggcgaact caacgccttc ttccgaaccc tgatcttcct    8700
ggttctggtg atggcgctgc tggtcggcgc gcagaacgtg atgagcacct tcttcggtcg    8760
tggtgccgaa atcgcggccc tcggcaacgg ggcgctgcac caggtgcaag tcgcggcggc    8820
ggatgccgtg cgtgcggtag cggctggacg gctcgcctaa tcatggctct gcgcacgatc    8880
cccatccgtc gcgcaggcaa ccgagaaaac ctgttcatgg gtggtgatcg tgaactggtg    8940
atgttctcgg gcctgatggc gtttgcgctg attttcagcg cccaagagct gcgggccacc    9000
gtggtcggtc tgatcctgtg gttcggggcg ctctatgcgt tccgaatcat ggcgaaggcc    9060
gatccgaaga tgcggttcgt gtacctgcgt caccgccggt acaagccgta ttacccggcc    9120
cgctcgaccc cgttccgcga gaacaccaat agccaaggga agcaataccg atgatccaag    9180
caattgcgat tgcaatcgcg ggcctcggcg cgcttctgtt gttcatcctc tttgcccgca    9240
tccgcgcggt cgatgccgaa ctgaaactga aaaagcatcg ttccaaggac gccggcctgg    9300
ccgatctgct caactacgcc gctgtcgtcg atgacgcgcg aatcgtgggc aagaacggca    9360
gctttatggc tgcctggctg tacaagggcg atgacaacgc aagcagcacc gaccagcagc    9420
gcgaagtagt gtccgcccgc atcaaccagg ccctcgcggg cctggaagtg ggtggatga    9480 tccatgtgga cgccgtgcgg cgtcctgctc cgaactacgc ggagcggggc ctgtcggcgt    9540
tccctgaccg tctgacggca gcgattgaag aagagcgctc ggtcttgcct tgctcgtcgg    9600
tgatgtactt caccagctcc gcgaagtcgc tcttcttgat ggagcgcatg gggacgtgct    9660
tggcaatcac gcgcaccccc cggccgtttt agcggctaaa aaagtcatgg ctctgccctc    9720
gggcggacca cgcccatcat gaccttgcca agctcgtcct gcttctcttc gatcttcgcc    9780
agcagggcga ggatcgtggc atcaccgaac cgcgccgtgc gcgggtcgtc ggtgagccag    9840
agtttcagca ggccgcccag gcggcccagg tcgccattga tgcgggccag ctcgcggacg    9900
tgctcatagt ccacgacgcc cgtgatttg tagccctggc cgacggccag caggtaggcc    9960
gacaggctca tgccggccgc cgccgccttt cctcaatcg ctcttcgttc gtctggaagg   10020
cagtacacct tgataggtgg gctgcccttc ctggttggct tggtttcatc agccatccgc   10080
ttgccctcat ctgttacgcc ggcggtagcc ggccagcctc gcagagcagg attcccgttg   10140
agcaccgcca ggtgcgaata agggacagtg aagaaggaac acccgctcgc gggtgggcct   10200
acttcaccta tcctgcccgg ctgacgccgt tggatacacc aaggaaagtc tacacgaacc   10260
```

```
ctttggcaaa atcctgtata tcgtgcgaaa aaggatggat ataccgaaaa aatcgctata   10320
atgaccccga agcagggtta tgcagcggaa aagcgctgct tccctgctgt tttgtggaat   10380
atctaccgac tggaaacagg caaatgcagg aaattactga actgagggga caggcgagag   10440
acgatgccaa agagctacac cgacgagctg gccgagtggg ttgaatcccg cgcggccaag   10500
aagcgccggc gtgatgaggc tgcggttgcg ttcctggcgg tgagggcgga tgtcgaggcg   10560
gcgttagcgt ccggctatgc gctcgtcacc atttgggagc acatgcggga aacggggaag   10620
gtcaagttct cctacgagac gttccgctcg cacgccaggc ggcacatcaa ggccaagccc   10680
gccgatgtgc ccgcaccgca ggccaaggct gcggaacccg cgccggcacc caagacgccg   10740
gagccacggc ggccgaagca ggggggcaag gctgaaaagc cggcccccgc tgcggccccg   10800
accggcttca ccttcaaccc aacaccggac aaaaaggatc tactgtaatg gcgaaaattc   10860
acatggtttt gcagggcaag ggcggggtcg gcaagtcggc catcgccgcg atcattgcgc   10920
agtacaagat ggacaagggg cagacaccct tgtgcatcga caccgacccg gtgaacgcga   10980
cgttcgaggg ctacaaggcc ctgaacgtcc gccggctgaa catcatggcc ggcgacgaaa   11040
ttaactcgcg caacttcgac accctggtcg agctgattgc gccgaccaag gatgacgtgg   11100
tgatcgacaa cggtgccagc tcgttcgtgc ctctgtcgca ttacctcatc agcaaccagg   11160
tgccggctct gctgcaagaa atggggcatg agctggtcat ccataccgtc gtcaccggcg   11220
gccaggctct cctggacacg gtgagcggct tcgcccagct cgccagccag ttcccggccg   11280
aagcgctttt cgtggtctgg ctgaacccgt attgggggcc tatcgagcat gagggcaaga   11340
gctttgagca gatgaaggcg tacacggcca acaaggcccg cgtgtcgtcc atcatccaga   11400
ttccggccct caaggaagaa acctacggcc gcgatttcag cgacatgctg caagagcggc   11460
tgacgttcga ccaggcgctg gccgatgaat cgctcacgat catgacgcgg caacgcctca   11520
agatcgtgcg gcgcggccct tttgaacagc tcgacgcggc ggccgtgcta tgagcgacca   11580
gattgaagag ctgatccggg agattgcggc caagcacggc atcgccgtcg gccgcgacga   11640
cccggtgctg atcctgcata ccatcaacgc ccggctcatg ccgacagtg cggccaagca   11700 agaggaaatc cttgccgcgt tcaaggaaga gctggaaggg atcgcccatc gttggggcga   11760
ggacgccaag gccaaagcgg agcggatgct gaacgcggcc ctggcggcca gcaaggacgc   11820
aatggcgaag gtaatgaagg acagcgccgc gcaggcggcc gaagcgatcc gcaggaaat   11880 cgacgacggc cttggccgcc agctcgcggc caaggtcgcg gacgcgcggc gcgtggcgat   11940
gatgaacatg atcgccggcg gcatggtgtt gttcgcggcc gccctggtgg tgtgggcctc   12000
gttatgaatc gcagaggcgc agatgaaaaa gcccggcgtt gccgggcttt gtttttgcgt   12060
tagctgggct tgtttgacag gcccaagctc tgactgcgcc cgcgctcgcg ctcctgggcc   12120
tgtttcttct cctgctcctg cttgcgcatc agggcctggt gccgtcgggc tgcttcacgc   12180
atcgaatccc agtcgccggc cagctcggga tgctccgcgc gcatcttgcg cgtcgccagt   12240
tcctcgatct tgggcgcgtg aatgcccatg ccttccttga tttcgcgcac catgtccagc   12300
cgcgtgtgca gggtctgcaa gcgggcttgc tgttgggcct gctgctgctg ccaggcggcc   12360
tttgtacgcg gcagggacag caagccgggg gcattggact gtagctgctg caaacgcgcc   12420
tgctgacggt ctacgagctg ttctaggcgg tcctcgatgc gctccacctg gtcatgcttt   12480
gcctgcacgt agagcgcaag ggtctgctgg taggtctgct cgatgggcgc ggattctaag   12540
agggcctgct gttccgtctc ggcctcctgg gccgcctgta gcaaatcctc gccgctgttg   12600
```

```
ccgctggact gctttactgc cggggactgc tgttgccctg ctcgcgccgt cgtcgcagtt    12660
cggcttgccc ccactcgatt gactgcttca tttcgagccg cagcgatgcg atctcggatt    12720
gcgtcaacgg acggggcagc gcggaggtgt ccggcttctc cttgggtgag tcggtcgatg    12780
ccatagccaa aggtttcctt ccaaaatgcg tccattgctg gaccgtgttt ctcattgatg    12840
cccgcaagca tcttcggctt gaccgccagg tcaagcgcgc cttcatgggc ggtcatgacg    12900
gacgccgcca tgaccttgcc gccgttgttc tcgatgtagc cgcgtaatga ggcaatggtg    12960
ccgcccatcg tcagcgtgtc atcgacaacg atgtacttct ggccggggat caccctccccc   13020 tcgaaagtcg ggttgaacgc caggcgatga tctgaaccgg ctccggttcg ggcgaccttc    13080
tcccgctgca caatgtccgt ttcgacctca aggccaaggc ggtcggccag aacgaccgcc    13140
atcatggccg gaatcttgtt gttccccgcc gcctcgacgg cgaggactgg aacgatgcgg    13200
ggcttgtcgt cgccgatcag cgtcttgagc tgggcaacag tgtcgtccga aatcaggcgc    13260
tcgaccaaat taagcgccgc ttccgcgtcg ccctgcttcg cagcctggta ttcaggctcg    13320
ttggtcaaag aaccaaggtc gccgttgcga accaccttcg ggaagtctcc ccacggtgcg    13380
cgctcggctc tgctgtagct gctcaagacg cctccctttt tagccgctaa aactctaacg    13440
agtgcgcccg cgactcaact tgacgctttc ggcacttacc tgtgccttgc cacttgcgtc    13500
ataggtgatg cttttcgcac tcccgatttc aggtacttta tcgaaatctg accgggcgtg    13560
cattacaaag ttcttcccca cctgttggta aatgctgccg ctatctgcgt ggacgatgct    13620
gccgtcgtgg cgctgcgact tatcggcctt ttgggccata tagatgttgt aaatgccagg    13680
tttcagggcc ccggctttat ctaccttctg gttcgtccat cgccttggt tctcggtctg     13740 gacaattctt tgcccattca tgaccaggag gcggtgtttc attgggtgac tcctgacggt    13800
tgcctctggt gttaaacgtg tcctggtcgc ttgccggcta aaaaaaagcc gacctcggca    13860
gttcgaggcc ggcttttccct agagccgggc gcgtcaaggt tgttccatct attttagtga   13920
actgcgttcg atttatcagt tactttcctc ccgctttgtg tttcctccca ctcgtttccg    13980
cgtctagccg accccctcaac atagcggcct cttcttgggc tgcctttgcc tcttgccgcg   14040
cttcgtcacg ctcggcttgc accgtcgtaa agcgctcggc ctgcctggcc gcctcttgcg    14100
ccgccaactt cctttgctcc tggtgggcct cggcgtcggc ctgcgccttc gctttcaccg    14160
ctgccaactc cgtgcgcaaa ctctccggctt cgcgcctggt ggcgtcgcgc tcgccgcgaa   14220
gcgcctgcat ttcctggttg gccgcgtcca gggtcttgcg gctctcttct ttgaatgcgc    14280
gggcgtcctg gtgagcgtag tccagctcgg cgcgcagctc ctgcgctcga cgctccacct    14340
cgtcggcccg ctgcgtcgcc agcgcggccc gctgctcggc tcctgccagg gcggtgcgtg    14400
cttcggccag ggcttgccgc tggcgtgcgg ccagctcggc cgcctcggcg gcctgctgct    14460
ctagcaatgt aacgcgcgcc tgggcttctt ccagctcgcg ggcctgcgcc tcgaaggcgt    14520
cggccagctc cccgcgcacg gcttccaact cgttgcgctc acgatcccag ccggcttgcg    14580
ctgcctgcaa cgattcattg gcaagggcct gggcggcttg ccagagggcg ccacggcct     14640 ggttgccggc ctgctgcacc gcgtccggca cctggactgc cagcggggcg gcctgcgccg    14700
tgcgctggcg tcgccattcg cgcatgccgg cgctggcgtc gttcatgttg acgcgggcgg    14760
ccttacgcac tgcatccacg gtcgggaagt tctcccggtc gccttgctcg aacagctcgt    14820
ccgcagccgc aaaaatgcgg tcgcgcgtct cttttgttcag ttccatgttg gctccggtaa   14880
ttggtaagaa taataaatact cttacctacc ttatcagcgc aagagtttag ctgaacagtt    14940
ctcgacttaa cggcaggttt tttagcggct gaagggcagg caaaaaaagc cccgcacggt    15000
```

```
cggcggggc  aaagggtcag  cgggaagggg  attagcgggc  gtcgggcttc  ttcatgcgtc  15060
ggggccgcgc  ttcttgggat  ggagcacgac  gaagcgcgca  cgcgcatcgt  cctcggccct  15120
atcggcccgc  gtcgcggtca  ggaacttgtc  gcgcgctagg  tcctccctgg  tgggcaccag  15180
gggcatgaac  tcggcctgct  cgatgtaggt  ccactccatg  accgcatcgc  agtcgaggcc  15240
gcgttccttc  accgtctctt  gcaggtcgcg  gtacgcccgc  tcgttgagcg  gctggtaacg  15300
ggccaattgg  tcgtaaatgg  ctgtcggcca  tgagcggcct  ttcctgttga  gccagcagcc  15360
gacgacgaag  ccggcaatgc  aggcccctgg  cacaaccagg  ccgacgccgg  gggcagggga  15420
tggcagcagc  tcgccaacca  ggaacccgc  gcgatgatg  ccgatgccgg  tcaaccagcc  15480
cttgaaacta  tccggccccg  aaacacccct  gcgcattgcc  tggatgctgc  gccggatagc  15540
ttgcaacatc  aggagccgtt  tcttttgttc  gtcagtcatg  gtccgccctc  accagttgtt  15600
cgtatcggtg  tcggacgaac  tgaaatcgca  agagctgccg  gtatcggtcc  agccgctgtc  15660
cgtgtcgctg  ctgccgaagc  acggcgaggg  gtccgcgaac  gccgcagacg  gcgtatccgg  15720
ccgcagcgca  tcgcccagca  tggccccggt  cagcgagccg  ccggccaggt  agcccagcat  15780
ggtgctgttg  gtcgccccgg  ccaccagggc  cgacgtgacg  aaatcgccgt  cattccctct  15840
ggattgttcg  ctgctcggcg  gggcagtgcg  ccgcgccggc  ggcgtcgtgg  atggctcggg  15900
ttggctggcc  tgcgacggcc  ggcgaaaggt  gcgcagcagc  tcgttatcga  ccggctgcgg  15960
cgtcggggcc  gccgccttgc  gctgcggtcg  gtgttccttc  ttcggctcgc  gcagcttgaa  16020
cagcatgatc  gcggaaacca  gcagcaacgc  cgcgcctacg  cctcccgcga  tgtagaacag  16080
catcggattc  attcttcggt  cctccttgta  gcggaaccgt  tgtctgtgcg  gcgcgggtgg  16140
cccgcgccgc  tgtctttggg  gatcagccct  cgatgagcgc  gaccagtttc  acgtcggcaa  16200
ggttcgcctc  gaactcctgg  ccgtcgtcct  cgtacttcaa  ccaggcatag  ccttccgccg  16260
gcggccgacg  gttgaggata  aggcgggcag  ggcgctcgtc  gtgctcgacc  tggacgatgg  16320
cctttttcag  cttgtccggg  tccggctcct  tcgcgccctt  ttccttggcg  tccttaccgt  16380
cctggtcgcc  gtcctcgccg  tcctggccgt  cgccggcctc  cgcgtcacgc  tcggcatcag  16440
tctggccgtt  gaaggcatcg  acggtgttgg  gatcgcggcc  cttctcgtcc  aggaactcgc  16500
gcagcagctt  gaccgtgccg  cgcgtgattt  cctgggtgtc  gtcgtcaagc  cacgcctcga  16560
cttcctccgg  gcgcttcttg  aaggccgtca  ccagctcgtt  caccacggtc  acgtcgcgca  16620
cgcggccggt  gttgaacgca  tcggcgatct  tctccggcag  gtccagcagc  gtgacgtgct  16680
gggtgatgaa  cgccggcgac  ttgccgattt  ccttggcgat  atcgcctttc  ttcttgccct  16740
tcgccagctc  gcggccaatg  aagtcggcaa  tttcgcgcgg  ggtcagctcg  ttgcgttgca  16800
ggttctcgat  aacctggtcg  gcttcgttgt  agtcgttgtc  gatgaacgcc  gggatggact  16860
tcttgccggc  ccacttcgag  ccacggtagc  ggcgggcgcc  gtgattgatg  atatagcggc  16920
ccggctgctc  ctggttctcg  cgcaccgaaa  tgggtgactt  caccccgcgc  tctttgatcg  16980
tggcaccgat  ttccgcgatg  ctctccgggg  aaaagccggg  gttgtcggcc  gtccgcggct  17040
gatgcggatc  ttcgtcgatc  aggtccaggt  ccagctcgat  agggccggaa  ccgccctgag  17100
acgccgcagg  agcgtccagg  aggctcgaca  ggtcgccgat  gctatccaac  ccaggccgg  17160
acggctgcgc  cgcgcctgcg  gcttcctgag  cggccgcagc  ggtgttttc  ttggtggtct  17220
tggcttgagc  cgcagtcatt  gggaaatctc  catcttcgtg  aacacgtaat  cagccagggc  17280
gcgaacctct  ttcgatgcct  tgcgcgcggc  cgttttcttg  atcttccaga  ccggcacacc  17340
```

```
ggatgcgagg gcatcggcga tgctgctgcg caggccaacg gtggccggaa tcatcatctt    17400 gggggtacgcg ccagcagct cggcttggtg gcgcgcgtgg cgcggattcc gcgcatcgac    17460
cttgctgggc accatgccaa ggaattgcag cttggcgttc ttctggcgca cgttcgcaat    17520
ggtcgtgacc atcttcttga tgccctggat gctgtacgcc tcaagctcga tggggacag    17580 cacatagtcg gccgcgaaga gggcggccgc caggccgacg ccaagggtcg gggccgtgtc    17640
gatcaggcac acgtcgaagc cttggttcgc cagggccttg atgttcgccc cgaacagctc    17700
gcgggcgtcg tccagcgaca gccgttcggc gttcgccagt accgggttgg actcgatgag    17760
ggcgaggcgc gcggcctggc cgtcgccggc tgcgggtgcg gtttcggtcc agccgccggc    17820
agggacagcg ccgaacagct tgcttgcatg caggccggta gcaaagtcct tgagcgtgta    17880
ggacgcattg ccctggggt ccaggtcgat cacggcaacc cgcaagccgc gctcgaaaaa     17940
gtcgaaggca agatgcacaa gggtcgaagt cttgccgacg ccgcctttct ggttggccgt    18000
gaccaaagtt ttcatcgttt ggtttcctgt ttttcttgg cgtccgcttc ccacttccgg     18060
acgatgtacg cctgatgttc cggcagaacc gccgttaccc gcgcgtaccc ctcgggcaag    18120
ttcttgtcct cgaacgcggc ccacacgcga tgcaccgctt gcgacactgc gcccctggtc    18180
agtcccagcg acgttgcgaa cgtcgcctgt ggcttcccat cgactaagac gccccgcgct    18240
atctcgatgg tctgctgccc cacttccagc ccctggatcg cctcctggaa ctggctttcg    18300
gtaagccgtt tcttcatgga taacacccat aatttgctcc gcgccttggt tgaacatagc    18360
ggtgacagcc gccagcacat gagagaagtt tagctaaaca tttctcgcac gtcaacacct    18420
ttagccgcta aaactcgtcc ttggcgtaac aaaacaaaag cccggaaacc gggctttcgt    18480
ctcttgccgc ttatggctct gcacccggct ccatcaccaa caggtcgcgc acgcgcttca    18540
ctcggttgcg gatcgacact gccagcccaa caaagccggt tgccgccgcc gccaggatcg    18600
cgccgatgat gccggccaca ccggccatcg cccaccaggt cgccgccttc cggttccatt    18660
cctgctggta ctgcttcgca atgctggacc tcggctcacc ataggctgac cgctcgatgg    18720
cgtatgccgc ttctcccctt ggcgtaaaac ccagcgccgc aggcggcatt gccatgctgc    18780
ccgccgcttt cccgaccacg acgcgcgcac caggcttgcg gtccagacct tcggccacgg    18840
cgagctgcgc aaggacataa tcagccgccg acttggctcc acgcgcctcg atcagctctt    18900
gcactcgcgc gaaatccttg gcctccacgg ccgccatgaa tcgcgcacgc ggcgaaggct    18960
ccgcagggcc ggcgtcgtga tcgccgccga gaatgcccct caccaagttc gacgacacga    19020
aaatcatgct gacggctatc accatcatgc agacggatcg cacgaacccg ctgaattgaa    19080
cacgagcacg gcaccgcga ccactatgcc aagaatgccc aaggtaaaaa ttgccggccc     19140
cgccatgaag tccgtgaatg ccccgacggc cgaagtgaag ggcaggccgc cacccaggcc    19200
gccgccctca ctgcccggca cctggtcgct gaatgtcgat gccagcacct gcggcacgtc    19260
aatgcttccg ggcgtcgcgc tcgggctgat cgcccatccc gttactgccc cgatcccggc    19320
aatggcaagg actgccagcg ctgccatttt tggggtgagg ccgttcgcgg ccgaggggcg    19380
cagcccctgg ggggatggga ggccgcgtt agcgggccgg gagggttcga aaggggggg     19440 cacccccctt cggcgtgcgc ggtcacgcgc acagggcgca gccctggtta aaaacaaggt    19500
ttataaatat tggtttaaaa gcaggttaaa agacaggtta gcggtggccg aaaaacgggc    19560 ggaaacccctt gcaaatgctg gattttctgc ctgtggacag cccctcaaat gtcaataggt   19620
gcgcccctca tctgtcagca ctctgcccct caagtgtcaa ggatcgcgcc cctcatctgt    19680
cagtagtcgc gccccctcaag tgtcaatacc gcagggcact tatccccagg cttgtccaca   19740
```

```
tcatctgtgg gaaactcgcg taaaatcagg cgttttcgcc gatttgcgag gctggccagc   19800
tccacgtcgc cggccgaaat cgagcctgcc cctcatctgt caacgccgcg ccgggtgagt   19860
cggcccctca agtgtcaacg tccgcccctc atctgtcagt gagggccaag ttttccgcga   19920
ggtatccaca acgccggcgg ccgcggtgtc tcgcacacgg cttcgacggc gtttctggcg   19980
cgtttgcagg gccatagacg gccgccagcc cagcggcgag ggcaaccagc ccggtgagcg   20040
tcggaaaggc gctggaagcc ccgtagcgac gcggagaggg gcgagacaag ccaagggcgc   20100
aggctcgatg cgcagcacga catagccggt tctcgcaagg acgagaattt ccctgcggtg   20160
cccctcaagt gtcaatgaaa gtttccaacg cgagccattc gcgagagcct tgagtccacg   20220
ctagatgaga gctttgttgt aggtggacca gttggtgatt ttgaactttt gctttgccac   20280
ggaacggtct gcgttgtcgg gaagatgcgt gatctgatcc ttcaactcag caaaagttcg   20340
atttattcaa caaagccacg ttgtgtctca aaatctctga tgttacattg cacaagataa   20400
aaatatatca tcatgaacaa taaaactgtc tgcttacata aacagtaata caaggggtgt   20460
tatgagccat attcaacggg aaacgtcttg ctcgactcta gagctcgttc ctcgaggcct   20520
cgaggcctcg aggaacggta cctgcgggga agcttacaat aatgtgtgtt gttaagtctt   20580
gttgcctgtc atcgtctgac tgactttcgt cataaatccc ggcctccgta acccagcttt   20640
gggcaagctc acggatttga tccggcgaaa cgggaatatc gagatgccgg gctgaacgct   20700
gcagttccag ctttcccttt cgggacaggt actccagctg attgattatc tgctgaaggg   20760
tcttggttcc acctcctggc acaatgcgaa tgattacttg agcgcgatcg ggcatccaat   20820
tttctcccgt caggtgcgtg gtcaagtgct acaaggcacc tttcagtaac gagcgaccgt   20880
cgatccgtcg ccgggatacg gacaaaatgg agcgcagtag tccatcgagg gcggcgaaag   20940
cctcgccaaa agcaatacgt tcatctcgca cagcctccag atccgatcga gggtcttcgg   21000
cgtaggcaga tagaagcatg gatacattgc ttgagagtat tccgatggac tgaagtatgg   21060
cttccatctt ttctcgtgtg tctgcatcta tttcgagaaa gccccccgatg cggcgcaccg   21120 caacgcgaat tgccatacta tccgaaagtc ccagcaggcg cgcttgatag gaaaaggttt   21180
catactcggc cgatcgcaga cgggcactca cgaccttgaa cccttcaact ttcagggatc   21240
gatgctggtt gatggtagtc tcactcgacg tggctctggt gtgttttgac atagcttcct   21300
ccaaagaaag cggaaggtct ggatactcca gcacgaaatg tgcccgggta gacggatgga   21360
agtctagccc tgctcaatat gaaatcaaca gtacatttac agtcaatact gaatatactt   21420
gctacatttg caattgtctt ataacgaatg tgaaataaaa atagtgtaac aacgctttta   21480
ctcatcgata atcacaaaaa catttatacg aacaaaaata caaatgcact ccggtttcac   21540
aggataggcg ggatcagaat atgcaacttt tgacgttttg ttctttcaaa ggggtgctg   21600 gcaaaaccac cgcactcatg ggcctttgcg ctgctttggc aaatgacggt aaacgagtgg   21660
ccctctttga tgccgacgaa aaccggcctc tgacgcgatg gagagaaaac gccttacaaa   21720
gcagtactgg gatcctcgct gtgaagtcta ttccgccgac gaaatgcccc ttcttgaagc   21780
agcctatgaa aatgccgagc tcgaaggatt tgattatgcg ttggccgata cgcgtggcgg   21840
ctcgagcgag ctcaacaaca caatcatcgc tagctcaaac ctgcttctga tccccaccat   21900
gctaacgccg ctcgacatcg atgaggcact atctacctac cgctacgtca tcgagctgct   21960
gttgagtgaa aatttggcaa ttcctacagc tgttttgcgc caacgcgtcc cggtcggccg   22020
attgacaaca tcgcaacgca ggatgtcaga gacgctagag agccttccag ttgtaccgtc   22080
```

```
tcccatgcat gaaagagatg catttgccgc gatgaaagaa cgcggcatgt tgcatcttac    22140
attactaaac acgggaactg atccgacgat gcgcctcata gagaggaatc ttcggattgc    22200
gatggaggaa gtcgtggtca tttcgaaact gatcagcaaa atcttggagg cttgaagatg    22260
gcaattcgca agcccgcatt gtcggtcggc gaagcacggc ggcttgctgg tgctcgaccc    22320
gagatccacc atcccaaccc gacacttgtt ccccagaagc tggacctcca gcacttgcct    22380
gaaaaagccg acgagaaaga ccagcaacgt gagcctctcg tcgccgatca catttacagt    22440
cccgatcgac aacttaagct aactgtggat gcccttagtc cacctccgtc cccgaaaaag    22500
ctccaggttt ttcttttcagc gcgaccgccc gcgcctcaag tgtcgaaaac atatgacaac    22560
ctcgttcggc aatacagtcc ctcgaagtcg ctacaaatga ttttaaggcg cgcgttggac    22620
gatttcgaaa gcatgctggc agatggatca tttcgcgtgg ccccgaaaag ttatccgatc    22680
ccttcaacta cagaaaaatc cgttctcgtt cagacctcac gcatgttccc ggttgcgttg    22740
ctcgaggtcg ctcgaagtca ttttgatccg ttggggttgg agaccgctcg agctttcggc    22800
cacaagctgg ctaccgccgc gctcgcgtca ttctttgctg gagagaagcc atcgagcaat    22860
tggtgaagag ggacctatcg gaacccctca ccaaatattg agtgtaggtt tgaggccgct    22920
ggccgcgtcc tcagtcacct tttgagccag ataattaaga gccaaatgca attggctcag    22980
gctgccatcg tcccccccgtg cgaaacctgc acgtccgcgt caaagaaata accggcacct    23040
cttgctgttt ttatcagttg agggcttgac ggatccgcct caagtttgcg gcgcagccgc    23100
aaaatgagaa catctatact cctgtcgtaa acctcctcgt cgcgtactcg actggcaatg    23160
agaagttgct cgcgcgatag aacgtcgcgg ggtttctcta aaaacgcgag gagaagattg    23220
aactcacctg ccgtaagttt cacctcaccg ccagcttcgg acatcaagcg acgttgcctg    23280
agattaagtg tccagtcagt aaaacaaaaa gaccgtcggt cttggagcg acaacgttg      23340
gggcgcacgc gcaaggcaac ccgaatgcgt gcaagaaact ctctcgtact aaacggctta    23400
gcgataaaat cacttgctcc tagctcgagt gcaacaactt tatccgtctc tcaaggcgg    23460
tcgccactga taattatgat tggaatatca gactttgccg ccagatttcg aacgatctca    23520
agcccatctt cacgacctaa atttagatca acaaccacga catcgaccgt cgcggaagag    23580
agtactctag tgaactgggt gctgtcggct accgcggtca cttttgaaggc gtggatcgta    23640
aggtattcga taataagatg ccgcatacg acatcgtcat cgataagaag aacgtgtttc      23700
aacggctcac ctttcaatct aaaatctgaa cccttgttca cagcgcttga gaaatttttca   23760
cgtgaaggat gtacaatcat ctccagctaa atgggcagtt cgtcagaatt gcggctgacc    23820
gcggatgacg aaaatgcgaa ccaagtatt caattttatg acaaaagttc tcaatcgttg     23880
ttacaagtga aacgcttcga ggttacagct actattgatt aaggagatcg cctatggtct    23940
cgccccggcg tcgtgcgtcc gccgcgagcc agatctcgcc tacttcataa acgtcctcat    24000
aggcacggaa tggaatgatg acatcgatcg ccgtagagag catgtcaatc agtgtgcgat    24060
cttccaagct agcaccttgg gcgctacttt tgacaaggga aaacagtttc ttgaatcctt    24120
ggattggatt cgcgccgtgt attgttgaaa tcgatcccgg atgtcccgag acgacttcac    24180
tcagataagc ccatgctgca tcgtcgcgca tctcgccaag caatatccgg tccggccgca    24240
tacgcagact tgcttggagc aagtgctcgg cgctcacagc acccagccca gcaccgttct    24300
tggagtagag tagtctaaca tgattatcgt gtggaatgac gagttcgagc gtatcttcta    24360
tggtgattag cctttcctgg gggggatgg cgctgatcaa ggtcttgctc attgttgtct     24420
tgccgcttcc ggtagggcca catagcaaca tcgtcagtcg gctgacgacg catgcgtgca    24480
```

```
gaaacgcttc caaatccccg ttgtcaaaat gctgaaggat agcttcatca tcctgatttt    24540
ggcgtttcct tcgtgtctgc cactggttcc acctcgaagc atcataacgg gaggagactt    24600
ctttaagacc agaaacacgc gagcttggcc gtcgaatggt caagctgacg gtgcccgagg    24660
gaacggtcgg cggcagacag atttgtagtc gttcaccacc aggaagttca gtggcgagaa    24720
gggggttacg tggtccgaca tcctgctttc tcagcgcgcc cgctaaaata gcgatatctt    24780
caagatcatc ataagagacg ggcaaaggca tcttggtaaa aatgccggct tggcgcacaa    24840
atgcctctcc aggtcgattg atcgcaattt cttcagtctt cgggtcatcg agccattcca    24900
aaatcggctt cagaagaaag cgtagttgcg gatccacttc catttacaat gtatcctatc    24960
tctaagcgga aatttgaatt cattaagagc ggcggttcct cccccgcgtg gcgccgccag    25020
tcaggcggag ctggtaaaca ccaaagaaat cgaggtcccg tgctacgaaa atggaaacgg    25080
tgtcaccctg attcttcttc agggttggcg gtatgttgat ggttgcctta agggctgtct    25140
cagttgtctg ctcaccgtta ttttgaaagc tgttgaagct catcccgcca cccgagctgc    25200
cggcgtaggt gctagctgcc tggaaggcgc cttgaacaac actcaagagc atagctccgc    25260
taaaacgctg ccagaagtgg ctgtcgaccg agcccggcaa tcctgagcga ccagttcgt    25320 ccgcgcttgg cgatgttaac gagatcatcg catggtcagg tgtctcggcg cgatcccaca    25380
acacaaaaac gcgcccatct ccctgttgca agccacgctg tatttcgcca acaacggtgg    25440
tgccacgatc aagaagcacg atattgttcg ttgttccacg aatatcctga ggcaagacac    25500
actttacata gcctgccaaa tttgtgtcga ttgcggtttg caagatgcac ggaattattg    25560
tcccttgcgt taccataaaa tcggggtgcg gcaagagcgt ggcgctgctg ggctgcagct    25620
cggtgggttt catacgtatc gacaaatcgt tctcgccgga cacttcgcca ttcggcaagg    25680
agttgtcgtc acgcttgcct tcttgtcttc ggcccgtgtc gccctgaatg gcgcgtttgc    25740
tgaccccttg atcgccgctg ctatatgcaa aaatcggtgt ttcttccggc cgtggctcat    25800
gccgctccgg ttcgcccctc ggcggtagag gagcagcagg ctgaacagcc tcttgaaccg    25860
ctggaggatc cggcggcacc tcaatcggag ctggatgaaa tggcttggtg tttgttgcga    25920
tcaaagttga cggcgatgcg ttctcattca ccttcttttg gcgcccacct agccaaatga    25980
ggcttaatga taacgcgaga acgacacctc cgacgatcaa tttctgagac cccgaaagac    26040
gccggcgatg tttgtcggag accagggatc cagatgcatc aacctcatgt gccgcttgct    26100
gactatcgtt attcatccct tcgccccctt caggacgcgt ttcacatcgg gcctcaccgt    26160
gcccgtttgc ggcctttggc caacgggatc gtaagcggtg ttccagatac atagtactgt    26220
gtggccatcc ctcagacgcc aacctcggga aaccgaagaa atctcgacat cgctccctt    26280 aactgaatag ttggcaacag cttccttgcc atcaggattg atggtgtaga tggagggtat    26340
gcgtacattg cccggaaagt ggaataccgt cgtaaatcca ttgtcgaaga cttcgagtgg    26400
caacagcgaa cgatcgcctt gggcgacgta gtgccaatta ctgtccgccg caccaagggc    26460
tgtgacaggc tgatccaata aattctcagc tttccgttga tattgtgctt ccgcgtgtag    26520
tctgtccaca acagccttct gttgtgcctc ccttcgccga ccgccgcat cgtcggcggg    26580 gtaggcgaat tggacgctgt aatagagatc gggctgctct ttatcgaggt gggacagagt    26640
cttgaaactt atactgaaaa cataacggcg catcccggag tcgcttgcgg ttagcacgat    26700
tactggctga ggcgtgagga cctggcttgc cttgaaaaat agataatttc cccgcggtag    26760
ggctgctaga tcttgctat ttgaaacggc aaccgctgtc accgtttcgt tcgtggcgaa    26820
```

-continued

```
tgttacgacc aaagtagctc caaccgccgt cgagaggcgc accacttgat cgggattgta   26880
agccaaataa cgcatgcgcg gatctagctt gcccgccatt ggagtgtctt cagcctccgc   26940
accagtcgca gcggcaaata acatgctaaa atgaaaagt gcttttctga tcatggttcg    27000
ctgtggccta cgtttgaaac ggtatcttcc gatgtctgat aggaggtgac aaccagacct   27060
gccgggttgg ttagtctcaa tctgccgggc aagctggtca ccttttcgta gcgaactgtc   27120
gcggtccacg tactcaccac aggcattttg ccgtcaacga cgagggtcct tttatagcga   27180
atttgctgcg tgcttggagt tacatcattt gaagcgatgt gctcgacctc caccctgccg   27240
cgtttgccaa gaatgacttg aggcgaactg ggattgggat agttgaagaa ttgctggtaa   27300
tcctggcgca ctgttggggc actgaagttc gataccaggt cgtaggcgta ctgagcggtg   27360
tcggcatcat aactctcgcg caggcgaacg tactcccaca atgaggcgtt aacgacggcc   27420
tcctcttgag ttgcaggcaa tcgcgagaca gacacctcgc tgtcaacggt gccgtccggc   27480
cgtatccata gatatacggg cacaagcctg ctcaacggca ccattgtggc tatagcgaac   27540
gcttgagcaa catttcccaa aatcgcgata gctgcgacag ctgcaatgag tttggagaga   27600
cgtcgcgccg atttcgctcg cgcggtttga aggcttcta cttccttata gtgctcggca   27660
aggctttcgc gcgccactag catggcatat tcaggccccg tcatagcgtc cacccgaatt   27720
gccgagctga agatctgacg gagtaggctg ccatcgcccc acattcagcg ggaagatcgg   27780
gcctttgcag ctcgctaatg tgtcgtttgt ctggcagccg ctcaaagcga caactaggca   27840
cagcaggcaa tacttcatag aattctccat tgaggcgaat ttttgcgcga cctagcctcg   27900
ctcaacctga gcgaagcgac ggtacaagct gctggcagat tgggttgcgc cgctccagta   27960
actgcctcca atgttgccgg cgatcgccgg caaagcgaca atgagcgcat cccctgtcag   28020
aaaaaacata tcgagttcgt aaagaccaat gatcttggcc gcggtcgtac cggcgaaggt   28080
gattacacca agcataaggg tgagcgcagt cgcttcggtt aggatgacga tcgttgccac   28140
gaggtttaag aggagaagca agagaccgta ggtgataagt tgcccgatcc acttagctgc   28200
gatgtcccgc gtgcgatcaa aaatatatcc gacgaggatc agaggcccga tcgcgagaag   28260
cactttcgtg agaattccaa cggcgtcgta aactccgaag gcagaccaga gcgtgccgta   28320
aaggacccac tgtgccccctt ggaaagcaag gatgtcctgg tcgttcatcg gaccgatttc   28380
ggatgcgatt ttctgaaaaa cggcctgggt cacggcgaac attgtatcca actgtgccgg   28440
aacagtctgc agaggcaagc cggttacact aaactgctga acaaagtttg ggaccgtctt   28500
ttcgaagatg gaaaccacat agtcttggta gttagcctgc ccaacaatta gagcaacaac   28560
gatggtgacc gtgatcaccc gagtgatacc gctacgggta tcgacttcgc cgcgtatgac   28620
taaaataccc tgaacaataa tccaaagagt gacacaggcg atcaatggcg cactcaccgc   28680
ctcctggata gtctcaagca tcgagtccaa gcctgtcgtg aaggctacat cgaagatcgt   28740
atgaatggcc gtaaacggcg ccggaatcgt gaaattcatc gattggacct gaacttgact   28800
ggtttgtcgc ataatgttgg ataaaatgag ctcgcattcg gcgaggatgc gggcggatga   28860
acaaatcgcc cagccttagg ggagggcacc aaagatgaca gcggtctttt gatgctcctt   28920
gcgttgagcg gccgcctctt ccgctcgtg aaggccggcc tgcgcggtag tcatcgttaa    28980
taggcttgtc gcctgtacat tttgaatcat tgcgtcatgg atctgcttga gaagcaaacc   29040
attggtcacg gttgcctgca tgatattgcg agatcgggaa agctgagcag acgtatcagc   29100 attgccgtc aagcgtttgt ccatcgtttc cagattgtca gccgcaatgc cagcgctgtt    29160
tgcggaaccg gtgatctgcg atcgcaacag gtccgcttca gcatcactac ccacgactgc   29220
```

-continued

```
acgatctgta tcgctggtga tcgcacgtgc cgtggtcgac attggcattc gcggcgaaaa    29280
catttcattg tctaggtcct tcgtcgaagg atactgattt ttctggttga gcgaagtcag    29340
tagtccagta acgccgtagg ccgacgtcaa catcgtaacc atcgctatag tctgagtgag    29400
attctccgca gtcgcgagcg cagtcgcgag cgtctcagcc tccgttgccg ggtcgctaac    29460
aacaaactgc gcccgcgcgg gctgaatata tagaaagctg caggtcaaaa ctgttgcaat    29520
aagttgcgtc gtcttcatcg tttcctacct tatcaatctt ctgcctcgtg gtgacgggcc    29580
atgaattcgc tgagccagcc agatgagttg ccttcttgtg cctcgcgtag tcgagttgca    29640
aagcgcaccg tgttggcacg ccccgaaagc acggcgacat attcacgcat atcccgcaga    29700
tcaaattcgc agatgacgct tccactttct cgtttaagaa gaaacttacg gctgccgacc    29760
gtcatgtctt cacggatcgc ctgaaattcc ttttcggtac atttcagtcc atcgacataa    29820
gccgatcgat ctgcggttgg tgatggatag aaaatcttcg tcatacattg cgcaaccaag    29880
ctggctccta gcgcgattc cagaacatgc tctggttgct gcgttgccag tattagcatc    29940
ccgttgtttt ttcgaacggt caggaggaat tgtcgacga cagtcgaaaa tttagggttt    30000
aacaaatagg cgcgaaactc atcgcagctc atcacaaaac ggcggccgtc gatcatggct    30060
ccaatccgat gcaggagata tgctgcagcg ggagcgcata cttcctcgta ttcgagaaga    30120
tgcgtcatgt cgaagccggt aatcgacgga tctaacttta cttcgtcaac ttcgccgtca    30180
aatgcccagc caagcgcatg gccccggcac cagcgttgga gccgcgctcc tgcgccttcg    30240
gcgggcccat gcaacaaaaa ttcacgtaac cccgcgattg aacgcatttg tggatcaaac    30300
gagagctgac gatggatacc acggaccaga cggcggttct cttccggaga aatcccaccc    30360
cgaccatcac tctcgatgag agccacgatc cattcgcgca gaaaatcgtg tgaggctgct    30420
gtgttttcta ggccacgcaa cggcgccaac ccgctgggtg tgcctctgtg aagtgccaaa    30480
tatgttcctc ctgtggcgcg aaccagcaat tcgccacccc ggtccttgtc aaagaacacg    30540
accgtacctg cacggtcgac catgctctgt tcgagcatgg ctagaacaaa catcatgagc    30600
gtcgtcttac ccctcccgat aggcccgaat attgccgtca tgccaacatc gtgctcatgc    30660
gggatatagt cgaaaggcgt tccgccattg gtacgaaatc gggcaatcgc gttgcccag    30720
tggcctgagc tggcgccctc tggaaagttt tcgaaagaga caaaccctgc gaaattgcgt    30780
gaagtgattg cgcagggcg tgtgcgccac ttaaaattcc ccggcaattg ggaccaatag    30840
gccgcttcca taccaatacc ttcttggaca accacggcac ctgcatccgc cattcgtgtc    30900
cgagcccgcg cgcccctgtc cccaagacta ttgagatcgt ctgcatagac gcaaaggctc    30960
aaatgatgtg agcccataac gaattcgttg ctcgcaagtg cgtcctcagc ctcggataat    31020
ttgccgattt gagtcacggc tttatcgccg gaactcagca tctggctcga tttgaggcta    31080
agtttcgcgt gcgcttgcgg gcgagtcagg aacgaaaaac tctgcgtgag aacaagtgga    31140
aaatcgaggg atagcagcgc gttgagcatg cccggccgtg ttttgcagg gtattcgcga    31200
aacgaataga tggatccaac gtaactgtct tttggcgttc tgatctcgag tcctcgcttg    31260
ccgcaaatga ctctgtcggt ataaatcgaa gcgccgagtg agccgctgac gaccggaacc    31320
ggtgtgaacc gaccagtcat gatcaaccgt agcgcttcgc caatttcggt gaagagcaca    31380
ccctgcttct cgcggatgcc aagacgatgc aggccatacg ctttaagaga gccagcgaca    31440
acatgccaaa gatcttccat gttcctgatc tggcccgtga gatcgttttc ccttttccg    31500
cttagcttgg tgaacctcct cttaccttc cctaaagccg cctgtgggta gacaatcaac    31560
```

```
gtaaggaagt gttcattgcg gaggagttgg ccggagagca cgcgctgttc aaaagcttcg    31620
ttcaggctag cggcgaaaac actacggaag tgtcgcggcg ccgatgatgg cacgtcggca    31680
tgacgtacga ggtgagcata tattgacaca tgatcatcag cgatattgcg caacagcgtg    31740
ttgaacgcac gacaacgcgc attgcgcatt tcagtttcct caagctcgaa tgcaacgcca    31800
tcaattctcg caatggtcat gatcgatccg tcttcaagaa ggacgatatg gtcgctgagg    31860
tggccaatat aagggagata gatctcaccg gatctttcgg tcgttccact cgcgccgagc    31920
atcacaccat tcctctccct cgtgggggaa ccctaattgg atttgggcta acagtagcgc    31980
ccccccaaac tgcactatca atgcttcttc ccgcggtccg caaaaatagc aggacgacgc    32040
tcgccgcatt gtagtctcgc tccacgatga gccgggctgc aaaccataac ggcacgagaa    32100
cgacttcgta gagcgggttc tgaacgataa cgatgacaaa gccggcgaac atcatgaata    32160
accctgccaa tgtcagtggc accccaagaa acaatgcggg ccgtgtggct gcgaggtaaa    32220
gggtcgattc ttccaaacga tcagccatca actaccgcca gtgagcgttt ggccgaggaa    32280
gctcgcccca acatgataa caatgccgcc gacgacgccg caaccagcc caagcgaagc    32340 ccgcccgaac atccaggaga tcccgatagc gacaatgccg agaacagcga gtgactggcc    32400
gaacggacca aggataaacg tgcatatatt gttaaccatt gtggcgggt cagtgccgcc    32460 acccgcagat tgcgctgcgg cgggtccgga tgaggaaatg ctccatgcaa ttgcaccgca    32520
caagcttggg gcgcagctcg atatcacgcg catcatcgca ttcgagagcg agaggcgatt    32580
tagatgtaaa cggtatctct caaagcatcg catcaatgcg cacctcctta gtataagtcg    32640
aataagactt gattgtcgtc tgcggatttg ccgttgtcct ggtgtggcgg tggcggagcg    32700
attaaaccgc cagcgccatc ctcctgcgag cggcgctgat atgaccccca aacatcccac    32760
gtctcttcgg attttagcgc ctcgtgatcg tcttttggag gctcgattaa cgcgggcacc    32820
agcgattgag cagctgtttc aacttttcgc acgtagccgt ttgcaaaacc gccgatgaaa    32880
ttaccggtgt tgtaagcgga gatcgcccga cgaagcgcaa attgcttctc gtcaatcgtt    32940
tcgccgcctg cataacgact tttcagcatg tttgcagcgg cagataatga tgtgcacgcc    33000
tggagcgcac cgtcaggtgt cagaccgagc atagaaaaat ttcgagagtt tatttgcatg    33060
aggccaacat ccagcgaatg ccgtgcatcg agacggtgcc tgacgacttg ggttgcttgg    33120
ctgtgatctt gccagtgaag cgtttcgccg gtcgtgttgt catgaatcgc taaggatca    33180 aagcgactct ccaccttagc tatcgccgca agcgtagatg tcgcaactga tggggcacac    33240
ttgcgagcaa catggtcaaa ctcagcagat gagagtggcg tggcaaggct cgacgaacag    33300
aaggagacca tcaaggcaag agaaagcgac cccgatctct taagcatacc ttatctcctt    33360
agctcgcaac taacaccgcc tctcccgttg gaagaagtgc gttgttttat gttgaagatt    33420
atcgggaggg tcggttactc gaaaatttc aattgcttct ttatgatttc aattgaagcg    33480
agaaacctcg cccggcgtct tggaacgcaa catggaccga gaaccgcgca tccatgacta    33540
agcaaccgga tcgacctatt caggccgcag ttggtcaggt caggctcaga acgaaaatgc    33600
tcggcgaggt tacgctgtct gtaaacccat tcgatgaacg ggaagcttcc ttccgattgc    33660
tcttggcagg aatattggcc catgcctgct tgcgctttgc aaatgctctt atcgcgttgg    33720
tatcatatgc cttgtccgcc agcagaaacg cactctaagc gattatttgt aaaaatgttt    33780
cggtcatgcg gcggtcatgg gcttgacccg ctgtcagcgc aagacggatc ggtcaaccgt    33840
cggcatcgac aacagcgtga atcttggtgg tcaaaccgcc acgggaacgt cccatacagc    33900
catcgtcttg atcccgctgt ttcccgtcgc cgcatgttgg tggacgcgga cacaggaact    33960
```

```
gtcaatcatg acgacattct atcgaaagcc ttggaaatca cactcagaat atgatcccag    34020
acgtctgcct cacgccatcg tacaaagcga ttgtagcagg ttgtacagga accgtatcga    34080
tcaggaacgt ctgcccaggg cgggcccgtc cggaagcgcc acaagatgac attgatcacc    34140
cgcgtcaacg cgcggcacgc gacgcggctt atttgggaac aaaggactga acaacagtcc    34200
attcgaaatc ggtgacatca aagcggggac gggttatcag tggcctccaa gtcaagcctc    34260
aatgaatcaa aatcagaccg atttgcaaac ctgatttatg agtgtgcggc ctaaatgatg    34320
aaatcgtcct tctagatcgc ctccgtggtg tagcaacacc tcgcagtatc gccgtgctga    34380
ccttggccag ggaattgact ggcaagggtg cttcacatg accgctcttt tggccgcgat    34440
agatgatttc gttgctgctt tgggcacgta aaggagaga agtcatatcg gagaaattcc    34500
tcctggcgcg agagcctgct ctatcgcgac ggcatcccac tgtcgggaac agaccggatc    34560
attcacgagg cgaaagtcgt caacacatgc gttataggca tcttcccttg aaggatgatc    34620
ttgttgctgc caatctggag gtgcggcagc cgcaggcaga tgcgatctca gcgcaacttg    34680
cggcaaaaca tctcactcac ctgaaaacca ctagcgagtc tcgcgatcag acgaaggcct    34740
tttacttaac gacacaatat ccgatgtctg catcacaggc gtcgctatcc cagtcaatac    34800
taaagcggtg caggaactaa agattactga tgacttaggc gtgccacgag gcctgagacg    34860
acgcgcgtag acagtttttt gaaatcatta tcaaagtgat ggcctccgct gaagcctatc    34920
acctctgcgc cggtctgtcg gagagatggg caagcattat tacggtcttc gcgcccgtac    34980
atgcattgga cgattgcagg gtcaatggat ctgagatcat ccagaggatt gccgccctta    35040
ccttccgttt cgagttggag ccagcccta aatgagacga catagtcgac ttgatgtgac    35100
aatgccaaga gagagatttg cttaacccga tttttttgct caagcgtaag cctattgaag    35160
cttgccggca tgacgtccgc gccgaaagaa tatcctacaa gtaaaacatt ctgcacaccg    35220
aaatgcttgg tgtagacatc gattatgtga ccaagatcct tagcagtttc gcttggggac    35280
cgctccgacc agaaataccg aagtgaactg acgccaatga caggaatccc ttccgtctgc    35340
agataggtac catcgataga tctgctgcct cgcgcgtttc ggtgatgacg gtgaaaacct    35400
ctgacacatg cagctcccgg agacggtcac agcttgtctg taagcggatg ccgggagcag    35460
acaagcccgt cagggcgcgt cagcgggtgt tggcgggtgt cggggcgcag ccatgaccca    35520
gtcacgtagc gatagcggag tgtatactgg cttaactatg cggcatcaga gcagattgta    35580
ctgagagtgc accatatgcg gtgtgaaata ccgcacagat gcgtaaggag aaaataccgc    35640
atcaggcgct cttccgcttc ctcgctcact gactcgctgc gctcggtcgt tcggctgcgg    35700
cgagcggtat cagctcactc aaaggcggta atacggttat ccacagaatc aggggataac    35760
gcaggaaaga acatgtgagc aaaaggccag caaaaggcca ggaaccgtaa aaaggccgcg    35820
ttgctggcgt ttttccatag gctccgcccc cctgacgagc atcacaaaaa tcgacgctca    35880
agtcagaggt ggcgaaaccc gacaggacta taaagatacc aggcgtttcc ccctggaagc    35940
tccctcgtgc gctctcctgt tccgaccctg ccgcttaccg gatacctgtc cgcctttctc    36000
ccttcgggaa gcgtggcgct ttctcatagc tcacgctgta ggtatctcag ttcggtgtag    36060
gtcgttcgct ccaagctggg ctgtgtgcac gaaccccccg ttcagcccga ccgctgcgcc    36120
ttatccggta actatcgtct tgagtccaac ccggtaagac acgacttatc gccactggca    36180
gcagccactg gtaacaggat tagcagagcg aggtatgtag gcggtgctac agagttcttg    36240
aagtggtggc ctaactacgg ctacactaga aggacagtat ttggtatctg cgctctgctg    36300
```

```
aagccagtta ccttcggaaa aagagttggt agctcttgat ccggcaaaca aaccaccgct    36360
ggtagcggtg gtttttttgt ttgcaagcag cagattacgc gcagaaaaaa aggatctcaa    36420
gaagatcctt tgatcttttc tacggggtct gacgctcagt ggaacgaaaa ctcacgttaa    36480
gggattttgg tcatgagatt atcaaaaagg atcttcacct agatcctttt aaattaaaaa    36540
tgaagtttta aatcaatcta agtatatat gagtaaactt ggtctgacag ttaccaatgc     36600
ttaatcagtg aggcacctat ctcagcgatc tgtctatttc gttcatccat agttgcctga    36660
ctccccgtcg tgtagataac tacgatacgg gagggcttac catctggccc cagtgctgca    36720
atgataccgc gagacccacg ctcaccggct ccagatttat cagcaataaa ccagccagcc    36780
ggaagggccg agcgcagaag tggtcctgca actttatccg cctccatcca gtctattaat    36840
tgttgccggg aagctagagt aagtagttcg ccagttaata gtttgcgcaa cgttgttgcc    36900
attgctgcag ggggggggg gggggggac ttccattgtt cattcacgg acaaaaacag       36960 agaaaggaaa cgacagaggc caaaaagcct cgctttcagc acctgtcgtt cctttctt     37020 tcagagggta ttttaaataa aaacattaag ttatgacgaa gaagaacgga aacgccttaa    37080
accggaaaat tttcataaat agcgaaaacc cgcgaggtcg ccgccccgta acctgtcgga    37140
tcaccggaaa ggaccgtaa agtgataatg attatcatct acatatcaca acgtgcgtgg    37200
aggccatcaa accacgtcaa ataatcaatt atgacgcagg tatcgtatta attgatctgc    37260
atcaacttaa cgtaaaaaca acttcagaca atacaaatca gcgacactga atacgggca    37320 acctcatgtc cccccccc ccccccctgc aggcatcgtg gtgtcacgct cgtcgtttgg     37380 tatgcttca ttcagctccg gttcccaacg atcaaggcga gttacatgat cccccatgtt     37440
gtgcaaaaaa gcggttagct ccttcggtcc tccgatcgtt gtcagaagta agttggccgc   37500
agtgttatca ctcatggtta tggcagcact gcataattct cttactgtca tgccatccgt   37560
aagatgcttt tctgtgactg gtgagtactc aaccaagtca ttctgagaat agtgtatgcg   37620
gcgaccgagt tgctcttgcc cggcgtcaac acgggataat accgcgccac atagcagaac   37680
tttaaaagtg ctcatcattg gaaaacgttc ttcgggcga aaactctcaa ggatcttacc    37740
gctgttgaga tccagttcga tgtaacccac tcgtgcaccc aactgatctt cagcatcttt   37800
tactttcacc agcgtttctg ggtgagcaaa acaggaagg caaaatgccg caaaaaggg     37860 aataagggcg acacggaaat gttgaatact catactcttc cttttttcaat attattgaag  37920 catttatcag ggttattgtc tcatgagcgg atacatattt gaatgtattt agaaaaataa   37980
acaaataggg gttccgcgca catttccccg aaaagtgcca cctgacgtct aagaaaccat   38040
tattatcatg acattaacct ataaaaatag gcgtatcacg aggccctttc gtcttcaaga   38100
attggtcgac gatcttgctg cgttcggata ttttcgtgga gttcccgcca cagacccgga   38160
ttgaaggcga gatccagcaa ctcgcgccag atcatcctgt gacggaactt tggcgcgtga   38220
tgactggcca ggacgtcggc cgaaagagcg acaagcagat cacgcttttc gacagcgtcg   38280
gatttgcgat cgaggatttt tcggcgctgc gctacgtccg cgaccgcgtt gagggatcaa   38340
gccacagcag cccactcgac cttctagccg acccagacga gccaagggat ctttttggaa   38400
tgctgctccg tcgtcaggct ttccgacgtt gggtggttg aacagaagtc attatcgtac    38460
ggaatgccaa gcactcccga ggggaaccct gtggttggca tgcacataca aatggacgaa   38520
cggataaacc ttttcacgcc cttttaaata tccgttattc taataaacgc tcttttctct   38580
taggtttacc cgccaatata tcctgtcaaa cactgatagt ttaaactgaa ggcgggaaac   38640
gacaatctga tcatgagcgg agaattaagg gagtcacgtt atgacccccg ccgatgacgc   38700
```

```
gggacaagcc gttttacgtt tggaactgac agaaccgcaa cgttgaagga gccactcagc  38760
ccaagctggt acgattgtaa tacgactcac tatagggcga attgagcgct gtttaaacgc  38820
tcttcaactg gaagagcggt taccagaggc cagaatggcc atctcggacc gatatcgcta  38880
tcaactttgt atagaaaagt tgggccgaat tcgagctcgg tacggccaga atggcccgga  38940
ccgggttacc gaattcgagc tcggtaccct gggatccgat atcgatgggc cctggccgaa  39000
gcttttttgga aggctaagga gaggaagccg gcgagaagga gggggcgttt tacgtgtcac  39060
tgtcctgtcg tgttggctgt tgacacgaat catttcttcc gcgcgtggga agaagaagat  39120
gcacattagc ggcctgaagt agagatgtca atggggaatt ccccagcggg gattaactcc  39180
ccagacccgt acccatgaac atagaccggc ccccatcccc gaacccgaac ccgacctcgg  39240
gtacgaaaat cctcccatac ccattcccga ccgggtacta atacccatg ggtatccata   39300
cccgacccga ttattcaaaa attaatgggc ttttatttg ttaaccggcg gacgcaatgc   39360
ttgggactct aggttttttt actttgttga ccggctggcg gctgggcttt ttcctacagg  39420
cccaaagttg gtcggcagcc actaggccac acgtcacagg cagcccacaa gtaaatgtcg  39480
ttggattgct ggatggtgga ataaaaatcc tagatgctag attgttctgg ttccgggtat   39540
ttttctccat ggctaatcgg gtttgggttt agccctccca aacccgaacc cgccataccc   39600
gatgggtaag ggatttattc caaatctata cccatgggga tttgtttaa cccataccct    39660
aaccctaata gaggaattcc ccacgggtaa tcgggtttcg ggcccattg acatctctag    39720
actgaaggcg tccaactcaa atcattaaaa agtgttgacg cacgcgctga tgcgccggcc   39780
gcacagcaca ggctgcacag cccgtttaat cagcgatgga gccccggccg tcagccagcc   39840
aggtccggcg tccgggtctg cgccctgcgg cgtcactgct gtcgcaccg tctccgatgg    39900
tcccacatcc atccagcggg ccgcgcgtgg tacaaaaggc tcttcctcgc cgtcaggtgc   39960
agctgcccaa acaccagaca cagactccac caccccgctt cgatcttctg ttgcagctga   40020
aatctgtcag attctgcagt tcattcctca tggctccgaa gaagaagcgc aaggtccaca   40080
tgaacaccaa gtacaacaag gagttcctcc tctacctggc aggtttcgtg gacggcgatg   40140
ggtctatcat cgcccagatt gatccgcaac agtcctacaa gttcaagcac tcgctgcggc   40200
tgaggttcac ggtcactcag aagacgcagc gcaggtggtt cctcgataag ctggtcgacg   40260
aaatcggagt cggcaaggtg cgggacaggg gctctgtcag cgactacatc ctctgtcaga   40320
tcaagccgct ccacaacttc ctgacccagc tgcagcccct tcctcaagctc aagcagaagc   40380
aggccaacct ggtgctcaag atcatcgagc agctgccatc tgccaaggag tcaccagaca   40440
agttccttga ggtaagtttc tgcttctacc tttgatatat atataataat tatcattaat   40500
tagtagtaat ataatatttc aaatattttt ttcaaaataa aagaatgtag tatatagcaa   40560
ttgctttttct gtagtttata agtgtgtata tttaatttta aacttttct aatatatgac    40620
caaaacatgg tgatgtgcag gtctgcacct gggtcgatca gatcgctgcc ctgaacgact   40680
ccaagacgag gaagaccacc tccgagaccg tcagggctgt gctggactca ctcccaggat   40740
ccgttggcgg tctcagccct tctcaggcta gctcggctgc ttcctcagcc agcagctcac   40800
ctggctccgg tatcagcgag gctctcagag caggtgccac caagtccaag gagttcctcc   40860
tgtacctggc aggcttcgtt gacggcgacg gctcgatctg cgcgtccatt gacccgaacc   40920
agtcgtgtaa gttcaagcat cagctgcgcc tgcgctttac cgtcacgcag aagacccaga   40980
ggcgctggtt cctggacaaa ctggtggacg agatcggggt cgggaaggtg tacgacagag   41040
```

```
ggagcgttag cgactaccgg ctgtgccaga tcaagccgct ccacaacttc ctgacgcagc   41100
tccaacccct cctgaagctg aagcagaagc aggcgaacct tgtgctgaag atcattgagc   41160
agctgccgag cgccaaggag agccctgaca agttcctgga ggtctgcacc tgggtcgacc   41220
agatcgctgc cctcaacgac tccaagacca ggaagaccac gagcgagacc gttcgggctg   41280
tcctggacag cctctccgag aagaagaagt cgagcccgta gggtaccaca tggttaacct   41340
agacttgtcc atcttctgga ttggccaact taattaatgt atgaaataaa aggatgcaca   41400
catagtgaca tgctaatcac tataatgtgg gcatcaaagt tgtgtgttat gtgtaattac   41460
tagttatctg aataaaagag aaagagatca tccatatttc ttatcctaaa tgaatgtcac   41520
gtgtctttat aattctttga tgaaccagat gcatttcatt aaccaaatcc atatacatat   41580
aaatattaat catatataat taatatcaat tgggttagca aaacaaatct agtctaggtg   41640
tgttttgcga atgcggccgc aagcttggtc acccggtccg ggcctagaag gccagcttca   41700
agtttgtaca aaaagcagg ctccggccag aatggcccgg accgggttac cgaattcgag   41760
ctcggtaccc tgggatccag cttcgcttag tttttagttt ttggcagaaa aaatgatcaa   41820
tgtttcacaa accaaatatt tttataactt ttgatgaaag aagatcacca cggtcatatc   41880 tagggggtggt aacaaattgc gatctaaatg tttcttcata aaaaataagg cttcttaata   41940 aatttttagtt caaataaat acgaataaag tctgattcta atctgattcg atccttaaat   42000
tttataatgc aaaatttaga gctcattacc acctctagtc atatgtctag tctgaggtat   42060
atccaaaaag ccctttctct aaattccaca cccaactcag atgtttgcaa ataaatactc   42120
cgactccaaa atgtaggtga agtgcaactt tctccatttt atatcaacat ttgttatttt   42180
ttgtttaaca tttcacactc aaaactaatt aataaaatac gtggttgttg aacgtgcgca   42240
catgtctccc ttacattatg tttttttatt tatgtattat tgttgttttc ctccgaacaa   42300
cttgtcaaca tatcatcatt ggtctttaat atttatgaat atggaagcct agttatttac   42360
acttggctac acactagttg tagttttgcc acttgtctaa catgcaactc tagtagtttt   42420
gccacttgcc tggcatgcaa ctctagtatt gacacttgta tagcatataa tgccaatacg   42480
acacctgcct tacatgaaac attatttttg acacttgtat accatgcaac attaccattg   42540
acatttgtcc atacacatta tatcaaatat attgagcgca tgtcacaaac tcgatacaaa   42600
gctggatgac cctccctcac cacatctata aaaacccgag cgctactgta aatcactcac   42660
aacacaacac atatcttta gtaacctttc aataggcgtc ccccaagaac tagtaaccat   42720
ggccctgtcc aacaagttca tcggcgacga catgaagatg acctaccaca tggacggctg   42780
cgtgaacggc cactacttca ccgtgaaggg cgagggcagc ggcaagccct acgagggcac   42840
ccagacctcc accttcaagg tgaccatggc caacggcggc ccctggcct tctccttcga   42900 catcctgtcc accgtgttca tgtacggcaa ccgctgcttc accgcctacc ccaccagcat   42960
gcccgactac ttcaagcagg ccttccccga cggcatgtcc tacgagaaa ccttcaccta   43020 cgaggacggc ggcgtggcca ccgccagctg ggagatcagc ctgaagggca actgcttcga   43080
gcacaagtcc accttccacg gcgtgaactt ccccgccgac ggccccgtga tggccaagaa   43140
gaccaccggc tgggacccct ccttcgagaa gatgaccgtg tgcgacgca tcttgaaggg   43200 cgacgtgacc gccttcctga tgctgcaggg cggcggcaac tacagatgcc agttccacac   43260
ctcctacaag accaagaagc ccgtgaccat gcccccaac cacgtggtgg agcaccgcat   43320
cgccagaacc gacctggaca agggcggcaa cagcgtgcag ctgaccgagc acgccgtggc   43380
ccacatcacc tccgtggtgc ccttctgaag cggcccatgg atattcgaac gcgtaggtac   43440
```

```
cacatggtta acctagactt gtccatcttc tggattggcc aacttaatta atgtatgaaa   43500
taaaaggatg cacacatagt gacatgctaa tcactataat gtgggcatca aagttgtgtg   43560
ttatgtgtaa ttactagtta tctgaataaa agagaaagag atcatccata tttcttatcc   43620
taaatgaatg tcacgtgtct ttataattct ttgatgaacc agatgcattt cattaaccaa   43680
atccatatac atataaatat taatcatata taattaatat caattgggtt agcaaaacaa   43740
atctagtcta ggtgtgtttt gcgaattccc atggacctcg agggggggcc cgggcaccca   43800
gctttcttgt acaaagtggc cgttaacgga tcggccagaa tggcccggac cgggttaccg   43860
aattcgagct cggtaccctg gatcggccg ctctagaact agtggatccc ccgggctgca   43920
ggaattccca tggagtcaaa gattcaaata gaggacctaa cagaactcgc cgtaaagact   43980
ggcgaacagt tcatacagag tctcttacga ctcaatgaca agaagaaaat cttcgtcaac   44040
atggtggagc acgacacgct tgtctactcc aaaaatatca agatacagt ctcagaagac    44100 caaagggcaa ttgagacttt tcaacaaagg gtaatatccg gaaacctcct cggattccat   44160
tgcccagcta tctgtcactt tattgtgaag atagtggaaa aggaaggtgg ctcctacaaa   44220
tgccatcatt gcgataaagg aaaggccatc gttgaagatg cctctgccga cagtggtccc   44280
aaagatggac ccccacccac gaggagcatc gtggaaaaag aagacgttcc aaccacgtct   44340
tcaaagcaag tggattgatg tgatatctcc actgacgtaa gggatgacgc acaatcccac   44400
taagcttcgg ccggggccca tcgatctggc gaaagggga tgtgctgcaa ggcgattaag    44460
ttgggtaacg ccagggtttt cccagtcacg acgttgtaaa acgacggcca gtgccaagct   44520
cagatcagct tggggctggt atcgataaat gttccacat agattttgca tatcataatg    44580
atgtttgtcg ttccgtatct atgtttcata caaattttt acgcatatcg caacacatgg    44640
gcacatacct agtgactgta taactctgca tgtatgagtg tatgactata tgatgtagta   44700
actaataaga agggtagaca tttgagtgat tctttttattc ctggacttgt aagacttgac   44760
atttctgcct tgagtgcgat acatcatatg gacaggggtt atgcatacac tgcttgtttg   44820
ttgtttatgt tctaagagca tctccaacaa cgtgacatat gaaaatgccc tacaatttaa   44880
aaatggttat attttataaa atttagggca taaataaaac atcccgctcc aacattaaag   44940
ccttaaatct attataggga agcccactat gatatagtat atttgaggca ctttagaggg   45000
tgccctataa ttttttgacc atttttttat gaaatgagac actattggag tattttttt     45060 ccgtagagca ccatatttca atttgagaca ccaatttaag gcattgttgg agatgttcta   45120
aatgttggtt tattttgtct gtatcgttgt ggttttgata gtggtgcctt tgcaatgtac   45180
atcttacatt gacaataata ataggtaaaa ctctacaaat ttttatcta atggactctt     45240 gtatgaaaca ttgtacttgc acacatctga tgtaaacact gcatactttt aacagtgaca   45300
agattctgtt tcatttagg gctagtttgg gaaccaaatt ttattagggt ttttatttc      45360 taagaaaaag taatttattt taccttgaga aaatataaat tacttgagaa aatagagttc   45420
caaactagct cttatctttg tcgaatcctc ctctattcaa atgtgacatt tctggcacgt   45480
gacaactggt gatgttgtag actgtgttaa gtaatacgtg tcattattac taaatgccat   45540
tttagtaaat gttgagtatg tactctacta cagtaagtat tattggtgta tttacactag   45600
acagttggcg gcctggcggg taaagttatc ctgtagaaag ttgggccagg ccaaaaccaa   45660
ccgccaaagg aaaggccttc cggcccgccc acctttgcgc gccgaaggtc agttccttca   45720
gtctcctccc gcttcagact ctgaccacgt cgacaatccg ggccgaaaca catctgcacc   45780
```

```
gtccacttgc gacagattga acacaccact tctatccacg tcagcgatcc gtggcactag    45840
cccttccacc aatcagccca agttgcccct ttcctttaaa ttcgccgcac ccattgctct    45900
tctcacggcc atagaaatcg accgagcgaa tccctcgcat cgcattcgca gcctttgctg    45960
catcacacca ccgcgaaacc ccagcagccg catctgcagg tcgactctag aggatccatg    46020
gcctcctccg aggacgtcat caaggagttc atgcgcttca aggtgcgcat ggagggctcc    46080
gtgaacggcc acgagttcga gatcgagggc gagggcgagg ccgcccctca cgagggcacc    46140
cagaccgcca agctgaaggt gaccaagggc ggcccctgc ccttcgcctg ggacatcctg    46200 tcccccagt tccagtacgg ctccaaggtg tacgtgaagc accccgccga catccccgac    46260
tacaagaagc tgtccttccc cgagggcttc aagtgggagc gcgtgatgaa cttcgaggac    46320
ggcggcgtgg tgacagtgac ccaggactcc tccctgcagg acggctcctt catctacaag    46380
gtgaagttca tcggcgtgaa cttcccctcc gacggccccg taatgcagaa gaagactatg    46440
ggctgggagg cctccaccga gcgcctgtac cccgcgacg gcgtgctgaa gggcgagatc    46500
cacaaggccc tgaagctgaa ggacggcggc cacgctagca tctgatggtg acgtacgtgc    46560
cctactcgat ggggctaggg ataacagggt aatactgaag ctactcaaaa cgtcgtgaga    46620
cagtttgcgg aggatatata tacctcacac gtacgcgtag ttcgctagca agggcggccc    46680
cctgcccttc gcctgggaca tcctgtcccc ccagttccag tacggctcca aggtgtacgt    46740
gaagcacccc gccgacatcc ccgactacaa gaagctgtcc ttccccgagg gcttcaagtg    46800
ggagcgcgtg atgaacttcg aggacggcgg cgtggtgaca gtgacccagg actcctccct    46860
gcaggacggc tccttcatct acaaggtgaa gttcatcggc gtgaacttcc cctccgacgg    46920
ccccgtaatg cagaagaaga ctatgggctg ggaggcctcc accgagcgcc tgtaccccg    46980 cgacggcgtg ctgaagggcg agatccacaa ggccctgaag ctgaaggacg gcggccacta    47040
cctggtggag ttcaagtcca tctacatggc caagaagccc gtgcagctgc ccggctacta    47100
ctacgtggac tccaagctgg acatcacctc ccacaacgag gactcacca tcgtggagca    47160 gtacgagcgc gccgagggcc gccaccacct gttcctgtag tcaggatctg agtcgaaacc    47220
tagacttgtc catcttctgg attggccaac ttaattaatg tatgaaataa aaggatgcac    47280
acatagtgac atgctaatca ctataatgtg gcatcaaag ttgtgtgtta tgtgtaatta    47340
ctagttatct gaataaaaga gaaagagatc atccatattt cttatcctaa atgaatgtca    47400
cgtgtcttta taattctttg atgaaccaga tgcatttcat taaccaaatc catatacata    47460
taaatattaa tcatatataa ttaatatcaa ttgggttagc aaaacaaatc tagtctaggt    47520
gtgttttgcg aatgcggccg ccaccgcggt ggagctcgaa ttccggtccg ggtcacccgg    47580
tccgggccta gaaggccagc ttgcggccgc cccgggcaac tttattatac aaagttgata    47640
gatatcggtc cgagcggcct agaaggcctt tggtcacctt tgtccaccaa gatggaactg    47700
cggccgctca ttaattaagt caggcgcgcc tctagttgaa gacacgttca tgtcttcatc    47760
gtaagaagac actcagtagt cttcggccag aatggcctaa ctcaaggcca tcgtggcctc    47820
ttgctcttca ggatgaagag ctatgtttaa acgtgcaagc gctactagac aattcagtac    47880
attaaaaacg tccgcaatgt gttattaagt tgtctaagcg tcaatttgtt tacaccacaa    47940
tatatcctgc caccagccag ccaacagctc cccgaccggc agctcggcac aaaatcacca    48000
ctcgatacag gcagcccatc agtccgggac ggcgtcagcg ggagagccgt tgtaaggcgg    48060
cagactttgc tcatgttacc gatgctattc ggaagaacgg caactaagct gccgggtttg    48120
aaacacggat gatctcgcgg agggtagcat gttgattgta acgatgacag agcgttgctg    48180
```

```
cctgtgatca aatatcatct ccctcgcaga gatccgaatt atcagccttc ttattcattt    48240
ctcgcttaac cgtgacaggc tgtcgatctt gagaactatg ccgacataat aggaaatcgc    48300
tggataaagc cgctgaggaa gctgagtggc gctatttctt tagaagtgaa cgttgacgat    48360
cgtcgaccgt accccgatga attaattcgg acgtacgttc tgaacacagc tggatactta    48420
cttgggcgat tgtcatacat gacatcaaca atgtacccgt tgtgtaacc gtctcttgga     48480 ggttcgtatg acactagtgg ttcccctcag cttgcgacta gatgttgagg cctaacattt    48540
tattagagag caggctagtt gcttagatac atgatcttca ggccgttatc tgtcagggca    48600
agcgaaaatt ggccatttat gacgaccaat gccccgcaga agctcccatc tttgccgcca    48660
tagacgccgc gcccccttt tggggtgtag aacatccttt tgccagatgt ggaaaagaag      48720
ttcgttgtcc cattgttggc aatgacgtag tagccggcga aagtgcgaga cccatttgcg    48780
ctatatataa gcctacgatt tccgttgcga ctattgtcgt aattggatga actattatcg    48840
tagttgctct cagagttgtc gtaatttgat ggactattgt cgtaattgct tatggagttg    48900
tcgtagttgc ttggagaaat gtcgtagttg gatggggagt agtcataggg aagacgagct    48960
tcatccacta aaacaattgg caggtcagca agtgcctgcc ccgatgccat cgcaagtacg    49020
aggcttagaa ccaccttcaa cagatcgcgc atagtcttcc ccagctctct aacgcttgag    49080
ttaagccgcg ccgcgaagcg gcgtcggctt gaacgaattg ttagacatta tttgccgact    49140
accttggtga tctcgccttt cacgtagtga acaaattctt ccaactgatc tgcgcgcgag    49200
gccaagcgat cttcttgtcc aagataagcc tgcctagctt caagtatgac gggctgatac    49260
tgggccggca ggcgctccat tgcccagtcg gcagcgacat ccttcggcgc gattttgccg    49320
gttactgcgc tgtaccaaat gcgggacaac gtaagcacta catttcgctc atcgccagcc    49380
cagtcgggcg gcgagttcca tagcgttaag gtttcattta gcgcctcaaa tagatcctgt    49440
tcaggaaccg gatcaaagag ttcctccgcc gctggaccta ccaaggcaac gctatgttct    49500
cttgcttttg tcagcaagat agccagatca atgtcgatcg tggctggctc gaagatacct    49560
gcaagaatgt cattgcgctg ccattctcca aattgcagtt cgcgcttagc tggataacgc    49620
cacggaatga tgtcgtcgtg cacaacaatg gtgacttcta cagcgcggag aatctcgctc    49680
tctccagggg aagccgaagt ttccaaaagg tcgttgatca aagctcgccg cgttgtttca    49740
tcaagcctta cagtcaccgt aaccagcaaa tcaatatcac tgtgtggctt caggccgcca    49800
tccactgcgg agccgtacaa atgtacggcc agcaacgtcg gttcgagatg gcgctcgatg    49860
acgccaacta cctctgatag ttgagtcgat acttcggcga tcaccgcttc cctcatgatg    49920
tttaactcct gaattaagcc gcgccgcgaa gcggtgtcgg cttgaatgaa ttgttaggcg    49980
tcatcctgtg ctcccgagaa ccagtaccag tacatcgctg tttcgttcga gacttgaggt    50040
ctagttttat acgtgaacag gtcaatgccg ccgagagtaa agccacattt tgcgtacaaa    50100
ttgcaggcag gtacattgtt cgtttgtgtc tctaatcgta tgccaaggag ctgtctgctt    50160
agtgcccact ttttcgcaaa ttcgatgaga ctgtgcgcga ctcctttgcc tcggtgcgtg    50220
tgcgacacaa caatgtgttc gatagaggct agatcgttcc atgttgagtt gagttcaatc    50280
ttcccgacaa gctcttggtc gatgaatgcg ccatagcaag cagagtcttc atcagagtca    50340
tcatccgaga tgtaatcctt ccggtagggg ctcacacttc tggtagatag ttcaaagcct    50400
tggtcggata ggtgcacatc gaacacttca cgaacaatga aatggttctc agcatccaat    50460
gtttccgcca cctgctcagg gatcaccgaa atcttcatat gacgcctaac gcctggcaca    50520
```

```
gcggatcgca aacctggcgc ggcttttggc acaaaaggcg tgacaggttt gcgaatccgt    50580
tgctgccact tgttaaccct tttgccagat ttggtaacta taatttatgt tagaggcgaa    50640
gtcttgggta aaaactggcc taaaattgct ggggatttca ggaaagtaaa catcaccttc    50700
cggctcgatg tctattgtag atatatgtag tgtatctact tgatcggggg atctgctgcc    50760
tcgcgcgttt cggtgatgac ggtgaaaacc tctgacacat gcagctcccg gagacggtca    50820
cagcttgtct gtaagcggat gccgggagca gacaagcccg tcagggcgcg tcagcgggtg    50880
ttggcgggtg tcggggcgca gccatgaccc agtcacgtag cgatagcgga gtgtatactg    50940
gcttaactat gcggcatcag agcagattgt actgagagtg caccatatgc ggtgtgaaat    51000
accgcacaga tgcgtaagga gaaaataccg catcaggcgc tcttccgctt cctcgctcac    51060
tgactcgctg cgctcggtcg ttcggctgcg cgagcggta tcagctcact caaaggcggt    51120
aatacggtta tccacagaat caggggataa cgcaggaaag aacatgtgag caaaaggcca    51180
gcaaaaggcc aggaaccgta aaaaggccgc gttgctggcg ttttttccata ggctccgccc    51240 ccctgacgag catcacaaaa atcgacgctc aagtcagagg tggcgaaacc cgacaggact    51300
ataaagatac caggcgtttc ccctggaag ctccctcgtg cgctctcctg ttccgaccct    51360
gccgcttacc ggatacctgt ccgcctttct cccttcggga agcgtggcgc tttctcatag    51420
ctcacgctgt aggtatctca gttcggtgta ggtcgttcgc tccaagctgg gctgtgtgca    51480 cgaaccccc gttcagcccg accgctgcgc cttatccggt aactatcgtc ttgagtccaa    51540
cccggtaaga cacgacttat cgccactggc agcagccact ggtaacagga ttagcagagc    51600
gaggtatgta ggcggtgcta cagagttctt gaagtggtgg cctaactacg gctacactag    51660
aaggacagta tttggtatct gcgctctgct gaagccagtt accttcggaa aaagagttgg    51720
tagctcttga tccggcaaac aaaccaccgc tggtagcggt ggtttttttg tttgcaagca    51780
gcagattacg cgcagaaaaa aaggatctca agaagatcct ttgatctttt ctacggggtc    51840
tgacgctcag tggaacgaaa actcacgtta agggattttg gtcatgagat tatcaaaaag    51900
gatcttcacc tagatccttt taaattaaaa atgaagtttt aaatcaatct aaagtatata    51960
tgagtaaact tggtctgaca gttaccaatg cttaatcagt gaggcaccta tctcagcgat    52020
ctgtctattt cgttcatcca tagttgcctg actccccgtc gtgtagataa ctacgatacg    52080
ggagggctta ccatctggcc ccagtgctgc aatgataccg cgagacccac gctcaccggc    52140
tccagattta tcagcaataa accagccagc cggaagggcc gagcgcagaa gtggtcctgc    52200
aactttatcc gcctccatcc agtctattaa ttgttgccgg gaagctagag taagtagttc    52260
gccagttaat agtttgcgca acgttgttgc cattgctgca                         52300

<210> SEQ ID NO 62
<211> LENGTH: 152
<212> TYPE: DNA
<213> ORGANISM: Sorghum bicolor

<400> SEQUENCE: 62
gacgcaggac cccaagggga tcctggagga cgacgtgctg ccggacggga cgaaggtgag     60
ggccggcggg atggtgacgt acgtgcccta ctcgatgggg cggatggagt acaactgggg    120
acccgacgcg gcgagcttcc ggccggagcg gt                                  152

<210> SEQ ID NO 63
<211> LENGTH: 150
<212> TYPE: DNA
<213> ORGANISM: artificial sequence
```

<220> FEATURE:
<223> OTHER INFORMATION: Modification at sorghum MS26 target site
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (145)..(147)
<223> OTHER INFORMATION: n is a, c, g, or t

<400> SEQUENCE: 63
gacgcaggac cccaagggga tcctggagga cgacgtgctg ccggacggga cgaaggtgag        60
ggccggcggg atggtgtacg tgccctactc natggggcgg atggagtaca actggggacc       120
cnacgcggcg agcttccggc cggannngtg                                        150

<210> SEQ ID NO 64
<211> LENGTH: 149
<212> TYPE: DNA
<213> ORGANISM: artificial sequence
<220> FEATURE:
<223> OTHER INFORMATION: Modification at sorghum MS26 target site
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t

<400> SEQUENCE: 64
gacgcaggac cccaagggga tcctggagga cgacgtgctg ccggacggga cgaaggtgag        60
ggccggcggg atggtgacgt gccctactcn atgggsgga tggagtacaa ctggggaccc       120
aacncggcga gcttccggcc ggagcggtg                                         149

<210> SEQ ID NO 65
<211> LENGTH: 134
<212> TYPE: DNA
<213> ORGANISM: artificial sequence
<220> FEATURE:
<223> OTHER INFORMATION: Modification at sorghum MS26 target site
<220> FEATURE:
<221> NAME/KEY: misc_feature
<222> LOCATION: (90)..(90)
<223> OTHER INFORMATION: n is a, c, g, or t

<400> SEQUENCE: 65
gacgcaggac cccaagggga tcctggagga cgacgtgctg ccggacggga cgaaggtgag        60
ggccggcggg atggtgacgt ccctactcn atgggcgga tggagtacaa ctggggaccc       120
aacgcggcga gctt                                                         134

<210> SEQ ID NO 66
<211> LENGTH: 144
<212> TYPE: DNA
<213> ORGANISM: artificial sequence
<220> FEATURE:
<223> OTHER INFORMATION: Modification at sorghum MS26 target site
<220> FEATURE:
<221> NAME/KEY: misc_feature
<222> LOCATION: (116)..(116)
<223> OTHER INFORMATION: n is a, c, g, or t

```
<400> SEQUENCE: 66
gacgcaggac cccaagggga tcctggagga cgacgtgctg ccggacggga cgaaggtgag      60
ggccggcggg atggtgacgt actcgatggg gcggatggag tacaactggg gacccnacgc    120
ggcgagcttc cggccggagc ggtg                                           144

<210> SEQ ID NO 67
<211> LENGTH: 138
<212> TYPE: DNA
<213> ORGANISM: artificial sequence
<220> FEATURE:
<223> OTHER INFORMATION: Modification at sorghum MS26 target site
<220> FEATURE:
<221> NAME/KEY: misc_feature
<222> LOCATION: (110)..(110)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t

<400> SEQUENCE: 67
gacgcaggac cccaagggga tcctggagga cgacgtgctg ccggacggga cgaaggtgag      60
ggccgacgtg ccctactcga tggggcggat ggagtacaac tggggacccn acgcggcgag    120
cttccngccg gagcggtg                                                  138

<210> SEQ ID NO 68
<211> LENGTH: 137
<212> TYPE: DNA
<213> ORGANISM: artificial sequence
<220> FEATURE:
<223> OTHER INFORMATION: Modification at sorghum MS26 target site

<400> SEQUENCE: 68
gacgcaggac cccaagggga tcctggagga cgacgtgctg ccggacggga cgaaggtgag      60
ggccggcggg atggtgacgt ggggcggatg gagtacaact ggggacccga cgcggcgagc    120
ttccggccgg agcggtg                                                   137

<210> SEQ ID NO 69
<211> LENGTH: 135
<212> TYPE: DNA
<213> ORGANISM: artificial sequence
<220> FEATURE:
<223> OTHER INFORMATION: Modification at sorghum MS26 target site
<220> FEATURE:
<221> NAME/KEY: misc_feature
<222> LOCATION: (96)..(96)
<223> OTHER INFORMATION: n is a, c, g, or t

<400> SEQUENCE: 69
gacgcaggac cccaagggga tcctggagga cgacgtgctg ccggacggga cgaaggtgag      60
ggccggcggg tactcgatgg ggcggatgga gtacanctgg ggacccgacg cggcgagctt    120
ccggccggag cggtg                                                     135

<210> SEQ ID NO 70
<211> LENGTH: 121
<212> TYPE: DNA
<213> ORGANISM: artificial sequence
<220> FEATURE:
<223> OTHER INFORMATION: Modification at sorghum MS26 target site
<220> FEATURE:
<221> NAME/KEY: misc_feature
<222> LOCATION: (86)..(86)
<223> OTHER INFORMATION: n is a, c, g, or t
```

```
<220> FEATURE:
<221> NAME/KEY: misc_feature
<222> LOCATION: (105)..(105)
<223> OTHER INFORMATION: n is a, c, g, or t

<400> SEQUENCE: 70
gacgcaggac cccaagggga tcctggagga cgacgtgctg ccggacggga cgaaggtgag      60
ggccggcggg atggtgacgg atggantaca actggggacc cgacncggcg agcttccggc    120
c                                                                    121

<210> SEQ ID NO 71
<211> LENGTH: 95
<212> TYPE: DNA
<213> ORGANISM: artificial sequence
<220> FEATURE:
<223> OTHER INFORMATION: Modification at sorghum MS26 target site

<400> SEQUENCE: 71
gacgcaggac cccaagggga tcctggagga cgacgtgctg ccggacggga cgaaggtgag      60
ggccgtctcg atggggcgga tggagtacaa ctggg                                 95

<210> SEQ ID NO 72
<211> LENGTH: 120
<212> TYPE: DNA
<213> ORGANISM: artificial sequence
<220> FEATURE:
<223> OTHER INFORMATION: Modification at sorghum MS26 target site

<400> SEQUENCE: 72
gacgcaggac cccaagggga tcctggagga cgacgtgctg ccggacggga cgaaggtgag      60
ggccggcggg atggagtaca actggggacc cgacgcggcg agcttccggc cggagcggtg    120

<210> SEQ ID NO 73
<211> LENGTH: 117
<212> TYPE: DNA
<213> ORGANISM: artificial sequence
<220> FEATURE:
<223> OTHER INFORMATION: Modification at sorghum MS26 target site
<220> FEATURE:
<221> NAME/KEY: misc_feature
<222> LOCATION: (104)..(105)
<223> OTHER INFORMATION: n is a, c, g, or t

<400> SEQUENCE: 73
gacgcaggac cccaagggga tcctggagga cgacgtgctg ccggacggga cgaaggtgag      60
ggggcggatg gagtacaact ggggacccga cgcggcgagc ttcnngccgg agcggtg       117

<210> SEQ ID NO 74
<211> LENGTH: 105
<212> TYPE: DNA
<213> ORGANISM: artificial sequence
<220> FEATURE:
<223> OTHER INFORMATION: Modification at sorghum MS26 target site
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t

<400> SEQUENCE: 74
gacgcaggac cccaagggga tcctggagga cgacgtgccc tactcnatgg ggcngatgga      60
```

```
gtacaactgg ggacccgacg cggcgagctt ccggccggag cggtg              105
```

```
<210> SEQ ID NO 75
<211> LENGTH: 95
<212> TYPE: DNA
<213> ORGANISM: artificial sequence
<220> FEATURE:
<223> OTHER INFORMATION: Modification at sorghum MS26 target site
<220> FEATURE:
<221> NAME/KEY: misc_feature
<222> LOCATION: (80)..(80)
<223> OTHER INFORMATION: n is a, c, g, or t

<400> SEQUENCE: 75
gacgcaggac cccaagggga tcctggagga cgacgtgctg ccggacggga cgaaggtgag    60
ggccggcggg atcctggaan ctcgccggag cggtg                               95
```

```
<210> SEQ ID NO 76
<211> LENGTH: 92
<212> TYPE: DNA
<213> ORGANISM: artificial sequence
<220> FEATURE:
<223> OTHER INFORMATION: Modification at sorghum MS26 target site
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t

<400> SEQUENCE: 76
gacgcaggac cccaagggga tccgccctac tcnatgggc ggatggagta caactgggga     60
cccnacgcgg cgagcttccg gccggagcgg tg                                  92
```

```
<210> SEQ ID NO 77
<211> LENGTH: 74
<212> TYPE: DNA
<213> ORGANISM: artificial sequence
<220> FEATURE:
<223> OTHER INFORMATION: Modification at sorghum MS26 target site
<220> FEATURE:
<221> NAME/KEY: misc_feature
<222> LOCATION: (15)..(15)
<223> OTHER INFORMATION: n is a, c, g, or t

<400> SEQUENCE: 77
gacgtgccct actcnatggg gcggatggag tacaactggg gacccgacgc ggcgagcttc    60
cggccggagc ggtg                                                      74
```

```
<210> SEQ ID NO 78
<211> LENGTH: 55
<212> TYPE: DNA
<213> ORGANISM: artificial sequence
<220> FEATURE:
<223> OTHER INFORMATION: Modification at sorghum MS26 target site

<400> SEQUENCE: 78
gacgcaggac cccaagggga tcctggagga cgacgtgctg ccggacggga cggtg         55
```

METHODS AND COMPOSITIONS FOR PRODUCING MALE STERILE PLANTS

CROSS-REFERENCE TO RELATED APPLICATIONS

This application claims the benefit of U.S. Provisional Application 61/499,441, filed Jun. 21, 2011, herein incorporated by reference in its entirety.

FIELD OF INVENTION

The invention relates to the field of plant molecular biology, particularly to methods for making targeted mutations in male fertility genes in plants.

REFERENCE TO SEQUENCE LISTING SUBMITTED

The Sequence Listing submitted Sep. 26, 2013 as a text file named "36446_0003U2_BB1992_US_NP_Updated_Sequence_Listing.txt," created on Sep. 25, 2013, and having a size of 336,076 bytes is hereby incorporated by reference pursuant to 37 C.F.R. §1.52(e)(5).

BACKGROUND

Development of hybrid plant breeding has made possible considerable advances in quality and quantity of crops produced. Increased yield and combination of desirable characteristics, such as resistance to disease and insects, heat and drought tolerance, along with variations in plant composition are all possible because of hybridization procedures. These procedures frequently rely heavily on providing for a male parent contributing pollen to a female parent to produce the resulting hybrid.

Field crops are bred through techniques that take advantage of the plant's method of pollination. A plant is self-pollinating if pollen from one flower is transferred to the same or another flower of the same plant or a genetically identical plant. A plant is cross-pollinated if the pollen comes from a flower on a different plant.

In certain species, such as *Brassica campestris*, the plant is normally self-sterile and can only be cross-pollinated. In self-pollinating species, such as soybeans and cotton, the male and female plants are anatomically juxtaposed. During natural pollination, the male reproductive organs of a given flower pollinate the female reproductive organs of the same flower.

Maize plants (*Zea mays* L.) can be bred by both self-pollination and cross-pollination techniques. Maize has male flowers, located on the tassel, and female flowers, located on the ear, on the same plant. It can self or cross pollinate. Natural pollination occurs in maize when wind blows pollen from the tassels to the silks that protrude from the tops of the incipient ears.

The development of maize hybrids requires the development of homozygous inbred lines, the crossing of these lines, and the evaluation of the crosses. Pedigree breeding and recurrent selection are two of the breeding methods used to develop inbred lines from populations. Breeding programs combine desirable traits from two or more inbred lines or various broad-based sources into breeding pools from which new inbred lines are developed by selfing and selection of desired phenotypes. A hybrid maize variety is the cross of two such inbred lines, each of which may have one or more desirable characteristics lacked by the other or which complement the other. The new inbreds are crossed with other inbred lines and the hybrids from these crosses are evaluated to determine which have commercial potential. The hybrid progeny of the first generation is designated $F_1$. In the development of hybrids only the $F_1$ hybrid plants are sought. The $F_1$ hybrid is more vigorous than its inbred parents. This hybrid vigor, or heterosis, can be manifested in many ways, including increased vegetative growth and increased yield.

Hybrid maize seed can be produced by a male sterility system incorporating manual detasseling. To produce hybrid seed, the male tassel is removed from the growing female inbred parent, which can be planted in various alternating row patterns with the male inbred parent. Consequently, providing that there is sufficient isolation from sources of foreign maize pollen, the ears of the female inbred will be fertilized only with pollen from the male inbred. The resulting seed is therefore hybrid ($F_1$) and will form hybrid plants.

Field variation impacting plant development can result in plants tasseling after manual detasseling of the female parent is completed. Or, a female inbred plant tassel may not be completely removed during the detasseling process. In any event, the result is that the female plant will successfully shed pollen and some female plants will be self-pollinated. This will result in seed of the female inbred being harvested along with the hybrid seed which is normally produced. Female inbred seed does not exhibit heterosis and therefore is not as productive as $F_1$ seed. In addition, the presence of female inbred seed can represent a germplasm security risk for the company producing the hybrid.

Alternatively, the female inbred can be mechanically detasseled by machine. Mechanical detasseling is approximately as reliable as hand detasseling, but is faster and less costly. However, most detasseling machines produce more damage to the plants than hand detasseling. Thus, no form of detasseling is presently entirely satisfactory, and a need continues to exist for alternatives which further reduce production costs and to eliminate self-pollination of the female parent in the production of hybrid seed.

Mutations that cause male sterility in plants have the potential to be useful in methods for hybrid seed production for crop plants such as maize and can lower production costs by eliminating the need for the labor-intensive removal of male flowers (also known as de-tasseling) from the maternal parent plants used to produce the hybrid seed. Mutations that cause male sterility in maize have been produced by a variety of methods such as X-rays or UV-irradiations, chemical treatments, or transposable element insertions (ms23, ms25, ms26, ms32) (Chaubal et al. (2000) *Am J Bot* 87:1193-1201). Conditional regulation of fertility genes through fertility/sterility "molecular switches" could enhance the options for designing new male-sterility systems for crop improvement (Unger et al. (2002) *Transgenic Res* 11:455-465).

Besides identification of novel genes impacting male fertility, there remains a need to provide a reliable system of producing genetic male sterility.

BRIEF SUMMARY OF THE INVENTION

The present invention provides methods for making a targeted modification in a male fertility gene in the genome of a plant. The methods involve contacting at least one plant cell comprising a target sequence in a male fertility gene with an engineered double-strand-break-inducing agent that is capable of inducing a double-strand break at the target sequence. The methods further involve identifying at least one cell comprising an alteration in its genome at the target sequence. If desired, the methods can further comprise regenerating a fertile plant comprising the alteration. The alterations include, but are not limited to, the replacement of at least one nucleotide in the target sequence, the deletion of at least one nucleotide in the target sequence, the insertion of at least one nucleotide in the target sequence or any combination thereof. For example, the alteration can be the insertion of a transgene in the target sequence of the male fertility gene or a null mutation, wherein a progeny plant that is homozygous for the null mutation is male sterile. In an embodiment of the invention, the insertion of a transgene in the target sequence of the male fertility gene is a null mutation in the male fertility gene.

In a first embodiment of methods for making a targeted modification in a male fertility gene in the genome of a plant, the male fertility gene is selected from the group consisting of MS26, MS45, BS92-7, 5126 and Msca1.

In a second embodiment, the methods further comprise regenerating a plant, particularly a fertile plant, comprising the alteration.

In a third embodiment, the engineered double-strand-break-inducing agent is an endonuclease, a zinc finger nuclease, a TAL effector nuclease, a transposase, or a site-specific recombinase. Preferably, the endonuclease is modified to specifically cut at the target sequence and no longer cuts at its wild-type endonuclease target sequence.

In a fourth embodiment, the methods further comprise selfing the fertile plant and selecting a progeny plant resulting therefrom, wherein said progeny plant is homozygous for the alteration.

In a fifth embodiment, the methods further comprise crossing the fertile plant with a second fertile plant comprising a null mutation in the male fertility gene and selecting a progeny plant resulting therefrom, wherein said progeny plant is male sterile.

In a sixth embodiment, the alteration comprises insertion of a transgene comprising a polynucleotide of interest. The transgene can further comprise a promoter operably linked to the polynucleotide of interest, wherein the promoter is capable of driving the expression of the polynucleotide of interest in a plant. For example, the polynucleotide of interest can encode a phenotypic marker or an RNA or protein providing an agronomic advantage to the plant.

In a seventh embodiment, the plant is selected from the group consisting of maize, sorghum, rice, wheat, rye, barley, millet, and oat.

In an eighth embodiment, the male fertility gene is MS26. For example, the target sequence for this embodiment can comprise the nucleotide sequence set forth in SEQ ID NO: 1. The engineered double-strand-break-inducing agent can, for example, be derived from I-CreI.

In a ninth embodiment, the step of contacting at least one plant cell comprising a target sequence in MS26 with the engineered double-strand-break-inducing agent comprises introducing into the at least one plant cell a nucleic acid construct comprising a nucleotide sequence encoding the engineered double-strand-break-inducing agent. The nucleotide sequence can be selected, for example, from the group consisting of the nucleotide sequences set forth in SEQ ID NO: 4, 5, 6, and 7; and a nucleotide sequence having at least 80% nucleotide sequence identity to at least one nucleotide sequence selected from the group consisting of the nucleotide sequences set forth in SEQ ID NOS: 4, 5, 6, and 7, wherein the nucleotide sequence encodes a polypeptide comprising endonuclease activity. If desired, the nucleic acid construct can further comprise a promoter operably linked to the nucleotide sequence encoding the engineered double-strand-break-inducing agent, wherein the promoter is capable of driving expression of the nucleotide sequence in a plant cell. For example, the promoter can be a maize ubiquitin promoter. Additionally, the nucleic acid construct can further comprise an operably linked coding sequence for a nuclear localization signal. Such nuclear localization signals can comprise, for example, an amino acid sequence selected from the group consisting of SEQ ID NOS: 2, 3, and 21.

In a tenth embodiment, the male fertility gene is MS45. For example, the target sequence for this embodiment can comprise the nucleotide sequence set forth in SEQ ID NO: 20. The engineered double-strand-break-inducing agent can, for example, be derived from I-CreI.

In an eleventh embodiment, the step of contacting at least one plant cell comprising a target sequence in MS45 with the engineered double-strand-break-inducing agent comprises introducing into the at least one plant cell a nucleic acid construct comprising a nucleotide sequence encoding the engineered double-strand-break-inducing agent. The nucleotide sequence can be selected, for example, from the group consisting of the nucleotide sequence set forth in SEQ ID NO: 22, 23, or 34; and a nucleotide sequence having at least 80% nucleotide sequence identity to at least one nucleotide sequence selected from the group consisting of the nucleotide sequences set forth in SEQ ID NOS: 22, 23, or 34, wherein the nucleotide sequence encodes a polypeptide comprising endonuclease activity. If desired, the nucleic acid construct can further comprise a promoter operably linked to the nucleotide sequence encoding the engineered double-strand-break-inducing agent, wherein the promoter is capable of driving expression of the nucleotide sequence in a plant cell. For example, the promoter can be a maize ubiquitin promoter. Additionally, the nucleic acid construct can further comprise an operably linked coding sequence for a nuclear localization signal. Such nuclear localization signals can comprise, for example, an amino acid sequence selected from the group consisting of SEQ ID NOS: 2, 3, and 21.

The present invention further provides isolated nucleic acid molecules comprising at least one male fertility gene with a targeted modification or alteration and plants, plant parts, plant cells, and seeds comprising at least one male fertility gene with a targeted modification or alteration. The plants of invention include, but are not limited to, a plant produced by any of the methods disclosed herein and a descendant of any plant produced by any of such methods, wherein the descendant comprises the alteration.

In one embodiment, the plant comprises a targeted modification in a male fertility gene in its genome, wherein the targeted modification is the insertion of a transgene, and wherein the male fertility gene is selected from the group consisting of MS26, MS45, BS92-7, 5126 and Msca1. For example, the insertion of a transgene can cause a null mutation in the male fertility gene, and a plant that is homozygous for the alteration is male sterile.

In another embodiment, the plant is selected from the group consisting of maize, sorghum, rice, wheat, rye, barley, millet, and oat.

In a further embodiment, the plant is a sorghum plant comprising a targeted modification in the male fertility gene MS26, wherein the MS26 gene comprises a nucleotide sequence selected from the group consisting of SEQ ID NOs: 63, 64, 65, 66, 67, 68, 69, 70, 71, 72, 73, 74, 75, 76, 77 and 78.

Additionally provided are isolated nucleic acid molecules encoding engineered double-strand-break-inducing agents that are capable of inducing a double-strand break in DNA comprising a target sequence of the invention. Expression cassettes comprising at least one isolated nucleic acid molecule encoding an engineered double-strand-break-inducing agent, and host cells, and plants comprising at least one of the expression cassettes are further provided.

In one embodiment of the invention, the expression cassettes comprise a promoter operably linked to a nucleotide sequence selected from the group consisting of SEQ ID NOS: 4, 5, 6, 7, 22, 23, and 34.

In another embodiment, the present invention provides a plant comprising an expression construct, which comprises a promoter operably linked to a nucleotide sequence encoding an endonuclease. The endonuclease is capable of specifically binding to and creating a double strand break in a target sequence selected from the group consisting of SEQ ID NOS: 1 and 20, wherein the promoter is capable of driving expression of an operably linked nucleotide sequence in a plant cell. The nucleotide sequence encoding the endonuclease can comprise a coding sequence of a DNA binding domain of an endonuclease, wherein the coding sequence is selected from the group consisting of:
  (a) nucleotides 100-261 and nucleotides 661-822 of SEQ ID NO: 4;
  (b) nucleotides 70-231 and nucleotides 631-792 of SEQ ID NO: 5;
  (c) nucleotides 70-231 and nucleotides 820-981 of SEQ ID NO: 6, 7 or 34; and
  (d) a degenerate coding sequence of (a), (b), or (c).

Preferably, the nucleotide sequence encoding the endonuclease is a nucleotide sequence selected from the group consisting of SEQ ID NOS: 4, 5, 6, 7, 22, 23, and 34.

BRIEF DESCRIPTION OF THE DRAWINGS AND THE SEQUENCE LISTING

The invention can be more fully understood from the following detailed description and the accompanying drawings and Sequence Listing, which form a part of this application. The sequence descriptions and sequence listing attached hereto comply with the rules governing nucleotide and amino acid sequence disclosures in patent applications as set forth in 37 C.F.R. §§1.821-1.825. The sequence descriptions contain the three letter codes for amino acids as defined in 37 C.F.R. §§1.821-1.825, which are incorporated herein by reference.

Figures

FIG. 1. DNA double-strand-break-induced DNA alteration of an endogenous target site. (A) A generalized endogenous target site with flanking genomic DNA sequences designated as DNA 1 and DNA 2 which can be used as DNA exchange regions by homologous recombination. (B) A generalized DNA construct that can be used to express a DNA endonuclease (nuclease gene) to recognize and cleave the endogenous target site. The DNA endonuclease gene can be physically linked to the donor DNA described in (C) or (D), or substituted by other double-strand-break-inducing agents. (C) A generalized donor DNA construct having two regions DNA1 and DNA 2 of homology to the genomic target, which flank a polynucleotide of interest and/or marker gene. (D) A generalized donor DNA construct that does not have regions of homology to the genomic target to flank a polynucleotide of interest and/or marker gene. Insertion of the DNA fragment will produce an insertion of the polynucleotide of interest at or near the recognition site. (E) One expected outcome when the polynucleotide of interest and/or marker gene of donor construct described in (C) or (D) is inserted at the endogenous target site by homologous recombination or non-homologous recombination, respectively. (F) Another outcome when the endogenous target site is altered by a deletion during the repair of the DNA double-strand break generated by the DNA endonuclease. The polynucleotide of interest and/or marker gene of donor construct described in (C) or (D) can be inserted at unrelated sites by random DNA integration. (G) Another outcome when the endogenous target site is altered by the insertion of an unrelated DNA during the repair of the DNA double-strand breaks cleaved by the DNA endonuclease. The polynucleotide of interest and/or marker gene of donor construct described in (C) or (D) can be inserted at unrelated sites by random DNA integration.

FIG. 2. Mutated alleles of the maize TS-MS26 target site. The mutated alleles found in the first generation maize transformants (T0 plants) were centered on the apparent 3' end GTAC overhang produced by the engineered MS26 endonuclease. Wild type (SEQ ID NO: 35), 3281 (SEQ ID NO: 36), 2963 (SEQ ID NO: 37), 2980 (SEQ ID NO: 38), 3861 (SEQ ID NO: 39), 3956 (SEQ ID NO: 40), 3990 (SEQ ID NO: 41), 6227 (SEQ ID NO: 42).

FIG. 3. Sequence homology across the TS-MS26 target site (MS26 TS, SEQ ID NO:1) between genomic regions of MS26 genes from maize (maize MS26, SEQ ID NO:13), rice (rice MS26, SEQ ID NO:14), sorghum (sorghum MS26, SEQ ID NO:15), and rye (rye MS26, SEQ ID NO:16).

Figure 4:
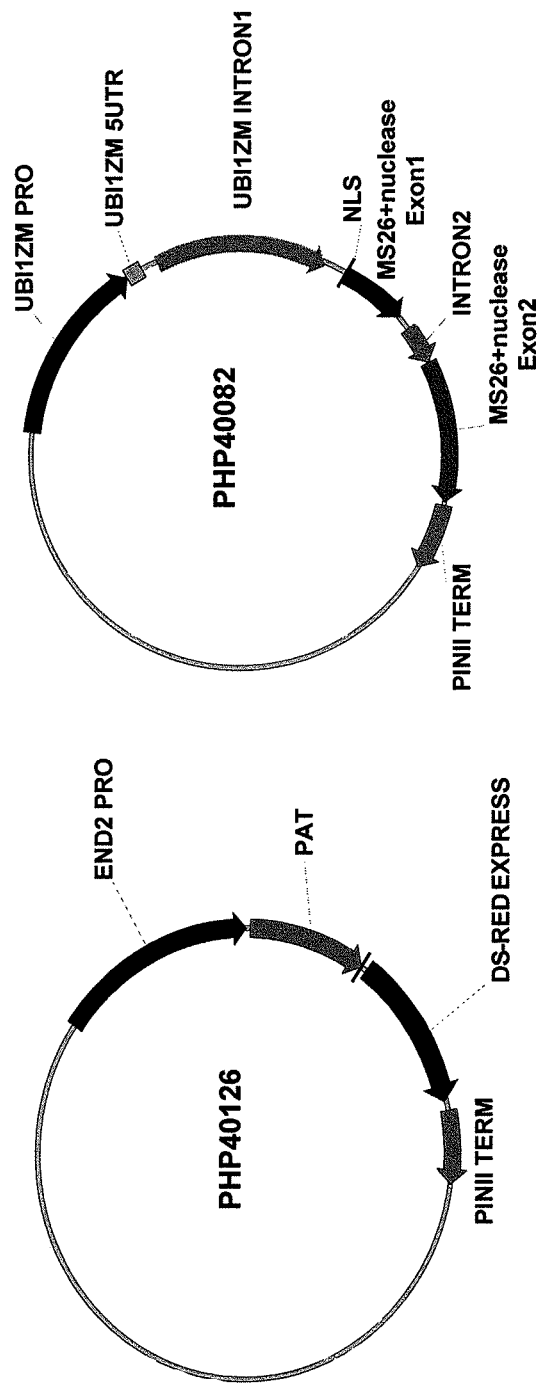

FIG. 4. Vectors for the biolistic transformation of rice.

Figure 5:
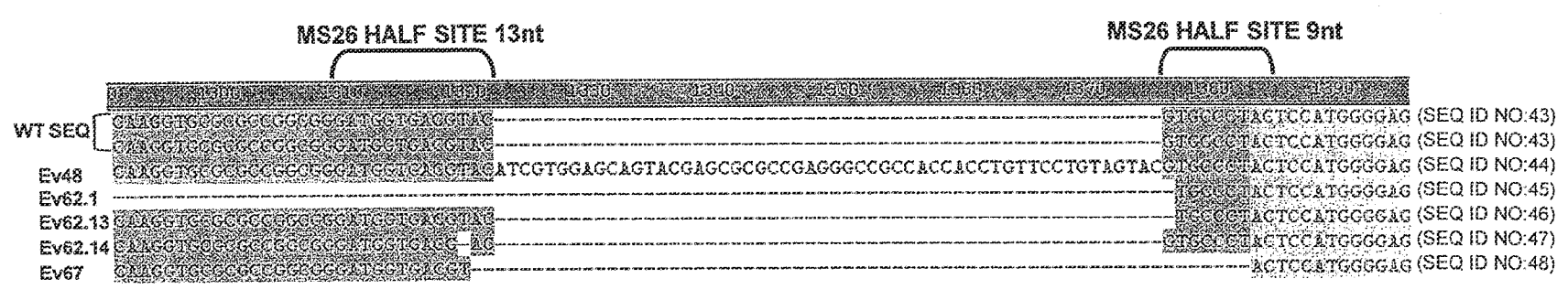

FIG. 5. Mutations at the rice MS26 gene introduced by biolistic transformation. Eva48 contains an insertion of 54 bp RFP. Ev62.1 contains a 200 bp deletion. Ev62.13 contains a 1 bp deletion. Ev62.14 contains a 1 bp deletion. Ev67 contains a 10 bp deletion.

Figure 6:
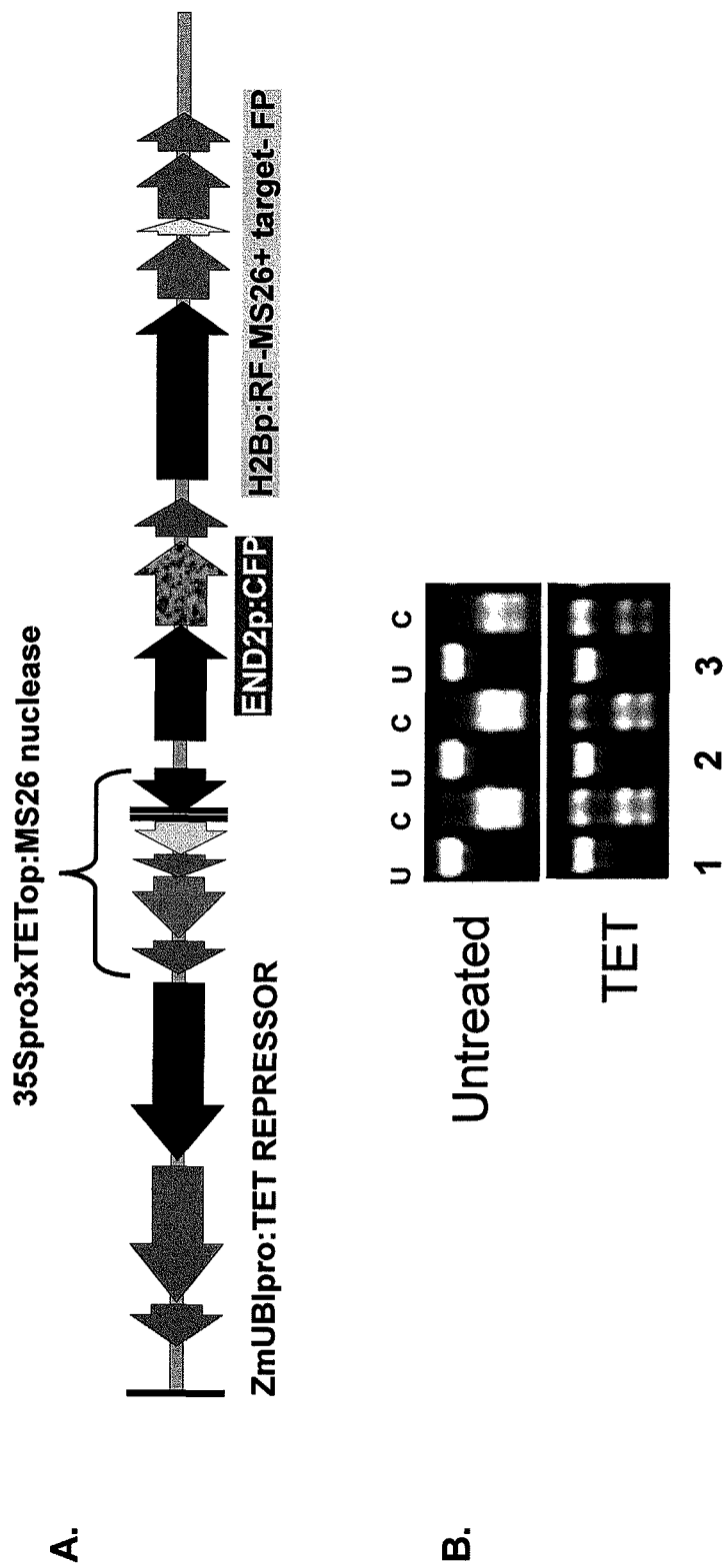

FIG. 6. A) Plasmid fragment of PHP40827 used for rice transformation. This plasmid contains a tetracycline repressor under the control of the maize Ubiquitin promoter, and a blue-fluorescence gene (CFP) regulated by the ZmEND2 promoter. In addition, this plasmid fragment contains a copy of a red fluorescence gene regulated by the maize Histone 2B promoter. A portion of the red fluorescence gene in this construct was duplicated in a direct orientation, consisting of two fragments of the RFP gene with 369 bp of overlap. The two fragments are separated by a 136-bp spacer which contains the TS-MS26 target site (FIG. 6A). B) PCR analysis for mutations at the TS-MS26 target site of TET treated events (1, 2, 3) compared to the PCR products of these same events not exposed to tetracycline (control).

FIG. 7. Mutations at the rice MS26 gene identified in PHP40827 callus events. Highlighted in gray is the wild-type TS-MS26 from rice. Wild-type rice MS26 (SEQ ID NO: 49), ms26.1 (SEQ ID NO: 50), ms26.2 (SEQ ID NO: 51), ms26.3 (SEQ ID NO: 52), ms26.4 (SEQ ID NO: 53), ms26.5 (SEQ ID NO 54), ms26.6 (SEQ ID NO: 55), ms26.7 (SEQ ID NO: 56), ms26.8 (SEQ ID NO: 57)

Figure 8:
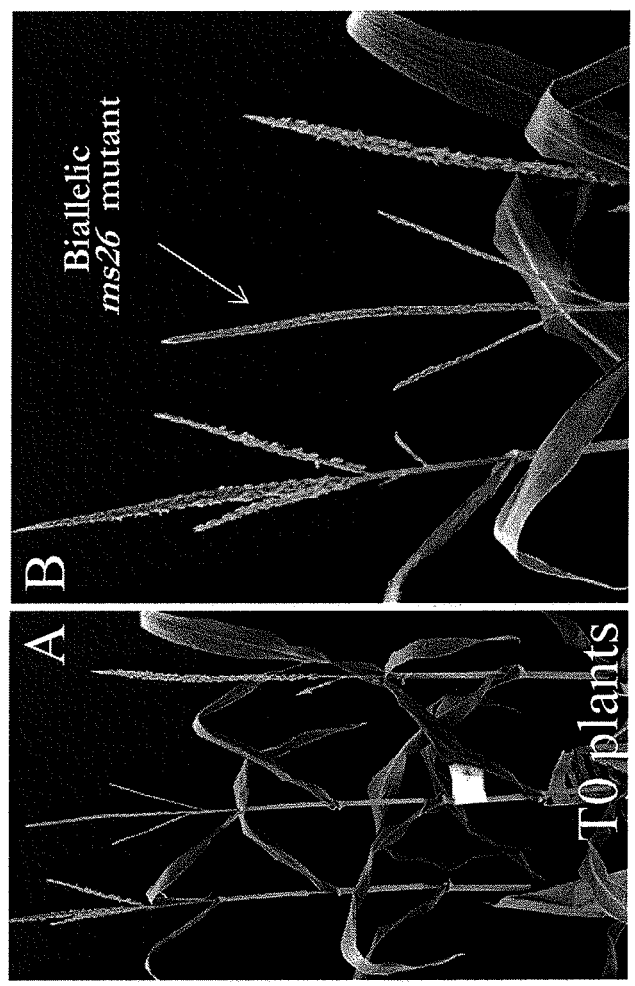

FIG. 8. Maize T0 plants at time of flowering. There was no obvious difference in the growth and development of T0 plants containing one mutated ms26 allele (two outside plants) as compared to the T0 biallelic event (the tagged plant) produced by the engineered MS26++ endonuclease (A). The biallelic event was sterile (the tassel at anthesis shown between two tassels from monoallelic events) (B).

Figure 9:
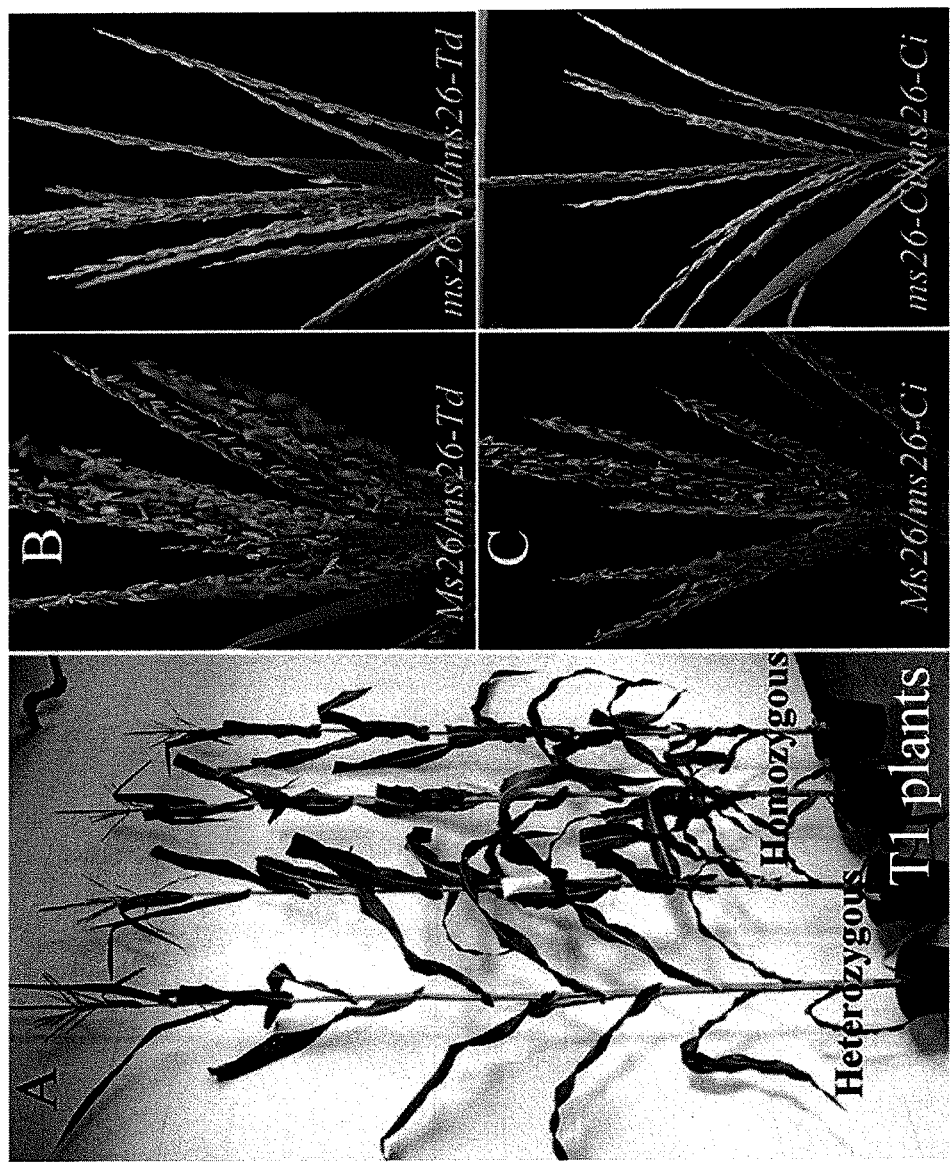

FIG. 9. Maize T1 progeny (A, B, C) plants at time of flowering. T1 progeny plants heterozygous for the ms26-Td or ms26-Ci mutant alleles (two plants at the left side) and two homozygous, sterile T1 plants at the right side are shown (A). There were no pleiotropic effects of the ms26 gene mutations on the growth and development of T1 progeny plants. Both mutant alleles (ms26-Td and ms26-Ci) produced a sterile phenotype only when in homozygous state in the T1 progeny plants (B and C).

Figure 10:
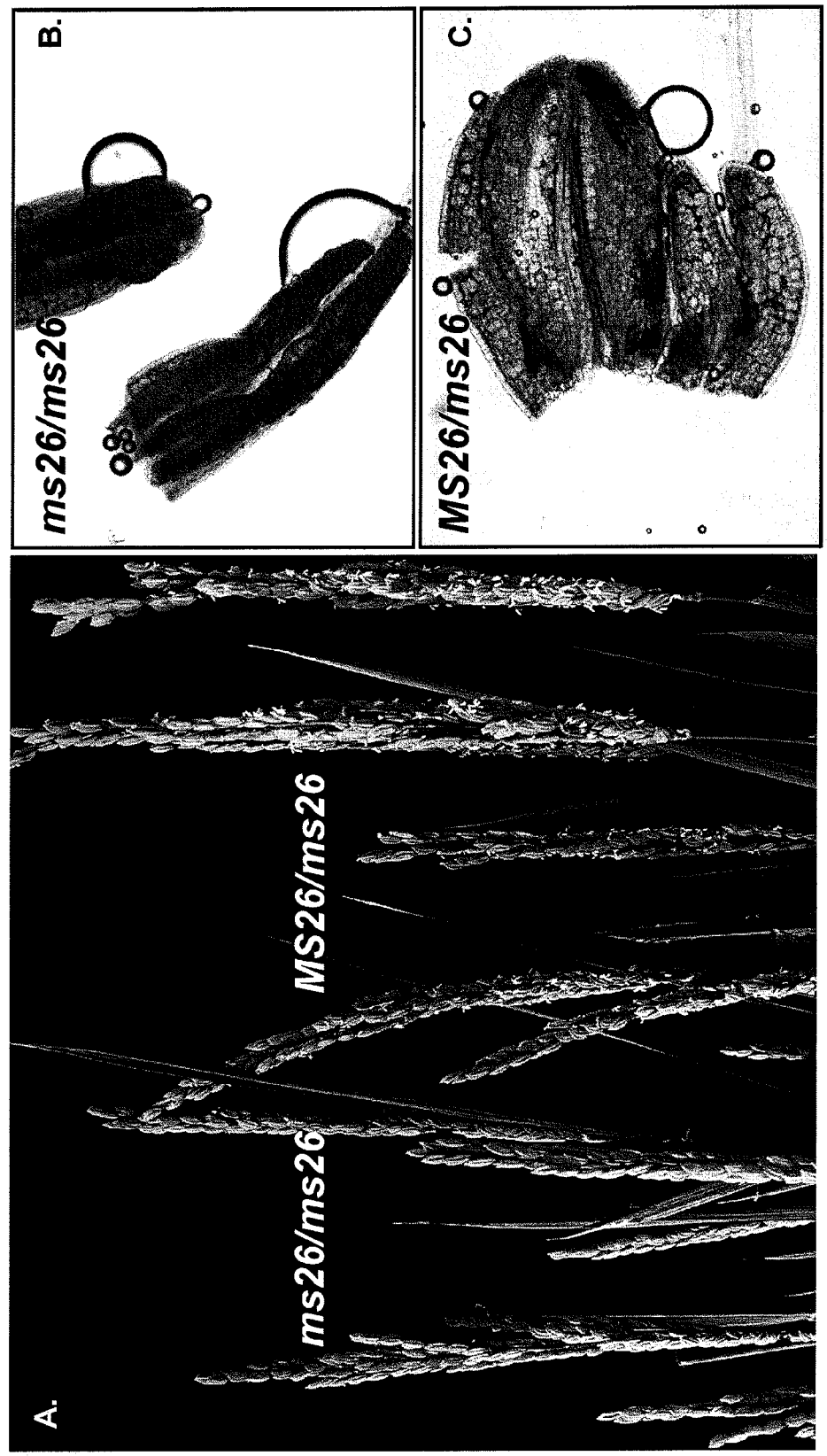
Figure 11E:
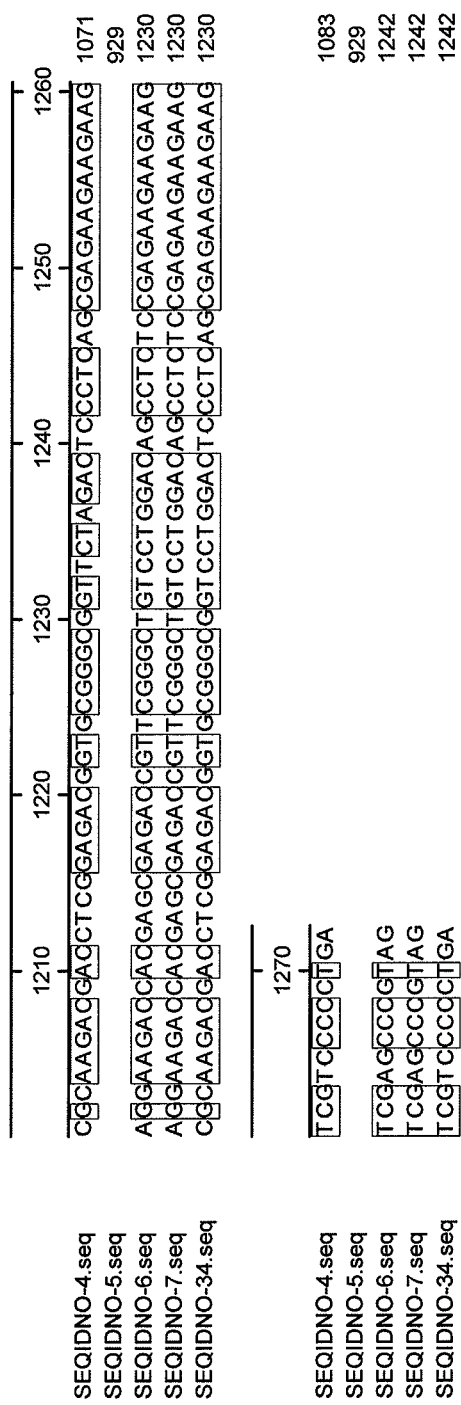

FIG. 10. Panicles and anthers from male sterile (ms26/ms26) and male fertile (MS26/ms26) rice plants. (A) Rice panicles showing male sterile homozygous ms26/ms26 plants on the left and male fertile heterozygous Ms26/ms26 plants on the right. Anther squashes from male sterile ms26/ms26 (B) and male fertile Ms26/ms26 (C) panicles shown in Panel A.

Figure 11B:
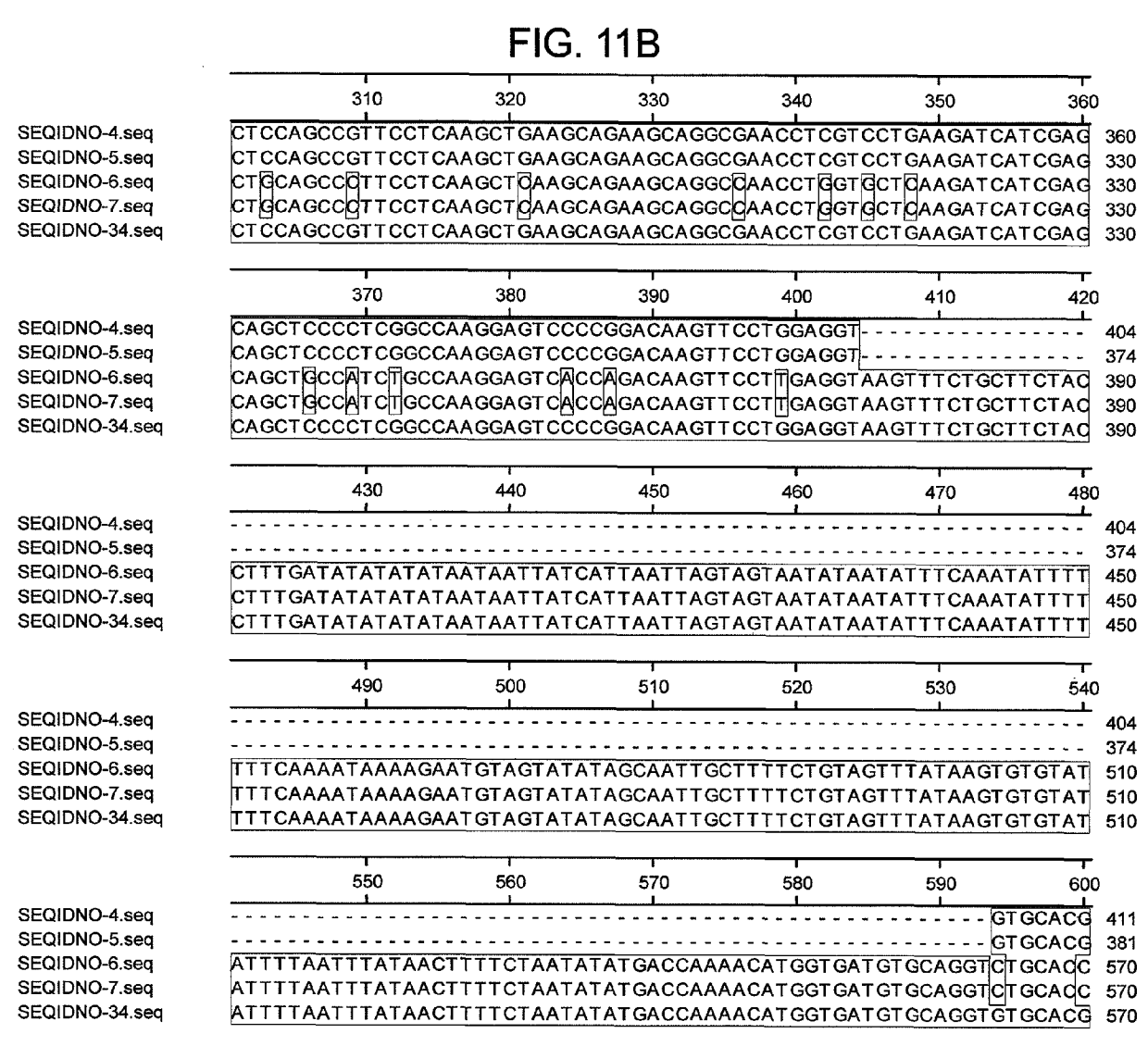
Figure 11C:
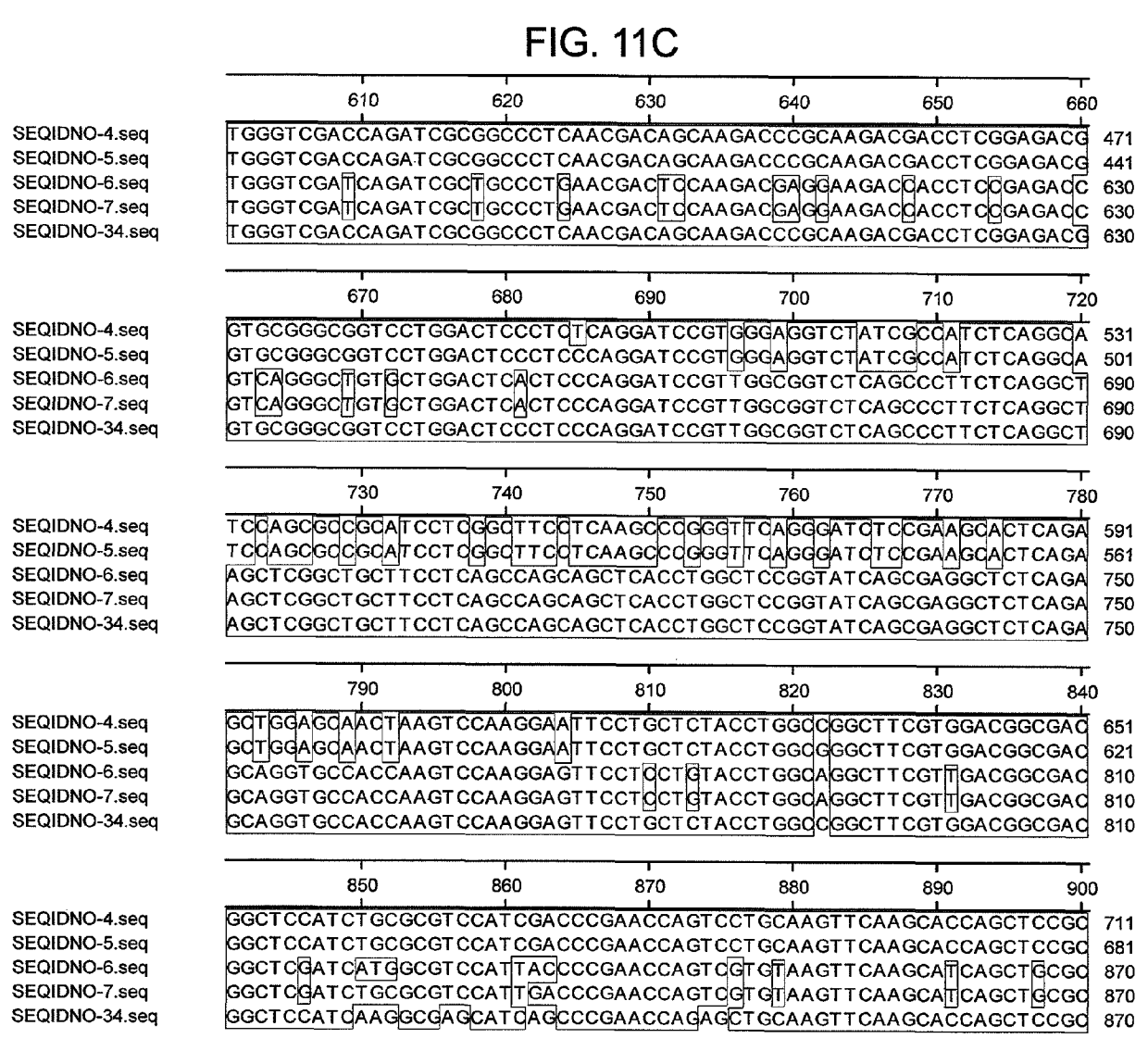
Figure 11D:
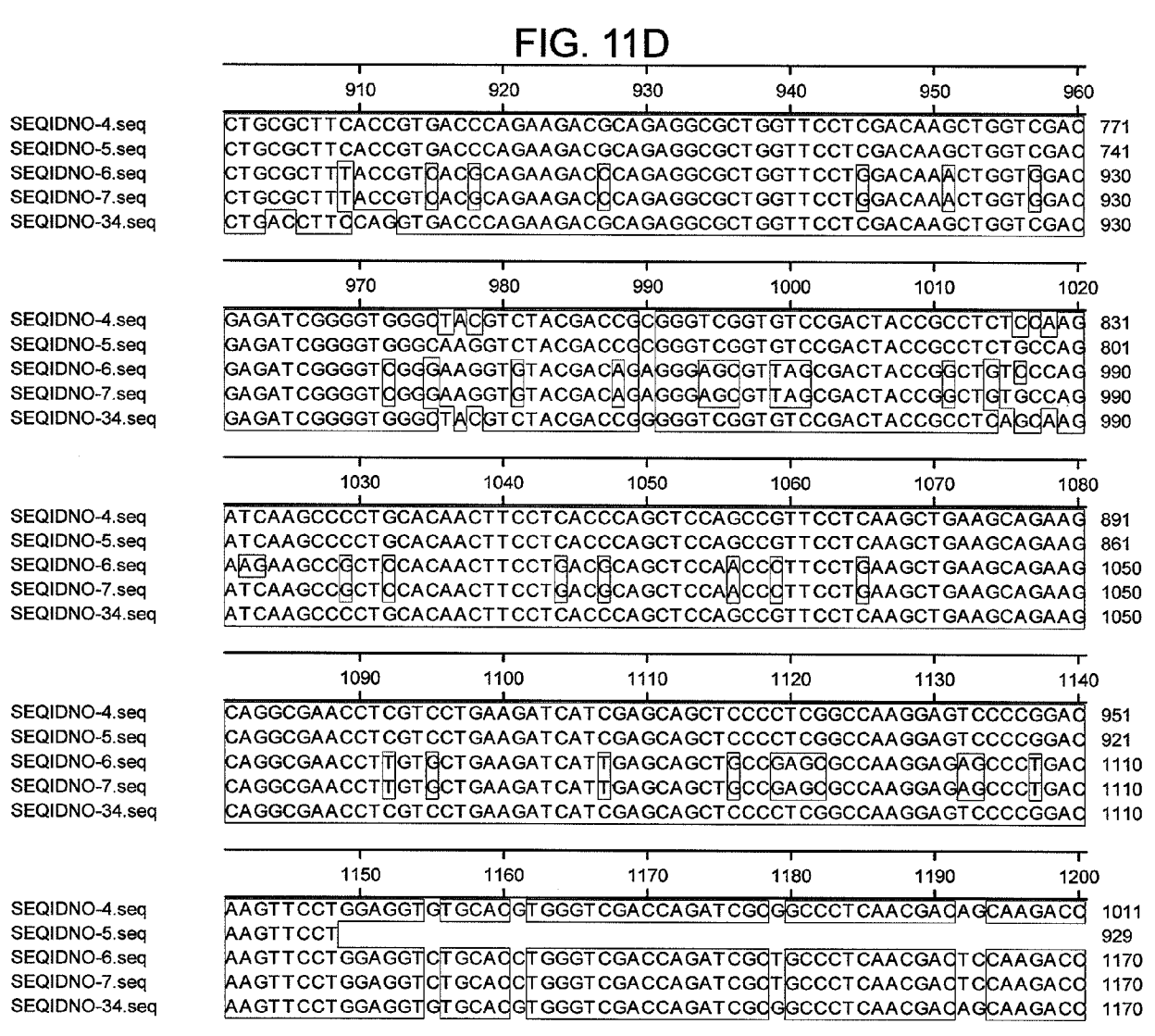

FIG. 11A-E. Alignment of fragments from the plant-optimized nucleotide sequence of meganucleases comprising the nucleotides 170-231 and nucleotides 820-981 of SEQ ID NO:6, 7 or 34, the nucleotides 70-231 and nucleotides 631-792 of SEQ ID NO: 5, and the nucleotides 100-261 and nucleotides 661-822 of SEQ ID NO: 4.

Figure 12:
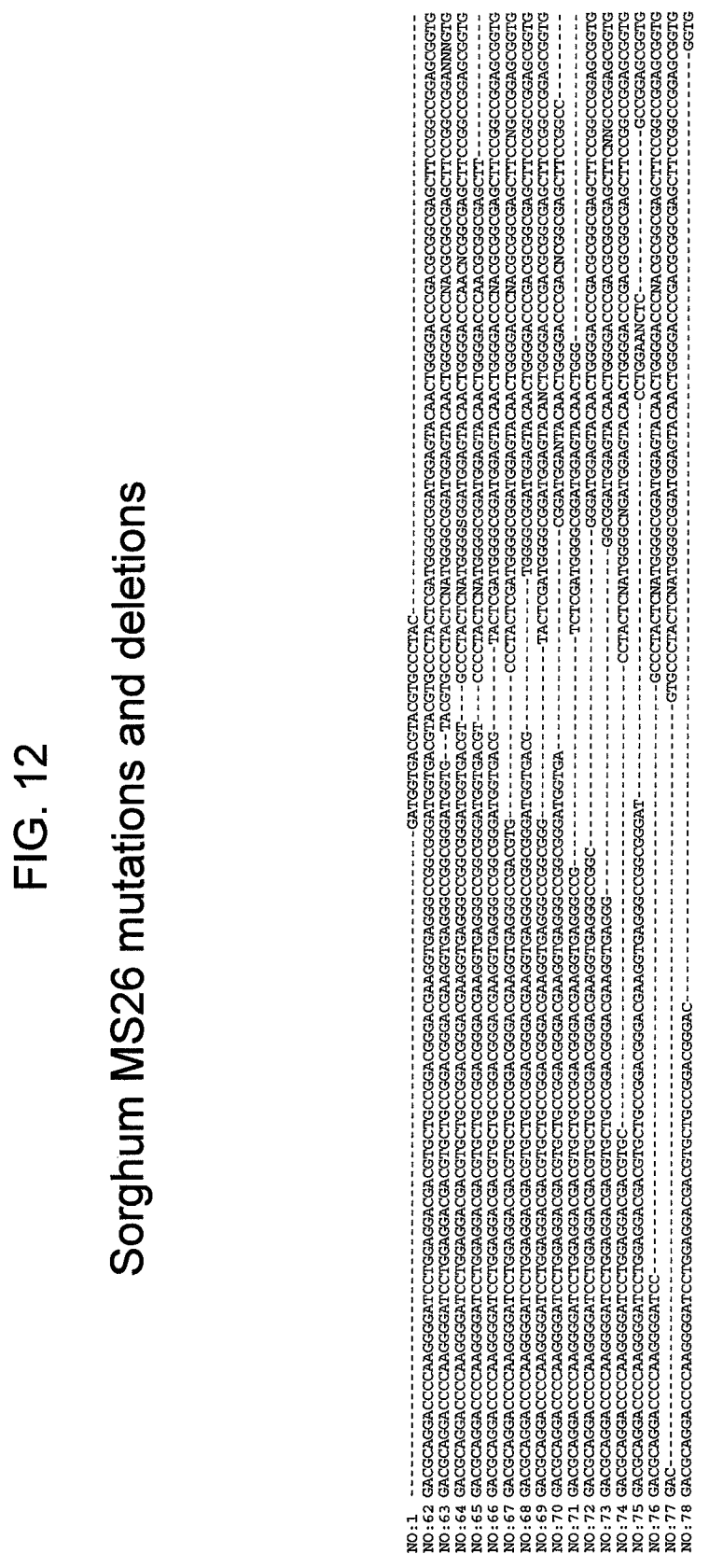

FIG. 12. Alignment of the MS26 recognition sequence and DNA sequences from different sorghum plants containing mutations and deletions at the TS-MS26 target site. NOs: 1 and 62-78 correspond to SEQ ID NOs: 1 and 62-78, respectively. SEQ ID NO:62 represents the wild-type sorgham MS26 nucleotide sequence.

Figure 13:

FIG. 13. (A) panicles of MS26/ms26.780 and (B) panicles of ms26.78Δ/ms26.78Δ sorghum plants.

Figure 14:
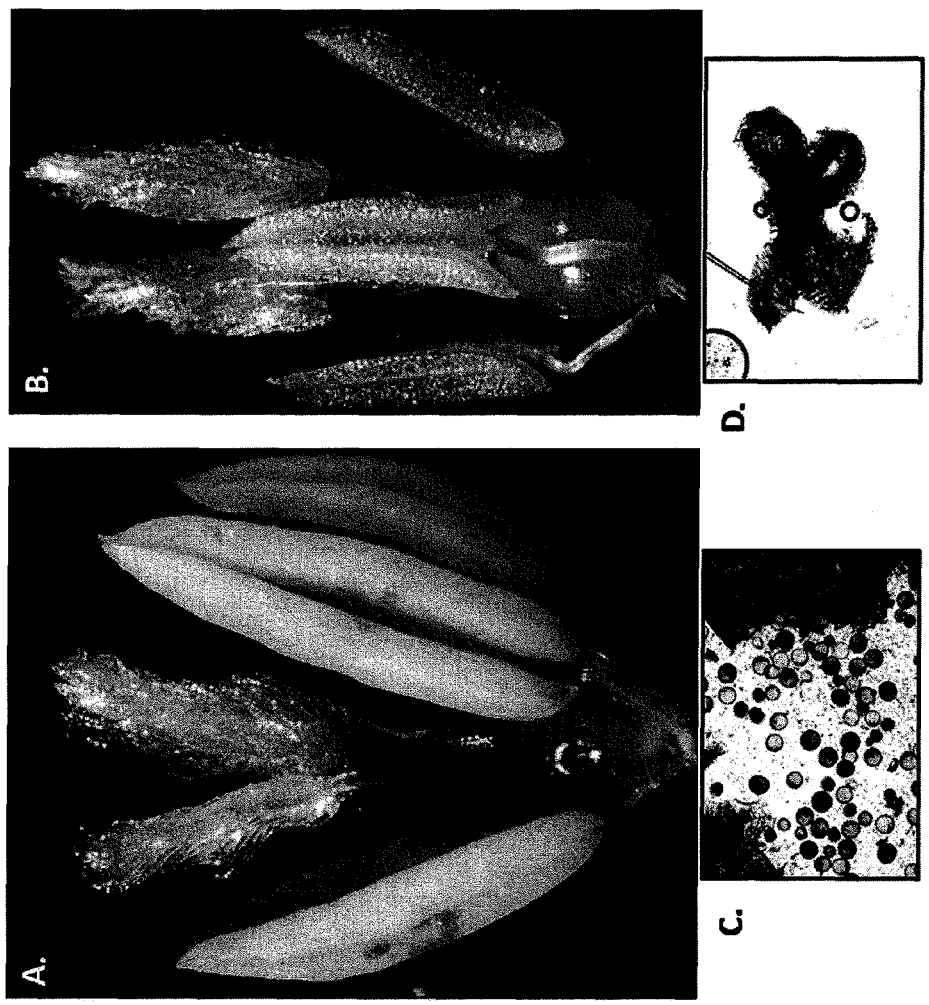

FIG. 14. Stigma, anthers and pollen from MS26/ms26.78Δ plants (FIG. 14A) and ms26.78Δ/ms26.78Δ plants (FIG. 14B). Pollen was easily detected in MS26/ms26.78Δ anthers (FIG. 14C), however pollen was not observed from anthers from ms26.78Δ/ms26.78Δ plants (FIG. 14D).

SEQUENCES

SEQ ID NO: 1 is the nucleotide sequence of the TS-MS26 target site recognized by the engineered MS26 endonuclease that is capable of inducing a double-strand break at that target sequence.

SEQ ID NO: 2 is a nuclear localization signal SV40 NLS-1.

SEQ ID NO: 3 is a nuclear localization signal SV40 NLS-2.

SEQ ID NO: 4 is the plant optimized nucleotide sequence (without an intron) encoding the engineered MS26 endonuclease.

SEQ ID NO: 5 is the plant optimized nucleotide sequence (without an intron) encoding the engineered MS26+ endonuclease.

SEQ ID NO: 6 is the plant optimized nucleotide sequence encoding the engineered MS26++ endonuclease. This nucleotide sequence has a GC content adjusted to less than 60% and contains an intron.

SEQ ID NO: 7 is the plant optimized nucleotide sequence encoding the engineered MS26+ endonuclease. This nucleotide sequence has a GC content adjusted to less than 60 and contains an intron.

SEQ ID NO: 8 is the nucleotide sequence of a male fertility gene encoding a cytochrome P450 (MS26) in maize (AF366297)

SEQ ID NO: 9 is the nucleotide sequence of a male fertility gene encoding a cytochrome P450 (MS26) in rice (LOC_Os03g07250)

SEQ ID NO: 10 is the nucleotide sequence of a male fertility gene encoding a cytochrome P450 (MS26) in sorghum.

SEQ ID NO: 11 is the nucleotide sequence of a male fertility gene encoding a cytochrome P450 (MS26) in rye (*Secale cereal*, FJ539083).

SEQ ID NO: 12 is the amino acid sequence of a male fertility gene (MS26) encoding a cytochrome P450 in maize (AAK52956.1).

SEQ ID NO: 13 is the maize genomic region comprising the maize TS-MS26 target site shown in FIG. 3.

SEQ ID NO: 14 is the rice genomic region comprising the rice TS-MS26 target site shown in FIG. 3.

SEQ ID NO: 15 is the sorghum genomic region comprising the sorghum TS-MS26 target site shown in FIG. 3.

SEQ ID NO: 16 is the rye genomic region comprising the rye TS-MS26 target site shown in FIG. 3.

SEQ ID NO: 17 is primer UNIMS26 5'-2.

SEQ ID NO: 18 is primer UNIMS26 3'-1.

SEQ ID NO: 19 is the maize genomic region comprising the maize-TS-MS26 target sequence.

SEQ ID NO: 20 is the TS-MS45 target sequence from maize.

SEQ ID NO: 21 is the nuclear localization amino acid sequence used in MAY1/MAY fusions.

SEQ ID NO: 22 is the plant optimized nucleotide sequence encoding MAY1.

SEQ ID NO: 23 is the plant optimized nucleotide sequence encoding MAY2.

SEQ ID NO: 24 is the nucleotide sequence of a male fertility gene encoding a chalcone and stilbene synthase (5126) in maize (AX060770).

SEQ ID NO: 25 is the nucleotide sequence of a male fertility gene encoding a chalcone and stilbene synthase (5126) in rice (LOC_Os07g22850).

SEQ ID NO: 26 is the nucleotide sequence of a male fertility gene encoding a dihydroflavonol 4-reductase (BS7) in maize (AF366295).

SEQ ID NO: 27 is the nucleotide sequence of a male fertility gene encoding a a dihydroflavonol 4-reductase (BS7) in rice (LOC_Os08g40440).

SEQ ID NO: 28 is the nucleotide sequence of a male fertility gene encoding a strictosidine synthase (MS45) in maize (AF360356).

SEQ ID NO: 29 is the nucleotide sequence of male fertility gene encoding a strictosidine synthase (MS45) in rice (LOC_Os03g15710).

SEQ ID NO: 30 is plasmid PHP31457.

SEQ ID NO: 31 is plasmid PHP31459.

SEQ ID NO: 32 is the nucleotide sequence of a male fertility gene encoding a MS22 protein in maize.

SEQ ID NO: 33 is a DNA sequence encoding the nuclear localization amino acid sequence used in MAY1/MAY fusions.

SEQ ID NO: 34 is a plant optimized gene encoding a MAY1-linker-MAY2 protein.

SEQ ID NO: 35 is the wild-type TS-MS26 DNA fragment shown in FIG. 2.

SEQ ID NO: 36 is the 3281 TS-MS26 DNA fragment shown in FIG. 2.

SEQ ID NO: 37 is the 2963 TS-MS26 DNA fragment shown in FIG. 2.

SEQ ID NO: 38 is the 2980 TS-MS26 DNA fragment shown in FIG. 2.

SEQ ID NO: 39 is the 3861 TS-MS26 DNA fragment shown in FIG. 2.

SEQ ID NO: 40 is the 3956 TS-MS26 DNA fragment shown in FIG. 2.

SEQ ID NO: 41 is the 3990 TS-MS26 DNA fragment shown in FIG. 2.

SEQ ID NO: 42 is the 6227 TS-MS26 DNA fragment shown in FIG. 2.

SEQ ID NO: 43 is the wild-type TS-MS26 DNA fragment shown in FIG. 5.

SEQ ID NO: 44 is the Ev48 TS-MS26 DNA fragment shown in FIG. 5.

SEQ ID NO: 45 is Ev62.1 TS-MS26 DNA fragment shown in FIG. 5.

SEQ ID NO: 46 is the Ev62.13 TS-MS26 DNA fragment shown in FIG. 5.

SEQ ID NO: 47 is the Ev62.14 TS-MS26 DNA fragment shown in FIG. 5.

SEQ ID NO: 48 is the Ev67 TS-MS26 DNA fragment shown in FIG. 5.

SEQ ID NO: 49 is the wild-type TS-MS26 DNA fragment shown in FIG. 7.

SEQ ID NO: 50 is the ms26.1 TS-MS26 DNA fragment shown in FIG. 7.

SEQ ID NO: 51 is the ms26.2 TS-MS26 DNA fragment shown in FIG. 7.

SEQ ID NO: 52 is the ms26.3 TS-MS26 DNA fragment shown in FIG. 7.

SEQ ID NO: 53 is the ms26.4 TS-MS26 DNA fragment shown in FIG. 7.

SEQ ID NO: 54 is the ms26.5 TS-MS26 DNA fragment shown in FIG. 7.

SEQ ID NO: 55 is the ms26.6 TS-MS26 DNA fragment shown in FIG. 7.

SEQ ID NO: 56 is the ms26.7 TS-MS26 DNA fragment shown in FIG. 7.

SEQ ID NO: 57 is the ms26.8 TS-MS26 DNA fragment shown in FIG. 7.

SEQ ID NO: 58 is the nucleotide sequence of plasmid PHP40082.

SEQ ID NO: 59 is the nucleotide sequence of plasmid PHP40126.

SEQ ID NO: 60 is the nucleotide sequence of plasmid PHP40827.

SEQ ID NO: 61 is the nucleotide sequence of plasmid PHP42063.

SEQ ID NO: 62-78 are the DNA fragments shown in FIG. 12. SEQ ID NO: 62 is the nucleotide sequence of a portion of the wild-type sorghum MS26 gene.

SEQ ID NOs: 63-78 set forth modifications to the nucleotide sequence of the wild-type sorghum MS26 gene set forth in SEQ ID NO: 62.

DETAILED DESCRIPTION OF THE INVENTION

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

As used herein and in the appended claims, the singular forms "a", "an", and "the" include plural reference unless the context clearly dictates otherwise. Thus, for example, reference to "a plant" includes a plurality of such plants; reference to "a cell" includes one or more cells and equivalents thereof known to those skilled in the art, and so forth.

A reliable system of producing genetic male sterility would provide advantages to develop hybrid plants. The laborious detasseling process can be avoided in some genotypes by using cytoplasmic male-sterile (CMS) inbreds. In the absence of a fertility restorer gene, plants of a CMS inbred are male sterile as a result of factors resulting from the cytoplasmic, as opposed to the nuclear, genome. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile. Usually seed from detasseled normal maize and CMS produced seed of the same hybrid must be blended to insure that adequate pollen loads are available for fertilization when the hybrid plants are grown and to insure cytoplasmic diversity.

Nuclear (genic) sterility can be either dominant or recessive. Dominant sterility can only be used for hybrid seed formation if propagation of the female line is possible (for example, via in vitro clonal propagation). Recessive sterility can be used if sterile and fertile plants are easily discriminated. Commercial utility of genic sterility systems is limited however by the expense of clonal propagation and roguing the female rows of self-fertile plants.

One type of genetic sterility is disclosed in U.S. Pat. Nos. 4,654,465 and 4,727,219 to Brar, et al. However, this form of genetic male sterility requires maintenance of multiple mutant genes at separate locations within the genome and requires a complex marker system to track the genes and make use of the system convenient. Patterson also described a genic system of chromosomal translocations which can be effective, but which are complicated. (See, U.S. Pat. Nos. 3,861,709 and 3,710,511.)

Many other attempts have been made to improve on these systems. For example, Fabijanski, et al., developed several methods of causing male sterility in plants (see EPO 89/3010153.8 publication no. 329,308 and PCT application PCT/CA90/00037 published as WO 90/08828). One method includes delivering into the plant a gene encoding a cytotoxic substance associated with a male tissue specific promoter. Another involves an antisense system in which a gene critical to fertility is identified and an antisense to the gene inserted in the plant. Fabijanski, et al. also shows several cytotoxic antisense systems. See EP0329308. Still other systems use "repressor" genes which inhibit the expression of another gene critical to male sterility. See PCT/GB90/00102, published as WO 90/08829. For yet another example see U.S. Pat. No. 6,281,348.

A still further improvement of this system is one described at U.S. Pat. No. 5,478,369 in which a method of imparting controllable male sterility is achieved by inactivating or otherwise silencing a gene native to the plant that is critical for male fertility and transforming that plant with the gene critical to male fertility linked to an inducible promoter controlling expression of the gene. That is, the expression of the endogenous sequence is prevented, by any of the methods known to a skilled person in the art for preventing expression of a sequence (such an antisense methods, cosuppression, mutation, use of ribozymes or hairpins, various repression systems and the like, discussed infra.) The plant is thus constitutively sterile, becoming fertile only when the promoter is induced and its linked male fertility gene is expressed.

In a number of circumstances, a male sterility plant trait is expressed by maintenance of a homozygous recessive condition. Difficulties arise in maintaining the homozygous condition, when a restoration gene must be used for maintenance. For example, a natural mutation in a gene critical to male fertility can impart a male sterility phenotype to plants when this mutant allele is in the homozygous state. But because this homozygosity results in male sterility, the homozygous male-sterile line cannot be maintained. Fertility is restored when the non-mutant form of the gene is introduced into the plant. However, this form of line maintenance removes the desired homozygous recessive condition, restores full male fertility in half of the resulting progeny, and prevents maintenance of pure male sterile maternal lines. These issues can be avoided where production of pollen containing the restoration gene is eliminated, thus providing a maintainer plant producing only pollen not containing the restoration gene, and the progeny retain their homozygous condition when fertilized by such pollen. An example of one approach is shown in Dellaporta et al., U.S. Pat. No. 6,743,968, in which a plant is produced having a hemizygotic construct comprising a gene that produces a product fatal to a cell, linked with a pollen-specific promoter, and the restoration gene. When crossed with the homozygous recessive male sterile plant, the progeny thus retains the homozygous recessive condition. Other approaches have been described, for example in U.S. Pat. No. 7,696,405.

As noted, an important aspect of much of the work underway with male sterility systems is the identification of genes impacting male fertility. Such a gene can be used in a variety of systems to control male fertility including those described above.

As used herein "genetic male sterility" results from a mutation, suppression, or other impact to one of the genes critical to a specific step in microsporogenesis, the term applied to the entire process of pollen formation. These genes can be collectively referred to as male fertility genes (or, alternatively, male sterility genes). There are many steps in the overall pathway where gene function impacts fertility, as demonstrated by the frequency of genetic male sterility in maize. New alleles of male sterility mutants are uncovered in materials that range from elite inbreds to unadapted populations.

In U.S. Pat. No. 5,478,369, a method is described by which the Ms45 male fertility gene was tagged and cloned on maize chromosome 9. Previously, there had been described a male fertility gene on chromosome 9, ms2, which had never been cloned and sequenced. It is not allelic to the gene referred to in the '369 patent. See Albertsen, M. and Phillips, R. L., "Developmental Cytology of 13 Genetic Male Sterile Loci in Maize" *Canadian Journal of Genetics & Cytology* 23:195-208 (January 1981). The only fertility gene cloned previously was the *Arabadopsis* gene described at Aarts, et al., supra.

Examples of genes that have been discovered subsequently that are important to male fertility are numerous and include the *Arabidopsis* ABORTED MICROSPORES (AMS) gene, Sorensen et al., *The Plant Journal* (2003) 33(2):413-423); the *Arabidopsis* MS1 gene (Wilson et al., *The Plant Journal* (2001) 39(2):170-181); the NEF1 gene (Ariizumi et al., The Plant Journal (2004) 39(2):170-181); *Arabidopsis* AtGPAT1 gene (Zheng et al., *The Plant Cell* (2003) 15:1872-1887); the *Arabidopsis* dde2-2 mutation was shown to be defective in the allene oxide syntase gene (Malek et al., Planta (2002)216:187-192); the *Arabidopsis* faceless pollen-1 gene (flp1) (Ariizumi et al, Plant Mol. Biol. (2003) 53:107-116); the *Arabidopsis* MALE MEIOCYTE DEATH1 gene (Yang et al., *The Plant Cell* (2003) 15: 1281-1295); the tapetum-specific zinc finger gene, TAZ1 (Kapoor et al., *The Plant Cell* (2002) 14:2353-2367); and the TAPETUM DETERMINANT1 gene (Lan et al, *The Plant Cell* (2003) 15:2792-2804).

Table 1 lists a number of known male fertility mutants or genes from *Zea mays*.

TABLE 1

| Male fertility mutants or genes from *Zea mays*. | | |
|---|---|---|
| GENE NAME | ALTERNATE NAME | REFERENCE |
| ms1 male sterile1 | male sterile1, ms1 | Singleton, W R and Jones, D F. 1930. J Hered 21: 266-268 |
| ms10 male sterile10 | male sterile10, ms10 | Beadle, G W. 1932. Genetics 17: 413-431 |
| ms11 male sterile11 | ms11, male sterile11 | Beadle, G W. 1932. Genetics 17: 413-431 |
| ms12 male sterile12 | ms12, male sterile12 | Beadle, G W. 1932. Genetics 17: 413-431 |
| ms13 male sterile13 | ms*-6060, male sterile13, ms13 | Beadle, G W. 1932. Genetics 17: 413-431 |
| ms14 male sterile14 | ms14, male sterile14 | Beadle, G W. 1932. *Genetics* 17: 413-431 |
| ms17 male sterile17 | ms17, male sterile17 | Emerson, R A. 1932. Science 75: 566 |
| ms2 male sterile2 | male sterile2, ms2 | Eyster, W H. 1931. J Hered 22: 99-102 |
| ms20 male sterile20 | ms20, male sterile20 | Eyster, W H. 1934. Genetics of *Zea mays*. Bibliographia Genetica 11: 187-392 |
| ms23 male sterile23 | : ms*-6059, ms*-6031, ms*-6027, ms*-6018, ms*-6011, ms35, male sterile23, ms*-Bear7, ms23 | West, D P and Albertsen, M C. 1985. MNL 59: 87 |
| ms24 male sterile24 | ms24, male sterile24 | West, D P and Albertsen, M C. 1985. MNL 59: 87 |

TABLE 1-continued

Male fertility mutants or genes from Zea mays.

| GENE NAME | ALTERNATE NAME | REFERENCE |
| --- | --- | --- |
| ms25 male sterile25 | ms*-6065, ms*-6057, ms25, male sterile25, ms*-6022 | Loukides, C A; Broadwater, A H; Bedinger, P A. 1995. Am J Bot 82: 1017-1023 |
| ms27 male sterile27 | ms27, male sterile27 | Albertsen, M C. 1996. MNL 70: 30-31 |
| ms28 male sterile28 | ms28, male sterile28 | Golubovskaya, I N. 1979. MNL 53: 66-70 |
| ms29 male sterile29 | male sterile29, ms*-JH84A, ms29 | Trimnell, M R et al. 1998. MNL 72: 37-38 |
| ms3 male sterile3 | Group 3, ms3, male sterile3 | Eyster, W H. 1931. J Hered 22: 99-102 |
| ms30 male sterile30 | ms30, msx, ms*-6028, ms*-Li89, male sterile30, ms*-LI89 | Albertsen, M C et al. 1999. MNL 73: 48 |
| ms31 male sterile31 | ms*-CG889D, ms31, male sterile31 | Trimnell, M R et al. 1998. MNL 72: 38 |
| ms32 male sterile32 | male sterile32, ms32 | Trimnell, M R et al. 1999. MNL 73: 48-49 |
| ms33 male sterile33 | : ms*-6054, ms*-6024, ms33, ms*-GC89A, ms*-6029, male sterile6019, Group 7, ms*-6038, ms*-Stan1, ms*-6041, ms*-6019, male sterile33 | Patterson, E B. 1995. MNL 69: 126-128 |
| ms34 male sterile34 | Group 1, ms*-6014, ms*-6010, male sterile34, ms34, ms*-6013, ms*-6004, male sterile6004 | Patterson, E B. 1995. MNL 69: 126-128 |
| ms36 male sterile36 | male sterile36, ms*-MS85A, ms36 | Trimnell, M R et al. 1999. MNL 73: 49-50 |
| ms37 male sterile 37 | ms*-SB177, ms37, male sterile 37 | Trimnell, M R et al. 1999. MNL 73: 48 |
| ms38 male sterile38 | ms30, ms38, ms*-WL87A, male sterile38 | Albertsen, M C et al. 1996. MNL 70: 30 |
| ms43 male sterile43 | ms43, male sterile43, ms29 | Golubovskaya, I N. 1979. Int Rev Cytol 58: 247-290 |
| ms45 male sterile45 | Group 6, male sterile45, ms*-6006, ms*-6040, ms*-BS1, ms*-BS2, ms*-BS3, ms45, ms45'-9301 | Albertsen, M C; Fox, T W; Trimnell, M R. 1993. Proc Annu Corn Sorghum Ind Res Conf 48: 224-233 |
| ms48 male sterile48 | male sterile48, ms*-6049, ms48 | Trimnell, M et al. 2002. MNL 76: 38 |
| ms5 male sterile5 | : ms*-6061, ms*-6048, ms*-6062, male sterile5, ms5 | Beadle, G W. 1932. Genetics 17: 413-431 |
| ms50 male sterile50 | ms50, male sterile50, ms*-6055, ms*-6026 | Trimnell, M et al. 2002. MNL 76: 39 |
| ms7 male sterile7 | ms7, male sterile7 | Beadle, G W. 1932. Genetics 17: 413-431 |
| ms8 male sterile8 | male sterile8, ms8 | Beadle, G W. 1932. Genetics 17: 413-431 |
| ms9 male sterile9 | Group 5, male sterile9, ms9 | Beadle, G W. 1932. Genetics 17: 413-431 |
| ms49 male sterile49 | ms*-MB92, ms49, male sterile49 | Trimnell, M et al. 2002. MNL 76: 38-39 |

U.S. Patent publication US 2008-0086783 A1 describes a male fertile gene referred to as "BS92-7" or "BS7" that is located on maize chromosome 7. BS92-7 can be used in the systems described above, and other systems impacting male fertility.

U.S. Pat. No. 5,750,868, issued May 12, 1998 describes a male fertile gene referred to as "5126" (SEQ ID NO: 24).

U.S. Pat. No. 5,478,369 issued Dec. 26, 1995 describes a male fertile gene referred to as "MS45".

U.S. Pat. No. 7,517,975, issued Apr. 14, 2009, describes a male fertile gene referred to as "MS26" (also known as SB200 or SBMu200) that is located on maize chromosome 1. MS26 can be used in the systems described above, and other systems impacting male fertility.

U.S. Patent publication US 2009-0038026 A1, published Feb. 5, 2009, describes a male fertile gene referred to as "Msca1" or "MS22" that is located on maize chromosome 7 and encodes a protein critical to male fertility. Mutations referred to as ms22 or msca1 were first noted as phenotypically male sterile with anthers which did not extrude from the tassel and lacked sporogenous tissue. West and Albertsen (1985) Maize Newsletter 59:87; Neuffer et al. (1977) Mutants of maize. Cold Spring Harbor Laboratory Press, Cold Spring Harbor, N.Y. The mutant locus was originally referred to as ms22 but was later changed to msca1, or male sterile converted anther. See Chaubal et al. "The transformation of anthers in the msca1 mutant of maize" *Planta* (2003) 216:778-788.

In the context of this disclosure, a number of terms and abbreviations are used. The following definitions are provided.

The term "recognition sequence" or "recognition site" as used herein refers to a DNA sequence at which a double-strand break is induced in the plant cell genome by a double-strand-break-inducing agent. The terms "recognition sequence" and "recognition site" are used interchangeably herein.

The terms "target site", "target sequence", "target locus", "genomic target site", "genomic target sequence" as used interchangeably herein refer to a polynucleotide sequence in the genome of a plant cell that comprises a recognition sequence for a double-strand-break-inducing agent.

An "artificial target sequence" is a target sequence that has been introduced into the genome of a plant. Such an artificial target sequence can be identical in sequence to an endogenous or native target sequence in the genome of a plant but be located in a different position (i.e., a non-endogenous or non-native position) in the genome of a plant.

An "endogenous target sequence" or "native target sequence" are used interchangeably herein to refer to a target sequence that is endogenous or native to the genome of a plant and is at the endogenous or native position of that target sequence in the genome of the plant.

An "altered target sequence" refers to a target sequence as disclosed herein that comprises at least one alteration of the invention when compared to non-altered target sequence. Such "alterations" of the invention include, for example: (i) replacement of at least one nucleotide, (ii) a deletion of at least one nucleotide, (iii) an insertion of at least one nucleotide, or (iv) any combination of (i)-(iii).

The term "double-strand-break-inducing agent" as used herein refers to any enzyme which produces a double-strand break in the target sequence. Producing the double-strand break in a target sequence or other DNA can be referred to herein as "cutting" or "cleaving" the target sequence or other DNA. In some embodiments of the invention, the double-strand-break-inducing agent has been engineered (or modified) to cut a specific endogenous target sequence, wherein the endogenous target sequence prior to being cut by the engineered double-strand-break-inducing agent was not a sequence that would have been recognized by a native (non-engineered or non-modified) double-strand-break-inducing agent.

An "engineered double-strand-break-inducing agent" is any double-strand-break-inducing agent, including but not limited to, native or wild-type double-strand-break-inducing agents and previously engineered double-strand-break-inducing agent that has been modified to produce a double-strand break at a target sequence of interest which has a different nucleotide sequence than the original target sequence of the double-strand-break-inducing agent prior to its modification. Preferably, an engineered double-strand-break-inducing agent of the invention is no longer capable of making a double-strand break at the original target sequence.

The term "endonuclease" refers to any enzyme that cleaves the phosphodiester bond within a polynucleotide chain, and includes restriction endonucleases that cleave DNA as specific sites without damaging the bases. Restriction endonucleases include Type I, Type II, Type III, and Type IV endonucleases, which further include subtypes. In the Type I and Type III systems, both the methylase and restriction activities are contained in a single complex.

Type I and Type III restriction endonucleases recognize specific recognition sites, but typically cleave at a variable position from the recognition site, which can be hundreds of base pairs away from the recognition site. In Type II systems the restriction activity is independent of any methylase activity, and cleavage typically occurs at specific sites within or near to the recognition site. Most Type II enzymes cut palindromic sequences, however Type IIa enzymes recognize non-palindromic recognition sites and cleave outside of the recognition site, Type IIb enzymes cut sequences twice with both sites outside of the recognition site, and Type IIs enzymes recognize an asymmetric recognition site and cleave on one side and at a defined distance of about 1-20 nucleotides from the recognition site.

Type IV restriction enzymes target methylated DNA. Restriction enzymes are further described and classified, for example in the REBASE database (webpage at rebase.neb.com; Roberts, et al., (2003) *Nucleic Acids Res* 31:418-20), Roberts, et al., (2003) *Nucleic Acids Res* 31:1805-12, and Belfort, et al., (2002) in *Mobile DNA II*, pp. 761-783, Eds. Craigie, et al., (ASM Press, Washington, D.C.).

Endonucleases also include meganucleases, also known as homing endonucleases (HEases), which like restriction endonucleases, bind and cut at a specific recognition sequence, however the recognition sites for meganucleases are typically longer, about 18 bp or more. Meganucleases have been classified into four families based on conserved sequence motifs; the families are the LAGLIDADG, GIY-YIG, H-N-H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing ORFs, introns, and inteins, respectively. For example, intron-, intein-, and freestanding gene encoded meganuclease from *Saccharomyces cerevisiae* are denoted I-SceI, PI-SceI, and F-SceII, respectively. Meganuclease domains, structure and function are known, see for example, Guhan and Muniyappa (2003) *Crit. Rev Biochem Mol Biol* 38:199-248; Lucas, et al., (2001) *Nucleic Acids Res* 29:960-9; Jurica and Stoddard, (1999) *Cell Mol Life Sci* 55:1304-26; Stoddard, (2006) *Q Rev Biophys* 38:49-95; and Moure, et al., (2002) *Nat Struct Biol* 9:764. In some examples an engineered meganuclease is used. Methods for modifying the kinetics, cofactor interactions, expression, optimal conditions, and/or recognition site specificity, and screening for activity are known. See, for example, Epinat, et al., (2003) *Nucleic Acids Res* 31:2952-62; Chevalier, et al., (2002) *Mol Cell* 10:895-905; Gimble, et al., (2003) *Mol Biol* 334:993-1008; Seligman, et al., (2002) *Nucleic Acids Res* 30:3870-9; Sussman, et al., (2004) *J Mol Biol* 342:31-41; Rosen, et al., (2006) *Nucleic Acids Res* 34:4791-800; Chames, et al., (2005) *Nucleic Acids Res* 33:e178; Smith, et al., (2006) *Nucleic Acids Res* 34:e149; Gruen, et al., (2002) *Nucleic Acids Res* 30:e29; Chen and Zhao, (2005) *Nucleic Acids Res* 33:e154; WO2005105989; WO2003078619; WO2006097854; WO2006097853; WO2006097784; and WO2004031346.

The endonuclease can be a modified endonuclease that binds a non-native or exogenous recognition sequence and does not bind a native or endogenous recognition sequence. Modification of the endonuclease can be as little as one nucleotide. A modified endonuclease is not capable of making a double-strand break within a wild-type target sequence. A wild-type (i.e., prior to being modified) endonuclease is capable of making a double-strand break within the wild-type target sequence.

The endonuclease can be provided via a polynucleotide encoding the endonuclease. Such a polynucleotide encoding an endonuclease can be modified to substitute codons having a higher frequency of usage in a plant, as compared to the naturally occurring polynucleotide sequence. For example the polynucleotide encoding the endonuclease can be modified to substitute codons having a higher frequency of usage in a maize or soybean plant, as compared to the naturally occurring polynucleotide sequence.

The term "engineered endonuclease" is any endonuclease that has been engineered (or modified) to cut a specific endogenous target sequence, wherein the endogenous target sequence prior to being cut by the engineered endonuclease was not a sequence that would have been recognized by a native (non-engineered or non-modified) endonuclease.

In some embodiments of the invention, the engineered endonuclease is an engineered MS26 endonuclease, an engineered MS26+ endonuclease, engineered MS26++ endonuclease or an engineered MS45 endonuclease.

As used herein, "physically linked," and "in physical linkage", and "genetically linked" are used to refer to any two or more genes, transgenes, native genes, mutated genes, alterations, target sites, markers, and the like that are part of the same DNA molecule or chromosome.

As used herein, a "polynucleotide of interest" within a genomic region of interest is any coding and/or non-coding portion of the genomic region of interest including, but not limited to, a transgene, a native gene, a mutated gene, and a genetic marker such as, for example, a single nucleotide polymorphism (SNP) marker and a simple sequence repeat (SSR) marker.

"Open reading frame" is abbreviated ORF.

As used herein, "nucleic acid" means a polynucleotide and includes a single or a double-stranded polymer of deoxyribonucleotide or ribonucleotide bases. Nucleic acids may also include fragments and modified nucleotides. Thus, the terms "polynucleotide", "nucleic acid sequence", "nucleotide sequence" or "nucleic acid fragment" are used interchangeably to denote a polymer of RNA and/or DNA that is single- or double-stranded, optionally containing synthetic, non-natural, or altered nucleotide bases. Nucleotides (usually found in their 5'-monophosphate form) are referred to by their single letter designation as follows: "A" for adenosine or deoxyadenosine (for RNA or DNA, respectively), "C" for cytosine or deoxycytosine, "G" for guanosine or deoxyguanosine, "U" for uridine, "T" for deoxythymidine, "R" for purines (A or G), "Y" for pyrimidines (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in suppression by linking a nucleic acid fragment or subfragment thereof, whether or not it encodes an active enzyme, in the sense or antisense orientation relative to a plant promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential to the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

Polynucleotide and polypeptide sequences, variants thereof, and the structural relationships of these sequences can be described by the terms "homology", "homologous", "substantially identical", "substantially similar" and "corresponding substantially" which are used interchangeably herein. These refer to polypeptide or nucleic acid fragments wherein changes in one or more amino acids or nucleotide bases do not affect the function of the molecule, such as the ability to mediate gene expression or to produce a certain phenotype. These terms also refer to modification(s) of nucleic acid fragments that do not substantially alter the functional properties of the resulting nucleic acid fragment relative to the initial, unmodified fragment. These modifications include deletion, substitution, and/or insertion of one or more nucleotides in the nucleic acid fragment.

Substantially similar nucleic acid sequences encompassed may be defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence in an in vitro hybridization assay. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salt(s)) at pH 7.0 to 8.3, and at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth, et al., (1984) *Anal Biochem* 138:267-284: $T_m=81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-Interscience, New York (1995). Hybridization and/or wash conditions can be applied for at least 10, 30, 60, 90, 120 or 240 minutes.

"Sequence identity" or "identity" in the context of nucleic acid or polypeptide sequences refers to the nucleic acid bases or amino acid residues in two sequences that are the same when aligned for maximum correspondence over a specified comparison window.

The term "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, 91%, 92%, 93%, 94%, 95%, 96%, 97%, 98%, or 99%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, (1989) *CABIOS* 5:151-153; Higgins, et al., (1992) *Comput Appl Biosci* 8:189-191) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

The "Clustal W method of alignment" corresponds to the alignment method labeled Clustal W (described by Higgins and Sharp, (1989) *CABIOS* 5:151-153; Higgins, et al., (1992) *Comput Appl Biosci* 8:189-191) and found in the MegAlign™ v6.1 program of the LASERGENE bioinformatics computing suite (DNASTAR Inc., Madison, Wis.). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

Unless otherwise stated, sequence identity/similarity values provided herein refer to the value obtained using GAP Version 10 (GCG, Accelrys, San Diego, Calif.) using the following parameters: % identity and % similarity for a nucleotide sequence using a gap creation penalty weight of 50 and a gap length extension penalty weight of 3, and the nwsgapdna.cmp scoring matrix; % identity and % similarity for an amino acid sequence using a GAP creation penalty weight of 8 and a gap length extension penalty of 2, and the BLOSUM62 scoring matrix (Henikoff and Henikoff, (1989) *Proc. Natl. Acad. Sci. USA* 89:10915). GAP uses the algorithm of Needleman and Wunsch, (1970) *J Mol Biol* 48:443-53, to find an alignment of two complete sequences that maximizes the number of matches and minimizes the number of gaps. GAP considers all possible alignments and gap positions and creates the alignment with the largest number of matched bases and the fewest gaps, using a gap creation penalty and a gap extension penalty in units of matched bases.

"BLAST" is a searching algorithm provided by the National Center for Biotechnology Information (NCBI) used to find regions of similarity between biological sequences. The program compares nucleotide or protein sequences to sequence databases and calculates the statistical significance of matches to identify sequences having sufficient similarity to a query sequence such that the similarity would not be predicted to have occurred randomly. BLAST reports the identified sequences and their local alignment to the query sequence.

It is well understood by one skilled in the art that many levels of sequence identity are useful in identifying polypeptides from other species or modified naturally or synthetically wherein such polypeptides have the same or similar function or activity. Useful examples of percent identities include, but are not limited to, 50%, 55%, 60%, 65%, 70%, 75%, 80%, 85%, 90% or 95%, or any integer percentage from 50% to 100%. Indeed, any integer amino acid identity from 50% to 100% may be useful in describing the present invention, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature, or at a different genetic locus than that found in nature. A "foreign" gene refers to a gene not normally found in the host organism, but that is introduced into the host organism by gene transfer. Foreign genes can comprise native genes inserted into a non-native organism, or chimeric genes.

A "mutated gene" is a native gene that has been altered through human intervention. Such a "mutated gene" has a sequence that differs from the sequence of the corresponding native gene by at least one nucleotide addition, deletion, or substitution. In certain embodiments of the invention, the mutated gene comprises an alteration that results from a double-strand-break-inducing agent as disclosed herein.

A "transgene" is a gene that has been introduced into the genome by a transformation procedure. A transgene can, for example encode one or more proteins or RNA that is not translated into protein. However, a transgene of the invention need not encode a protein and/or non-translated RNA. In certain embodiments of the invention, the transgene comprises one or more chimeric genes, including chimeric genes comprising, for example, a gene of interest, phenotypic marker, a selectable marker, and a DNA for gene silencing.

As used herein, a "targeted modification" is a modification in a target sequence in the genome of an organism that was made by altering a target sequence within the native gene using a method involving a double-strand-break-inducing agent that is capable of inducing a double-strand break in the DNA of the target sequence as disclosed herein or known in the art. A "targeted mutation" is a mutation in a native gene that was made by altering a target sequence within the native gene using a method involving a double-strand-break-inducing agent that is capable of inducing a double-strand break in the DNA of the target sequence as disclosed herein or known in the art. A "targeted mutation" is one type of "targeted modification."

When used herein with respect to DNA, genes, and other nucleic acids, the terms "alteration," "modification," and "mutation" are to be considered equivalent terms unless it is apparent from the context that a different meaning is intended for any one or more of these terms.

A "null mutation" is a mutation in a gene that leads to it not being transcribed into RNA and/or translated into a functional protein product. An allele that comprises the null mutation is referred to a "null allele." A null mutation in a gene can be caused, for example, by an alteration in the gene including (i) replacement of at least one nucleotide, (ii) a deletion of at least one nucleotide, (iii) an insertion of at least one nucleotide, or (iv) any combination of (i)-(iii).

As used herein, a "male fertility gene" is a gene that is critical to steps leading to and including microsporogenesis, the term applied to the entire process of pollen formation. These genes can be collectively referred to as male fertility genes (or, alternatively, male sterility genes). The terms "male fertility gene", "male fertile gene", "male sterility gene" and "male sterile gene" are used interchangeably.

A "fertile plant" is a plant that is capable of producing a progeny plant. In certain embodiments of the invention, a fertile plant is a plant that produces viable male and female gametes and is self fertile. Such a self-fertile plant can produce a progeny plant without the contribution from any other plant of a gamete and the genetic material contained therein. Other embodiments of the invention can involve the use of a plant that is not self fertile because the plant does not produce male or female gametes that are viable or otherwise capable of fertilization. As used herein, a "male sterile plant" is a plant that does not produce male gametes that are viable or otherwise capable of fertilization. As used herein, a "female sterile plant" is a plant that does not produce female gametes that are viable or otherwise capable of fertilization. It is recognized that male-sterile and female-sterile plants can be female-fertile and male-fertile, respectively. It is further recognized that a male-fertile (but female-sterile) plant can produce viable progeny when crossed with a female-fertile plant, and that a female-fertile (but male-sterile) plant can produce viable progeny when crossed with a male fertile plant.

The term "genome" as it applies to a plant cell encompasses not only chromosomal DNA found within the nucleus, but organelle DNA found within subcellular components (e.g., mitochondria, or plastid) of the cell.

A "codon-modified gene" or "codon-preferred gene" or "codon-optimized gene" is a gene having its frequency of codon usage designed to mimic the frequency of preferred codon usage of the host cell.

An "allele" is one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus.

"Coding sequence" refers to a polynucleotide sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, 5' untranslated sequences, 3' untranslated sequences, introns, polyadenylation recognition sequences, RNA processing sites, effector binding sites, and stem-loop structures.

"Promoter" refers to a DNA sequence capable of controlling the expression of a coding sequence or functional RNA. The promoter sequence consists of proximal and more distal upstream elements, the latter elements often referred to as enhancers. An "enhancer" is a DNA sequence that can stimulate promoter activity, and may be an innate element of the promoter or a heterologous element inserted to enhance the activity or tissue-specificity of a promoter. Promoters may be derived in their entirety from a native gene, or be composed of different elements derived from different promoters found in nature, and/or comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters". New promoters of various types useful in plant cells are constantly being discovered; numerous examples may be found in the compilation by Okamuro and Goldberg, (1989) In *The Biochemistry of Plants*, Vol. 115, Stumpf and Conn, eds (New York, N.Y.: Academic Press), pp. 1-82.

"Translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (e.g., Turner and Foster, (1995) *Mol Biotechnol* 3:225-236).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by effecting the addition of polyadenylic acid tracts to the 3' end of the mRNA precursor. The use of different 3' non-coding sequences is exemplified by Ingelbrecht, et al., (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript. A RNA transcript is referred to as the mature RNA when it is a RNA sequence derived from post-transcriptional processing of the primary transcript. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (see, e.g., U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In another example, the complementary RNA regions can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook, et al., *Molecular Cloning: A Laboratory Manual; Cold Spring Harbor Laboratory*: Cold Spring Harbor, N.Y. (1989). Transformation methods are well known to those skilled in the art and are described infra.

"PCR" or "polymerase chain reaction" is a technique for the synthesis of specific DNA segments and consists of a series of repetitive denaturation, annealing, and extension cycles. Typically, a double-stranded DNA is heat denatured, and two primers complementary to the 3' boundaries of the target segment are annealed to the DNA at low temperature, and then extended at an intermediate temperature. One set of these three consecutive steps is referred to as a "cycle".

The term "recombinant" refers to an artificial combination of two otherwise separated segments of sequence, e.g., by chemical synthesis, or manipulation of isolated segments of nucleic acids by genetic engineering techniques.

The terms "plasmid", "vector" and "cassette" refer to an extra chromosomal element often carrying genes that are not part of the central metabolism of the cell, and usually in the form of double-stranded DNA. Such elements may be autonomously replicating sequences, genome integrating sequences, phage, or nucleotide sequences, in linear or circular form, of a single- or double-stranded DNA or RNA, derived from any source, in which a number of nucleotide sequences have been joined or recombined into a unique construction which is capable of introducing a polynucleotide of interest into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for expression of that gene in a foreign host.

The terms "recombinant DNA molecule", "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not all found together in nature. For example, a chimeric construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells. The skilled artisan will also recognize that different independent transformation events may result in different levels and patterns of expression (Jones, et al., (1985) *EMBO J.* 4:2411-2418; De Almeida, et al., (1989) *Mol Gen Genetics* 218:78-86), and thus that multiple events are typically screened in order to obtain lines displaying the desired expression level and pattern. Such screening may be accomplished standard molecular biological, biochemical, and other assays including Southern analysis of DNA, Northern analysis of mRNA expression, PCR, real time quantitative PCR (qPCR), reverse transcription PCR (RT-PCR), immunoblotting analysis of protein expression, enzyme or activity assays, and/or phenotypic analysis.

The term "expression", as used herein, refers to the production of a functional end-product (e.g., an mRNA or a protein) in either precursor or mature form.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid, or mitochondrial DNA), converted into an autonomous replicon, or transiently expressed (e.g., transfected mRNA).

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or other DNA-containing organelle, of a host organism resulting in gene expression without integration or stable inheritance. Host organisms containing the transformed nucleic acid fragments are referred to as "transgenic" organisms.

As used herein, "transgenic" refers to a plant or a cell which comprises within its genome a heterologous polynucleotide. Typically, the heterologous polynucleotide is stably integrated within the genome such that the polynucleotide is passed on to successive generations. The heterologous polynucleotide may be integrated into the genome alone or as part of an expression construct. Transgenic is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

The term "plant" refers to whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores. Plant parts include differentiated and undifferentiated tissues including, but not limited to roots, stems, shoots, leaves, pollen, seeds, tumor tissue and various forms of cells and culture (e.g., single cells, protoplasts, embryos, and callus tissue). The plant tissue may be in plant or in a plant organ, tissue or cell culture. The term "plant organ" refers to plant tissue or a group of tissues that constitute a morphologically and functionally distinct part of a plant. The term "genome" refers to the entire complement of genetic material (genes and non-coding sequences) that is present in each cell of an organism, or virus or organelle; and/or a complete set of chromosomes inherited as a (haploid) unit from one parent. "Progeny" comprises any subsequent generation of a plant.

The present invention finds use in the production of hybrid plants. Mutations that cause male sterility in plants are useful in hybrid seed production methods for crop plants such as, for example, maize. The use of male sterile plants in hybrid maize seed production eliminates the need for the labor-intensive removal of male flowers (also known as de-tasseling when maize is the plant) from the maternal parent plants used to produce the hybrid seed. Mutations that cause male sterility in maize have been produced by a variety of methods such as X-rays or UV-irradiations, chemical treatments, or transposable element insertions (ms23, ms25, ms26, ms32) (Chaubal et al. (2000) *Am J Bot* 87:1193-1201). However, such methods are random mutagenesis methods that induce mutations randomly throughout the genome and not just in the gene of interest. Typically, with such random mutagenesis methods, it requires considerable effort to identify a plant that contains a mutation in the gene of interest and it is by no means certain that such a plant will be identified. Furthermore, with random mutagenesis methods, each plant tested is likely to carry multiple mutations. Therefore, a plant that is identified with the mutation in the gene of interest must be backcrossed for several or more generations to eliminate the undesired mutations that are not within the gene of interest.

In contrast to such random mutagenesis methods, the present invention provides improved methods for producing male sterile plants by making targeted mutations or alterations in a male fertility gene of interest in any plant, particularly any crop plant. Because the mutations are targeted to the male fertility gene of interest, it is not necessary to screen a population of thousands of plants carrying random mutations in order to identify a plant with a mutation in the male fertility gene of interest. Furthermore, undesired mutations outside of the gene of interest are rare, and if they occur are all in a particular plant produced by the methods of the present invention. Therefore, the need to backcross a plant to remove undesired mutations that are not in the gene of interest is eliminated or at least reduced.

In a first aspect, the present invention provides methods for making a targeted modification in a male fertility gene in the genome of a plant. The methods involve contacting at least one plant cell comprising a target sequence in a male fertility gene with an engineered double-strand-break-inducing agent capable of inducing a double-strand break at the target sequence and then identifying at least one cell comprising an alteration in its genome at the target sequence. The methods can further comprise regenerating a fertile plant or a male sterile plant comprising the alteration.

The methods involve the use of an engineered double-strand-break-inducing agent that is capable of inducing a double-strand break in DNA comprising the target sequence in a male fertility gene of interest. The methods of the invention do not depend on a particular engineered double-strand-break-inducing agent but only that the engineered double-strand-break-inducing agent is capable of inducing a double-strand break in DNA in a target sequence of the invention. Any such engineered double-strand-break-inducing agent that is disclosed herein or known in the art can be used in the methods of the present invention. Furthermore, the invention encompasses the use of any engineered double-strand-break-inducing agent that is made by methods disclosed herein or known in the art.

The methods of the invention comprise contacting at least one plant cell comprising a target sequence in a male fertility gene with an engineered double-strand-break-inducing agent capable of inducing a double-strand break at the target sequence. Such contacting can involve, for example, introducing a polypeptide comprising the double-strand-break-inducing agent directly into the plant cell or introducing into the plant cell a nucleic acid construct comprising a nucleotide sequence encoding the engineered double-strand-break-inducing agent, whereby the engineered double-strand-break-inducing agent is produced in the cell. The nucleic acid construct can comprise, for example, a promoter operably linked to a nucleotide sequence encoding an engineered double-strand-break-inducing agent of the invention. Any promoter disclosed herein or known in the art that can drive the expression of the operably linked nucleotide sequence in the plant cell can be used in the methods of the present invention.

If desired or necessary to achieve nuclear localization of the engineered double-strand-break-inducing agent, the nucleotide construct can further comprise an operably linked nucleotide sequence encoding a nuclear localization signal. Any nuclear localization signal that can facilitate nuclear localization of the engineered double-strand-break-inducing agent that is disclosed herein or known in the art can be used in the methods of the present invention. Such nuclear localization signals include, but are not limited to, a nuclear localization signal comprising an amino acid sequence set forth in SEQ ID NO: 2, 3 or 21.

The methods of the invention involve making an alteration at the target sequence. Such an alteration includes, for example, a replacement of at least one nucleotide, a deletion of at least one nucleotide, an insertion of at least one nucleotide, and any combination of one or more replacements, deletions, and insertions.

In one embodiment of the invention, the alteration is an insertion of a transgene. Such a transgene can comprise, for example, one, two, three, four, or more polynucleotides of interest. If desired, a polynucleotide of interest can be operably linked to promoter that is capable of driving the expression of the polynucleotide of interest in a plant. Polynucleotides of interest include, but are not limited to, a phenotypic marker and an RNA or protein providing an agronomic advantage to the plant.

In another embodiment of the invention, the alteration in the target sequence of the male fertility gene is a null mutation. When a plant is homozygous for such a null mutation (i.e., has two null alleles at the male fertility gene of interest), the plant is male sterile. Such a null mutation can result from any of the alterations disclosed hereinabove including, for example, the insertion of a transgene. In certain embodiments of the invention, the transgene comprises a phenotypic marker, particularly a selectable marker. It is recognized that when the null mutation is caused by the insertion of a transgene comprising a phenotypic marker, particularly a selectable marker, identifying plants comprising at least one null allele at the male fertility gene of interest can comprise identifying a plant comprising the phenotypic maker, particularly the selectable marker.

The methods of the invention can further comprise selfing the fertile plant comprising the alteration in the male fertility gene and selecting a progeny plant resulting therefrom, wherein said progeny plant is homozygous for the alteration. In an embodiment of the invention, the methods further comprise selfing the fertile plant comprising an alteration that is a null mutation in the male fertility gene and selecting a progeny plant resulting therefrom, wherein said progeny plant is homozygous for the alteration and is male sterile.

In another embodiment of the invention, the methods of the invention further comprise crossing a first fertile plant comprising a null mutation in the male fertility gene with a second fertile plant comprising a null mutation in the male fertility gene and selecting a progeny plant resulting therefrom, wherein the progeny plant is male sterile. Both the first and second male sterile plants can be produced by the methods as disclosed herein or can be descendants of a fertile plant that is produced by the methods as disclosed herein. The first and second male sterile plants can comprise the same null mutation in the male fertility gene. Alternatively, the first male sterile plant can comprise a first null mutation in the male fertility gene, and the second male sterile plant can comprise a second null mutation in the male fertility gene wherein the first null mutation is not identical to the second null mutation. In one embodiment of the invention, the first null mutation comprises the insertion of a first transgene comprising a first phenotypic marker, particularly a first selectable marker, and the second null mutation comprises the insertion of a second transgene comprising a second phenotypic marker, particularly a second selectable marker. Thus, when the first fertile plant is crossed to the second fertile plant, male sterile progeny which comprise both the first null mutation and the second null mutation can be identified as those progeny plants comprising both the first and second phenotypic markers.

The methods of the invention can be employed to make targeted modifications in any male fertility gene in a plant and thus provide for the production of male sterile plants in any plant comprising a male fertility gene. Male fertility genes of interest include, but are not limited to, the genes disclosed in Table1 and MS26, MS45, BS92-7, 5126 and Msca1.

In one embodiment of the invention, the methods of the invention involve making a targeted modification in the male fertility gene, MS26, in the genome of a plant, such as for example, a maize plant or a sorghum plant. The methods involve contacting at least one plant cell comprising a target sequence in the MS26 gene with an engineered double-strand-break-inducing agent capable of inducing a double-strand break at the target sequence and then identifying at least one cell comprising an alteration, particularly a null mutation, in its genome at the target sequence. The methods further comprise regenerating a fertile plant comprising the alteration.

An example of a target sequence in the MS26 gene that can be used in this embodiment is set forth in TS-MS26 (SEQ ID NO: 1). In this example, any double-strand-break-inducing agent capable of inducing a double-strand break at this target sequence can be used.

The engineered double-strand-break-inducing agent that is cable of inducing a double strand break in the TS-MS26 target sequence comprising SEQ ID NO: 1 can be introduced into a plant as a nucleotide construct comprising a promoter operably linked to a nucleotide sequence encoding the engineered double-strand-break-inducing agent. Any promoter disclosed herein or known in the art that can drive expression of the operably linked nucleotide sequence encoding the engineered double-strand-break-inducing agent in the plant cell can be used in the methods of the present invention. The nucleotide sequence encoding the engineered double-strand-break-inducing agent can be selected from the group consisting of: the nucleotide sequences set forth in SEQ ID NOS: 4 to 7; and a nucleotide sequence having at least 80% nucleotide sequence identity to at least one nucleotide sequence selected from the group consisting of the nucleotide sequences set forth in SEQ ID NOS: 4 to 7. The nucleic acid construct can further comprise an operably linked nuclear localization signal.

In one embodiment, the plant produced by the methods of the invention is a sorghum plant comprising a targeted modification in the male fertility gene MS26, wherein the MS26 gene comprises a nucleotide sequence selected from the group consisting of SEQ ID NOs: 63, 64, 65, 66, 67, 68, 69, 70, 71, 72, 73, 74, 75, 76, 77 and 78.

In another embodiment of the invention, the methods of the invention involve making a targeted modification in the male fertility gene, MS45, in the genome of a plant, such as for example, a maize plant. The methods involve contacting at least one plant cell comprising a target sequence in the MS45 gene with an engineered double-strand-break-inducing agent capable of inducing a double-strand break at the target sequence and then identifying at least one cell comprising an alteration, particularly a null mutation, in its genome at the target sequence. The methods further comprise regenerating a fertile plant comprising the alteration.

An example of a target sequence in the MS45 gene that can be used in this embodiment is set forth in the TS-MS45 target site (SEQ ID NO: 20). The nucleotide sequence encoding the engineered double-strand-break-inducing agent can be selected from the group consisting of: the nucleotide sequences set forth in SEQ ID NOS: 22, 23, and 34; and a nucleotide sequence having at least 80% nucleotide sequence identity to at least one nucleotide sequence selected from the group consisting of the nucleotide sequences set forth in SEQ ID NOS: 22, 23, and 34. The nucleic acid construct can further comprise an operably linked nuclear localization signal.

In this example, any double-strand-break-inducing agent capable of inducing a double-strand break at this target sequence can be used: in one embodiment a first polypeptide encoded by the nucleotide sequence set forth in SEQ ID NO: 22 and a second polypeptide encoded by the nucleotide sequence set forth in SEQ ID NO: 23 can be used. The engineered double-strand-break-inducing agent that is capable of inducing double strand breaks in the TS-MS45 target site (SEQ ID NO: 20) can be introduced into a plant as a nucleotide construct comprising a promoter operably linked to a nucleotide sequence encoding the engineered double-strand-break-inducing agent. Any promoter disclosed herein or known in the art that can drive expression of the operably linked nucleotide sequence encoding the engineered double-strand-break-inducing agent in the plant cell can be used in the methods of the present invention. The nucleotide sequence encoding the engineered double-strand-break-inducing agents includes, but is not limited to, the nucleotide sequence set forth in SEQ ID NO: 22, 23, or 34. The nucleic acid construct can further comprise an operably linked nuclear localization signal.

In a second aspect, the present invention provides a plant comprising in its genome at least one male fertility gene with a targeted modification and descendants thereof that comprise at least one of the male fertility genes with a targeted modification. Such targeted modifications comprise the alterations in a male fertility gene as disclosed hereinabove. The plants of the invention can be made by the methods disclosed herein for making a targeted modification in the genome of a plant including, but not limited to, fertile plants that are heterozygous for a null mutation in a male fertility gene, male sterile plants that are homozygous for a null mutation in the male fertility gene, and plants comprising an alteration in a male fertility gene, wherein the alteration comprises the insertion of a transgene. In one embodiment of the invention, a plant of the invention comprises in its genome the insertion of a transgene in the male fertility gene and such insertion is a null mutation.

In a third aspect, the present invention provides isolated nucleic acid molecules comprising a male fertility gene with at least one targeted modification. Such targeted modifications comprise one or more alterations in a male fertility gene as disclosed hereinabove.

In a fourth aspect, the present invention provides isolated plant-optimized nucleic acid molecules encoding engineered double-strand-break-inducing agents, particularly an engineered double-strand-break-inducing agent derived from I-CreI, more particularly an engineered double-strand-break-inducing agent derived from I-CreI that is capable of inducing double-strand breaks in DNA in a TS-MS26 or TS-MS45 target sequence, most particularly an engineered double-strand-break-inducing agent derived from I-CreI that encodes an engineered MS26 endonuclease or an engineered MS45 endonuclease. Nucleic acid molecules of the invention include, but are not limited to, nucleic acid molecules comprising the nucleotide sequence set forth in SEQ ID NO: 4, 5, 6, 7, 22, 23, or 34, nucleotide sequences and fragments and variants thereof that encode an engineered MS26 endonuclease, an engineered MS26+ endonuclease, an engineered MS26++ endonuclease or an engineered MS45 endonuclease. In one embodiment of the invention, the nucleic acid molecules comprise nucleotide sequences that have been optimized for expression in a plant of interest.

Compositions of the invention include endonucleases that are double-strand-break-inducing agents capable of inducing a double-strand break in a specific recognition or target sequence in a DNA molecule. In particular, the present invention provides for isolated polynucleotides comprising nucleotide sequences encoding endonucleases. The invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Fragments and variants of the disclosed polynucleotides and proteins encoded thereby are also encompassed by the present invention. By "fragment" is intended a portion of the polynucleotide or a portion of the amino acid sequence and hence protein encoded thereby. Fragments of a polynucleotide may encode protein fragments that retain biological activity of the exemplified protein and hence comprise target-sequence-specific endonuclease active, particularly nuclease activity at the TS-MS26 or TS-MS45 target site, as described herein. Thus, fragments of a nucleotide sequence may range from at least about 200 nucleotides, about 400 nucleotides, and up to the full-length polynucleotide encoding the proteins of the invention.

"Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in a polynucleotide sequence disclosed herein. For polynucleotides, conservative variants include those sequences that, because of the degeneracy of the genetic code, encode the amino acid sequence of one of the endonuclease polypeptides of the invention. Variant polynucleotides also include synthetically derived polynucleotides, such as those generated, for example, by using site-directed mutagenesis but which still encode an endonuclease protein of the invention. Generally, variants of a particular polynucleotide of the invention will have at least about 80%, 85%, 90%, 91%, 92%, 93%, 94%, 95%, 96%, 97%, 98%, 99% or more sequence identity to that particular polynucleotide as determined by sequence alignment programs and parameters as described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant proteins encompassed by the present invention are biologically active, that is they continue to possess the desired biological activity of the native protein, that is nuclease activity at the TS-MS26 or TS-MS45 target site, as described herein. Biologically active variants of an endonuclease protein of the invention will have at least about 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants and fragments of the endonuclease proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Variant polypeptides will continue to possess the desired nuclease activity at the TS-MS26 or TS-MS45 target site. Obviously, the mutations that will be made in the DNA encoding the variant must not place the sequence out of reading frame and optimally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays (Lucas et al. 2001 (*Nucl. Acids Res.* 29: 960-969).

Variant polynucleotides and proteins also encompass sequences and proteins derived from a mutagenic and recombinogenic procedure such as DNA shuffling. With such a procedure, one or more different endonuclease sequences can be manipulated to create a new endonuclease possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The methods of the present invention involve the use of one or more double-strand-break-inducing agents. A double-strand-break-inducing agent of the present invention is any agent that recognizes and/or binds to a specific polynucleotide recognition sequence to produce a break in the target sequence at or near the recognition sequence. Examples of double-strand-break-inducing agents include, but are not limited to, endonucleases, site-specific recombinases, transposases, topoisomerases, TAL effector nucleases, and zinc finger nucleases, and include modified derivatives, variants, and fragments thereof.

A recognition sequence is any polynucleotide sequence that is specifically recognized and/or bound by a double-strand-break-inducing agent. The length of the recognition site sequence can vary, and includes, for example, sequences that are at least 4, 6, 8, 10, 12, 14, 16, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more nucleotides in length.

It is possible that the recognition site could be palindromic, that is, the sequence on one strand reads the same in the opposite direction on the complementary strand. The nick/cleavage site could be within the recognition sequence or the nick/cleavage site could be outside of the recognition sequence. In another variation, the cleavage could occur at nucleotide positions immediately opposite each other to produce a blunt end cut or, in other cases, the incisions could be staggered to produce single-stranded overhangs, also called "sticky ends", which can be either 5' overhangs, or 3' overhangs. The recognition sequence can be endogenous or exogenous. When the recognition site is an endogenous sequence, it may be a recognition sequence recognized by a naturally-occurring, or native double-strand-break-inducing agent. Alternatively, an endogenous recognition site could be recognized and/or bound by a modified or engineered double-strand-break-inducing agent designed or selected to specifically recognize the endogenous recognition sequence to produce a double-strand break. A modified double-strand-break-inducing agent can be derived from a native, naturally-occurring double-strand-break-inducing agent or it could be artificially created or synthesized.

A variety of methods are available to identify those cells having an altered genome at or near the recognition sequence without using a screenable marker phenotype. Such methods can be viewed as directly analyzing a recognition sequence to detect any change in the recognition sequence, including but not limited to PCR methods, sequencing methods, nuclease digestion, Southern blots, and any combination thereof.

Proteins may be altered in various ways including amino acid substitutions, deletions, truncations, and insertions. Methods for such manipulations are generally known. For example, amino acid sequence variants of the protein(s) can be prepared by mutations in the DNA. Methods for mutagenesis and nucleotide sequence alterations include, for example, Kunkel, (1985) *Proc. Natl. Acad. Sci. USA* 82:488-92; Kunkel, et al., (1987) *Meth Enzymol* 154:367-82; U.S. Pat. No. 4,873,192; Walker and Gaastra, eds. (1983) *Techniques in Molecular Biology* (MacMillan Publishing Company, New York) and the references cited therein. Guidance regarding amino acid substitutions not likely to affect biological activity of the protein is found, for example, in the model of Dayhoff, et al., (1978) *Atlas of Protein Sequence and Structure* (Natl Biomed Res Found, Washington, D.C.). Conservative substitutions, such as exchanging one amino acid with another having similar properties, may be preferable. Conservative deletions, insertions, and amino acid substitutions are not expected to produce radical changes in the characteristics of the protein, and the effect of any substitution, deletion, insertion, or combination thereof can be evaluated by routine screening assays. Assays for double-strand-break-inducing activity are known and generally measure the overall activity and specificity of the agent on DNA substrates containing recognition sites.

Any meganuclease can be used as a double-strand break inducing agent including, but not limited to, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NcIIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-Scat, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any variant or derivative thereof.

A site-specific recombinase, also referred to as a recombinase, is a polypeptide that catalyzes conservative site-specific recombination between its compatible recombination sites, and includes native polypeptides as well as derivatives, variants and/or fragments that retain activity, and native polynucleotides, derivatives, variants, and/or fragments that encode a recombinase that retains activity.

One step in the recombination process involves polynucleotide cleavage at or near the recognition site. This cleaving activity can be used to produce a double-strand break. For reviews of site-specific recombinases and their recognition sites, see, Sauer (1994) *Curr Op Biotechnol* 5:521-7; and Sadowski, (1993) *FASEB* 7:760-7.

The Integrase family of recombinases has over one hundred members and includes, for example, FLP, Cre, lambda integrase, and R. The Integrase family has been grouped into two classes based on the structure of the active sites, serine recombinases and tyrosine recombinases. The tyrosine family, which includes Cre, FLP, SSV1, and lambda (λ) integrase, uses the catalytic tyrosine's hydroxyl group for a nucleophilic attack on the phosphodiester bond of the DNA. Typically, members of the tyrosine family initially nick the DNA, which later forms a double-strand break. In the serine recombinase family, which includes phiC31 (φC31) integrase, a conserved serine residue forms a covalent link to the DNA target site (Grindley et al., (2006) *Ann Rev Biochem* 16:16). For other members of the Integrase family, see for example, Esposito et al., (1997) *Nucleic Acids Res* 25:3605-14 and Abremski et al., (1992) *Protein Eng* 5:87-91.

Other recombination systems include, for example, the streptomycete bacteriophage phiC31 (Kuhstoss, et al., (1991) *J Mol Biol* 20:897-908); the SSV1 site-specific recombination system from *Sulfolobus shibatae* (Maskhelishvili, et al., (1993) *Mol Gen Genet.* 237:334-42); and a retroviral integrase-based integration system (Tanaka, et al., (1998) *Gene* 17:67-76).

Sometimes the recombinase is one that does not require cofactors or a supercoiled substrate, including but not limited to Cre, FLP, and active derivatives, variants or fragments thereof. FLP recombinase catalyzes a site-specific reaction during DNA replication and amplification of the two-micron plasmid of *S. cerevisiae*. FLP recombinase catalyzes site-specific recombination between two FRT sites. The FLP protein has been cloned and expressed (Cox, (1993) *Proc. Natl. Acad. Sci. USA* 80:4223-7). Functional derivatives, variants, and fragments of FLP are known (Buchholz, et al., (1998) *Nat Biotechnol* 16:617-8, Hartung, et al., (1998) *J Biol Chem* 273:22884-91, Saxena, et al., (1997) *Biochim Biophys Acta* 1340:187-204, and Hartley, et al., (1980) *Nature* 286:860-4).

The bacteriophage recombinase Cre catalyzes site-specific recombination between two lox sites (Guo, et al., (1997) *Nature* 389:40-6; Abremski, et al., (1984) *J Biol Chem* 259:1509-14; Chen, et al., (1996) *Somat Cell Mol Genet.* 22:477-88; Shaikh, et al., (1977) *J Biol Chem* 272:5695-702; and, Buchholz, et al., (1998) *Nat Biotechnol* 16:617-8). Examples of site-specific recombinases that can be used to produce a double-strand break at a recognition sequence, including for example FLP, Cre, SSV1, lambda Int, phi C31, HK022, and R. Examples of site-specific recombination systems used in plants can be found in U.S. Pat. No. 5,929,301; U.S. Pat. No. 6,175,056; WO99/25821; U.S. Pat. No. 6,331,661; WO99/25855; WO99/25841, and WO99/25840, the contents of each are herein incorporated by reference.

Methods for modifying the kinetics, cofactor interaction and requirements, expression, optimal conditions, and/or recognition site specificity, and screening for activity of recombinases and variants are known, see for example Miller, et al., (1980) *Cell* 20:721-9; Lange-Gustafson and Nash, (1984) *J Biol Chem* 259:12724-32; Christ, et al., (1998) *J Mol Biol* 288:825-36; Lorbach, et al., (2000) *J Mol Biol* 296:1175-81; Vergunst, et al., (2000) *Science* 290:979-82; Dorgai, et al., (1995) *J Mol Biol* 252:178-88; Dorgai, et al., (1998) *J Mol Biol* 277:1059-70; Yagu, et al., (1995) *J Mol Biol* 252:163-7; Sclimente, et al., (2001) *Nucleic Acids Res* 29:5044-51; Santoro and Schultze, (2002) *Proc. Natl. Acad. Sci. USA* 99:4185-90; Buchholz and Stewart, (2001) *Nat Biotechnol* 19:1047-52; Voziyanov, et al., (2002) *Nucleic Acids Res* 30:1656-63; Voziyanov, et al., (2003) *J Mol Biol* 326:65-76; Klippel, et al., (1988) *EMBO J.* 7:3983-9; Arnold, et al., (1999) *EMBO J.* 18:1407-14; WO03/08045; WO99/25840; and WO99/25841. The recognition sites range from about 30 nucleotide minimal sites to a few hundred nucleotides.

Any recognition site for a recombinase can be used, including naturally occurring sites, and variants. Variant recognition sites are known, see for example Hoess, et al., (1986) *Nucleic Acids Res* 14:2287-300; Albert, et al., (1995) *Plant J* 7:649-59; Thomson, et al., (2003) *Genesis* 36:162-7; Huang, et al., (1991) *Nucleic Acids Res* 19:443-8; Siebler and Bode, (1997) *Biochemistry* 36:1740-7; Schlake and Bode, (1994) *Biochemistry* 33:12746-51; Thygarajan, et al., (2001) *Mol Cell Biol* 21:3926-34; Umlauf and Cox, (1988) *EMBO J.* 7:1845-52; Lee and Saito, (1998) *Gene* 216:55-65; WO01/23545; WO99/25821; WO99/25851; WO01/11058; WO01/07572 and U.S. Pat. No. 5,888,732.

A recombinase can be provided via a polynucleotide that encodes the recombinase or it can be provided via a modified polynucleotide encoding the recombinase. For example, the polynucleotide (encoding a recombinase) can be modified to substitute codons having a higher frequency of usage in a plant, as compared to the naturally occurring polynucleotide sequence, or it can be modified to substitute codons having a higher frequency of usage in a maize or soybean plant, as compared to the naturally occurring polynucleotide sequence.

TAL effector nucleases are a new class of sequence-specific nucleases that can be used to make double-strand breaks at specific target sequences in the genome of a plant or other organism. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al. (2010) *PNAS* 10.1073/pnas.1013133107; Scholze & Boch (2010) *Virulence* 1:428-432; Christian et al. *Genetics* (2010) 186:757-761; Li et al. (2010) *Nuc. Acids Res*. (2010) doi:10.1093/nar/gkq704; and Miller et al. (2011) *Nature Biotechnology* 29:143-148; all of which are herein incorporated by reference.

Transposases are polypeptides that mediate transposition of a transposon from one location in the genome to another. Transposases typically induce double-strand breaks to excise the transposon, recognize subterminal repeats, and bring together the ends of the excised transposon; in some systems other proteins are also required to bring together the ends during transposition.

Examples of transposons and transposases include, but are not limited to, the Ac/Ds, Dt/rdt, Mu-M1/Mn, and Spm(En)/dSpm elements from maize, the Tam elements from snapdragon, the Mu transposon from bacteriophage, bacterial transposons (Tn) and insertion sequences (IS), Ty elements of yeast (retrotransposon), Ta1 elements from *Arabidopsis* (retrotransposon), the P element transposon from *Drosophila* (Gloor, et al., (1991) *Science* 253:1110-1117), the Copia, Mariner and Minos elements from *Drosophila*, the Hermes elements from the housefly, the PiggyBack elements from *Trichplusia ni*, Tc1 elements from *C. elegans*, and IAP elements from mice (retrotransposon). In some examples the transposase is provided via a polynucleotide that encodes the transposase.

It is possible to modify the polynucleotide encoding the transposase by substituting codons having a higher frequency of usage in a plant, as compared to the naturally occurring polynucleotide sequence, by substituting codons having a higher frequency of usage in a maize or soybean plant, as compared to the naturally occurring polynucleotide sequence.

DNA topoisomerases modulate DNA secondary and higher order structures and functions related primarily to replication, transcription, recombination and repair. Topoisomerases share two characteristics: (i) the ability to cleave and reseal the phosphodiester backbone of DNA in two successive transesterification reactions; and (ii) once a topoisomerase-cleaved DNA intermediate is formed, the enzyme allows the severed DNA ends to come apart, allowing the passage of another single- or double-stranded DNA segment. DNA topoisomerases can be classified into three evolutionarily independent families: type IA, type IB and type II.

Those that cleave one strand of DNA and allow single step changes in the linking number of circular DNA are defined as type I DNA topoisomerases. The *Escherichia coli* topoisomerase I and topoisomerase III, *Saccharomyces cerevisiae* topoisomerase III and reverse gyrase belong to the type IA or type I-5' subfamily as the protein link is to a 5' phosphate in the DNA. The prototype of type IB or I-3' enzymes are found in all eukaryotes and also in vaccinia virus topoisomerase I where the protein is attached to a 3' phosphate. Despite differences in mechanism and specificity between the bacterial and eukaryotic enzymes, yeast DNA topoisomerase I can complement a bacterial DNA topoisomerase I mutant (Bjornsti, et al., (1987) *Proc. Natl. Acad. Sci. USA* 84:8971-5). Type IA topoisomerases relax negatively supercoiled DNA and require magnesium and a single-stranded region of DNA. Topoisomerases IB relax both positively and negatively supercoiled DNA with equal efficiency and do not require a single-stranded region of DNA or metal ions for function.

The type II family includes *E. coli* DNA gyrase, *E. coli* topoisomerase IV (par E), eukaryotic type II topoisomerases, and archaic topoisomerase VI. Type II enzymes are homodimeric (eukaryotic topoisomerase II) or tetrameric (gyrase), cleaving both strands of a duplex. Preferred cutting sites are known for available topoisomerases.

Zinc finger nucleases (ZFNs) are engineered double-strand-break-inducing agents comprised of a zinc finger DNA binding domain and a double-strand-break-inducing agent domain. Recognition site specificity is conferred by the zinc finger domain, typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs consist of an engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, where a 3 finger domain recognizes a sequence of 9 contiguous nucleotides, with a dimerization requirement of the nuclease, two sets of zinc finger triplets are used to bind an 18 nucleotide recognition sequence. A recognition sequence of 18 nucleotides is long enough to be unique in a mammalian genome ($4^{18}=6.9\times10^{10}$).

To date, designer zinc finger modules predominantly recognize GNN and ANN triplets (Dreier, et al., (2001) *J Biol Chem* 276:29466-78; Dreier, et al., (2000) *J Mol Biol* 303:489-502; Liu, et al., (2002) *J Biol Chem* 277:3850-6), but examples using CNN or TNN triplets are also known (Dreier, et al., (2005) *J Biol Chem* 280:35588-97; Jamieson, et al., (2003) *Nature Rev Drug Discov* 2:361-8). See also, Durai, et al., (2005) *Nucleic Acids Res* 33:5978-90; Segal, (2002) *Methods* 26:76-83; Porteus and Carroll, (2005) *Nat Biotechnol* 23:967-73; zinc-finger consortium (website at www.zincfinger.org); Pabo, et al., (2001) *Ann Rev Biochem* 70:313-40; Wolfe, et al., (2000) *Ann Rev Biophys Biomol Struct* 29:183-212; Segal and Barbas, (2001) *Curr Opin Biotechnol* 12:632-7; Segal, et al., (2003) *Biochemistry* 42:2137-48; Beerli and Barbas, (2002) *Nat Biotechnol* 20:135-41; Carroll, et al., (2006) *Nature Protocols* 1:1329; Ordiz, et al., (2002) *Proc. Natl. Acad. Sci. USA* 99:13290-5; Guan, et al., (2002) *Proc. Natl. Acad. Sci. USA* 99:13296-301; WO2002099084; WO00/42219; WO02/42459; WO2003062455; U.S. Patent Application Publication No. 20030059767; U.S. Patent Application Publication No. 2003/0108880; U.S. Pat. Nos. 6,140,466, 6,511,808 and 6,453,242.

Alternatively, engineered zinc finger DNA binding domains can be fused to other double-strand-break-inducing agents or derivatives thereof that retain DNA nicking/cleaving activity. For example, this type of fusion can be used to direct the double-strand-break-inducing agent to a different target site, to alter the location of the nick or cleavage site, to direct the inducing agent to a shorter target site, or to direct the inducing agent to a longer target site. In some examples a zinc finger DNA binding domain is fused to a site-specific recombinase, transposase, topoisomerase, or a derivative thereof that retains DNA nicking and/or cleaving activity.

It is possible to provide a zinc-finger nuclease via a polynucleotide that encodes the zinc-finger nuclease. This polynucleotide encoding the zinc-finger nuclease can be modified by substituting codons having a higher frequency of usage in a plant, as compared to the naturally occurring polynucleotide sequence or by substituting codons having a higher frequency of usage in a maize or soybean plant, as compared to the naturally occurring polynucleotide sequence.

Sufficient homology or sequence identity indicates that two polynucleotide sequences have sufficient structural similarity to act as substrates for a homologous recombination reaction. The structural similarity includes overall length of each polynucleotide fragment, as well as the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

The amount of homology or sequence identity shared by a target and a donor polynucleotide can vary and includes total lengths and/or regions having unit integral values in the ranges of about 1-20 bp, 20-50 bp, 50-100 bp, 75-150 bp, 100-250 bp, 150-300 bp, 200-400 bp, 250-500 bp, 300-600 bp, 350-750 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, 5-10 kb, or up to and including the total length of the target site. These ranges include every integer within the range, for example, the range of 1-20 bp includes 1, 2, 3, 4, 5, 6, 7, 8, 9, 10, 11, 12, 13, 14, 15, 16, 17, 18, 19 and 20 bp. The amount of homology can also described by percent sequence identity over the full aligned length of the two polynucleotides which includes percent sequence identity of about at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. Sufficient homology includes any combination of polynucleotide length, global percent sequence identity, and optionally conserved regions of contiguous nucleotides or local percent sequence identity, for example sufficient homology can be described as a region of 75-150 bp having at least 80% sequence identity to a region of the target locus. Sufficient homology can also be described by the predicted ability of two polynucleotides to specifically hybridize under high stringency conditions, see, for example, Sambrook, et al., (1989) *Molecular Cloning: A Laboratory Manual*, (Cold Spring Harbor Laboratory Press, NY); *Current Protocols in Molecular Biology*, Ausubel, et al., Eds (1994) Current Protocols, (Greene Publishing Associates, Inc. and John Wiley & Sons, Inc); and, Tijssen, (1993) *Laboratory Techniques in Biochemistry and Molecular Biology—Hybridization with Nucleic Acid Probes*, (Elsevier, New York).

Any means can be used to bring together the various components needed to alter the genome of a dicot plant cell. For example, in in vitro systems, the double-strand-break-inducing agent and the polynucleotide(s) comprising the recognition site(s) can be provided by contacting the components under the appropriate conditions for DNA cleavage.

Alternatively a variety of methods are known for the introduction of nucleotide sequences and polypeptides into an organism, including, for example, transformation, sexual crossing, and the introduction of the polypeptide, DNA, or mRNA into the cell.

Methods for contacting, providing, and/or introducing a composition into various organisms are known and include but are not limited to, stable transformation methods, transient transformation methods, virus-mediated methods, and sexual breeding. Stable transformation indicates that the introduced polynucleotide integrates into the genome of the organism and is capable of being inherited by progeny thereof. Transient transformation indicates that the introduced composition is only temporarily expressed or present in the organism.

Protocols for introducing polynucleotides and polypeptides into plants may vary depending on the type of plant or plant cell targeted for transformation, such as monocot or dicot. Suitable methods of introducing polynucleotides and polypeptides into plant cells and subsequent insertion into the plant genome include microinjection (Crossway, et al., (1986) *Biotechniques* 4:320-34 and U.S. Pat. No. 6,300,543), meristem transformation (U.S. Pat. No. 5,736,369), electroporation (Riggs, et al., (1986) *Proc. Natl. Acad. Sci. USA* 83:5602-6, *Agrobacterium*-mediated transformation (U.S. Pat. Nos. 5,563,055 and 5,981,840), direct gene transfer (Paszkowski, et al., (1984) *EMBO J.* 3:2717-22), and ballistic particle acceleration (U.S. Pat. Nos. 4,945,050; 5,879,918; 5,886,244; 5,932,782; Tomes, et al., (1995) "Direct DNA Transfer into Intact Plant Cells via Microprojectile Bombardment" in *Plant Cell, Tissue, and Organ Culture: Fundamental Methods*, ed. Gamborg & Phillips (Springer-Verlag, Berlin); McCabe, et al., (1988) *Biotechnology* 6:923-6; Weissinger, et al., (1988) *Ann Rev Genet.* 22:421-77; Sanford, et al., (1987) *Particulate Science and Technology* 5:27-37 (onion); Christou, et al., (1988) *Plant Physiol* 87:671-4 (soybean); Finer and McMullen, (1991) *In Vitro Cell Dev Biol* 27P:175-82 (soybean); Singh, et al., (1998) *Theor Appl Genet.* 96:319-24 (soybean); Datta, et al., (1990) *Biotechnology* 8:736-40 (rice); Klein, et al., (1988) *Proc. Natl. Acad. Sci. USA* 85:4305-9 (maize); Klein, et al., (1988) *Biotechnology* 6:559-63 (maize); U.S. Pat. Nos. 5,240,855; 5,322,783 and 5,324,646; Klein, et al., (1988) *Plant Physiol* 91:440-4 (maize); Fromm, et al., (1990) *Biotechnology* 8:833-9 (maize); Hooykaas-Van Slogteren, et al., (1984) *Nature* 311:763-4; U.S. Pat. No. 5,736,369 (cereals); Bytebier, et al., (1987) *Proc. Natl. Acad. Sci. USA* 84:5345-9 (*Liliaceae*); De Wet, et al., (1985) in *The Experimental Manipulation of Ovule Tissues*, ed. Chapman, et al., (Longman, N.Y.), pp. 197-209 (pollen); Kaeppler, et al., (1990) *Plant Cell Rep* 9:415-8) and Kaeppler, et al., (1992) *Theor Appl Genet.* 84:560-6 (whisker-mediated transformation); D'Halluin, et al., (1992) *Plant Cell* 4:1495-505 (electroporation); Li, et al., (1993) *Plant Cell Rep* 12:250-5; Christou and Ford (1995) *Annals Botany* 75:407-13 (rice) and Osjoda, et al., (1996) *Nat Biotechnol* 14:745-50 (maize via *Agrobacterium tumefaciens*).

Alternatively, polynucleotides may be introduced into plants by contacting plants with a virus or viral nucleic acids. Generally, such methods involve incorporating a polynucleotide within a viral DNA or RNA molecule. In some examples a polypeptide of interest may be initially synthesized as part of a viral polyprotein, which is later processed by proteolysis in vivo or in vitro to produce the desired recombinant protein. Methods for introducing polynucleotides into plants and expressing a protein encoded therein, involving viral DNA or RNA molecules, are known, see, for example, U.S. Pat. Nos. 5,889,191, 5,889,190, 5,866,785, 5,589,367 and 5,316,931. Transient transformation methods include, but are not limited to, the introduction of polypeptides, such as a double-strand-break-inducing agent, directly into the organism, the introduction of polynucleotides such as DNA and/or RNA polynucleotides, and the introduction of the RNA transcript, such as an mRNA encoding a double-strand-break-inducing agent, into the organism. Such methods include, for example, microinjection or particle bombardment. See, for example Crossway, et al., (1986) *Mol Gen Genet.* 202:179-85; Nomura, et al., (1986) *Plant Sci* 44:53-8; Hepler, et al., (1994) *Proc. Natl. Acad. Sci. USA* 91:2176-80; and, Hush, et al., (1994) *J Cell Sci* 107:775-84.

Standard DNA isolation, purification, molecular cloning, vector construction, and verification/characterization methods are well established, see, for example Sambrook, et al., (1989) *Molecular Cloning: A Laboratory Manual*, (Cold Spring Harbor Laboratory Press, NY). Vectors and constructs include circular plasmids, and linear polynucleotides, comprising a polynucleotide of interest and optionally other components including linkers, adapters, regulatory regions, introns, restriction sites, enhancers, insulators, selectable markers, nucleotide sequences of interest, promoters, and/or other sites that aid in vector construction or analysis. In some examples a recognition site and/or target site can be contained within an intron, coding sequence, 5' UTRs, 3' UTRs, and/or regulatory regions.

Any promoter can be used, and can be selected based on the desired outcome. A promoter is a region of DNA involved in recognition and binding of RNA polymerase and other proteins to initiate transcription. A plant promoter is a promoter capable of initiating transcription in a plant cell; for a review of plant promoters, see, Potenza, et al., (2004) *In Vitro Cell Dev Biol* 40:1-22. Constitutive promoters include, for example, the core promoter of the Rsyn7 promoter and other constitutive promoters disclosed in WO99/43838 and U.S. Pat. No. 6,072,050; the core CaMV 35S promoter (Odell, et al., (1985) *Nature* 313:810-2); rice actin (McElroy, et al., (1990) *Plant Cell* 2:163-71); ubiquitin (Christensen, et al., (1989) *Plant Mol Biol* 12:619-32; Christensen, et al., (1992) *Plant Mol Biol* 18:675-89); pEMU (Last, et al., (1991) *Theor Appl Genet.* 81:581-8); MAS (Velten, et al., (1984) *EMBO J.* 3:2723-30); ALS promoter (U.S. Pat. No. 5,659,026), and the like. Other constitutive promoters are described in, for example, U.S. Pat. Nos. 5,608,149; 5,608,144; 5,604,121; 5,569,597; 5,466,785; 5,399,680; 5,268,463; 5,608,142 and 6,177,611. In some examples an inducible promoter may be used. Pathogen-inducible promoters induced following infection by a pathogen include, but are not limited to those regulating expression of PR proteins, SAR proteins, beta-1,3-glucanase, chitinase, etc.

Chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. Chemical-inducible promoters include, but are not limited to, the maize In2-2 promoter, activated by benzene sulfonamide herbicide safeners (De Veylder, et al., (1997) Plant Cell Physiol 38:568-77), the maize GST promoter (GST-II-27, WO93/01294), activated by hydrophobic electrophilic compounds used as pre-emergent herbicides, and the tobacco PR-1a promoter (Ono, et al., (2004) Biosci Biotechnol Biochem 68:803-7) activated by salicylic acid. Other chemical-regulated promoters include steroid-responsive promoters (see, for example, the glucocorticoid-inducible promoter (Schena, et al., (1991) Proc. Natl. Acad. Sci. USA 88:10421-5; McNellis, et al., (1998) Plant J 14:247-257); tetracycline-inducible and tetracycline-repressible promoters (Gatz, et al., (1991) Mol Gen Genet. 227:229-37; U.S. Pat. Nos. 5,814,618 and 5,789,156).

Tissue-preferred promoters can be utilized to target enhanced expression within a particular plant tissue. Tissue-preferred promoters include, for example, Kawamata, et al., (1997) Plant Cell Physiol 38:792-803; Hansen, et al., (1997) Mol Gen Genet. 254:337-43; Russell, et al., (1997) Transgenic Res 6:157-68; Rinehart, et al., (1996) Plant Physiol 112:1331-41; Van Camp, et al., (1996) Plant Physiol 112:525-35; Canevascini, et al., (1996) Plant Physiol 112:513-524; Lam, (1994) Results Probl Cell Differ 20:181-96; and Guevara-Garcia, et al., (1993) Plant J 4:495-505. Leaf-preferred promoters include, for example, Yamamoto, et al., (1997) Plant J 12:255-65; Kwon, et al., (1994) Plant Physiol 105:357-67; Yamamoto, et al., (1994) Plant Cell Physiol 35:773-8; Gotor, et al., (1993) Plant J 3:509-18; Orozco, et al., (1993) Plant Mol Biol 23:1129-38; Matsuoka, et al., (1993) Proc. Natl. Acad. Sci. USA 90:9586-90; Simpson, et al., (1958) EMBO J. 4:2723-9; Timko, et al., (1988) Nature 318:57-8. Root-preferred promoters include, for example, Hire, et al., (1992) Plant Mol Biol 20:207-18 (soybean root-specific glutamine synthase gene); Miao, et al., (1991) Plant Cell 3:11-22 (cytosolic glutamine synthase (GS)); Keller and Baumgartner, (1991) Plant Cell 3:1051-61 (root-specific control element in the GRP 1.8 gene of French bean); Sanger, et al., (1990) Plant Mol Biol 14:433-43 (root-specific promoter of A. tumefaciens mannopine synthase (MAS)); Bogusz, et al., (1990) Plant Cell 2:633-41 (root-specific promoters isolated from Parasponia andersonii and Trema tomentosa); Leach and Aoyagi, (1991) Plant Sci 79:69-76 (A. rhizogenes rolC and rolD root-inducing genes); Teeri, et al., (1989) EMBO J. 8:343-50 (Agrobacterium wound-induced TR1' and TR2' genes); VfENOD-GRP3 gene promoter (Kuster, et al., (1995) Plant Mol Biol 29:759-72); and rolB promoter (Capana, et al., (1994) Plant Mol Biol 25:681-91; phaseolin gene (Murai, et al., (1983) Science 23:476-82; Sengopta-Gopalen, et al., (1988) Proc. Natl. Acad. Sci. USA 82:3320-4). See also, U.S. Pat. Nos. 5,837,876; 5,750,386; 5,633,363; 5,459,252; 5,401,836; 5,110,732 and 5,023,179.

Seed-preferred promoters include both seed-preferred promoters active during seed development, as well as seed-germinating promoters active during seed germination. See, Thompson, et al., (1989) BioEssays 10:108. Seed-preferred promoters include, but are not limited to, Cim1 (cytokinin-induced message); cZ19B1 (maize 19 kDa zein); and milps (myo-inositol-1-phosphate synthase) (WO00/11177; and U.S. Pat. No. 6,225,529). For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa gamma zein, waxy, shrunken 1, shrunken 2, globulin 1, oleosin, and nuc1. See also, WO00/12733, where seed-preferred promoters from END1 and END2 genes are disclosed.

A phenotypic marker is a screenable or selectable marker that includes visual markers and selectable markers, whether it is a positive or negative selectable marker. Any phenotypic marker can be used. Specifically, a selectable or screenable marker comprises a DNA segment that allows one to identify, or select for or against, a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products which provide resistance against otherwise toxic compounds including antibiotics, such as, spectinomycin, ampicillin, kanamycin, tetracycline, Basta, neomycin phosphotransferase II (NEO) and hygromycin phosphotransferase (HPT)); DNA segments that encode products which are otherwise lacking in the recipient cell (e.g., tRNA genes, auxotrophic markers); DNA segments that encode products which can be readily identified (e.g., phenotypic markers such as β-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequence required for a specific modification (e.g., methylation) that allows its identification.

Additional selectable markers include genes that confer resistance to herbicidal compounds, such as glufosinate ammonium, bromoxynil, imidazolinones, and 2,4-dichloro-phenoxyacetate (2,4-D). See for example, Yarranton, (1992) Curr Opin Biotech 3:506-11; Christopherson, et al., (1992) Proc. Natl. Acad. Sci. USA 89:6314-8; Yao, et al., (1992) Cell 71:63-72; Reznikoff, (1992) Mol Microbiol 6:2419-22; Hu, et al., (1987) Cell 48:555-66; Brown, et al., (1987) Cell 49:603-12; Figge, et al., (1988) Cell 52:713-22; Deuschle, et al., (1989) Proc. Natl. Acad. Sci. USA 86:5400-4; Fuerst, et al., (1989) Proc. Natl. Acad. Sci. USA 86:2549-53; Deuschle, et al., (1990) Science 248:480-3; Gossen, (1993) Ph.D. Thesis, University of Heidelberg; Reines, et al., (1993) Proc. Natl. Acad. Sci. USA 90:1917-21; Labow, et al., (1990) Mol Cell Biol 10:3343-56; Zambretti, et al., (1992) Proc. Natl. Acad. Sci. USA 89:3952-6; Baim, et al., (1991) Proc. Natl. Acad. Sci. USA 88:5072-6; Wyborski, et al., (1991) Nucleic Acids Res 19:4647-53; Hillen and Wissman, (1989) Topics Mol Struc Biol 10:143-62; Degenkolb, et al., (1991) Antimicrob Agents Chemother 35:1591-5; Klein-schnidt, et al., (1988) Biochemistry 27:1094-104; Bonin, (1993) Ph.D. Thesis, University of Heidelberg; Gossen, et al., (1992) *Proc. Natl. Acad. Sci. USA* 89:5547-51; Oliva, et al., (1992) *Antimicrob Agents Chemother* 36:913-9; Hlavka, et al., (1985) *Handbook of Experimental Pharmacology*, Vol. 78 (Springer-Verlag, Berlin); Gill, et al., (1988) *Nature* 334:721-4.

A cell having the introduced sequence may be grown or regenerated into a plant using conventional conditions, see for example, McCormick, et al., (1986) *Plant Cell Rep* 5:81-4. This plant may then be grown, and either pollinated with the same transformed strain or with a different transformed or untransformed strain, and the resulting progeny having the desired characteristic and/or comprising the introduced polynucleotide or polypeptide identified. Two or more generations may be grown to ensure that the polynucleotide is stably maintained and inherited, and seeds harvested.

Any plant can be used, including moncot and dicot plants. Examples of monocot plants that can be used include, but are not limited to, corn (*Zea mays*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), wheat (*Triticum aestivum*), sugarcane (*Saccharum* spp.), oats (*Avena*), barley (*Hordeum*), pineapple (*Ananas comosus*), banana (*Musa* spp.), palm, ornamentals, and grasses. Examples of dicot plants that can be used include, but are not limited to, soybean (*Glycine max*), canola (*Brassica napus* and *B. campestris*), alfalfa (*Medicago sativa*), tobacco (*Nicotiana tabacum*), Arabidopsis (*Arabidopsis thaliana*), sunflower (*Helianthus annuus*), cotton (*Gossypium arboreum*), and peanut (*Arachis hypogaea*), tomato (*Solanum lycopersicum*), potato (*Solanum tuberosum*) etc.

The transgenes, recombinant DNA molecules, DNA sequences of interest, and polynucleotides of interest can comprise one or more genes of interest. Such genes of interest can encode, for example, a protein that provides agronomic advantage to the plant. Genes of interest can be reflective of the commercial markets and interests of those involved in the development of the crop. Crops and markets of interest change, and as developing nations open up world markets, new crops and technologies will emerge also. In addition, as understanding of agronomic traits and characteristics such as yield and heterosis increases, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) *Eur. J. Biochem.* 165:99-106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497-502; herein incorporated by reference); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) *Gene* 48:109); and the like.

Genes encoding disease resistance traits include detoxification genes, such as against fumonosin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene); glyphosate (e.g., the EPSPS gene and the GAT gene; see, for example, U.S. Publication No. 20040082770 and WO 03/092360); or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development. Interference with pollen formation, function, or dispersal may be accomplished by disrupting starch accumulation as described in U.S. Pat. No. 7,969,405 and U.S. Pat. No. 7,612,251.

The quality of grain is reflected in traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802, and 5,990,389.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) *J. Bacteriol.* 170:5837-5847) facilitate expression of polyhyroxyalkanoates (PHAs).

Exogenous products include plant enzymes and products as well as those from other sources including procaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

The transgenes, recombinant DNA molecules, DNA sequences of interest, and polynucleotides of interest can be comprise one or more DNA sequences for gene silencing. Methods for gene silencing involving the expression of DNA sequences in plant are known in the art include, but are not limited to, cosuppression, antisense suppression, double-stranded RNA (dsRNA) interference, hairpin RNA (hpRNA) interference, intron-containing hairpin RNA (ihpRNA) interference, transcriptional gene silencing, and micro RNA (miRNA) interference Cosuppression may be used to inhibit the expression of plant genes to produce plants having undetectable protein levels for the proteins encoded by these genes. See, for example, Broin et al. (2002) *Plant Cell* 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell et al. (1994) *Proc. Natl. Acad. Sci. USA* 91:3490-3496; Jorgensen et al. (1996) *Plant Mol. Biol.* 31:957-973; Johansen and Carrington (2001) *Plant Physiol.* 126:930-938; Broin et al. (2002) *Plant Cell* 14:1417-1432; Stoutjesdijk et al (2002) *Plant Physiol.* 129:1723-1731; Yu et al. (2003) *Phytochemistry* 63:753-763; and U.S. Pat. Nos. 5,034,323, 5,283,184, and 5,942,657; each of which is herein incorporated by reference. The efficiency of cosuppression may be increased by including a poly-dT region in the expression cassette at a position 3' to the sense sequence and 5' of the polyadenylation signal. See, U.S. Patent Publication No. 20020048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323; herein incorporated by reference.

Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550, or greater may be used. Methods for using antisense suppression to inhibit the expression of endogenous genes in plants are described, for example, in Liu et al (2002) *Plant Physiol.* 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, U.S. Patent Publication No. 20020048814, herein incorporated by reference.

Methods for using dsRNA interference to inhibit the expression of endogenous plant genes are described in Waterhouse et al. (1998) *Proc. Natl. Acad. Sci. USA* 95:13959-13964, Liu et al. (2002) *Plant Physiol.* 129:1732-1743, and WO 99/49029, WO 99/53050, WO 99/61631, and WO 00/49035; each of which is herein incorporated by reference.

Methods of hpRNA interference are described in Waterhouse and Helliwell (2003) *Nat. Rev. Genet.* 4:29-38 and the references cited therein. These methods are highly efficient at inhibiting the expression of endogenous genes. See, for example, Chuang and Meyerowitz (2000) *Proc. Natl. Acad. Sci. USA* 97:4985-4990; Stoutjesdijk et al. (2002) *Plant Physiol.* 129:1723-1731; and Waterhouse and Helliwell (2003) *Nat. Rev. Genet.* 4:29-38. Methods for using hpRNA interference to inhibit or silence the expression of genes are described, for example, in Chuang and Meyerowitz (2000) *Proc. Natl. Acad. Sci. USA* 97:4985-4990; Stoutjesdijk et al. (2002) *Plant Physiol.* 129:1723-1731; Waterhouse and Helliwell (2003) *Nat. Rev. Genet.* 4:29-38; Pandolfini et al. *BMC Biotechnology* 3:7, and U.S. Patent Publication No. 20030175965; each of which is herein incorporated by reference. A transient assay for the efficiency of hpRNA constructs to silence gene expression in vivo has been described by Panstruga et al. (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith et al. (2000) *Nature* 407:319-320. In fact, Smith et al. show 100% suppression of endogenous gene expression using ihpRNA-mediated interference. Methods for using ihpRNA interference to inhibit the expression of endogenous plant genes are described, for example, in Smith et al. (2000) *Nature* 407: 319-320; Wesley et al. (2001) *Plant J.* 27:581-590; Wang and Waterhouse (2001) *Curr. Opin. Plant Biol.* 5:146-150; Waterhouse and Helliwell (2003) *Nat. Rev. Genet.* 4:29-38; Helliwell and Waterhouse (2003) *Methods* 30:289-295, and U.S. Patent Publication No. 20030180945, each of which is herein incorporated by reference.

Transcriptional gene silencing (TGS) may be accomplished through use of hpRNA constructs wherein the inverted repeat of the hairpin shares sequence identity with the promoter region of a gene to be silenced. Processing of the hpRNA into short RNAs which can interact with the homologous promoter region may trigger degradation or methylation to result in silencing (Aufsatz et al. (2002) *PNAS* 99 (Suppl. 4):16499-16506; Mette et al. (2000) *EMBO J.* 19(19):5194-5201).

The inhibition of the expression of a target protein may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example Javier et al. (2003) *Nature* 425: 257-263, herein incorporated by reference. For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). miRNA molecules are highly efficient at inhibiting the expression of endogenous genes, and the RNA interference they induce is inherited by subsequent generations of plants.

The frequency of homologous recombination is influenced by a number of factors. Different organisms vary with respect to the amount of homologous recombination and the relative proportion of homologous to non-homologous recombination. Generally, the length of the region of homology affects the frequency of homologous recombination events, the longer the region of homology, the greater the frequency. The length of the homology region needed to observe homologous recombination is also species-variable. In many cases, at least 5 kb of homology has been utilized, but homologous recombination has been observed with as little as 25-50 bp of homology. The minimum length of homology needed has been estimated at 20-50 bp in *E. coli* (Singer, et al., (1982) *Cell* 31:25-33; Shen and Huang, (1986) *Genetics* 112:441-57; Watt, et al., (1985) *Proc. Natl. Acad. Sci. USA* 82:4768-72), 63-89 bp in *Sacchromyces cerevisaie* (Sugawara and Haber, (1992) *Mol Cell Biol* 12:563-75), and 163-300 bp in mammalian cells (Rubnitz and Subramani, (1984) *Mol Cell Biol* 4:2253-8; Ayares, et al., (1986) *Proc. Natl. Acad. Sci. USA* 83:5199-203; Liskay, et al., (1987) *Genetics* 115:161-7).

Homologous recombination has been demonstrated in insects. In *Drosophila*, Dray and Gloor found that as little as 3 kb of total template:target homology sufficed to copy a large non-homologous segment of DNA into the target with reasonable efficiency (Dray and Gloor, (1997) *Genetics* 147:689-99). Using FLP-mediated DNA integration at a target FRT in *Drosophila*, Golic, et al., showed integration was approximately 10-fold more efficient when the donor and target shared 4.1 kb of homology as compared to 1.1 kb of homology (Golic, et al., (1997) *Nucleic Acids Res* 25:3665). Data from *Drosophila* indicates that 2-4 kb of homology is sufficient for efficient targeting, but there is some evidence that much less homology may suffice, on the order of about 30 bp to about 100 bp (Nassif and Engels, (1993) *Proc. Natl. Acad. Sci. USA* 90:1262-6; Keeler and Gloor, (1997) *Mol Cell Biol* 17:627-34).

Homologous recombination has also been accomplished in other organisms. For example, at least 150-200 bp of homology was required for homologous recombination in the parasitic protozoan *Leishmania* (Papadopoulou and Dumas, (1997) *Nucleic Acids Res* 25:4278-86). In the filamentous fungus *Aspergillus nidulans*, gene replacement has been accomplished with as little as 50 bp flanking homology (Chaveroche, et al., (2000) *Nucleic Acids Res* 28:e97). Targeted gene replacement has also been demonstrated in the ciliate Tetrahymena thermophila (Gaertig, et al., (1994) *Nucleic Acids Res* 22:5391-8). In mammals, homologous recombination has been most successful in the mouse using pluripotent embryonic stem cell lines (ES) that can be grown in culture, transformed, selected and introduced into a mouse embryo. Embryos bearing inserted transgenic ES cells develop as genetically chimeric offspring. By interbreeding siblings, homozygous mice carrying the selected genes can be obtained. An overview of the process is provided in Watson, et al., (1992) Recombinant DNA, 2nd Ed., (Scientific American Books distributed by WH Freeman & Co.); Capecchi, (1989) *Trends Genet.* 5:70-6; and Bronson, (1994) *J Biol Chem* 269:27155-8. Homologous recombination in mammals other than mouse has been limited by the lack of stem cells capable of being transplanted to oocytes or developing embryos. However, McCreath, et al., *Nature* 405:1066-9 (2000) reported successful homologous recombination in sheep by transformation and selection in primary embryo fibroblast cells.

Error-prone DNA repair mechanisms can produce mutations at double-strand break sites. The nonhomologous end-joining (NHEJ) pathways are the most common repair mechanism to bring the broken ends together (Bleuyard, et al., (2006) *DNA Repair* 5:1-12). The structural integrity of chromosomes is typically preserved by the repair, but deletions, insertions, or other rearrangements are possible. The two ends of one double-strand break are the most prevalent substrates of NHEJ (Kirik, et al., (2000) *EMBO J.* 19:5562-6), however if two different double-strand breaks occur, the free ends from different breaks can be ligated and result in chromosomal deletions (Siebert and Puchta, (2002) *Plant Cell* 14:1121-31), or chromosomal translocations between different chromosomes (Pacher, et al., (2007) *Genetics* 175: 21-9).

Episomal DNA molecules can also be ligated into the double-strand break, for example, integration of T-DNAs into chromosomal double-strand breaks (Chilton and Que, (2003) *Plant Physiol* 133:956-65; Salomon and Puchta, (1998) *EMBO J.* 17:6086-95). Once the sequence around the double-strand breaks is altered, for example, by exonuclease activities involved in the maturation of double-strand breaks, gene conversion pathways can restore the original structure if a homologous sequence is available, such as a homologous chromosome in non-dividing somatic cells, or a sister chromatid after DNA replication (Molinier, et al., (2004) *Plant Cell* 16:342-52). Ectopic and/or epigenic DNA sequences may also serve as a DNA repair template for homologous recombination (Puchta, (1999) *Genetics* 152: 1173-81).

Alteration of the genome of a plant cell, for example, through homologous recombination (HR), is a powerful tool for genetic engineering. Despite the low frequency of homologous recombination in higher plants, there are a few examples of successful homologous recombination of plant endogenous genes. The parameters for homologous recombination in plants have primarily been investigated by rescuing introduced truncated selectable marker genes. In these experiments, the homologous DNA fragments were typically between 0.3 kb to 2 kb. Observed frequencies for homologous recombination were on the order of $10^{-4}$ to $10^{-5}$. See, for example, Halfter, et al., (1992) *Mol Gen Genet.* 231:186-93; Offring a, et al., (1990) *EMBO J.* 9:3077-84; Offring a, et al., (1993) *Proc. Natl. Acad. Sci. USA* 90:7346-50; Paszkowski, et al., (1988) *EMBO J.* 7:4021-6; Hourda and Paszkowski, (1994) *Mol Gen Genet.* 243:106-11; and Risseeuw, et al., (1995) *Plant J* 7:109-19.

An endogenous, non-selectable gene was targeted in *Arabidopsis* using a targeting vector containing a region of about 7 kb homologous to the target gene and the targeting frequency was estimated to be at least $3.9 \times 10^{-4}$ (Maio and Lam, (1995) *Plant J* 7:359-65). In another example, using a positive-negative selection scheme and a targeting vector containing up to 22.9 kb of sequence homologous to the target, homologous recombination was detected with a frequency less than $5.3 \times 10^{-5}$, despite the large flanking sequences available for recombination (Thykjær, et al., (1997) *Plant Mol Biol* 35:523-30). In *Arabidopsis*, the AGL5 MADS-box gene was knocked out by homologous recombination using a targeting construct consisting of a kanamycin-resistance cassette inserted into the AGL5 sequence roughly 3 kb from the 5' end and 2 kb from the 3' end. Of the 750 kanamycin-resistant transgenic lines that were generated, one line contained the anticipated insertion (Kempin, et al., (1997) *Nature* 389:802-3). Hanin, et al., obtained homologous recombination events at a basal frequency of 7×10 using 3 kb 5'-end and 2 kb 3'-end homology to the *Arabidopsis* PPO gene encoding protoporphyrinogen oxidase (Hanin, et al., (2001) *Plant J* 28:671-7). Terada, et al., targeted the Waxy locus in rice using an *Agrobacterium*-mediated transformation procedure. Negative selection, in the form of two copies of the diphteria toxin gene placed at both ends of T-DNA, was used to eliminate random integration of T-DNAs, allowing for enrichment of rare homologous recombination events in the selected material, and their transformation system generated thousands of events from just 150 rice seeds. The reported frequency of homologous recombination of the waxy gene in rice was $0.65 \times 10^{-3}$, without inclusion of elements to enhance homologous recombination (Terada, et al., (2002) *Nat Biotech* 20:1030-4).

DNA double-strand breaks (DSBs) appear to be an effective factor to stimulate homologous recombination pathways in every organism tested to date (Puchta, et al., (1995) *Plant Mol Biol* 28:281-92; Tzfira and White, (2005) *Trends Biotechnol* 23:567-9; Puchta, (2005) *J Exp Bot* 56:1-14). Using DNA-breaking agents, two- to nine-fold increase of homologous recombination was observed between artificially constructed homologous DNA repeats in plants (Puchta, et al., (1995) *Plant Mol Biol* 28:281-92). In maize protoplasts, experiments with linear DNA molecules demonstrated enhanced homologous recombination between plasmids (Lyznik, et al., (1991) *Mol Gen Genet.* 230:209-18).

The effects of DSBs on homologous recombination have been investigated by using rare-cutting as well as transposons such as Ac and Mutator (Chiurazzi, et al., (1996) *Plant Cell* 8:2057-66; Puchta, et al., (1996) *Proc. Natl. Acad. Sci. USA* 93:5055-60; Xiao and Peterson, (2000) *Mol Gen Genet.* 263:22-9; and Shalev and Levy (1997) *Genetics* 146:1143-51). Chiurazzi, et al., (1996) *Plant Cell* 8:2057-66) introduced DSBs into an *Arabidopsis* chromosome using HO-endonuclease and observed 10-fold increase in the frequency of homologous recombination between repeats flanking the HO recognition site. Excision of Ac transposable elements also stimulated homologous recombination between repeats flanking the elements at an even higher frequency (Xiao and Peterson (2000) *Mol Gen Genet.* 263: 22-9). Puchta et al. reported that homologous recombination frequency at an artificial target locus was increased by up to two orders of magnitude when DSBs were generated using I-SceI (Puchta, et al., (1996) *Proc. Natl. Acad. Sci. USA* 93:5055-60). In experiment of Puchta et al., I-SceI expression cassette was introduced into transgenic tobacco target lines together with targeting construct by co-inoculation with the two respective *Agrobacterium* strains. Homologous recombination between T-DNA containing the targeting construct and the target site reconstituted the kanamycin-resistance gene (nptII). There was an apparent correlation between frequency of homologous recombination and the amount of I-SceI expression cassette, suggesting that more DSBs yielded higher homologous recombination frequency.

High frequency of homologous recombination at a pre-introduced artificial target site was obtained using a zinc-finger nuclease (ZFN) in tobacco (Wright, et al., (2005) *Plant J* 44:693-705). The zinc-finger nuclease expression cassette and donor DNA were introduced into protoplasts by co-electroporation and targeted modification was monitored by kanamycin resistance and GUS activity. One modified event was observed in approximately every 10 transformants, however, only 20% of the modified events contained the desired homologous recombination products as indicated by Southern blot analysis.

Zinc finger nucleases are engineered endonucleases with altered specificities, for example by fusion of an engineered DNA binding domain to an endonuclease, for example, FokI (Durai, et al., (2005) *Nucleic Acids Res* 33:5978-90; Mani, et al., (2005) *Biochem Biophys Res Comm* 335:447-57). Wright, et al., and Lloyd, et al., reported a high frequency mutagenesis at a DNA target site integrated into tobacco or *Arabidopsis* chromosomal DNA using zinc-finger nucleases (Wright, et al., (2005) *Plant J* 44:693-705; Lloyd, et al., (2005) *Proc. Natl. Acad. Sci. USA* 102:2232-7). Using a designed zinc-finger nuclease recognizing a tobacco endogenous acetolactate synthase (ALS) gene locus, a mutated ALS gene known to confer resistance to imidazolinone and sulphonylurea herbicides was introduced to replace the endogenous ALS gene at frequencies exceeding 2% of transformed cells (Townsend, et al., (2009) *Nature* 459:442-5). The knock-out of an endogenous gene and the expression of a transgene can be achieved simultaneously by gene targeting. The IPK1 gene, which encodes inositol-1,3,4,5,6-pentakisphosphate 2-kinase needed in the final step of phytate biosynthesis in maize seeds, was targeted using a designed zinc-finger nuclease to insert via homologous recombination a PAT gene, which encodes phosphinothricin acetyl transferase tolerance to glufosinate ammonium herbicides such as bialaphos. The disruption of the IPK1 gene with the insertion of the PAT gene resulted in both herbicide tolerance and the expected alteration of the inositol phosphate profile in developing seeds (Shukla, et al., (2009) *Nature* 459:437-41).

Members of the serine family of recombinases produce double-strand breaks at the recombination sites as a part of their catalytic activities (Grindley, et al., (2006) *Ann Rev Biochem* 16:16). The R/RS system in sweet orange appeared to induce mutations of RS sites leading to chromosomal deletions not associated with site-specific recombination reactions per se (Ballester, et al., (2006) *Plant Cell Rep* 26:39-45).

Another approach uses protein engineering of existing homing endonucleases to alter their target specificities. Homing endonucleases, such as I-SceI or I-CreI, bind to and cleave relatively long DNA recognition sequences (18 bp and 22 bp, respectively). These sequences are predicted to naturally occur infrequently in a genome, typically only 1 or 2 sites/genome. The cleavage specificity of a homing endonuclease can be changed by rational design of amino acid substitutions at the DNA binding domain and/or combinatorial assembly and selection of mutated monomers (see, for example, Arnould, et al., (2006) *J Mol Biol* 355:443-58; Ashworth, et al., (2006) *Nature* 441:656-9; Doyon, et al., (2006) *J Am Chem Soc* 128:2477-84; Rosen, et al., (2006) *Nucleic Acids Res* 34:4791-800; and Smith, et al., (2006) *Nucleic Acids Res* 34:e149; Lyznik, et al., (2009) U.S. Patent Application Publication No. 20090133152A1; Smith, et al., (2007) U.S. Patent Application Publication No. 20070117128A1). Engineered meganucleases have been demonstrated that can cleave cognate mutant sites without broadening their specificity. An artificial recognition site specific to the wild type yeast I-SceI homing nuclease was introduced in maize genome and mutations of the recognition sequence were detected in 1% of analyzed F1 plants when a transgenic I-SceI was introduced by crossing and activated by gene excision (Yang, et al., (2009) *Plant Mol Biol* 70:669-79). More practically, the maize liguleless locus was targeted using an engineered single-chain endonuclease designed based on the I-CreI meganuclease sequence. Mutations of the selected liguleless locus recognition sequence were detected in 3% of the T0 transgenic plants when the designed homing nuclease was introduced by *Agrobacterium*-mediated transformation of immature embryos (Gao, et al., (2010) *Plant J* 61:176-87).

The DNA repair mechanisms of cells are the basis of transformation to introduce extraneous DNA or induce mutations of endogenous genes. DNA homologous recombination is a specialized way of DNA repair in which the cells repair DNA damage using a homologous sequence. In plants, DNA homologous recombination happens at frequencies too low to be used in transformation until it has been found that the process can be stimulated by DNA double-strand breaks (Bibikova et al. (2001) *Mol. Cell. Biol.* 21:289-297; Puchta and Baltimore (2003) *Science* 300:763; Wright et al. (2005) *Plant J.* 44:693-705).

EXAMPLES

The present invention is further defined in the following Examples, in which parts and percentages are by weight and degrees are Celsius, unless otherwise stated. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Such modifications are also intended to fall within the scope of the appended claims.

The meaning of abbreviations is as follows: "sec" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kb" means kilobase(s).

Example 1

DNA Double-Strand-Break-Induced Alteration of an Endogenous Target Site

When a DNA double-strand-break-inducing agent recognizes and cleaves the specific recognition sequence at a target site in the genome, a DNA double-strand break is formed, triggering the cell DNA repair mechanisms to mobilize to repair the damage that could be fatal to the cell. The process can be utilized in plant transformation to introduce mutations specifically at the target site to knock out the gene residing at the target site or to insert a donor DNA of interest at the target site. Once the DNA double-strand break is formed, depending on the designs of the DNA constructs involved and the actual processes of DNA repair, different outcomes can be obtained serving different transformation purposes.

For simple site-specific gene mutations, a target site containing a recognition sequence (FIG. 1A) and a DNA double-strand break agent such as a endonuclease (FIG. 1B) that recognizes specifically the recognition sequence have to be present in the same cell. After the endonuclease recognizes and cuts the DNA, the two free ends can be repaired through end joining by the cell DNA repair machinery without the intervention of any external factors. The two ends can be repaired to the original state so no change can be detected, or they can be altered before being repaired resulting in detectable changes after they are connected again such as the deletion of one or more nucleotides of the recognition sequence and possibly extra surrounding sequences (FIG. 1F). Mutations are introduced at the target site by the latter process.

To achieve site-specific DNA insertions, a donor DNA containing the DNA of interest has to be simultaneously present in the cell in addition to the target site and the endonuclease. The donor DNA can contain the same DNA sequences that flank the target site to flank the DNA of interest, i.e., the homologous sequences (FIG. 1C). The DNA of interest can be inserted at the target site by homologous recombination (FIG. 1E), a process that is stimulated by the DNA double-strand break at the target site. The donor DNA can also contain only the DNA of interest without any flanking homologous sequences (FIG. 1D). The DNA of interest can still be inserted at the target site, though in a less predictable fashion, through non-homologous recombination. Similarly, any unrelated DNA that happens to be present when the DNA ends are repaired can be inserted at the target site (FIG. 1G). The different outcomes (FIGS. 1E-G) can be obtained simultaneously in the same transformation experiment.

Any means to make a DNA double-strand break in vivo can be used as the DNA double-strand-break-inducing agent such as the most commonly used meganucleases which recognize >18 bp sequences long enough to be unique in most genomes. Numerous meganucleases have been found and characterized to recognize many different sequences, but such sequences are often not naturally present in important crops such as soybean or maize. Even if similar sequences can be found in crop genomes, the limited numbers of these sequences are still too small to be useful. Certain meganucleases such as I-CreI can be modified by protein engineering in such a way that it will no longer preferentially recognize the recognition sequence of wild type I-CreI and instead will preferentially recognize specifically selected sequences of interest. Taking advantage of the flexibility of the I-CreI endonuclease, one can design and make a modified I-CreI to cleave a target site of choice in the genome and subsequently introduce mutations or insert genes of interest at the selected target site. The precise genetic engineering that this methodology provides will solve many problems that traditional plant transformation methods such as *Agrobacterium* infection and biolistic bombardment currently face, such as unpredictable integration, unwanted endogenous gene interruption, unpredicted transgene expression, etc.

Example 2

Male-Sterile Maize Plants Produced by the Targeted Mutagenesis of a Cytochrome P450-Like Gene, MS26, Using an Engineered MS26 Endonuclease ZmMS26 is a locus of interest for making a male sterile mutation in maize located on the short arm of chromosome 1. The maize MS26 gene (SEQ ID NO: 8; AF366297) consists of five exons and it encodes an amino acid sequence (SEQ ID NO 12; AAK52956.1) that shows substantial homology to the CYP70481-Zm gene—a member of the extensive (over 26 genes) family of the maize cytochrome P450 monooxygenases. The heme domain, essential for catalytic activity, is found in the fifth exon (U.S. Pat. No. 7,517,975). Null mutants of the maize MS26 gene cause premature termination of microspore development in anther locules as this gene has been implicated in pollen wall formation (Li et al. (2010) Plant Cell; 22:173). Frameshift or premature termination mutations in this region are expected to knockout the maize MS26 gene function.

An engineered I-CreI-based homing endonuclease, referred to as engineered MS26 endonuclease, was able to produce double-strand breaks in the maize MS26 gene leading to the introduction of mutations that knockout function of the MS26 protein. The process is advantageous because it does not require a dedicated selection step or a modification of routine transformation protocols. As anticipated, single-nucleotide deletions or insertions at the MS26 coding sequence produced sterile maize plants.

A. TS-MS26 Target Site and Engineered MS26 Endonucleases

A target site designated "TS-MS26" target site (SEQ ID NO: 1) was selected for design of a custom double-strand-break-inducing agent. The TS-MS26 target site is a 22 bp polynucleotide positioned 62 bps from the 5' end of the fifth exon of the maize MS26 gene and having the following sequence:

gatggtgacgtac^gtgccctac.    (SEQ ID NO: 1)

The double strand break site and overhang region is underlined; the enzyme cuts after C13, as indicated by the ^. Plant optimized nucleotide sequences for three engineered endonucleases (SEQ ID NO:4 encoding engineered MS26 endonuclease; SEQ ID NO: 5 and 7 encoding engineered MS26+ endonuclease; SEQ ID NO: 6 encoding engineered MS26++ endonuclease) were designed based on the I-CreI homing endonuclease to bind and make double-strand breaks at the selected TS-MS26 target site (SEQ ID NO: 1).

B. Vector Construction for Plant Expression Vectors Encoding the Engineered MS26 Endonucleases and Repair DNAs for Transgene Integration by Homologous Recombination Vectors comprising expression cassettes for the appropriate engineered endonuclease were constructed using standard molecular biological techniques.

Plant expression cassettes contained the plant codon-optimized nucleotide sequence encoding the engineered MS26 endonuclease for better performance in maize cells. These plant optimized sequences were also supplemented with DNA sequences encoding nuclear localization signals added to the N-terminus of the protein (SEQ ID NO: 2) for the engineered MS26 endonuclease and SEQ ID NO: 3 for the engineered MS26++ endonuclease. The maize ubiquitin promoter and the potato proteinase inhibitor II gene terminator sequences completed the gene designs. In some cases, the plant optimized nucleotide sequence encoding the engineered MS26+ endonuclease (SEQ ID NO:5) was additionally modified by addition of the ST-LS1 intron to the coding sequence of the first endonuclease monomer in order to eliminate its expression in E. coli and Agrobacterium (SEQ ID NO 7). The expression cassette containing the plant optimized nucleotide sequence encoding the engineered MS26++ endonuclease (SEQ ID NO:6) also contained the ST-LS1 intron inserted into the coding sequences of the first monomer in order to eliminate its expression in E. coli and Agrobacterium and its codon sequence was optimized for GC content.

These expression cassettes were inserted into T-DNA molecules that were also equipped with a BAR or a moPAT selectable marker gene allowing for selection of transgenic events on media containing bialaphos. No selection was applied for mutations at the TS-MS26 target site.

C. Production of Transgenic Plants

Maize (Zea mays) immature embryos were transformed by a modified Agrobacterium-mediated transformation procedure as described in (Djukanovic et al. 2006). Ten to eleven day old immature embryos (1.3-1.8 mm) were dissected from sterilized kernels and placed into 2 ml of liquid medium [4.0 g/L N6 Basal Salts (Sigma C-1416; Sigma-Aldrich Co., St. Louis, Mo., USA), 1.0 ml/L Eriksson's Vitamin Mix (Sigma E-1511), 1.0 mg/L thiamine HCl, 1.5 mg/L 2,4-dichlorophenoxyacetic acid (2,4-D), 0.690 g/L L-proline, 68.5 g/L sucrose, 36.0 g/L glucose, pH 5.2]. The Agrobacterium suspension was diluted down to O.D. of 0.175 at 550 nm. The embryo-containing medium was replaced with 1 ml of the Agrobacterium suspension and the embryos were allowed to incubate for five minutes at room temperature. After incubating, the embryos (40 embryos/plate) were transferred, embryo axis down, onto a plate containing 4.0 g/L N6 Basal Salts (Sigma C-1416), 1.0 ml/L Eriksson's Vitamin Mix (Sigma E-1511), 1.0 mg/L thiamine HCl, 1.5 mg/L 2,4-D, 0.690 g/L L-proline, 30.0 g/L sucrose, 0.85 mg/L silver nitrate, 0.1 nM acetosyringone, 3.0 g/L Gelrite, pH 5.8. Embryos were incubated in the dark for 3-4 days at 21° C. and then transferred to media containing 4.0 g/L N6 Basal Salts (Sigma C-1416), 1.0 ml/L Eriksson's Vitamin Mix (Sigma E-1511), 0.5 mg/L thiamine HCl, 1.5 mg/L 2,4-D, 0.690 g/L L-proline, 30.0 g/L sucrose, 0.5 g/L 2-(N-morpholino)ethanesulphonic acid (MES) Buffer, 0.85 mg/L silver nitrate, 100 mg/L carbenicillin, and 8 g/L Sigma Agar for an additional four days of incubation in the dark at 28° C. The embryos were then transferred (19 embryos/plate) onto new plates containing 4.0 g/L N6 Basal Salts (Sigma C-1416), 1.0 ml/L Eriksson's Vitamin Mix (Sigma E-1511), 0.5 mg/L thiamine HCl, 1.5 mg/L 2,4-D, 0.69 g/L L-proline, 30.0 g/L sucrose, 0.5 g/L MES buffer, 0.85 mg/L silver nitrate, 1.5 mg/L Bialaphos, 100 mg/L carbenicillin, 8.0 g/L agar, pH 5.8, and placed in the dark at 28° C. After three weeks, the responding callus (7 calli/plate) was subcultured onto media containing 4.0 g/L N6 Basal Salts (Sigma C-1416), 1.0 ml/L Eriksson's Vitamin Mix (Sigma E-1511), 0.5 mg/L thiamine HCl, 1.5 mg/L 2,4-D, 0.69 g/L L-proline, 30.0 g/L sucrose, 0.5 g/L MES buffer, 0.85 mg/L silver nitrate, 3.0 mg/L Bialaphos, 100 mg/L carbenicillin, 8.0 g/L agar, pH 5.8. After five weeks in the dark at 28° C. somatic embryogenesis was induced by transferring a small amount of selected tissue onto a regeneration medium (1 transgenic event/plate) containing 4.3 g/L Murashige and Skoog (MS) salts (Gibco 11117; Gibco, Grand Island, N.Y.), 5.0 ml/L MS Vitamins Stock Solution (Sigma M3900), 100 mg/L myo-inositol, 0.1 DM abscisic acid (ABA), 1 mg/L indoleacetic acid (IAA), 0.5 mg/L zeatin, 60.0 g/L sucrose, 3.0 mg/L Bialaphos, 100 mg/L carbenicillin, 6.0 g/L Ultra-pure Agar, pH 5.6. The plates were incubated in the dark for 2-3 weeks at 28° C. All material with visible shoots and roots was transferred (5-10 shoots per event/plate) onto media containing 4.3 g/L MS salts (Gibco 11117), 5.0 ml/L MS Vitamins Stock Solution (Sigma M3900), 100 mg/L myo-inositol, 40.0 g/L sucrose, 3 mg/L Bialaphos, 100 mg/L Benomyl 6.0 g/L Bacto-Agar, pH 5.6, and incubated under artificial light at 28° C. One week later, plantlets were moved into glass tubes (1 plantlet/tube) containing the same medium minus the Bialaphos and grown under artificial light until they were sampled and/or transplanted into soil.

Four versions of plant optimized sequences encoding the engineered endonuclease targeting the TS-MS26 target site (SEQ. ID NO:4, SEQ. ID NO:5, SEQ ID NO:6 or SEQ. ID NO:7) were delivered by *Agrobacterium*-mediated transformation of immature maize embryos. Over 1,000 T0 plants were produced, each plant regenerated from an independent callus tissue selected on media containing 1.5 mg/L Bialaphos. Transformation efficiency represented the percentage of co-cultivated embryos that produced transformation events. The transformation frequency ranged from 14% to 35% for the engineered MS26 endonuclease; this was within the routine transformation frequencies recorded for other genes used for genetic transformation of the maize embryos with similar *Agrobacterium* strains.

D. Screening for Mutations at the TS-MS26 Target Site and Selecting Mutant Plants.

T0 plants were screened for mutations at the TS-MS26 target site by PCR amplification of the TS-MS26 target site region and subsequent digestion of the PCR product with the BsiWI restriction enzyme, which cuts within TS-MS26 target site, followed by gel electrophoresis of the restriction digestion products. Failure to cut the PCR amplified target site region to completion with BsiWI indicated that a mutation had occurred. Three mutated MS26 alleles were identified among 300 T0 plants from the transformation experiment using SEQ ID NO:5 (Table 2) and three mutated MS26 alleles were identified among 257 analyzed T0 plants from the experiment using SEQ ID NO: 7. No mutant MS26 alleles were found in the transformation experiment using SEQ ID NO: 4. The highest frequency of mutant alleles was observed when SEQ ID NO: 6 was used in the transformation experiment, yielding 15 mutations among 344 analyzed T0 plants (Table 2).

The results are presented in Table 2. Mutation rate represents the percentage of T0 analyzed plants containing a mutation at the TS-MS26 target site. The mutated ms26 alleles found in the T0 plants were centered on the apparent 3' end GTAC overhang produced by the engineered endonucleases (FIG. 2).

TABLE 2

Mutation rate at the TS-MS26 target site of T0 maize plants expressing engineered endonucleases

| Endonuclease (Plant optimized sequence) | # analyzed T0 plants | # mutations | Mutation rate* |
|---|---|---|---|
| MS26 (SEQ ID NO: 4) | 229 | 0 | 0 |
| MS26+ (SEQ ID NO: 5) | 300 | 3 | 1% |
| MS26+ (SEQ ID NO: 7) | 257 | 3 | 1.2% |
| MS26++ (SEQ ID NO: 6) | 344 | 15 | 5.8% |

T0 plants at time of flowering are shown in FIG. 8. There was no obvious difference in the growth and development of T0 plants containing one mutated ms26 allele (two outside plants) as compared to the T0 biallelic event (the tagged plant) produced by the engineered MS26++ endonuclease (A). The biallelic event was sterile (the tassel at anthesis shown between two tassels from monoallelic events) (B).

Selected T0 plants containing one nucleotide insertion (ms26-Ci) or one nucleotide deletion (ms26-Td) in the endogenous MS26 gene were grown in a greenhouse and self-pollinated to produce T1 progeny plants. The MS26 alleles present in the T1 plants were determined by PCR assays on leaf DNA samples of T1 plants. Segregation of the ms26-Ci (one nucleotide insertion) and ms26-Td (one nucleotide deletion) alleles in the T1 progeny is shown in Table 3.

TABLE 3

Segregation data of progeny from T0 plants that were self pollinated.

| T0 allele (mutation) | # T1 seeds planted | # T1seeds germinated | MS26/ MS26 | Genotype MS26/ms26 | ms26/ ms26 |
|---|---|---|---|---|---|
| ms26-Ci | 100 | 69 | 25 | 27 | 17 |
| ms26-Td | 100 | 93 | 26 | 50 | 17 |

E. Sterility Induced by the Mutations at the TS-MS26 Target Site.

T1 sibling maize plants derived from selfing two original T0 plants each carrying a mutation in the MS26 gene (ms26-Ci and ms26-Td) were cultivated under standard growing conditions. FIG. 9A shows one heterozygous MS26/ms26– and one homozygous ms26–/ms26– plant derived from each T0 event at flowering time. All plants were similar in stature and reached maturity at similar times. The silks emerged from the husks at the tips of the ears over a period of few days in all. The close-up photos of mature tassel inflorescences at anthesis are shown in FIGS. 9B and 9C. The plants produced spikelet-containing tassels with central rachis and branches. Only heterozygous MS26/ms26-C1 and MS26/ms26-Td T1 sibling plants developed anthers that were hanging on elongated filaments. The tassels of the ms26-Ci/ms26-Ci and ms26-Td/ms26-Td homozygous sibling plants contained spikelets with no evidence of emerging anthers, indicating male sterility.

Example 3

Male-Sterile Rice Plants Produced by the Targeted Mutagenesis of a Cytochrome P450-Like Gene, MS26, Using an Engineered MS26 Endonuclease The maize MS26 gene (ZmMS26, Accession No. AF366297; SEQ ID NO: 8) and its orthologues in rice (Accession No. LOC_Os03g07250; SEQ ID NO: 9) sorghum (SEQ ID NO: 10) and rye (SEQ ID NO: 11) encode a cytochrome P450, CYP704B family (U.S. Pat. App. Pub. No. 2009/0183284), proposed to catalyze the production of omega-hydroxylated fatty acids with 16 and 18 carbon chains (Li et al. (2010) *Plant Cell* 22:173). Homozygous recessive mutations that disrupt the coding frame of the maize (U.S. Pat. No. 7,517,975) or rice MS26 genes result in the plant's inability to generate functional pollen grains which is likely due to reduced production of fatty acids critical to pollen wall formation (Li et al. (2010) *Plant Cell* 22:173). The MS26 genes from maize, rice, sorghum and rye all contain an identical 22 nucleotide sequence, referred to as the "TS-MS26" target site, within the last exon of the genes (FIG. 3).

A. TS-MS26 Target Site and Engineered MS26 Endonucleases

As described in Example 2, the TS-MS26 target site was selected for design of engineered MS26 endonucleases. Both Indica and *japonica* rice varieties contain this endogenous TS-MS26 target site in their genome. The genomic region comprising the TS-MS26 target site in rice is shown in FIG. 3 (SEQ ID NO: 14). FIG. 3 also shows the genomic region comprising the TS-MS26 target site in maize (SEQ ID NO: 13), rice (SEQ ID NO: 14), sorghum (SEQ ID NO: 15) and rye (SEQ ID NO: 16) and illustrates that these genomic regions can contain some base pair differences between species and still be a functional target site for an engineered MS26 endonuclease.

B. Vectors and Transformation

Young rice callus (*Oryza sativa* ssp. *japonica* cv. Nipponbare or Kitaake) containing an endogenous TS-MS26 target site was used as transformation targets for *Agrobacterium*- or biolistic-mediated DNA delivery. For biolistic transformation, the vectors PHP40082 and PHP40126 (FIG. 4; SEQ ID NOs: 58 and 59, respectively) were co-bombarded into two-week-old, seed-derived callus by modifying a protocol described by Chen et al. ((1998) *Plant Cell Rep.* 18:25-31). PHP40082 contains a plant optimized sequence (SEQ ID NO:5) encoding a single-chain engineered MS26+ endonuclease placed under the transcriptional control of the maize Ubiquitin promoter. PHP40126 contains the herbicide resistance selectable marker fused to the Red-fluorescence gene (RFP) and placed under the regulation of the maize END2 promoter.

PHP40827 was used to generate rice events by *Agrobacterium*-mediated transformation. PHP40827 contains a plant optimized nucleotide sequence (SEQ. ID NO:5), encoding a single-chain engineered MS26+ endonuclease, placed under the transcriptional control of a CAMV35S promoter containing 3 copies of the Tet operator. This plasmid also contains the tetracycline repressor under the control of the maize Ubiquitin promoter, and a blue-fluorescence gene (CFP) regulated by the ZmEND2 promoter. In addition, PHP40827 contains a copy of a red fluorescence gene regulated by the maize Histone 2B promoter. A portion of the red fluorescence gene in this construct was duplicated in a direct orientation, consisting of two fragments of the RFP gene with 369 bp of overlap. The two fragments are separated by a 136-bp spacer which contains the TS-MS26 target site (FIG. 6A). In the absence of tetracycline, callus fluoresce blue due to the expression of the CFP-marker. In the presence of tetracycline, derepression of the engineered MS26+ meganuclease would lead to double-strand breaks at the TS-MS26 target site between the two overlapping sequences to promote intramolecular recombination and produce a functional RFP gene, which is revealed by the appearance of red fluorescing cells against a background of blue fluorescence. Red fluorescing callus events were selected for additional characterization and plant regeneration.

C. Identification of Mutations at the TS-MS26 Target Site in Plant Tissues

Bialaphos-resistant red fluorescing callus or blue and red fluorescing callus events generated by biolistic or *Agrobacterium*-mediated transformation, respectively were screened for TS-MS26 target site mutations by amplification of the region by PCR using the primer pair UNIMS26 5'-2 (GACGTGGTGCTCAACTTCGTGAT) (SEQ ID NO: 17) and UNIMS26 3'-1 (GCCATGGAGAGGATGGTCATCAT) (SEQ ID NO: 18) and digestion of the amplified products with the DNA restriction enzyme, BsiWI, which recognizes the sequence 5'-CGTACG-3'. Products of these reactions were electrophoresed on 1% agarose gels and screened for BsiWI digestion resistant bands indicative of mutations at the TS-MS26 target site.

Twenty two of the 292 bialaphos-resistant events generated by co-bombardment PHP40082 and PHP40126 events contained PCR products resistant to BsiWI restriction enzyme digestion indicating mutations at TS-MS26 target site. Subcloning and DNA sequence analysis of these PCR products revealed a variety of mutations across the TS-MS26 target site, including point mutations, as well as deletions and insertions ranging from one to greater than 250 nucleotides. Examples of these mutations are shown in FIG. 5. In several cases the insertion at the TS-MS26 target site-consisted of fragments of sequences derived from the co-bombarded vector (for example, see, FIG. 5; Event 48 (Ev.48) contains 54 base pairs of RFP).

Blue fluorescing rice callus events containing PHP40827 were also screened for the presence of mutations at the TS-MS26 target site after treatment with tetracycline (FIG. 6B). Eight independent PHP40827 events were placed onto callus maintenance media containing 1 mg/liter tetracycline (TET) for 24 hours at 37° C.; genomic DNA was isolated and analyzed by PCR for mutations at the TS-MS26 target site and compared to the PCR products of these same events not exposed to tetracycline (control) (FIG. 6B). Six of the eight PHP40827 events yielded BsiWI resistant PCR products that were dependent upon tetracycline application. PCR products from TET and control treatments were subcloned and subjected to DNA sequence analysis. The majority of the PCR products from the uncut control treatment reactions did not reveal mutations across the TS-MS26 target site. In contrast, the majority of the DNA sequences from BSIWI resistant PCR products revealed a high proportion of deletions and insertions across the TS-MS26 target site (see, examples in FIG. 7). Plants were regenerated from callus events containing mutations at the TS-MS26 target site for phenotypic analysis.

D. Phenotypic Analysis of Rice Plants Containing MS26 Mutations

Herbicide resistant plants regenerated from callus events co-bombarded with PHP40082 and PHP40126 as well as plants from blue fluorescing callus containing PHP40827 were grown under greenhouse conditions, analyzed for mutations in MS26 and allowed to set selfed seed (T1 seed). Male fertility was screened by selecting T1 seed from 6 plants (3 PHP40082/PHP40126 and 3 PHP40827) containing non-identical MS26 mutations but lacking the vectors used for transformation. Male fertility was determined by examining anthers for the development of starch filling pollen grains coupled with the plant's ability to set self seed. Plantlets were screened by PCR for mutations at the TS-MS26 target site target site; MS26/ms26 heterozygous and ms26/ms26 homozygous mutant plants were advanced and scored for their ability to generate functional pollen (FIG. 10A). In summary, 34 of 34 of the MS26/ms26 plants were male fertile, while, with two exceptions, 27 of the 29 ms26/ms26 plants were male sterile (Table 4). Microscopic examination of anthers derived from ms26/ms26 plants staged at late uninucleate microspore development revealed a reduced number and abnormally shaped microspores (FIG. 10B). In contrast, anthers from MS26/ms26 plants contained many normal microspores (FIG. 10C) similar to observations reported by Li et al. (Plant Cell 2010; 22:173). The male sterile plants were female fertile as demonstrated by their ability to set seed when fertilized with wild-type rice pollen.

TABLE 4

Fertility scores of rice plants from selfed seed

| SOURCE | | | MS26/ms26 | | ms26/ms26 | |
|---|---|---|---|---|---|---|
| PHP40082/PHP40126 | MUTATION | Num. plants | FERTILE | STERILE | FERTILE | STERILE |
| EVENT 1 | 66bp INSERTION | 8 | 4 | | 1* | 3 |
| EVENT 2 | 36 bp deletion | 23 | 17 | | | 6 |
| EVENT 3 | 56bp deletion | 8 | 4 | | | 4 |
| PHP40827 | | | | | | |
| EVENT 4 | 51bp deletion | 8 | 3 | | | 5 |
| EVENT 5 | LARGE DELETION | 8 | 3 | | 1* | 4 |
| EVENT 6 | 3 bp deletion | 8 | 3 | | | 5 |

*incorrect genotype

Example 4

Targeted Mutations in the Maize MS45 Gene

Maize lines comprising an endogenous target recognition sequence in their genome were contacted with an engineered meganuclease designed to specifically recognize and create a double-strand break in the endogenous target sequence in the MS45 gene. Immature embryos comprising an endogenous target site were contacted with the components described below, events selected and characterized.

A. Maize TS-MS45 Target Site and Engineered MS45 Endonuclease

An endogenous maize genomic target site located in the MS45 gene and referred to as the TS-MS45 target site (SEQ ID NO: 20), was selected for design of an engineered double-strand-break-inducing agent.

The genomic region comprising the TS-MS45 target site has the following sequence, with the TS-MS45 target site shown underlined:

```
                                          (SEQ ID NO: 19)
GGAGTTCTGCGGCCGGCCGCTCGGCCTGAGGTTCCACGGGGAGACCGGCG

AGCTCTACGTCGCCGACGCGTACTACGGTCTCATGGTCGT
```

The TS-MS45 target site is a 22 bp polynucleotide having the following sequence:

```
CGGGGAGACCGGC^GAGCTCTAC        (SEQ ID NO: 20)
```

The double strand beak site and overhang region is shown in bold, the enzyme cuts after nucleotide 13, as indicated by the ^.

An engineered MS45 endonuclease designed to recognize the TS-MS45 target site was produced under contract with Precision BioSciences, Inc. (Durham, N.C. USA). The engineered MS45 endonuclease is a heterodimer. One monomer is designated MAY1 and the other is designated MAY2.

A nucleus localization signal (SEQ ID NO: 21) was added to the amino terminus of each monomer to improve transport of the protein into the nucleus.

Plant optimized nucleotide sequences encoding MAY1 (SEQ ID NO: 22) or MAY2 (SEQ ID NO: 23) were constructed.

B. Vector Construction for Plant Expression Vectors Encoding the Engineered MS45 Endonuclease and Repair DNAs for Transgene Integration by Homologous Recombination The strategies employed for generating and selecting genomic alterations produced do not employ reconstitution of a selectable marker expression cassette, therefore the double-strand-break-inducing agent vectors do not have a fragment of a selectable marker cassette. In this example, the double-strand-break-inducing agent vectors had a phenotypic marker expression cassette encoding phosphinothricin acetyltransferase, which was used to validate successful delivery of the vector.

Vectors containing the plant optimized coding sequences encoding an MS45 endonuclease were constructed using standard molecular biology techniques. PHP31456 comprises the following operably linked components: Ubi pro:: ubi 5' UTR::cMAY1::pinII::Ubi pro::ubi 5' UTR::cMAY2::pinII::35 S CaMV pro::BAR::pinII; wherein ubi pro is the maize ubiquitin promoter, ubi 5' UTR is the 5' untranslated region of the maize ubiquitin gene, cMAY1 and cMAY2 are the DNA sequences encoding the MAY1 and MAY2 monomers, respectively, designed to specifically recognize and induce a double-strand break at the endogenous TS-MS45 maize genome target site, 35S CaMV pro is the 35S Cauliflower Mosaic Virus promoter, BAR encodes phosphinothricin acetyltransferase, and pinII is the transcription termination sequence from potato proteinase inhibitor II. PHP31458 comprises the following operably linked components: Ubi pro::ubi 5' UTR::NLS::cMAY1::pinII::Ubi pro::ubi 5' UTR::NLS::cMAY2::pinII::35 S CaMV pro::BAR::pinII; wherein ubi pro is the maize ubiquitin promoter, ubi 5' UTR is the 5' untranslated region of the maize ubiquitin gene, NLS is a DNA fragment encoding an SV40 nuclear localization signal, cMAY1 and cMAY2 are the DNA sequences encoding the MAY1 and MAY2 monomers, respectively, designed to specifically recognize and induce a double strand break at the endogenous TS-MS45 maize genome target site, 35S CaMV pro is the 35S Cauliflower Mosaic Virus promoter, BAR encodes phosphinothricin acetyltransferase, and pinII is the transcription termination sequence from potato proteinase inhibitor II.

These vectors were designed to induce double-strand breaks at the TS-MS45 target site and thereby produce alterations of the TS-MS45 target site. The vector components of PHP31456 and PHP31458 were inserted between the right border and left border of T-DNA for *Agrobacterium* mediated introduction into plant cells creating vectors PHP31457 AND PHP31459.

Maize immature embryos 9-12 days after pollination (DAP) were transformed with vector PHP31457 (SEQ ID NO: 30) or PHP31459 (SEQ ID NO: 31) using *Agrobacterium*-mediated methods as described in Example 2C.

Bialaphos resistance was used to identify putative transformation events by callus selection on media containing 3 mg/L bialaphos. Callus tissue and/or plants regenerated from stable transformants using standard culture and regeneration conditions were screened for modification(s) of the endogenous target site.

C. Evaluation of Transformed Maize for Modification of TS-MS45 Target Site

Any standard protocol for isolation, manipulation, and characterization of polynucleotides and or proteins can be used to identify, select, and characterize putative modification events.

PCR products were produced from genomic DNA obtained from transformed maize cells using primers flanking the target site and purified by Qiaquick (Qiagen Inc., Valencia, N. Mex., USA). The double-strand-break-inducing enzyme or a restriction enzyme contained in the target site was added to the purified target site PCR product DNA to test if the target site had been modified. This mixture was digested at 37° C. for about 0.5 hr to overnight (approximately 17 hr), the digestion time depending on the enzyme used. Samples with meganuclease enzyme were treated with 0.5 µL proteinase K and 0.2 µL 20% SDS to denature the protein. The digestion products were separated on a 1.5 to 2% agarose gel. Undigested products indicate that the target site was modified.

Bialaphos-resistant callus and/or T0 plant events were screened for mutations at the TS-MS45 target site by PCR amplification of the target site region using a primer pair which produced a 389 bp product. Samples that yielded the 389 bp PCR product were subjected to enzyme digestion with an engineered MS45 endonuclease. In some cases the PCR product was directly cloned and sequenced. No transformation events with modifications of TS-MS45 target site were identified in approximately 300 transformed plants analyzed.

D. Improvements of the Engineered MS45 Endonuclease

Further evaluation of the engineered MS45 endonuclease indicated that the activity of this nuclease was lower than other nucleases, e.g. MS26+ and MS26++, that were able to produce modifications of endogenous maize target sites.

An improvement in the design of the engineered MS45 endonuclease expected to increase nuclease activity in maize is a single chain protein comprising the MAY1 and MAY2 monomers fused using a linker polypeptide. The MAY1 and MAY2 monomers can be linked to create a single chain protein of the form MAY1-linker-MAY2 or MAY2-linker-MAY1. A plant optimized gene encoding a MAY1-linker-MAY2 protein is shown in SEQ ID NO: 34. If desired, a nuclear localization signal (e.g., SEQ ID NO: 21) can be added to the amino terminus of this protein.

E. Alternate Method for Delivery of Engineered MS45 Endonuclease Genes into Maize Cells Introduction of an engineered MS45 endonuclease gene via a direct DNA delivery method, e.g. particle bombardment, increases the copy number of the meganuclease gene, as compared to introduction of the meganuclease gene via *Agrobacterium*; the increased meganuclease gene copy number increases frequency of the target site modifications 10-50 fold. Immature maize embryos from greenhouse or field grown High type II (Hill) donor plants are bombarded with at least one polynucleotide construct described above. If the construct does not include a selectable marker, another polynucleotide containing a selectable marker gene can be co-precipitated on the particles used for bombardment.

Ears are harvested 8-12 days after pollination for the isolation of fertilized embryos. The harvested ears are surface sterilized in 50% Clorox® bleach plus 0.5% Micro detergent for 20 minutes, then rinsed twice with sterile water. The immature embryos are isolated and placed embryo axis side down (scutellum side up), 25 embryos per plate. These are cultured on 560L agar medium 4 days in the dark prior to bombardment. Medium 560L is an N6-based medium containing Eriksson's vitamins, thiamine, sucrose, 2,4-D, and silver nitrate. The day of bombardment, the embryos are transferred to 560Y medium for 4 hours and are arranged within the 2.5-cm target zone. Medium 560Y is a high osmoticum medium (560L with high sucrose concentration).

Particles are prepared by precipitating the DNA to be delivered onto 1.0 µm (average diameter) gold pellets using a $CaCl_2$ precipitation procedure as follows: 100 µL prepared gold particles (0.6 mg) in water, 20 µL (2 µg) DNA in TrisEDTA buffer (1 µg total), 100 µL 2.5 M $CaCl_2$, 40 µl 0.1 M spermidine. Each reagent is added sequentially to the gold particle suspension. The final mixture is sonicated briefly. After the precipitation period, the particles are centrifuged briefly, washed with 500 µL 100% ethanol, pelleted again and resuspended in 60 µL 100% ethanol to make the final suspension. Macrocarriers are prepared by briefly sonicating the final preparation, spotting 5 µL onto the center of each macrocarrier, and drying for about 2 minutes before bombardment. The sample plates are bombarded at a distance of 8 cm from the stopping screen to the tissue, using a DuPont biolistics helium particle gun. All samples receive a single shot at 650 PSI, with a total of ten aliquots taken from each tube of prepared particles/DNA.

Alternatively, DNA to be delivered is associated with microparticles using a reagent comprising a cationic lipid solution. For example, DNA solutions are added to 50 µL of a gold-particle stock solution (0.1 µg/µL of 0.6 micron gold particles). A DNA stock, 10 µL of a 0.1 µg/µL plasmid solution, is added to 30 µL of water. To this DNA mixture, 50 µL of the gold stock solution is added and the mixture briefly sonicated. Next 5 µL of TFX-50™ (Promega Corp, Madison Wis.) is added, and the mixture is placed on a rotary shaker at 100 rpm for 10 minutes. The mixture is briefly centrifuged to pellet the gold particles and remove supernatant. After removal of the excess DNA/TFX solution, 120 µL of absolute EtOH is added, and 10 µL aliquots are dispensed onto the macrocarriers typically used with the DuPont PDS-1000 Helium Particle Gun. The gold particles with adhered DNA are allowed to dry onto the carriers and then these are used for standard particle bombardment.

Four to 12 hours post bombardment, the embryos are moved to a low osmoticum callus initiation medium for 3-7 days at 28° C., then transferred to selection medium and subcultured every 2 weeks. Incubation of the embryos post bombardment for about 48 hrs at 32° C. increases the frequency of target site modifications 2-4 fold for most meganucleases. After about 10 weeks, embryos are transferred to regeneration media. Following 2-4 weeks of somatic embryo maturation, well-developed somatic embryos are transferred to germination medium in a lighted culture room. Approximately 7-10 days later, developing plantlets are transferred to tubes until plantlets are well established and can be transplanted into flats and/or pots and grown to maturity.

Example 5

Male-Sterile *Sorghum* Plants Produced by the Targeted Mutagenesis of a Cytochrome P450-Like Gene, MS26, Using an Engineered MS26 Endonuclease A. TS-MS26 Target Site and Engineered MS26 Endonucleases As described in Example 2, the TS-MS26 target site was selected for design of engineered MS26 endonucleases. The genomic region comprising the TS-MS26 target site in sorghum (*Sorghum bicolor*) is shown in FIG. 3 (SEQ ID NO: 15).

B. Vectors and Transformation

Immature sorghum (*Sorghum bicolor*) embryos containing an endogenous MS26 target site (TS-MS26, SEQ ID NO: 1) were used as transformation targets for *Agrobacterium* DNA delivery. PHP42063 (SEQ ID NO: 61) was used to generate sorghum callus events by *Agrobacterium*-mediated transformation. PHP42063 contains a single chain MS26+ endonuclease (described in Example 2) placed under the transcriptional control of the maize CAS1 promoter. The CAS1 promoter has been shown to be transcriptionally induced by either the sulfonylurea-safener, 2-CBSU, or by elevated temperature (U.S. Patent application 61/648,758, filed May 18, 2012). PHP42063 also contains a blue-fluorescence gene (CFP) regulated by the ZmEND2 promoter which is used as visual marker for the selection of integration of the T-DNA into sorghum cells. In addition, PHP42063 also contains a copy of a red fluorescence gene regulated by the maize Histone 2B promoter. A portion of the red fluorescence gene in this construct was duplicated in a direct orientation, consisting of two fragments of the RFP gene with 369 bp of overlap. The two fragments are separated by a 136-bp spacer which contains an MS26 target site as described for PHP40827 (FIG. 6, SEQ ID NO:60). Immature embryos were transformed with PHP42063 according to Zhao et al (*Plant Molecular Biology* 44: 789-798, 2000). Blue fluorescing calli were selected and used for regeneration of plants and grown in the greenhouse to maturity and seed set. *Sorghum* plants containing DNA insertions of PHP42063 were verified by copy-number analysis. Four independent single or low-copy PHP42063 transformed plants were selected for additional experimentation. Blue fluorescing immature embryos were harvested 14-20 days after pollination, sterilized, placed on maintenance media (PHI-U without PPT selection) and incubated in the dark at either room temperature (23 C-26 C) or at the elevated temperature of 37 C for 24 to 48 hours. At the end of this period, embryos incubated at the elevated temperature were moved to room temperature (<260) and embryos were allowed to grow in the dark. As described above, embryos containing PHP42063 and maintained at 26 C post harvest only fluoresce blue due to the expression of the CFP-marker. In contrast, approximately 72 hours after treatment at elevated temperature, embryos incubated at 37 C begin to develop red fluorescing sectors on the embryo. This observation suggests that the heat inducible gene cassette, CAS1:MS26+, has resulted in double-strand breaks at the MS26 target site between the two overlapping sequences of the RF-FP reporter promoting intramolecular recombination and producing a functional RPF gene which is revealed by the appearance of red fluorescing cells against a background of blue fluoresce. Red fluorescing callus events were selected for plant regeneration and additional molecular and phenotype characterization.

C. Identification of Mutations at the TS-MS26 Target Site in *Sorghum* Tissues

Regenerated plants were screened for mutations at the TS-MS26 target site by amplification of the region by PCR using the primer pair UNIMS26 5'-2 (GACGTGGTGCT-CAACTTCGTGAT, SEQ ID NO: 17) and UNIMS26 3'-1 (GCCATGGAGAGGATGGTCATCAT, SEQ ID NO: 18) and digestion of the amplified products with the DNA restriction enzyme, BsiWI, which recognizes the sequence 5'-CGTACG-3'. Products of these reactions were electrophoresed on 1% agarose gels and screened for BsiWI digestion resistant bands indicative of mutations at the TS-MS26 target site.

One hundred twenty nine out of the 389 regenerated plants from PHP42063 heat treated embryos generated contained PCR products resistant to BsiWI restriction enzyme digestion indicating mutations at the TS-MS26 target site. Subcloning and DNA sequence analysis of these PCR products revealed a variety of mutations across the TS-MS26 region which consisted of primarily deletions within and across the TS-MS26 target site ranging from 3 to 98 nucleotides. Occasionally, small insertions of single to 11 nucleotides were detected. In total, 16 non-identical mutations were identified in these regenerated sorghum plants (FIG. 12, SEQ ID NOs: 62-78). Plants containing mutations at the TS-MS26 target site were used for phenotypic analysis.

D. Phenotypic Analysis of *Sorghum* Plants Containing MS26 Mutations

Regenerated plants containing mutations at TS-MS26 in *Sorghum* were grown under greenhouse conditions and allowed to set selfed seed (T1 seed). Male fertility phenotype was screened by planting T1 seed from plants containing the 78 bp deletion (ms26.78Δ across the TS-MS26 target site and allowing these plants to flower. Prior to flowering, seedlings were screened by PCR for mutations at the TS-MS26 target site; MS26/MS26 (wild-type), MS26/ms26.78Δ (heterozygous) and ms26.78Δ/ms26.78Δ (recessive) plants were identified and advanced. Male fertility was determined by examining anthers for the development of starch filling pollen grains coupled with the plant's ability to set self seed. As shown in FIG. 13A, panicles of MS26/ms26.78Δ revealed anther extrusion, pollen shed and seed set. In contrast, ms26.78Δ/ms26.78Δ plants (FIG. 13B) extruded small shriveled anthers, did not shed pollen and did not set seed. In contrast to examination of anthers from MS26/ms26.78Δ plants (FIG. 14A), anthers from ms26.78Δ/ms26.78Δ plants were small (FIG. 14B). In addition, when anthers from these plants were more closely examined, pollen was easily detected in MS26/ms26.78Δ anthers (FIG. 14C), however pollen was not observed from anthers from ms26.78Δ/ms26.78Δ plants (FIG. 14D). Good correlation of the fertility phenotype and the MS26 genotype was observed. In summary, all MS26/MS26 and MS26/ms26.78Δ plants were male fertile, while all ms26.78Δ/ms26.78Δ plants were male sterile (Table 5). These male sterile plants were female fertile as demonstrated by their ability to set seed when fertilized with wild-type sorghum pollen (data not shown).

TABLE 5

Fertility scores of *Sorghum* plants

| Genotype | Fertile | Sterile |
| --- | --- | --- |
| MS26/MS26 | 3 | 0 |
| MS26/ms26.78Δ | 7 | 0 |
| ms26.78Δ/ms26.78Δ | 0 | 8 |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for making a targeted modification in a male fertility gene in the genome of a plant, said method comprising: (a) contacting at least one plant cell comprising, in a MS26 male fertility gene, a target sequence comprising SEQ ID NO.: 1 with an engineered meganuclease that is capable of inducing a double-strand break at the target sequence in the MS26 male fertility gene, wherein the engineered meganuclease is modified to specifically cut at the target sequence, and wherein the engineered meganuclease no longer cuts at its wild-type meganuclease target sequence; and (b) identifying at least one cell from step (a)

comprising an alteration in its genome at the target sequence wherein the alteration is selected from the group consisting of (i) replacement of at least one nucleotide, (ii) a deletion of at least one nucleotide, (iii) an insertion of at least one nucleotide, and (iv) any combination of (i) through (iii); wherein the alteration of the male fertility gene is a null mutation.

2. The method of claim 1, wherein a plant that is homozygous for the null mutation is male sterile.

3. The method of claim 1, further comprising selfing the plant and selecting a progeny plant resulting therefrom, wherein said progeny plant is homozygous for the alteration.

4. The method of claim 1, further comprising crossing the plant with a second fertile plant comprising a null mutation in the male fertility gene and selecting a progeny plant resulting therefrom, wherein said progeny is male sterile.

5. The method of claim 1, wherein the alteration comprises insertion of a transgene comprising a polynucleotide of interest.

6. The method of claim 5, wherein the transgene further comprises a promoter operably linked to the polynucleotide of interest, and wherein the promoter is capable of driving the expression of the polynucleotide of interest in a plant.

7. The method of claim 1, wherein the plant is selected from the group consisting of maize, sorghum, rice, wheat, rye, barley, millet and oat.

8. The method of claim 1, wherein the engineered meganuclease is derived from I-CreI.

9. The method of claim 1, wherein step (a) further comprises introducing into the at least one plant cell a nucleic acid construct comprising a nucleotide sequence encoding the engineered meganuclease.

10. The method of claim 9, wherein the nucleotide sequence is the nucleotide sequence set forth in SEQ ID NO: 4, 5, 6, or 7.

11. The method of claim 10, wherein the nucleic acid construct further comprises a promoter operably linked to the nucleotide sequence encoding the engineered meganuclease, wherein the promoter is capable of driving expression of the nucleotide sequence in a plant cell.

12. The method of claim 11, wherein the promoter is a maize ubiquitin promoter.

13. The method of claim 10, wherein the nucleic acid construct further comprises an operably linked nucleotide sequence encoding a nuclear localization signal.

14. The method of claim 13, wherein the nuclear localization signal comprises an amino acid sequence selected from the group consisting of SEQ ID NOS: 2, and 3.

* * * * *